(12) United States Patent
Wu et al.

(10) Patent No.: US 7,964,706 B2
(45) Date of Patent: Jun. 21, 2011

(54) HIGH AFFINITY ANTIBODIES AGAINST HMGB1 AND METHODS OF USE THEREOF

(75) Inventors: Herren Wu, Boyds, MD (US);
Changshou Gao, Potomac, MD (US);
Ling-Ling An, Boyds, MD (US); Peter Kiener, Potomac, MD (US); Su-Yau Mao, Gaithersburg, MD (US); Anthony Coyle, Washington, DC (US); Jane Tian, North Potomac, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 12/094,447

(22) PCT Filed: Nov. 27, 2006

(86) PCT No.: PCT/US2006/061258
§ 371 (c)(1),
(2), (4) Date: Sep. 29, 2008

(87) PCT Pub. No.: WO2007/084253
PCT Pub. Date: Jul. 26, 2007

(65) Prior Publication Data
US 2009/0169546 A1 Jul. 2, 2009

Related U.S. Application Data

(63) Continuation-in-part of application No. 11/254,679, filed on Oct. 21, 2005.

(60) Provisional application No. 60/739,938, filed on Nov. 28, 2005, provisional application No. 60/765,746, filed on Feb. 7, 2006, provisional application No. 60/799,639, filed on May 12, 2006, provisional application No. 60/822,044, filed on Aug. 10, 2006, provisional application No. 60/822,041, filed on Aug. 10, 2006, provisional application No. 60/620,726, filed on Oct. 22, 2004, provisional application No. 60/651,512, filed on Feb. 10, 2005, provisional application No. 60/658,572, filed on Mar. 7, 2005, provisional application No. 60/662,944, filed on Mar. 18, 2005, provisional application No. 60/713,712, filed on Sep. 6, 2005.

(51) Int. Cl.
*C07K 16/00* (2006.01)
(52) U.S. Cl. .................... 530/387.9; 424/142.1
(58) Field of Classification Search .............. None
See application file for complete search history.

(56) References Cited

U.S. PATENT DOCUMENTS

| | | |
|---|---|---|
| 5,545,806 A | 8/1996 | Lonberg et al. |
| 5,545,807 A | 8/1996 | Surani et al. |
| 5,594,114 A | 1/1997 | Goodearl et al. |
| 5,605,690 A | 2/1997 | Jacobs et al. |
| 5,656,272 A | 8/1997 | Le et al. |
| 5,859,205 A | 1/1999 | Adair et al. |
| 6,177,077 B1 | 1/2001 | Tobinick |
| 6,303,321 B1 | 10/2001 | Tracey et al. |
| 6,323,329 B1 | 11/2001 | Bullerdiek |
| 6,448,233 B1 | 9/2002 | Lefevre et al. |
| 6,468,533 B1 | 10/2002 | Tracey et al. |
| 7,304,034 B2 | 12/2007 | Tracey et al. |
| 2002/0009749 A1 | 1/2002 | Ozaki et al. |
| 2003/0017155 A1 | 1/2003 | Tracey et al. |
| 2003/0060410 A1 | 3/2003 | Tracey et al. |
| 2003/0113323 A1 | 6/2003 | Tracey et al. |
| 2003/0143194 A1 | 7/2003 | Tracey et al. |
| 2004/0053841 A1 | 3/2004 | Tracey et al. |
| 2004/0120953 A1 | 6/2004 | Tracey et al. |
| 2004/0141948 A1 | 7/2004 | O'Keefe |
| 2005/0118688 A1 | 6/2005 | Freeze et al. |
| 2005/0152903 A1 | 7/2005 | Newman et al. |
| 2006/0057679 A1 | 3/2006 | O'Keefe et al. |
| 2006/0099207 A1 | 5/2006 | Wu et al. |

FOREIGN PATENT DOCUMENTS

| | | |
|---|---|---|
| EP | 1 079 849 B1 | 1/2002 |
| JP | 62-166897 A | 7/1987 |
| JP | 2003-096099 | 4/2003 |
| WO | WO-96-25493 A1 | 8/1996 |
| WO | WO-97-23611 A2 | 7/1997 |
| WO | WO-99-59609 A2 | 11/1999 |
| WO | WO-00-47104 A2 | 8/2000 |
| WO | WO-02-074337 A1 | 9/2002 |
| WO | WO-02-092004 | 11/2002 |

(Continued)

OTHER PUBLICATIONS

Abaza, M. S., et al. "Effects of Amino Acid Substitutions Outside an Antigenic Site on Protein Binding to Monoclonal Antibodies of Predetermined Specificity obtained by Peptide Immunization: Demonstration with Region 94-100 (Antigenic Site 3) of Myoglobin." *J. Protein Chem.* (1992) 11: 433-44.

(Continued)

*Primary Examiner* — Michael Pak
(74) *Attorney, Agent, or Firm* — Hamilton, Brook, Smith & Reynolds, P.C.

(57) ABSTRACT

Compositions and methods are disclosed for inhibiting the release of a proinflammatory cytokine from a vertebrate cell, and for inhibiting an inflammatory cytokine cascade in a patient. The compositions comprise, for example, high affinity antibodies that specifically bind HMG1 and antigenic fragments thereof. The high affinity antibodies of the present invention and pharmaceutical compositions comprising the same are useful for many purposes, for example, as therapeutics against a wide range of inflammatory diseases and disorders such as sepsis, rheumatoid arthritis, peritonitis, Crohn s disease, reperfusion injury, septicemia, endotoxic shock, cystic fibrosis, endocarditis, psoriasis, psoriatic arthritis, arthritis, anaphylactic shock, organ ischemia, reperfusion injury, and allograft rejection. In addition, the high affinity antibodies of the present inventions are useful as diagnostic antibodies.

16 Claims, 87 Drawing Sheets

FOREIGN PATENT DOCUMENTS

Figure 2E:
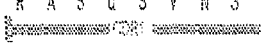

| WO | WO-02-092004 A2 | 11/2002 |
| --- | --- | --- |
| WO | WO-2004-004763 A2 | 1/2004 |
| WO | WO-2005-034952 A2 | 4/2005 |
| WO | WO 2007/011606 A2 | 1/2007 |
| WO | WO-2007-054090 A1 | 5/2007 |
| WO | WO-2007-076200 A2 | 7/2007 |
| WO | WO-2007-084253 A2 | 7/2007 |

OTHER PUBLICATIONS

Abraham, E., et al. "HMG-1 as a Mediator of Acute Lung Inflammation." *J.Immunol.* (2000) 165:2950-4.

An, L-L, and et al. "Targeting Different Isoforms of HMGB1 Leads to Different Beneficial Effects in Preclinical Models of Sepsis and Inflammatory Arthritis (Abstract and Presentation)." 94th Annual AAI Meeting. Miami Beach, FL, May 18-22, 2007. pp. 1-10.

Andersson, U., et al. "High Mobility Group 1 Protein (HMG-1) Stimulates Proinflammatory Cytokine Synthesis in Human Monocytes." *J.Exp.Med.* (2000) 192: 565-70.

Ayer, L. M., et al. "Antibodies to HMG Proteins in Patients with Drug-Induced Autoimmunity" *Arthritis Rheum.* (1994) 37:98 -103.

Banks, G. C., et al. "The HMG-I(Y) A.T-Hook Peptide Motif Confers DNA-Binding Specificity to a Structured Chimeric Protein." *J.Biol. Chem.* (1999) 274: 16536-44.

Baxevanis, A. D., et al. "The HMG-1 Box Protein Family: Classification and Functional Relationships." *Nucleic Acids Res.* (1995) 23: 1604-13.

Benjamini, E. "Antigenicity." *Immunology, A Short Course.*, 1991. 40.Wiley-LissNew York.

Bianchi, M. E., et al. "Specific Recognition of Cruciform DNA by Nuclear Protein HMG1." *Science* (1989) 243: 1056-9.

Bianchi, M. E., et al. "The DNA Binding Site of HMG1 Protein is Composed of Two Similar Segments (HMG Boxes), both of which have Counterparts in Other Eukaryotic Regulatory Proteins." *EMBO J.* (1992) 11: 1055-63.

Bustin, M. "Revised Nomenclature for High Mobility Group (HMG) Chromosomal Proteins." *Trends Biochem.Sci.* (2001) 26: 152-3.

Bustin, M. "Regulation of DNA-Dependent Activities by the Functional Motifs of the High-Mobility-Group Chromosomal Proteins." *Mol.Cell.Biol.* (1999) 19: 5237-46.

Bustin, M., et al. "Antigenic Determinants of High Mobility Group Chromosomal Proteins 1 and 2." *Biochemistry* (1982) 21: 6773-7.

Bustin, M., et al "Immunological Relatedness of High Mobility Group Chromosomal Proteins from Calf Thymus." *J.Biol.Chem.* (1978) 253: 1694-9.

Cattaneo, A., et al. "The Selection of Intracellular Antibodies." *Trends in biotechnology* 17.3 (1999): 115-21.

Chou, D. K., et al. "Identity of Nuclear High-Mobility-Group Protein, HMG-1, and Sulfoglucuronyl Carbohydrate-Binding Protein, SBP-1, in Brain." *J.Neurochem.* (2001) 77: 120-31.

Clackson, T., et al. "Making Antibody Fragments using Phage Display Libraries." *Nature* (1991) 352: 624-8.

Colman, P. M. "Effects of Amino Acid Sequence Changes on Antibody-Antigen Interactions." *Res.Immunol.* (1994) 145: 33-6.

Coyle, A. J. "HMBG1—New Role for an Old Protein a Mediator of Inflammation and Autoimmune Disease (Presentation)." National Cancer Institute. Frederick, MD, Jun. 21, 2007. pp. 1-32.

Coyle, A. J., and et al. "HMBG1—New Role for an Old Protein a Mediator of Inflammation and Autoimmune Disease (Abstract and Presentation)." British Society of Biochemistry. Cambridge, UK, Aug. 8-10. pp. 1-32.

Czura, C. J., et al. "High Mobility Group Box-1 as a Therapeutic Target Downstream of Tumor Necrosis Factor." *J.Infect.Dis.* (2003) 187 Suppl 2: S391-6.

Czura, C. J., et al. "Dual Roles for HMGB1: DNA Binding and Cytokine." *J.Endotoxin Res.* (2001) 7: 315-21.

Daston, M. M., et al. "Expression of P30, a Protein with Adhesive Properties, in Schwann Cells and Neurons of the Developing and Regenerating Peripheral Nerve." *J.Cell Biol.* (1991) 112: 1229-39.

Degryse, B., et al. "The High Mobility Group (HMG) Boxes of the Nuclear Protein HMG1 Induce Chemotaxis and Cytoskeleton Reorganization in Rat Smooth Muscle Cells." *J.Cell Biol.* (2001) 152: 1197-206.

Dumitriu, I. E., et al. "Requirement of HMGB1 and RAGE for the Maturation of Human Plasmacytoid Dendritic Cells." *Eur.J.Immunol.* (2005) 35: 2184-90.

Falciola, L., et al. "High Mobility Group 1 Protein is Not Stably Associated with the Chromosomes of Somatic Cells." *J.Cell Biol.* (1997) 137: 19-26.

Freeman, B. D., et al. "The Role of Inflammation in Sepsis and Septic Shock: A Meta-Analysis of both Clinical and Preclinical Trials of Anti-Inflammatory Therapies." *Inflammation: Basic Principals and Clinical Correlates.*, 1999.pp. 965-975. Gallin, J.I.; Snyderman, R.eds., Lippincott, Williams & Wilkins Philadelphia.

GenBank. "Accession No. AAA64970, "HMG-1," (1995) [Online] [Retrieved on Sep. 30, 2004]. Retrieved from the Internet: <URL:Http://www.Ncbi.Nlm.Nih.gov/entrez/viewer. Fcgi?db=protein&val=184251>."

GenBank. "Accession No. AAB08987, "Non-Histone Chromatin Protein HMG1 [*Homo sapiens*]," (1996) [Online] [Retrieved on Mar. 21, 2006]. Retrieved from the Internet: <URL:Http://www.Ncbi. Nlm.Nih.gov/entrez/viewer.Fcgi?db=protein&val=1435197>."

GenBank. "Accession No. PO7155, "High Mobility Group Protein 1 (HMG-1) (Amphoterin) (Heparin-Binding Protein p30)," (2004) [Online] [Retrieved on Mar. 21, 2006]. Retrieved from the Internet: <URL:Http://www.Ncbi.Nlm.Nih.gov/entrez/viewer. Fcgi?db=protein&val=1708258>."

GenBank. "Accession No. AAA20508, "HMG-I," (1994) [Online] [Retrieved on Mar. 21, 2006]. Retrieved from the Internet: <URL:Http://www.Ncbi.Nlm.Nih.gov/entrez/viewer. Fcgi?db=protein&val=437102>."

GenBank. "Accession No. S29857, "Nonhistone Chromosomal Protein HMG-1—Human," (1999) [Online] [Retrieved on Mar. 21, 2006]. Retrieved from the Internet: <URL:Http://www.Ncbi.Nlm. Nih.gov/entrez/viewer.Fcgi?db=protein&val=478813>."

GenBank. "Accession No. P09429, "High Mobility Group Protein 1 (HMG-1) (High Mobility Group Protein B1," (1989) [Online] [Retrieved on Mar. 21, 2006]. Retrieved from the Internet: <URL:Http://www.Ncbi.Nlm.Nih.gov/entrez/viewer. Fcgi?db=protein&val=123369>."

GenBank. "Accession No. NP_002119, "High-Mobility Group Box 1 [*Homo sapiens*]," (2006) [Online] [Retrieved on Mar. 21, 2006]. Retrieved from the Internet: <URL:Http://www.Ncbi.Nlm.Nih.gov/entrez/viewer.Fcgi?db=protein&val=4504425>."

GenBank. "Accession No. CAA31110, "Unnamed Protein Product [*Homo sapiens*]," (2005) [Online] [Retrieved on Mar. 21, 2006]. Retrieved from the Internet: <URL: Http://www.Ncbi.Nlm.Nih.gov/entrez/viewer.Fcgi?db=protein&val=32327>."

GenBank. "Accession No. S02826, "Nonhistone Chromosomal Protein HMG-1—Human," (1999) [Online] [Retrieved on Apr. 18, 2006] . Retrieved from the Internet: <URL: Http://www.Ncbi.nlm. Nih.gov/entrez/viewer.Fcgi?db=protein&val=88270>."

GenBank. "Accession No. U00431, "Mus Musculus HMG-1 mRNA, Complete Cds" (1994) [Online] [Retrieved on 0312 Jan. 2006]. Retrieved from the Internet: <URL:Http://www.Ncbi.Nlm.Nih.gov/entrez/viewer.Fcgi?db=nuccore&val=437101>."

GenBank. "Accession No. X67668, "M. Musculus mRNA for High Mobility Group 2 Protein," (2005) [Online] [Retrieved on Mar. 21, 2006]. Retrieved from the Internet: <URL: Http://www.Ncbi.Nlm. Nih.gov/entrez/viewer.Fcgi?db=nuccore &val=51338>."

GenBank. "Accession No. NP_005333, "High-Mobility Group Box 3 [*Homo sapiens*]," (2005) [Online] [Retrieved on Mar. 21, 2006]. Retrieved from the Internet: <URL: Http://www.Ncbi.Nlm.Nih.gov/entrez/viewer.Fcgi?db=protein&val=71143137>."

GenBank. "Accession No. NM_016957, "Mus Musculus High Mobility Group Nucleosomal Binding Domain 2 (Hmgn2), mRNA," (2006) [Online] [Retrieved on Mar. 21, 2006]. Retrieved from the Internet: <URL:Http://www.Ncbi.nlm.Nih.gov/entrez/viewer. Fcgi?db=nuccore&val=86198321>."

GenBank. "Accession No. J04197, "Rattus Norvegicus 6-Phosphofructo-2-kinase/fructose-2,6-Bisphosphatase mRNA, Complete Cds," (1995) [Online] [Retrieved on Mar. 21, 2006]. Retrieved from the Internet: <URL:Http://www.Ncbi.Nlm.Nih.gov/entrez/viewer.Fcgi?db=nuccore&val=202557>."

GenBank. "Accession No. U51677, "Human Non-Histone Chromatin Protein HMG1 (HMG1) Gene Complete Cds," (1996) [Online]

[Retrieved on Mar. 21, 2006]. Retrieved from the Internet: <URL:Http://www.Ncbi.Nlm.Nih.gov/entrez/viewer.Fcgi?db=nuccore&val=1435196>."

GenBank. "Accession No. M83665, "Human High Mobility Group 2 Protein (HMG-2) Gene, Complete Cds," (1994) [Online] [Retrieved on Sep. 24, 2004]. Retrieved from the Internet: <URL:Http://www.Ncbi.Nlm.Nih.gov/entrez/viewer.Fcgi?db=nuccore&val=184235>."

GenBank. "Accession No. NM_005342, "*Homo sapiens* High-Mobility Group Box 3 (HMGB3), mRNA," (2005) [Online] [Retrieved on Mar. 21, 2006]. Retrieved from the Internet: <URL:Http://www.Ncbi.Nlm.Nih.gov/entrez/viewer.Fcgi?db=nuccore & val=71143136>."

GenBank. "Accession No. PO5114, "Nonhistone Chromosomal Protein HMG-14 (High-Mobility Group Nucleosome-Binding Domain I)," (1987) [Online] [Retrieved on Mar. 24, 2006]. Retrieved from the Internet: <URL:Http://www.Ncbi.Nlm.Nih.gov/entrez/viewer.Fcgi?db=protein&val=123101>."

GenBank. "Accession No. X13546, "Human HMG-17 Gene for Non-Histone Chromosomal Protein HMG-17," (1997) [Online] [Retrieved on Mar. 21, 2006]. Retrieved from the Internet: <URL:Http:Www.Ncbi.Nlm.Nih.gov/entrez/viewer.Fcgi?db=nuccore&val=32328>."

GenBank. "Accession No. L17131, "*Homo sapiens* High Mobility Group Protein (HMG-I(Y)) Gene Exons 1-8, Complete Cds" (1999) [Online] [Retrieved on Mar. 21, 2006]. Retrieved from the Internet: <URL:Http:L/www.Ncbi.Nlm.Nih.gov/entrez/viewer.Fcgi?db=nuccore&val=306868>."

GenBank. "Accession No. M23618, "Human HMG-Y Protein Isoform mRNA (HMGI Gene), Clone 1ID," (1996) [Online] [Retrieved on Mar. 21, 2006]. Retrieved from the Internet: <URL:Http:/www.Ncbi.Nlm.Nih.gov/entrez/viewer.Fcgi?db=nuccore&val=184258>."

GenBank. "Accession No. X02666, "Trout mRNA for High Mobility Group Protein HMG-T," (2005) [Online] [Retrieved on Mar. 21, 2006]. Retrieved from the Internet: <URL:Http://www.Ncbi.Nlm.Nih.gov/cntrcz/vicwcr.Fcgi?db=nuccore&val=64327>."

GenBank. "Accession No. L32859, "Rainbow Trout HMG-I Gene Exons 2-5, Complete Cds," (1995) [Online] [Retrieved on Mar. 21, 2006]. Retrieved from the Internet: <URL:Http://www.Ncbi.Nlm.Nih.gov/entrez/viewer.Fcgi?db=nuccore&val=609550>."

GenBank. "Accession No. D30765, "Xenopus Laevis mRNA for HMG-X Protein, Complete Cds," (1999) [Online] [Retrieved on Mar. 21, 2006]. Retrieved from the Internet: <URL:Http://www.Ncbi.Nlm.Nih.gov/entrez/viewer.Fcgi?db=nuccore&va~=639690>."

GenBank. "Accession No. X71138, "D. Melanogaster HMG-D rnRNA," (1993) [Online] [Retrieved on Mar. 21, 2006]. Retrieved from the Internet: <URL:Http://www.Ncbi.Nlm.Nih.gov/entrez/viewer.Fcgi?db—nuccore&val-296942>."

GenBank. "Accession No. X71139, "D. Mclanogaster HMG-Z mRNA," (2005) [Online] [Rctricvcd on Mar. 21, 2006]. Retrieved from the Internet: <URL: Http://www.Ncbi.Nlm.Nih.gov/entrez/viewer.Fcgi?db=nuccore&val=296944>."

GenBank. "Accession No. Z48008, "S. Cerevisiae Chromosome IV Cosmid 8119," (2005) [Online] [Retrieved on Mar. 21, 2006]. Retrieved from the Internet: <URL:Http//www.Ncbi.Nlm.Nih.gov/entrez/viewer.Fcgi?db=nuccore&val=642799>."

GenBank. "Accession No. 000479, "Nonhistone Chromosomal Protein HMG-17-Like 3 (Non-Histone Chromosomal Protein) (High-Mobility Group Nucleosome Binding Domain 4)," (2005) [Online] [Retrieved on Mar. 21, 2006]. Retrieved Fiom the Internet: <URL: Http://www.Ncbi.Nlm.Nih.gov/entrez/viewer.Fcgi?db=protein&val=20138140>."

GenBank. "Accession No. Z11540, "T. Acstivum mRNA for High Mobility Group Protein (HMGW)," (2005) [Online] [Retrieved on Mar. 21, 2006]. Retrieved from the Internet: <URL:Http://www.Ncbi.Nlm.Nih.gov/entrez/viewer.Fcgi?db=nuccore&val=21802>."

GenBank. "Accession No. X53390, "Human mRNA for Upstream Binding Factor (hUBF)," (1999) [Online] [Retrieved on Mar. 21, 2006]. Retrieved from the Internet: <URL:Http://www.Ncbi.nlm.Nih.gov/entrez/viewer.Fcgi?db=nuccore&val=509240>."

GenBank. "Accession No. U13695, "Human Homolog of Yeast mutL (hPMS1) Gene, Complete Cds," (1995) [Online] [Retrieved on Mar. 21, 2006]. Retrieved from the Internet: <URL:Http://www.Ncbi.Nlm.Nih.gov/entrez/viewer.Fcgi?db=nuccore&val=535512>."

GenBank. "Accession No. M86737, "Human High Mobility Group Box (SSRP1) rnRNA, Complete Cds," (1 994) [Online] [Rctricvcd on Mar. 21, 2006]. Rctricvcd from thc Intcrnct: <URL:Http://www.Ncbi.Nlm.Nih.gov/entrez/viewer.Fcgi?db=nuccore&val=184241>."

GenBank. "Accession No. M74017, "T. Brucei Rhodesiense HMG1-Like Protein mRNA, Complete Cds" (1993) [Online] [Retrieved on Mar. 21, 2006]. Retrieved from the Internet: URL:Http://www.Ncbi.Nlm.Nih.gov/entrez/viewer.Fcgi?db=nuccore&val=162108>."

GenBank. "Accession No. X53772, "*H. sapiens* SRY Gene," (1997) [Online] [Retrieved on Mar. 21, 2006]. Retrieved from the Internet: <URL: Http://www.Ncbi.Nlm.Nih.gov/entrez/viewer.Fcgi?db=nuccore &val=36604>."

GenBank. "Accession No. AB009451, "Alternaria Alternata MAT1 Gene, Complete Cds," (2002) [Online] [Retrieved on Mar. 21, 2006]. Retrieved from the Internet: <URL:Http://www.Ncbi.Nlm.Nih.gov/cntrcz/vicwcr.Fcgi?db=nuccore&val=4520345>."

GenBank. "Accession No. X53431, "Yeast Gene for STE11," (2005) [Online] [Retrieved on Mar. 21, 2006]. Retrieved from the Internet: <URL:Http://www.Ncbi.Nlm.Nih.gov/entrez/viewer.Fcgi?db=nuccore&val=4553>."

GenBank. "Accession No. AF107043, "*Homo sapiens* Clone pCL11 DNA-Binding Protein SOX14 (SOX14) Gene, Complete Cds," (1998) [Online] [Retrieved on Mar. 21, 2006]. Retrieved from the Internet: <URL:Http://www.Ncbi.Nlm.Nih.gov/entrez/viewer.Fcgi?db=nuccore&val=4008100>."

GenBank. "Accession No. Y13436, "*Homo sapiens* Sox 1 Gene," (2005) [Online] [Retrieved on Mar. 21, 2006]. Retrieved from the Internet: <URL:Http://www.Ncbi.Nlm.Nih.gov/entrez/viewer.Fcgi?db=nuccore&val=4128158>."

GenBank. "Accession No. Z31560, "*H. sapicns* Sox-2 mRNA (Partial)," (2005) [Onlinc] [Rctricvcd on Mar. 21, 2006]. Retrieved from the Internet: <URL:Http://www.Ncbi.Nlm.Nih.gov/entrez/viewer.Fcgi?db=nuccore&val=854181>."

GenBank. "Accession No. X71135, "*H. sapiens* Sox3 Gene," (2005) [Online] [Retrieved on Mar. 21, 2006]. Retrieved from the Internet: <URL:Http://www.Ncbi.Nlm.Nih.gov/entrez/viewer.Fcgi?db=nuccore&val=4687 90>."

GenBank. "Accession No. AF309034, "*Homo sapiens* SOX6 mRNA, Complete Cds," (2001) [Online] [Retrieved on Mar. 21, 2006]. Retrieved from the Internet: <URL:Http://www.Ncbi.Nlm.Nih.gov/entrez/viewer.Fcgi?db=nuccore&val=13435017>."

GenBank. "Accession No. AF226675, "*Homo sapiens* Transcription Factor SOX8 mRNA, Complete Cds," (2000) [Online] [Rctricvcd on Mar. 21, 2006]. Rctricvcd from the Intcrnct: <URL:Http://www.Ncbi.Nlm.Nih.gov/entrez/viewer.Fcgi?db=nuccore&val=7025446>."

GenBank. "Accession No. AJ001183, "*Homo sapiens* mRNA for Sox 10 Protein," (2005) [Online] [Retrieved on Mar. 21, 2006]. Retrieved from the Internet: <URL:Http://www.Ncbi.Nlm.Nih.gov/entrez/viewer.Fcgi?db=nuccore&val=2909359>."

GenBank. "Accession No. X73039, "*H. sapiens* SOX-12 Gene," (2005) [Online] [Retrieved on Mar. 21, 2006]. Retrieved from the Internet: <URL: Http://www.Ncbi.Nlm.Nih.gov/entrez/viewer.Fcgi?db=nuccore &val=312151>. "

GenBank. "Accession No. AF107044, "*Homo sapiens* Clone pCL4 DNA-Binding Protein SOX21 (SOX21) Gene, Complete Cds," (1998) [Online] [Retrieved on Mar. 21, 2006]. Retrieved from the Internet: <URL : Http://www.Ncbi.Nlm.Nih.gov/cntrcz/vicwcr.Fcgi?db=nuccorc&val=4008102>."

GenBank. "Accession No. X58636, "Mouse LEF1 mRNA for Lymphoid Enhancer Binding Factor 1," (1999) [Online] [Retrieved on Mar. 21, 2006]. Retrieved from the Internet: URL:Http://www.Ncbi.Nlm.Nih.gov/entrez/viewer.Fcgi?db—nuccore&val=52887>."

GenBank. "Accession No. X59869, "Human TCF-1 mRNA for T Cell Factor 1 (Splice Form A)," (2005) [Online] [Retrieved on Mar. 21, 2006]. Retrieved from the Internet: <URL: Http://www.Ncbi.Nlm.Nih.gov/entrez/viewer.Fcgi?db=nuccore &val=36785>. "

GenBank. "Accession No. M62810, "Human Mitochondrial Transcription Factor 1 mRNA, Complete Cds," (1995) [Online] [Retrieved on Mar. 21, 2006]. Retrieved from the Internet:

<URL:Http://www.Ncbi.Nlm.Nih.gov/entrez/viewer. Fcgi?db=nuccore&val=188563>."

GenBank. "Accession No. U36501, "Human SP 100-B (SP 100-B) mRNA, Complete Cds," (1996) [Online] [Retrieved on Mar. 21, 2006]. Retrieved from the Internet: <URL: Http://www.Ncbi.Nlm. Nih.gov/entrez/viewer.Fcgi?db=nuccore &val=1173655>. "

GenBank. "Accession No. AF076674, "*Homo sapiens* High Mobility Group 1-Like Protein L1 (HMG1L1) Retropseudogene Sequence," (1999) [Online] [Retrieved on Apr. 18, 2006]. Retrieved from the Internet: <URL:Http:/www.Ncbi.Nlm.Nih.gov/entrez/viewer. Fcgi?db=nuccore&val=4884556>."

GenBank. "Accession No. AF076676, "*Homo sapiens* High Mobility Group 1-Like Protein L4 (HMG1L4) Retropseudogene Sequence," (1999) [Online] [Retrieved on Apr. 18, 2006]. Retrieved from the Internet: <URL:Http://www.Ncbi.Nlm.Nih. gov/entrez/viewer. Fcgi?db=nuccore&val=4884558>."

GenBank. "Accession No. AF165168, "*Homo sapiens* High Mobility Group 1-Like Protein L9 (HMG1L9) Retropseudogene, Complete Sequence," (2001) [Online] [Retrieved on Apr. 18, 2006]. Retrieved from the Internet: <URL:Http://www.Ncbi.Nlm.Nih.gov/entrez/viewer.Fcgi?db=nuccore&val=15027609>."

GenBank. "Accession No. AF165167, "*Homo sapiens* High Mobility Group 1-Like Protein L8 (HMG1L8) Retropseudogene, Complete Sequence," (2001) [Online] [Retrieved on Apr. 18, 2006]. Retrieved from the Internet: <URL:Http://www.Ncbi.Nlm.Nih.gov/entrez/viewer.Fcgi?db=nuccore&val=15027608>."

GenBank. "Accession No. AC010149, "*Homo sapiens* BAC Clone RP11-395A23 From 2, Complete Sequence," (2005) [Online] [Retrieved on Apr. 18, 2006]. Retrieved from the Internet: <URL:Http://www.Ncbi.Nlm.Nih.gov/entrez/viewer. Fcgi?db=nuccore&val=14151041>."

GenBank. "Accession No. X67668, "M.musculus mRNA for High Mobility Group 2 Protein," (2005) [Online] [Retrieved on Apr. 18, 2006]. Retrieved from the Internet: <URL: Http://www.Ncbi.Nlm. Nih.gov/entrez/viewer.Fcgi?db=nuccore &val=51338 >."

GenBank. "Accession No. NG_000897, "*Homo sapiens* High-Mobility Group (Nonhistone Chromosomal) Protein 1-Like 5 (HMG1L5) Pseudogene on Chromosome 3," (2006) [Online] [Retrieved on 04/18/20061. Retrieved from the Internet: <URL:Http://www.Ncbi.Nlm.Nih.gov/entrez/viewer. Fcgi?db=nuccore&val=27502364>."

GenBank. "Accession No. XM_063129, "*Homo sapiens* Similar to High Mobility Group 1 (LOC122441), rnRNA," (2002) [Online] [Retrieved on Apr. 18, 2006]. Retrieved Fiom the Internet: <URL:Http://www.Ncbi.Nlm.Nih.gov/entrez/viewer. Fcgi?db=nuccore&val=17453404>."

GenBank. "Accession No. XM_066789, "*Homo sapiens* Similar to High Mobility Group 1 (LOC139603), mRNA," (2002) [Online] [Retrieved on Apr. 18, 2006]. Retrieved from the Internet: <URL:Http://www.Ncbi.Nlm.Nih.gov/entrez/viewer. Fcgi?db=nuccore&val=17486193>."

Hatada, T., et al. "Plasma Concentrations and Importance of High Mobility Group Box Protein in the Prognosis of Organ Failure in Patients with Disseminated Intravascular Coagulation." *Thromb. Haemost.* (2005) 94:975-9.

Hori, O., et al. "The Receptor for Advanced Glycation End Products (RAGE) is a Cellular Binding Site for Amphoterin. Mediation of Neurite Outgrowth and Co-Expression of Rage and Amphoterin in the Developing Nervous System." *J.Biol.Chem.* (1995) 270: 25752-61.

Huttunen, H. J., et al. "Receptor for Advanced Glycation End Products-Binding COOH-Terminal Motif of Amphoterin Inhibits Invasive Migration and Metastasis." *Cancer Res.* (2002) 62: 4805-11.

Imamura, T., et al. "Interaction with p53 Enhances Binding of Cisplatin-Modified DNA by High Mobility Group 1 Protein." *J.Biol. Chem.* (2001) 276: 7534-40.

Ise, T., et al. "Transcription Factor Y-Box Binding Protein 1 Binds Preferentially to Cisplatin-Modified DNA and Interacts with Proliferating Cell Nuclear Antigen." *Cancer Res.* (1999) 59: 342-6.

Jakobovits, A., et al. "Germ-Line Transmission and Expression of a Human-Derived Yeast Artificial Chromosome." *Nature* (1993) 362: 255-8.

Jakobovits, A., et al. "Analysis of Homozygous Mutant Chimeric Mice: Deletion of the Immunoglobulin Heavy-Chain Joining Region Blocks B-Cell Development and Antibody Production." *Proc.Natl. Acad.Sci.U.S.A.* (1993) 90: 2551-5.

Jantzen, H. M., et al. "Nucleolar Transcription Factor hUBF Contains a DNA-Binding Motif with Homology to HMG Proteins." *Nature* (1990) 344: 830-6.

Johns, E. W., et al. "History, Definitions and Problems." *The HMG Chromosomal Problems*. 1982, Chapter 1, pp. 1-7.Academic Press, London.

Jung, F., et al. "Antibodies Against a Peptide Sequence Located in the Linker Region of the HMG-1/2 Box Domains in Sera from Patients with Juvenile Rheumatoid Arthritis." *Arthritis Rheum.* (1997) 40: 1803-9.

Kokkola, R., et al. "Successful Treatment of Collagen-Induced Arthritis in Mice and Rats by Targeting Extracellular High Mobility Group Box Chromosomal Protein 1 Activity." *Arthritis Rheum.* (2003) 48: 2052-8.

Kolodrubetz, D. "Consensus Sequence for HMG1-Like DNA Binding Domains." *Nucleic Acids Res.* (1990) 18: 5565.

Kuby, J. *Immunology*. 1992, Chapter 1, pp. 1-20, W.H. Freeman and Company, New York.

Landsman, D., et al. "A Signature for the HMG-1 Box DNA-Binding Proteins." *BioEssays* (1993) 15: 539-46.

Laudet, V., et al. "Ancestry and Diversity of the HMG Box Superfamily." *Nucleic Acids Res.* (1993) 21: 2493-501.

Lederman, S., et al. "A Single Amino Acid Substitution in a Common African Allele of the CD4 Molecule Ablates Binding of the Monoclonal Antibody, OKT4." *Mol.Immunol.* (1991) 28: 1171-81.

Li, C. H., et al. "Beta-Endorphin Omission Analogs: Dissociation of Immunoreactivity from Other Biological Activities." *Proc.Natl. Acad.Sci.U.S.A.* (1980) 77: 3211-4.

Lotze, M. T., et al. "High-Mobility Group Box 1 Protein (HMGB1): Nuclear Weapon in the Immune Arsenal." *Nat.Rev.Immunol.* (2005) 5: 331-42.

Ma, W., et al. "Detection of Anti-Neutrophil Cytoplasmic Antibodies in MRL/Mp-lpr/lpr Mice and Analysis of their Target Antigens." *Autoimmunity* (2000) 32: 281-91.

Majumdar, A., et al. "Sequence of Human HMG2 cDNA." *Nucleic Acids Res.* (1991) 19: 6643.

Mao, S-Y, and et al. "Antagonizing HMGB1 Inhibits Proteinuria in a Murine Model of Lupus-Like Disease (Abstract and Presentation)." 94th Annual AAI Meeting. Miami Beach, FL, May 18-22, 2007. pp. 1-2.

Mao, S-Y, and et al. "Antagonizing HMGB1 Blocks Inflammation and Tissue Damage in Experimental Arthritis(Abstract and Presentation)." ACR/ARHP 2007 Meeting. Boston, MA, Nov. 6-11, 2007. pp. 1-17.

Marks, J. D., et al. "By-Passing Immunization: Building High Affinity Human Antibodies by Chain Shuffling." *Biotechnology (N. Y)* (1992) 10: 779-83.

MedImmune. "The International Search Report and the Written Opinion of the International Searching Authority for PCT/US2006/061258" : 1-17.

MedImmune. "International Search Report and Written Opinion of the International Searching Authority for PCT/US2006/061257": 1-17.

MedImmune, Inc. "International Preliminary Report on Patentability and Written Opinion of the International Searching Authority for PCT/US2005/037734":1-5.

Melloni, E., et al. "Extracellular Release of the 'Differentiation Enhancing Factor', a HMG1 Protein Type, is an Early Step in Murine Erythroleukemia Cell Differentiation." *FEBS Lett.* (1995) 368: 466-70.

Melloni, E., et al. "Identity in Molecular Structure between "Differentiation Enhancing Factor" of Murine Erythroleukemia Cells and the 30 kD Heparin-Binding Protein of Developing Rat Brain." *Biochem.Biophys.Res.Commun.* (1995) 210: 82-9.

Merenmies, J., et al. "30-kDa Heparin-Binding Protein of Brain (Amphoterin) Involved in Neurite Outgrowth Amino Acid Sequence and Localization in the Filopodia of the Advancing Plasma Membrane." *J.Biol.Chem.* (1991) 266: 16722-9.

Milev, P., et al. "High Affinity Binding and Overlapping Localization of Neurocan and phosphacan/protein-Tyrosine Phosphatase-zeta/beta with Tenascin-R, Amphoterin, and the Heparin-Binding Growth-Associated Molecule." *J.Biol.Chem.* (1998) 273: 6998-7005.

Mohan, P. S., et al. "Sulfoglycolipids Bind to Adhesive Protein Amphoterin (P30) in the Nervous System." *Biochem.Biophys.Res. Commun.* (1992) 182: 689-96.

Muller, S., et al. "Regulated Expression and Subcellular Localization of HMGB1, a Chromatin Protein with a Cytokine Function." *J. Intern. Med.* (2004) 255: 332-43.

Ohlin, M., et al. "Human Monoclonal Antibodies Against a Recombinant HIV Envelope Antigen Produced by Primary in Vitro Immunization. Characterization and Epitope Mapping." *Immunology* (1989) 68: 325-31.

Ozaki, S., et al. "Epitope Mapping of Autoantibodies o High Mobility Group (HMG) Proteins HMG1 and HMG2." *Clin. Exp. Immunol.*, 2000. 53.

Padlan, E. A. "Anatomy of the Antibody Molecule." Molecular immunology 31.3 (1994): 169-217.

Parkkinen, J., et al. "Amphoterin, the 30-kDa Protein in a Family of HMG1-Type Polypeptides. Enhanced Expression in Transformed Cells, Leading Edge Localization, and Interactions with Plasminogen Activation." *J.Biol.Chem.* (1993) 268: 19726-38.

Parkkinen, J., et al. "Interactions of Plasminogen and Tissue Plasminogen Activator (t-PA) with Amphoterin. Enhancement of t-PA-Catalyzed Plasminogen Activation by Amphoterin." *J.Biol. Chem.* (1991) 266: 16730-5.

Parrish, W., et al. "High-Mobility Group Box-1 Isoforms as Potential Therapeutic Targets in Sepsis." *Methods in Molecular Biology*, 2007. 145-62.Clifton, NJ.

Passalacqua, M., et al. "Stimulated Astrocytes Release High-Mobility Group 1 Protein, an Inducer of LAN-5 Neuroblastoma Cell Differentiation." *Neuroscience* (1998) 82: 1021-8.

Portolano, S., et al. "Lack of Promiscuity in Autoantigen-Specific H and L Chain Combinations as Revealed by Human H and L Chain "Roulette"." Journal of immunology (Baltimore, Md.: 1950) 150.3 (1993): 880-7.

Rauvala, H., et al. "The Adhesive and Neurite-Promoting Molecule p30: Analysis of the Amino-Terminal Sequence and Production of Antipeptide Antibodies that Detect p30 at the Surface of Neuroblastoma Cells and of Brain Neurons." *J.Cell Biol.* (1988) 107: 2293-305.

Rauvala, H., et al. "Isolation and some Characteristics of an Adhesive Factor of Brain that Enhances Neurite Outgrowth in Central Neurons." *J.Biol.Chem.* (1987) 262: 16625-35.

Redlitz, A., et al. "Receptors for Plasminogen and t-PA: An Update." *Bailliere's Clin.Haemetol.* (1995) 8: 313-27.

Reeves, R. "Molecular Biology of HMGA Proteins: Hubs of Nuclear Function." *Gene* (2001) 277: 63-81.

Romani, M., et al. "Serological Analysis of Species Specificity in the High Mobility Group Chromosomal Proteins." *J.Biol.Chem.* (1979) 254: 2918-22.

Rosenberg, AM, et al. "Relationship between Sex and Antibodies to High Mobility Group Proteins 1 and 2 in Juvenile Idiopathic Arthritis." *J.Rheumatol.* (2000) 27: 2489-93.

Salmivirta, M., et al. "Neurite Growth-Promoting Protein (Amphoterin, p30) Binds Syndecan." *Exp.Cell Res.* (1992) 200:444-51.

Scaffidi, P., et al. "Release of Chromatin Protein HMGB1 by Necrotic Cells Triggers Inflammation." *Nature* (2002) 418: 191-5.

Shirakawa, H., et al. "Structure of a Gene Coding for Human HMG2 Protein." *J.Biol.Chem.* (1992) 267: 6641-5.

Sjogren-Jansson, E., et al. "Production of Human Monoclonal Antibodies in Dialysis Tubing." *Hybridoma*(1991) 10: 411-9.

Sobajima, J., et al. "High Mobility Group (HMG) Non-Histone Chromosomal Proteins HMG1 and HMG2 are Significant Target Antigens of Perinuclear Anti-Neutrophil Cytoplasmic Antibodies in Autoimmune Hepatitis." *Gut* (1999) 44: 867-73.

Sobajima, J., et al. "Prevalence and Characterization of Perinuclear Anti-Neutrophil Cytoplasmic Antibodies (P-ANCA) Directed Against HMG1 and HMG2 in Ulcerative Colitis (UC)." *Clin.Exp. Immunol.* (1998) 111: 402-7.

Sobajima, J., et al. "Novel Autoantigens of Perinuclear Anti-Neutrophil Cytoplasmic Antibodies (P-ANCA) in Ulcerative Colitis: Non-Histone Chromosomal Proteins, HMG1 and HMG2." *Clin.Exp. Immunol.* (1997) 107: 135-40.

Sobajima, J., et al. "Anti-Neutrophil Cytoplasmic Antibodies (ANCA) in Ulcerative Colitis: Anti-Cathepsin G and a Novel Antibody Correlate with a Refractory Type." *Clin.Exp.Immunol.* (1996) 105: 120-4.

Sparatore, B., et al. "Extracellular High-Mobility Group 1 Protein is Essential for Murine Erythroleukaemia Cell Differentiation." *Biochem.J.* (1996) 320 ( Pt 1): 253-6.

Suda, T., et al. "A Novel Activity of HMG Domains: Promotion of the Triple-Stranded Complex Formation between DNA Containing (GGA/TCC)11 and d(GGA)11 Oligonucleotides." *Nucleic Acids Res.* (1996) 24:4733-40.

Thomas, Jean O., et al. "HMG1 and 2, and Related 'Architectural' DNA-Binding Proteins." *TRENDS in Biochemical Sciences.*, 2001. 167-74.

Tian, J., et al. "Toll-Like Receptor 9-Dependent Activation by DNA-Containing Immune Complexes is Mediated by HMGB1 and RAGE." *Nat.Immunol.* (2007) 8: 487-96.

Tian, J., and et al. "Regulation of TLR9 Dependent DNA Immune Complex Mediated Cell Activation by High Mobility Group Box Protein 1 (HMGB1) and Receptor for Advanced Glycation End Products (RAGE) (Abstract and Presentation)." 94th Annual AAI Meeting. Miami Beach, FL, May 18-22, 2007. pp. 1-17.

Tomita, N., et al. "Direct in Vivo Gene Introduction into Rat Kidney." *Biochem.Biophys.Res.Commun.* (1992) 186:129-34.

Tsuneoka, M., et al. "Monoclonal Antibody Against Non-Histone Chromosomal Protein High Mobility Group 1 Co-Migrates with High Mobility Group 1 into the Nucleus." *J.Biol.Chem.* (1986) 261: 1829-34.

Uesugi, H., et al. "Prevalence and Characterization of Novel pANCA, Antibodies to the High Mobility Group Non-Histone Chromosomal Proteins HMG1 and HMG2, in Systemic Rheumatic Diseases." *J.Rheumatol.* (1998) 25: 703-9.

Vanderbilt, J. N., et al. "Monoclonal Antibodies as Probes for the Complexity, Phylogeny, and Chromatin Distribution of High Mobility Group Chromosomal Proteins 1 and 2." *J.Biol.Chem.* (1985) 260: 9336-45.

Vassalli, J. D., et al. "The Plasminogen activator/plasmin System." *J.Clin.Invest.* (1991) 88: 1067-72.

Wang, H., et al. "HMG-1 as a Late Mediator of Endotoxin Lethality in Mice." *Science* (1999) 285: 248-51.

Wang, H., et al. "Proinflammatory Cytokines (Tumor Necrosis Factor and Interleukin 1) Stimulate Release of High Mobility Group Protein-1 by Pituicytes." *Surgery* (1999) 126: 389-92.

Wen, L., et al. "A Human Placental cDNA Clone that Encodes Nonhistone Chormosomal Protein HMG-1." *Nucleic Acids Res.* (1989) 17: 1197-213.

Wittemann, B., et al. "Autoantibodies to Nonhistone Chromosomal Proteins HMG-1 and HMG-2 in Sera of Patients with Juvenile Rheumatoid Arthritis." *Arthritis Rheum.* (1990) 33: 1378-83.

Yamada, S., et al. "High Mobility Group Protein 1 (HMGB1) Quantified by ELISA with a Monoclonal Antibody that does Not Cross-React with HMGB2." *Clin.Chem.* (2003) 49: 1535-7.

Yamawaki, M., et al. "Generation and Characterization of Anti-Sulfoglucuronosyl Paragloboside Monoclonal Antibody NGR50 and its Immunoreactivity with Peripheral Nerve." *J.Neurosci.Res.* (1996) 44: 586-93

Zhang, M. and Tracey, K.J. "Tumor Necrosis Factor." *The Cytokine Handbook.*, 1998. 517-47.Academic Press Limited.

Dumitriu, Ingrid E., et al., 2005, "Requirement of HMGB1 and RAGE for the maturation of human plasmacytoid dendritic cells," Eur. J. Immunol. 35:2184-2190.

Li, Jianhua, et al., 2003, "Structural Basis for the Proinflammatory Cytokine Activity of High Mobility Group Box 1," Molecular Medicine, 9(1-2): 37-45.

Popovic, Karin, et al. 2005, "Increased Expression of the Novel Proinflammatory Cytokine High Mobility Group Box Chromosomal Protein 1 in Skin Lesions of Patients With Lupus Erythematosus," Arthritis & Rheumatism, 52(11): 3639-3645.

Rovere-Querini, Patrizia, et al., 2005, "Environmental adjuvants, apoptosis and the censorship over autoimmunity," Autoimmunity Reviews, Elsevier, vol. 4. pp. 555-560.

Sanford, Amy N. et al., 2005, "Apoptotic cells, autoantibodies, and the role of HMGB1 in the subcellular localization of an autoantigen," Journal of Autoimmunity, Elsevier, vol. 25. pp. 264-271.

Tian, Jane, et al., 2007, "Toll-like receptor 9-dependent activation by DNA-containing immune complexes is mediated by HMGB1 and RAGE," Nature Immunology, 8(5):487-496.

European Search Report dated Nov. 24, 2009 for PCT/US2006/061257.

|       | 10 | 20 | 30 | 40 | 50 |
|---|---|---|---|---|---|
| HMGB1 | MGKGDPKKPTGKMSSYAFFVQTCREEHKKKHPDASVNFSEFSKKCSERWK |
| HMGB2 | MGKGDPNKPRGKMSSYAFFVQTCREEHKKKHPDSSVNFAEFSKKCSERWK |

|       | 60 | 70 | 80 | 90 | 100 |
|---|---|---|---|---|---|
| HMGB1 | TMSAKEKGKFEDMAKADKARYEREMKTYIPPKGETKKKFKDPNAPKRLPS |
| HMGB2 | TMSAKEKSKFEDMAKSDKARYDREMKNYVPPKGDKKGKKKDPNAPKRPPS |

|       | 110 | 120 | 130 | 140 | 150 |
|---|---|---|---|---|---|
| HMGB1 | AFFLFCSEYRPKIKGEHPGLSIGDVAKKLGEMWNNTAADDKQPYEKKAAK |
| HMGB2 | AFFLFCSEHRPKIKSEHPGLSIGDTAKKLGEMWSEQSAKDKQPYEQKAAK |

|       | 160 | 170 | 180 | 190 | 200 |
|---|---|---|---|---|---|
| HMGB1 | LKEKYEKDIAAYRAKGKPDAAKKGVKAEKSKKKKEEEEDEEDEEDEEE |
| HMGB2 | LKEKYEKDIAAYRAKGKSEAGKKGPGRPTGSKKKNEPEDEEEEEEEDED |

|       | 210 | | |
|---|---|---|---|
| HMGB1 | EDEEDEEDEEDDDDE | SEQ ID NO.: 1 |
| HMGB2 | EEEEDE------DEE | SEQ ID NO.: 21 |

Fig. 1

SEQ ID NO:
6 GCACAAGACATCCAGATGACCCAGTCTCCAGACTCCCTGGCTGTGTCTCTGGGCGAGAGGGCCACCATCAACTGCAAGTCCAGCC       85

5 [A Q] D I Q M T Q S P D S L A V S L G E R A T I N C K S S
   Extra

AGAGTGTTTTATACAGCTCCAACAATAAGAACTACTTAGCTTGGTACCAGCAGAAACCAGGACAGCCTCCTAAGCTGCTCATTTA      170

Q S V L Y S S N N K N Y L A W Y Q Q K P G Q P P K L L I Y
              CDR1

CTGGGCATCTACCCGGGAATCCGGGGTCCCTGACCGATTCAGTGGCAGCGGGTCTGGGACAGATTTCACTCTCACCATCAGCAGC      255

W A S T R E S G V P D R F S G S G S G T D F T L T I S S
    CDR2

CTGCAGGCTGAAGATGTGGCAGTTTATTACTGTCAGCAATATTATAGTACTCCTCGGACGTTCGGCCAAGGGACCAAGGTGGAAA      340

L Q A E D V A V Y Y C Q Q Y Y S T P R T F G Q G T K V E
                         CDR3

TCAAA      345
I K

Fig. 2A

SEQ ID NO:

8 GAAGTTCAATTGTTAGAGTCTGGTGGCGGTCTTGTTCAGCCTGGTGGTTCTTTACGTCTTTCTTGCGCTGCTTCCGGATTCACTTTCTCT 90

7 E V Q L L E S G G G L V Q P G G S L R L S C A A S G F T F S

GGTTACATGATGGTTTGGGTTCGCCAAGCTCCTGGTAAAGGTTTGGAGTGGGTTTCTCGTATCTCTCCTTCTGGTGGCCAGACTGGTTAT 180

G Y M M V W V R Q A P G K G L E W V S R I S P S G G Q T G Y
◾◾◾CDR1◾◾◾                                    ◾◾◾◾◾◾◾◾ CDR2

GCTGACTCCGTTAAAGGTCGCTTCACTATCTCTAGAGACAACTCTAAGAATACTCTCTACTTGCAGATGAACAGCTTAAGGGCTGAGGAC 270

A D S V K G R F T I S R D N S K N T L Y L Q M N S L R A E D
◾◾◾ CDR2 ◾

ACGGCCGTGTATTACTGTGCGAGAGAAGAGGGTGGGAGCTACGGGGCTTTTGATATCTGGGGCCAAGGGACAATGGTCACCGTCTCAAGC 360

T A V Y Y C A R E E G G S Y G A F D I W G Q G T M V T V S S
                ◾◾◾◾◾ CDR3 ◾◾◾◾◾

Fig. 2B

SEQ ID NO:
10  GCACAAGACATCCAGATGACCCAGTCTCCATCCTCCCTGTCTGCATCTGTAGGAGACAGAGTCACCATCACTTGCCGGGCAAGTCAGAGC  90

9   A Q  D I Q M T Q S P S S L S A S V G D R V T I T C R A S Q S
    Extra                                                                  CDR1

ATTAGCAGCTATTTAAATTGGTATCAGCAGAAACCAGGGAAAGCCCCTAAACTCCTGATCTATGCTGCATCCAGTTTGCAAAGTGGGGTC  180

I S S Y L N W Y Q Q K P G K A P K L L I Y A A S S L Q S G V
                CDR1                                        CDR2

CCCTCAAGGTTCAGTGGCAGTGGATCTGGGACAGATTTCACTCTCACCATCAGCAGTCTGCAACCTGAAGATTTTGCAACTTACTACTGT  270

P S R F S G S G S G T D F T L T I S S L Q P E D F A T Y Y C

CAACAGAGTTACAGTACCCCTCGGACGTTCGGCCAAGGGACCAAGGTGGAAATCAAA  357

Q Q S Y S T P R T F G Q G T K V E I K
              CDR3

Fig. 2C

SEQ ID NO:
12 GAAGTTCAATTGTTAGAGTCTGGTGGCGGTCTTGTTCAGCCTGGTGGTTCTTTACGTCTTTCTTGCGCTGCTTCCGGATTCACTTTCTCT 90

11 E V Q L L E S G G G L V Q P G G S L R L S C A A S G F T F S
TGGTACGATATGTCTTGGGTTCGCCAAGCTCCTGGTAAAGGTTTGGAGTGGGTTTCTCGTATCTCTCCTTCTGGTGGCTATACTATGTAT 180

W Y D M S W V R Q A P G K G L E W V S R I S P S G G Y T M Y
  ▬▬ CDR1 ▬▬                                ▬▬▬▬▬ CDR2 ▬▬▬▬▬
GCTGACTCCGTTAAAGGTCGCTTCACTATCTCTAGAGACAACTCTAAGAATACTCTCTACTTGCAGATGAACAGCTTAAGGGCTGAGGAC 270

A D S V K G R F T I S R D N S K N T L Y L Q M N S L R A E D
  ▬▬▬ CDR2 ▬▬▬
ACGGCCGTGTATTACTGTGCGAGACTCGAGGTGGGAGCTACTTCGGGGGGTACGGCTTTTGATATCTGGGGCCAAGGGACAATGGTCACC 360

T A V Y Y C A R L E V G A T S G G T A F D I W G Q G T M V T
                  ▬▬▬▬▬▬▬▬ CDR3 ▬▬▬▬▬▬▬▬

GTCTCAAGC 369

V S S

Fig. 2D

SEQ ID NO:
16 GAAGTTCAATTGTTAGAGTCTGGTGGCGGTCTTGTTCAGCCTGGTGGTTCTTTACGTCTTTCTTGCGCTGCTTCCGGATTCACTTTCTCT 90

15 E V Q L L E S G G G L V Q P G G S L R L S C A A S G F T F S

TGGTACTCTATGCTTTGGGTTCGCCAAGCTCCTGGTAAAGGTTTGGAGTGGGTTTCTTATATCTCTCCTTCTGGTGGCTTTACTAATTAT 180

W Y S M L W V R Q A P G K G L E W V S Y I S P S G G F T N Y
—— CDR1 ——                                    —— CDR2 ——

GCTGACTCCGTTAAAGGTCGCTTCACTATCTCTAGAGACAACCTAAGAATACTCTCTACTTGCAGATGAACAGCTTAAGGGCTGAGGAC 270

A D S V K G R F T I S R D N S K N T L Y L Q M N S L R A E D
—— CDR2 ——

ACGGCCGTGTATTACTGTGCGAGGTGGGACTACAACAGTGGCTGGTACTATGACCACTGGGGCCAGGGCACCCTGGTCACCGTCTCAAGC 360

T A V Y Y C A R W D Y N S G W Y Y D H W G Q G T L V T V S S
                —— CDR3 ——

Fig. 2F

SEQ ID NO:
18 GCACAAGACATCCAGATGACCCAGTCTCCAGGCACCCTGTCTTTGTCTCCAGGGGAAGGAGCCACCCTCTCCTGCAGGGCCAGTCAGAGTGTTAGCAGCA 100

17 A Q D I Q M T Q S P G T L S L S P G E G A T L S C R A S Q S V S S
   Extra                                                    CDR1

CCTACTTAGCCTGGTACCAGCAGAAACCTGGCCAGGCTCCCAGGCTCCTCATCTATGAAGCGTCCAAGAGGGCCACAGGCACCCCAGCCAGGTTCAGTGG 200

T Y L A W Y Q Q K P G Q A P R L L I Y E A G K R A T G T P A R F S G
    CDR1                                      CDR2

CAGTGGGTCTGGGACAGACTTCACTCTCAGCATCAGCAGCCTAGAGCCTGAAGATTTTGCAGTTTATTACTGTCAGCACCGTCACAACTGGCCTCCACAG 300

G S G T D F T L S I S S L E P E D F A V Y Y C Q H R H N W P P Q
                                              CDR3

TGGACGTTCGGCCAAGGGACCAAGGTGGAGGTCAAA 336

W T F G Q G T K V E V K
   end CDR3

Fig. 2G

SEQ ID NO:
20 GAAGTTCAATTGTTAGAGTCTGGTGGCGGTCTTGTTCAGCCTGGTGGTTCTTTACGTCTTTCTTGCGCTGCTTCCGGATT 80

19  E  V  Q  L  L  E  S  G  G  G  L  V  Q  P  G  G  S  L  R  L  S  C  A  A  S  G  F

CACTTTCTCTTGGTACGATATGACTTGGGTTCGCCAAGCTCCTGGTAAAGGTTTGGAGTGGGTTTCTTCCATCTCTCCTT 160

T  F  S  W  Y  D  M  T  W  V  R  Q  A  P  G  K  G  L  E  W  V  S  S  I  S  P
            ▨▨▨ CDR1 ▨▨▨                                              ▬ CDR2 ▬▬▬

CTGGTGGCTATACTAAGTATGCTGACTCCGTTAAAGGTCGCTTCACTATCTCTAGAGACAACTCTAAGAATACTCTCTAC 240

G  G  Y  T  K  Y  A  D  S  V  K  G  R  F  T  I  S  R  D  N  S  K  N  T  L  Y
   ▬▬▬▬▬▬▬▬▬▬▬▬ CDR2 ▬▬▬▬▬▬▬▬▬▬▬▬▬

TTGCAGATGAACAGCTTAAGGGCTGAGGACACAGCCGTGTATTACTGTACCACAGAATTCTACGATTACCTGGACGTCTG 320

L  Q  M  N  S  L  R  A  E  D  T  A  V  Y  Y  C  T  T  E  F  Y  D  Y  L  D  V  W
                                                    ▨▨▨▨▨ CDR3 ▨▨▨▨▨

GGGCAAAGGGACCACGGTCACCGTCTCAAGC 351

G  K  G  T  T  V  T  V  S  S

Fig. 2H

```
GCACAAGACATCCAGATGACCCAGTCTCCAGGCACCCTGTCTTTGTCTCCAGGGGAAAGAGCCACCCTCTCCTGCAGGGCCAGTCAGAGT
                                                                                              90
 A  Q  D  I  Q  M  T  Q  S  P  G  T  L  S  L  S  P  G  E  R  A  T  L  S  C  R  A  S  Q  S
Extra                                                                          CDR1

GTTAGGAGCAACTTCTTGGCCTGGTACCAGCAGAAACCTGGCCAGGCTCCCAGGCTCCTCATATATGGTGCATCCAGGAGGGCCAGTGGC
                                                                                              180
 V  R  S  N  F  L  A  W  Y  Q  Q  K  P  G  Q  A  P  R  L  L  I  Y  G  A  S  R  R  A  S  G
        CDR1                                                         CDR2

ATCCCAGACAGGTTCAGTGGCAGTGGGTTTGGGGCAGACTTCACTCTCAGCATCAGCAGACTGGAGCCTGAAGATTTCGCAGTGTATTAC
                                                                                              270
 I  P  D  R  F  S  G  S  G  F  G  A  D  F  T  L  S  I  S  R  L  E  P  E  D  F  A  V  Y  Y
TGTCAGCAGTATGGTAGCTCACCCAACACTTTTGGCCAGGGGTCCAaGGTGGAGATCAAA  25
                                                              SEQ ID NO.                      330
 C  Q  Q  Y  G  S  S  P  N  T  F  G  Q  G  S  K  V  E  I  K   24
        CDR3
```

Fig. 2I

```
GAAGTTCAATTGTTAGAGTCTGGTGGCGGTCTTGTTCAGCCTGGTGGTTCTTTACGTCTTTCTTGCGCTGCTTCCGGATTCACTTTCTCT
++++|++++|++++|++++|++++|++++|++++|++++|++++|++++|++++|++++|++++|++++|++++|++++|++++|++++| 90
 E   V   Q   L   L   E   S   G   G   G   L   V   Q   P   G   G   S   L   R   L   S   C   A   A   S   G   F   T   F   S
CGTTACCAGATGAATTGGGTTCGCCAAGCTCCTGGTAAAGGTTTGGAGTGGGTTTCTTCTATCTCTCCTTCTGGTGGCCATACTCATTAT
++++|++++|++++|++++|++++|++++|++++|++++|++++|++++|++++|++++|++++|++++|++++|++++|++++|++++| 180
 R   Y   Q   M   N   W   V   R   Q   A   P   G   K   G   L   E   W   V   S   S   I   S   P   S   G   G   H   T   H   Y
▓═══ CDR1 ═══▓                                             ■━━━━━━━ CDR2 ━━━━━━━
GCTGACTCCGTTAAAGGTCGCTTCACTATCTCTAGAGACAACTCTAAGAATACTCTCTACTTGCAGATGAACAGCTTAAGGGCTGAGGAC
++++|++++|++++|++++|++++|++++|++++|++++|++++|++++|++++|++++|++++|++++|++++|++++|++++|++++| 270
 A   D   S   V   K   G   R   F   T   I   S   R   D   N   S   K   N   T   L   Y   L   Q   M   N   S   L   R   A   E   D
━━━━ CDR2 ━━━■
ACGGCCGTGTATTACTGTGCGAAAGATGGACGACAGGGTAAAATAAGTACGGTTGACCACTGGGGCCAGGGAACCCTCGTCACCGTCTCA
++++|++++|++++|++++|++++|++++|++++|++++|++++|++++|++++|++++|++++|++++|++++|++++|++++|++++| 360
 T   A   V   Y   Y   C   A   K   D   G   R   Q   G   K   I   S   T   V   D   H   W   G   Q   G   T   L   V   T   V   S
                 ▓═══════════════════ CDR3 ═══════════════════▓
AGC   27
+++       SEQ ID NO.                                                                          363
 S    26
```

Fig. 2J

G4-VH

1. Donor site predictions:

| Start | End | Score | Exon | Intron |
|-------|-----|-------|------|--------|
| 86 | 100 | 0.64 | tctcttggtacgata | |
| 118 | 132 | 0.41 | gctcctggtaaaggt | |

2. Acceptor site predictions for:

| Start | End | Score | Intron | Exon |
|-------|-----|-------|--------|------|
| 195 | 235 | 0.64 | aggtcgcttcactatctctagagacaactctaagaatactc | |
| 226 | 266 | 0.76 | aagaatactctctacttgcagatgaacagcttaagggctga | |

Start and stop nucleotide positions are based on SEQ ID NO.: 20

S6-VH

1. Donor site predictions for 199.68.16.14.13114.0 :

| Start | End | Score | Exon | Intron |
|-------|-----|-------|------|--------|
| 86 | 100 | 0.64 | tctcttggtacgata | |
| 118 | 132 | 0.41 | gctcctggtaaaggt | |
| 294 | 308 | 0.70 | actcgaggtgggagc | |

2. Acceptor site predictions for 199.68.16.14.13114.0 :

| Start | End | Score | Intron | Exon |
|-------|-----|-------|--------|------|
| 195 | 235 | 0.64 | aggtcgcttcactatctctagagacaactctaagaatactc | |
| 226 | 266 | 0.76 | aagaatactctctacttgcagatgaacagcttaagggctga | |

Start and stop nucleotide positions are based on SEQ ID NO.: 12

Fig. 2K

| | | |
|---|---|---|
| 1 | GAAGTTCAATTGTTAGAGTCTGGTGGCGGTCTTGTTCAGC | VH-G4 |
| 1 | GAAGTTCAATTGTTAGAGTCTGGTGGCGGTCTTGTTCAGC | VH-SP G4 |
| 41 | CTGGTGGTTCTTTACGTCTTTCTTGCGCTGCTTCCGGATT | VH-G4 |
| 41 | CTGGTGGTTCTTTACGTCTTTCTTGCGCTGCTTCCGGATT | VH-SP G4 |
| 81 | CACTTTCTCTTGGTA[C]GATATGACTTGGGTTCGCCAAGCT | VH-G4 |
| 81 | CACTTTCTCTTGGTA[T]GATATGACTTGGGTTCGCCAAGCT | VH-SP G4 |
| 121 | CCTGGTAAAGGTTTGGAGTGGGTTTCTTCCATCTCTCCTT | VH-G4 |
| 121 | CCTGGTAAAGGTTTGGAGTGGGTTTCTTCCATCTCTCCTT | VH-SP G4 |
| 161 | CTGGTGGCTATACTAAGTATGCTGACTCCGTTAAAGGTCG | VH-G4 |
| 161 | CTGGTGGCTATACTAAGTATGCTGACTCCGTTAAAGGTCG | VH-SP G4 |
| 201 | CTTCACTATCTCT[A]GAGACAACTCTAAGAATACTCTCTAC | VH-G4 |
| 201 | CTTCACTATCTCT[C]GAGACAACTCTAAGAATACTCTCTAC | VH-SP G4 |
| 241 | TTGCA[G]ATGAACAGCTTAAGGGCTGAGGACACAGCCGTGT | VH-G4 |
| 241 | TTGCA[A]ATGAACAGCTTAAGGGCTGAGGACACAGCCGTGT | VH-SP G4 |
| 281 | ATTACTGTACCACAGAATTCTACGATTACCTGGACGTCTG | VH-G4 |
| 281 | ATTACTGTACCACAGAATTCTACGATTACCTGGACGTCTG | VH-SP G4 |

SEQ ID NO:

| | | | |
|---|---|---|---|
| 321 | GGGCAAAGGGACCACGGTCACCGTCTCAAGC | 20 | VH-G4 |
| 321 | GGGCAAAGGGACCACGGTCACCGTCTCAAGC | 110 | VH-SP G4 |

Donor site: TAC-TAT: Tyr
Acceptor sites: AGA-CGA: Arg
CAG-CAA: Gln

Fig. 2L

Average of fore and hind paws at day 14
* P < 0.01

Average of fore paws at day 14
*P < 0.01

1. Vector transfected+CpG/HMGB1      IP: HA
2. RAGE transfected.+med.            IP: HA
3. RAGE transfected +CpG/Hmgb1 45min IP: HA
4. RAGE transfected +CpG/Hmgb1 90min IP: HA

SEQUENCE LISTING

```
<160> NUMBER OF SEQ ID NOS: 110

<210> SEQ ID NO 1
<211> LENGTH: 215
<212> TYPE: PRT
<213> ORGANISM: Homo sapiens

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
```

```
                195                 200                 205
Glu Glu Asp Asp Asp Asp Glu
    210                 215

<210> SEQ ID NO 2
<211> LENGTH: 215
<212> TYPE: PRT
<213> ORGANISM: Homo sapiens

<400> SEQUENCE: 2

Met Gly Lys Gly Asp Pro Lys Lys Pro Thr Gly Lys Met Ser Ser Tyr
1               5                   10                  15

Ala Phe Phe Val Gln Thr Cys Arg Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Leu Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Asp Glu Glu
            180                 185                 190

Asp Glu Glu Asp Glu Glu Glu Glu Asp Glu Glu Asp Glu Glu Asp
        195                 200                 205

Glu Glu Asp Asp Asp Asp Glu
    210                 215

<210> SEQ ID NO 3
<211> LENGTH: 77
<212> TYPE: PRT
<213> ORGANISM: Homo sapiens

<400> SEQUENCE: 3

Pro Thr Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 4
```

```
<211> LENGTH: 74
<212> TYPE: PRT
<213> ORGANISM: Homo sapiens

<400> SEQUENCE: 4

Phe Lys Asp Pro Asn Ala Pro Lys Arg Leu Pro Ser Ala Phe Phe Leu
1               5                   10                  15

Phe Cys Ser Glu Tyr Arg Pro Lys Ile Lys Gly Glu His Pro Gly Leu
                20                  25                  30

Ser Ile Gly Asp Val Ala Lys Lys Leu Gly Glu Met Trp Asn Asn Thr
            35                  40                  45

Ala Ala Asp Asp Lys Gln Pro Tyr Glu Lys Lys Ala Ala Lys Leu Lys
        50                  55                  60

Glu Lys Tyr Glu Lys Asp Ile Ala Ala Tyr
65                  70

<210> SEQ ID NO 5
<211> LENGTH: 115
<212> TYPE: PRT
<213> ORGANISM: Homo sapiens

<400> SEQUENCE: 5

Ala Gln Asp Ile Gln Met Thr Gln Ser Pro Asp Ser Leu Ala Val Ser
1               5                   10                  15

Leu Gly Glu Arg Ala Thr Ile Asn Cys Lys Ser Ser Gln Ser Val Leu
                20                  25                  30

Tyr Ser Ser Asn Asn Lys Asn Tyr Leu Ala Trp Tyr Gln Gln Lys Pro
            35                  40                  45

Gly Gln Pro Pro Lys Leu Leu Ile Tyr Trp Ala Ser Thr Arg Glu Ser
        50                  55                  60

Gly Val Pro Asp Arg Phe Ser Gly Ser Gly Ser Gly Thr Asp Phe Thr
65                  70                  75                  80

Leu Thr Ile Ser Ser Leu Gln Ala Glu Asp Val Ala Val Tyr Tyr Cys
                85                  90                  95

Gln Gln Tyr Tyr Ser Thr Pro Arg Thr Phe Gly Gln Gly Thr Lys Val
            100                 105                 110

Glu Ile Lys
        115

<210> SEQ ID NO 6
<211> LENGTH: 345
<212> TYPE: DNA
<213> ORGANISM: Homo sapiens

<400> SEQUENCE: 6
gcacaagaca tccagatgac ccagtctcca gactccctgg ctgtgtctct gggcgagagg      60
gccaccatca actgcaagtc cagccagagt gttttataca gctccaacaa taagaactac     120
ttagcttggt accagcagaa accaggacag cctcctaagc tgctcattta ctgggcatct     180
acccgggaat ccggggtccc tgaccgattc agtggcagcg gtctgggaca gatttcact     240 ctcaccatca gcagcctgca ggctgaagat gtggcagttt attactgtca gcaatattat     300
agtactcctc ggacgttcgg ccaagggacc aaggtggaaa tcaaa                    345

<210> SEQ ID NO 7
<211> LENGTH: 120
<212> TYPE: PRT
<213> ORGANISM: Homo sapiens

<400> SEQUENCE: 7
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Met Met Val Trp Val Arg Gln Ala Pro Gly Lys Gly Leu Glu Trp Val
        35                  40                  45

Ser Arg Ile Ser Pro Ser Gly Gly Gln Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Gly Gly Ser Tyr Gly Ala Phe Asp Ile Trp Gly Gln
            100                 105                 110

Gly Thr Met Val Thr Val Ser Ser
        115                 120
```

<210> SEQ ID NO 8
<211> LENGTH: 360
<212> TYPE: DNA
<213> ORGANISM: Homo sapiens

<400> SEQUENCE: 8

```
gaagttcaat tgttagagtc tggtggcggt cttgttcagc ctggtggttc tttacgtctt    60
tcttgcgctg cttccggatt cactttctct ggttacatga tggtttgggt tcgccaagct   120
cctggtaaag gtttggagtg ggtttctcgt atctctcctt ctggtggcca gactggttat   180
gctgactccg ttaaaggtcg cttcactatc tctagagaca actctaagaa tactctctac   240
ttgcagatga acagcttaag ggctgaggac acggccgtgt attactgtgc gagagaagag   300
ggtgggagct acggggcttt tgatatctgg ggccaaggga caatggtcac cgtctcaagc   360
```

<210> SEQ ID NO 9
<211> LENGTH: 109
<212> TYPE: PRT
<213> ORGANISM: Homo sapiens

<400> SEQUENCE: 9

```
Ala Gln Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Ser
            20                  25                  30

Ser Tyr Leu Asn Trp Tyr Gln Gln Lys Pro Gly Lys Ala Pro Lys Leu
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Ser Thr
                85                  90                  95

Pro Arg Thr Phe Gly Gln Gly Thr Lys Val Glu Ile Lys
            100                 105
```

<210> SEQ ID NO 10
<211> LENGTH: 327
<212> TYPE: DNA
<213> ORGANISM: Homo sapiens -continued

<400> SEQUENCE: 10

```
gcacaagaca tccagatgac ccagtctcca tcctccctgt ctgcatctgt aggagacaga    60
gtcaccatca cttgccgggc aagtcagagc attagcagct atttaaattg gtatcagcag   120
aaaccaggga aagcccctaa actcctgatc tatgctgcat ccagtttgca aagtggggtc   180
ccctcaaggt tcagtggcag tggatctggg acagatttca ctctcaccat cagcagtctg   240
caacctgaag attttgcaac ttactactgt caacagagtt acagtacccc tcggacgttc   300
ggccaaggga ccaaggtgga aatcaaa                                       327
```

<210> SEQ ID NO 11
<211> LENGTH: 123
<212> TYPE: PRT
<213> ORGANISM: Homo sapiens

<400> SEQUENCE: 11

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Tyr
            20                  25                  30

Asp Met Ser Trp Val Arg Gln Ala Pro Gly Lys Gly Leu Glu Trp Val
        35                  40                  45

Ser Arg Ile Ser Pro Ser Gly Gly Tyr Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Glu Val Gly Ala Thr Ser Gly Gly Thr Ala Phe Asp Ile
               100                 105                 110

Trp Gly Gln Gly Thr Met Val Thr Val Ser Ser
           115                 120
```

<210> SEQ ID NO 12
<211> LENGTH: 369
<212> TYPE: DNA
<213> ORGANISM: Homo sapiens

<400> SEQUENCE: 12

```
gaagttcaat tgttagagtc tggtggcggt cttgttcagc ctggtggttc tttacgtctt    60
tcttgcgctg cttccggatt cactttctct tggtacgata tgtcttgggt cgccaagct   120
cctggtaaag gtttggagtg ggtttctcgt atctctcctt ctggtggcta ctatgtat    180
gctgactccg ttaaaggtcg cttcactatc tctagagaca actctaagaa tactctctac   240
ttgcagatga acagcttaag ggctgaggac acggccgtgt attactgtgc gagactcgag   300
gtgggagcta cttcgggggg tacggctttt gatatctggg gccaagggac aatggtcacc   360
gtctcaagc                                                          369
```

<210> SEQ ID NO 13
<211> LENGTH: 109
<212> TYPE: PRT
<213> ORGANISM: Homo sapiens

<400> SEQUENCE: 13

```
Ala Gln Asp Ile Gln Met Thr Gln Ser Pro Asp Thr Leu Ser Leu Ser
 1               5                  10                  15

Pro Gly Glu Arg Ala Thr Leu Ser Cys Arg Ala Ser Gln Ser Val Asn
```

```
            20                  25                  30
Ser Arg Asn Leu Ala Trp Tyr Gln Gln Lys Pro Gly Gln Ala Pro Arg
        35                  40                  45

Leu Leu Ile Tyr Gly Ala Ser Thr Arg Ala Thr Gly Ile Pro Asp Arg
50                  55                  60

Phe Ser Gly Ser Val Ser Gly Thr Glu Phe Thr Leu Thr Ile Ser Ser
65                  70                  75                  80

Leu Gln Pro Asp Asp Phe Ala Thr Tyr Tyr Cys Gln Gln Tyr Asn Ser
                85                  90                  95

Tyr Phe Thr Phe Gly Gln Gly Thr Lys Leu Glu Ile Lys
            100                 105

<210> SEQ ID NO 14
<211> LENGTH: 327
<212> TYPE: DNA
<213> ORGANISM: Homo sapiens

<400> SEQUENCE: 14
gcacaagaca tccagatgac ccagtctcca gacaccctgt ctttgtctcc aggggaaaga     60
gccaccctct cctgcagggc cagtcagagt gttaacagca ggaacttagc ctggtaccag    120
cagaaacctg gccaggctcc caggctcctc atctatggtg catccaccag ggccactggc    180
atcccagaca ggttcagtgg cagtgtatct gggacagaat tcactctcac catcagcagc    240
ctgcagcctg atgatttgc aacttattac tgccagcaat ataacagtta tttcactttt    300
ggccagggga ccaagctgga gatcaaa                                        327

<210> SEQ ID NO 15
<211> LENGTH: 120
<212> TYPE: PRT
<213> ORGANISM: Homo sapiens

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Leu Trp Val Arg Gln Ala Pro Gly Lys Gly Leu Glu Trp Val
        35                  40                  45

Ser Tyr Ile Ser Pro Ser Gly Gly Phe Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Asp Tyr Asn Ser Gly Trp Tyr Tyr Asp His Trp Gly Gln
            100                 105                 110

Gly Thr Leu Val Thr Val Ser Ser
        115                 120

<210> SEQ ID NO 16
<211> LENGTH: 360
<212> TYPE: DNA
<213> ORGANISM: Homo sapiens

<400> SEQUENCE: 16
gaagttcaat tgttagagtc tggtggcggt cttgttcagc ctggtggttc tttacgtctt     60
tcttgcgctg cttccggatt cactttctct tggtactcta tgctttgggt tcgccaagct    120
```

```
cctggtaaag gtttggagtg ggtttcttat atctctcctt ctggtggctt tactaattat    180
gctgactccg ttaaaggtcg cttcactatc tctagagaca actctaagaa tactctctac    240
ttgcagatga acagcttaag ggctgaggac acggccgtgt attactgtgc gaggtgggac    300
tacaacagtg gctggtacta tgaccactgg ggccagggca ccctggtcac cgtctcaagc    360
```

<210> SEQ ID NO 17
<211> LENGTH: 112
<212> TYPE: PRT
<213> ORGANISM: Homo sapiens

<400> SEQUENCE: 17

```
Ala Gln Asp Ile Gln Met Thr Gln Ser Pro Gly Thr Leu Ser Leu Ser
1               5                   10                  15

Pro Gly Glu Gly Ala Thr Leu Ser Cys Arg Ala Ser Gln Ser Val Ser
            20                  25                  30

Ser Thr Tyr Leu Ala Trp Tyr Gln Gln Lys Pro Gly Gln Ala Pro Arg
        35                  40                  45

Leu Leu Ile Tyr Glu Ala Ser Lys Arg Ala Thr Gly Thr Pro Ala Arg
    50                  55                  60

Phe Ser Gly Ser Gly Ser Gly Thr Asp Phe Thr Leu Ser Ile Ser Ser
65                  70                  75                  80

Leu Glu Pro Glu Asp Phe Ala Val Tyr Tyr Cys Gln His Arg His Asn
                85                  90                  95

Trp Pro Pro Gln Trp Thr Phe Gly Gln Gly Thr Lys Val Glu Val Lys
            100                 105                 110
```

<210> SEQ ID NO 18
<211> LENGTH: 336
<212> TYPE: DNA
<213> ORGANISM: Homo sapiens

<400> SEQUENCE: 18

```
gcacaagaca tccagatgac ccagtctcca ggcaccctgt ctttgtctcc aggggaagga    60
gccaccctct cctgcagggc cagtcagagt gttagcagca cctacttagc ctggtaccag    120
cagaaacctg gccaggctcc caggctcctc atctatgaag cgtccaagag ggccacaggc    180 acccccagcca ggttcagtgg cagtgggtct gggacagact tcactctcag catcagcagc    240
ctagagcctg aagattttgc agtttattac tgtcagcacc gtcacaactg gcctccacag    300
tggacgttcg gccaagggac caaggtggag gtcaaa                               336
```

<210> SEQ ID NO 19
<211> LENGTH: 117
<212> TYPE: PRT
<213> ORGANISM: Homo sapiens

<400> SEQUENCE: 19

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Asp Met Thr Trp Val Arg Gln Ala Pro Gly Lys Gly Leu Glu Trp Val
        35                  40                  45

Ser Ser Ile Ser Pro Ser Gly Gly Tyr Thr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Thr Thr Glu Phe Tyr Asp Tyr Leu Asp Val Trp Gly Lys Gly Thr Thr
            100                 105                 110

Val Thr Val Ser Ser
        115

<210> SEQ ID NO 20
<211> LENGTH: 351
<212> TYPE: DNA
<213> ORGANISM: Homo sapiens

<400> SEQUENCE: 20
gaagttcaat tgttagagtc tggtggcggt cttgttcagc ctggtggttc tttacgtctt      60
tcttgcgctg cttccggatt cactttctct tggtacgata tgacttgggt tcgccaagct    120
cctggtaaag gtttggagtg gtttcttcc atctctcctt ctggtggcta tactaagtat     180
gctgactccg ttaaaggtcg cttcactatc tctagagaca actctaagaa tactctctac    240
ttgcagatga acagcttaag ggctgaggac acagccgtgt attactgtac cacagaattc    300
tacgattacc tggacgtctg ggcaaaggg accacggtca ccgtctcaag c              351

<210> SEQ ID NO 21
<211> LENGTH: 209
<212> TYPE: PRT
<213> ORGANISM: Homo sapiens

<400> SEQUENCE: 21

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Lys Asp Pro Asn Ala Pro Lys
                85                  90                  95

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Glu Asp Glu Glu Glu Asp Glu Asp Glu
        195                 200                 205

Glu
```

```
<210> SEQ ID NO 22
<211> LENGTH: 77
<212> TYPE: PRT
<213> ORGANISM: Homo sapiens

<400> SEQUENCE: 22

Pro Arg Gly Lys Met Ser Ser Tyr Ala Phe Phe Val Gln Thr Cys Arg
1               5                   10                  15

Glu Glu His Lys Lys His Pro Asp Ser Ser Val Asn Phe Ala Glu
            20                  25                  30

Phe Ser Lys Lys Cys Ser Glu Arg Trp Lys Thr Met Ser Ala Lys Glu
        35                  40                  45

Lys Ser Lys Phe Glu Asp Met Ala Lys Ser Asp Lys Ala Arg Tyr Asp
    50                  55                  60

Arg Glu Met Lys Asn Tyr Val Pro Pro Lys Gly Asp Lys
65                  70                  75

<210> SEQ ID NO 23
<211> LENGTH: 75
<212> TYPE: PRT
<213> ORGANISM: Homo sapiens

<400> SEQUENCE: 23

Lys Lys Lys Asp Pro Asn Ala Pro Lys Arg Pro Pro Ser Ala Phe Phe
1               5                   10                  15

Leu Phe Cys Ser Glu His Arg Pro Lys Ile Lys Ser Glu His Pro Gly
            20                  25                  30

Leu Ser Ile Gly Asp Thr Ala Lys Lys Leu Gly Glu Met Trp Ser Glu
        35                  40                  45

Gln Ser Ala Lys Asp Lys Gln Pro Tyr Glu Gln Lys Ala Ala Lys Leu
    50                  55                  60

Lys Glu Lys Tyr Glu Lys Asp Ile Ala Ala Tyr
65                  70                  75

<210> SEQ ID NO 24
<211> LENGTH: 110
<212> TYPE: PRT
<213> ORGANISM: Homo sapiens

<400> SEQUENCE: 24

Ala Gln Asp Ile Gln Met Thr Gln Ser Pro Gly Thr Leu Ser Leu Ser
1               5                   10                  15

Pro Gly Glu Arg Ala Thr Leu Ser Cys Arg Ala Ser Gln Ser Val Arg
            20                  25                  30

Ser Asn Phe Leu Ala Trp Tyr Gln Gln Lys Pro Gly Gln Ala Pro Arg
        35                  40                  45

Leu Leu Ile Tyr Gly Ala Ser Arg Arg Ala Ser Gly Ile Pro Asp Arg
    50                  55                  60

Phe Ser Gly Ser Gly Phe Gly Ala Asp Phe Thr Leu Ser Ile Ser Arg
65                  70                  75                  80

Leu Glu Pro Glu Asp Phe Ala Val Tyr Tyr Cys Gln Gln Tyr Gly Ser
                85                  90                  95

Ser Pro Asn Thr Phe Gly Gln Gly Ser Arg Val Glu Ile Lys
            100                 105                 110

<210> SEQ ID NO 25
<211> LENGTH: 330
<212> TYPE: DNA
<213> ORGANISM: Homo sapiens
```

<400> SEQUENCE: 25

```
gcacaagaca tccagatgac ccagtctcca ggcaccctgt ctttgtctcc aggggaaaga    60
gccaccctct cctgcagggc cagtcagagt gttaggagca acttcttggc ctggtaccag   120
cagaaacctg gccaggctcc caggctcctc atatatggtg catccaggag ggccagtggc   180
atcccagaca ggttcagtgg cagtgggttt ggggcagact tcactctcag catcagcaga   240
ctggagcctg aagatttcgc agtgtattac tgtcagcagt atggtagctc acccaacact   300
tttggccagg ggtccagggt ggagatcaaa                                    330
```

<210> SEQ ID NO 26
<211> LENGTH: 121
<212> TYPE: PRT
<213> ORGANISM: Homo sapiens

<400> SEQUENCE: 26

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Arg Tyr
            20                  25                  30
Gln Met Asn Trp Val Arg Gln Ala Pro Gly Lys Gly Leu Glu Trp Val
        35                  40                  45
Ser Ser Ile Ser Pro Ser Gly Gly His Thr His Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Gly Arg Gly Lys Ile Ser Thr Val Asp His Trp Gly
            100                 105                 110
Gln Gly Thr Leu Val Thr Val Ser Ser
        115                 120
```

<210> SEQ ID NO 27
<211> LENGTH: 363
<212> TYPE: DNA
<213> ORGANISM: Homo sapiens

<400> SEQUENCE: 27

```
gaagttcaat tgttagagtc tggtggcggt cttgttcagc ctggtggttc tttacgtctt    60
tcttgcgctg cttccggatt cactttctct cgttaccaga tgaattgggt tcgccaagct   120
cctggtaaag gtttggagtg gtttcttcta tctctccttc tggtggcca tactcattat   180
gctgactccg ttaaaggtcg cttcactatc tctagagaca actctaagaa tactctctac   240
ttgcagatga acagcttaag ggctgaggac acggccgtgt attactgtgc gaaagatgga   300
cgacagggta aataagtac ggttgaccac tggggccagg gaaccctggt caccgtctca   360
agc                                                                363
```

<210> SEQ ID NO 28
<211> LENGTH: 79
<212> TYPE: PRT
<213> ORGANISM: Homo sapiens

<400> SEQUENCE: 28

```
Asp Pro Asn Ala Pro Lys Arg Leu Pro Ser Ala Phe Phe Leu Phe Cys
1               5                   10                  15
Ser Glu Tyr Arg Pro Lys Ile Lys Gly Glu His Pro Gly Leu Ser Ile
```

```
                    20                  25                  30
Gly Asp Val Ala Lys Lys Leu Gly Glu Met Trp Asn Asn Thr Ala Ala
                35                  40                  45

Asp Asp Lys Gln Pro Tyr Glu Lys Lys Ala Ala Lys Leu Lys Glu Lys
    50                  55                  60

Tyr Glu Lys Asp Ile Ala Ala Tyr Arg Ala Lys Gly Lys Pro Asp
65                  70                  75

<210> SEQ ID NO 29
<211> LENGTH: 34
<212> TYPE: PRT
<213> ORGANISM: Homo sapiens

<400> SEQUENCE: 29

Lys Leu Lys Glu Lys Tyr Glu Lys Asp Ile Ala Ala Tyr Arg Ala Lys
1               5                   10                  15

Gly Lys Pro Asp Ala Ala Lys Lys Gly Val Val Lys Ala Glu Lys Ser
                20                  25                  30

Lys Lys

<210> SEQ ID NO 30
<211> LENGTH: 111
<212> TYPE: PRT
<213> ORGANISM: Homo sapiens

<400> SEQUENCE: 30

Ala Gln Ser Glu Leu Thr Gln Pro Pro Ser Val Ser Glu Ala Pro Gly
1               5                   10                  15

Gln Arg Val Thr Ile Ser Cys Ser Gly Ser Thr Ser Asn Ile Gly Asn
                20                  25                  30

Asn Ala Val Ile Trp Tyr Gln Gln Leu Pro Gly Lys Ala Pro Lys Leu
            35                  40                  45

Leu Ile Tyr Tyr Asp Asp Leu Leu Pro Ser Gly Val Ser Asp Arg Phe
        50                  55                  60

Ser Gly Ser Lys Ser Gly Thr Ser Gly Ser Leu Ala Ile Ser Gly Leu
65                  70                  75                  80

Gln Ser Glu Asp Glu Ala Asp Tyr Tyr Cys Ala Ser Trp Asp Asp Asn
                85                  90                  95

Leu Asn Gly Pro Leu Phe Gly Gly Gly Thr Lys Leu Thr Val Leu
            100                 105                 110

<210> SEQ ID NO 31
<211> LENGTH: 333
<212> TYPE: DNA
<213> ORGANISM: Homo sapiens

<400> SEQUENCE: 31
gcacagagcg aattgactca gccaccctcg gtgtctgaag cccccgggca gagggtcacc    60
atctcctgtt ctggaagcac ctccaacatc ggaaataatg ctgtaatctg gtaccagcag   120
ctcccaggaa aggctcccaa actcctcatc tattatgatg atctgctgcc ctcaggggtc   180
tctgaccgat tctctggctc caagtctggc acctcaggct ccctggccat cagtgggctc   240
cagtctgagg atgaggctga ctattactgt gcatcatggg atgacaacct gaatggtccg   300
ctgttcggcg gagggaccaa gttgaccgtc cta                                333

<210> SEQ ID NO 32
<211> LENGTH: 122
<212> TYPE: PRT
```

```
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Lys Met Gln Trp Val Arg Gln Ala Pro Gly Lys Gly Leu Glu Trp Val
        35                  40                  45

Ser Gly Ile Ser Pro Ser Gly Gly Ser Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Gly Leu Phe Asn Thr Gly Asn Ser Tyr Val Asp Tyr Trp
            100                 105                 110

Gly Gln Gly Thr Leu Val Thr Val Ser Ser
        115                 120

<210> SEQ ID NO 33
<211> LENGTH: 366
<212> TYPE: DNA
<213> ORGANISM: Homo sapiens

<400> SEQUENCE: 33
gaagttcaat tgttagagtc tggtggcggt cttgttcagc ctggtggttc tttacgtctt      60
tcttgcgctg cttccggatt cactttctct tggtacaaga tgcagtgggt cgccaagct    120 cctggtaaag gtttggagtg gtttctggt atctctcctt ctggtggctc tactgcttat    180
gctgactccg ttaaaggtcg cttcactatc tctagagaca actctaagaa tactctctac    240
ttgcagatga acagcttaag ggctgaggac acggccgtgt attactgtgc gaaaatgggg    300
ctttttaata ctgggaattc ctacgttgac tactggggac agggaaccct ggtcaccgtc    360
tcaagc                                                               366

<210> SEQ ID NO 34
<211> LENGTH: 110
<212> TYPE: PRT
<213> ORGANISM: Homo sapiens

<400> SEQUENCE: 34

Ala Gln Asp Ile Gln Met Thr Gln Ser Pro Gly Thr Leu Ser Leu Ser
1               5                   10                  15

Pro Gly Glu Arg Ala Thr Leu Ser Cys Arg Ala Ser Gln Ser Val Arg
            20                  25                  30

Ser Ser Tyr Leu Ala Trp Tyr Gln Gln Lys Pro Gly Gln Ala Pro Arg
        35                  40                  45

Leu Leu Ile Tyr Gly Ala Ser Thr Arg Ala Thr Gly Ile Pro Asp Arg
    50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys Gln Gln Tyr Gly Thr
                85                  90                  95

Ser Arg Trp Thr Phe Gly Gln Gly Thr Lys Val Glu Ile Lys
            100                 105                 110
```

<210> SEQ ID NO 35
<211> LENGTH: 330
<212> TYPE: DNA
<213> ORGANISM: Homo sapiens

<400> SEQUENCE: 35

```
gcacaagaca tccagatgac ccagtctcca ggcaccctgt ctttgtctcc aggggaaaga       60
gccaccctct cctgcagggc cagtcagagt gttaggagca gctacttagc ctggtaccag      120
cagaaacctg gccaggctcc caggctcctc atctatggtg catccaccag ggccactggc      180
atcccagaca ggttcagtgg cagtgggtct gggacagact tcactctcac catcagcaga      240
ctggagcctg aagattttgc agtgtattac tgtcagcagt atggtacctc acggtggacg      300
ttcggccaag ggaccaaggt ggaaatcaaa                                       330
```

<210> SEQ ID NO 36
<211> LENGTH: 122
<212> TYPE: PRT
<213> ORGANISM: Homo sapiens

<400> SEQUENCE: 36

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Asp Met Phe Trp Val Arg Gln Ala Pro Gly Lys Gly Leu Glu Trp Val
        35                  40                  45
Ser Arg Ile Ser Pro Ser Gly Gly Tyr Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Leu Arg Tyr Phe Asp Ser Arg Gly Tyr Ala Phe Asp Ile Trp
            100                 105                 110
Gly Gln Gly Thr Met Val Thr Val Ser Ser
        115                 120
```

<210> SEQ ID NO 37
<211> LENGTH: 366
<212> TYPE: DNA
<213> ORGANISM: Homo sapiens

<400> SEQUENCE: 37

```
gaagttcaat tgttagagtc tggtggcggt cttgttcagc ctggtggttc tttacgtctt       60
tcttgcgctg cttccggatt cactttctct tcttacgata tgttttgggt tcgccaagct      120
cctggtaaag gtttggagtg gtttctcgt atctctcctt ctggtggcta tacttattat      180
gctgactccg ttaaaggtcg cttcactatc tctagagaca actctaagaa tactctctac      240
ttgcagatga acagcttaag ggctgaggac acggccgtgt attactgtgc gaggctacga      300
tattttgact aagggggcta tgcttttgat atctggggcc aagggacaat ggtcaccgtc      360
tcaagc                                                                366
```

<210> SEQ ID NO 38
<211> LENGTH: 110
<212> TYPE: PRT
<213> ORGANISM: Homo sapiens

<400> SEQUENCE: 38

Ala Gln Asp Ile Gln Met Thr Gln Ser Pro Gly Thr Leu Ser Leu Ser
1               5                   10                  15

Pro Gly Glu Arg Ala Thr Leu Ser Cys Arg Ala Ser Glu Ser Leu Thr
            20                  25                  30

Ser Thr Tyr Val Ala Trp Tyr Gln His Lys Pro Gly Gln Ala Pro Arg
        35                  40                  45

Leu Leu Ile His Gly Gly Ser Thr Arg Ala Thr Gly Ile Pro Val Arg
50                  55                  60

Phe Ser Gly Ser Gly Ser Gly Thr Asp Phe Thr Leu Thr Ile Ala Thr
65                  70                  75                  80

Leu Glu Pro Glu Asp Phe Ala Val Tyr Tyr Cys Gln Gln Tyr Gly Ser
            85                  90                  95

Ser Pro Tyr Thr Phe Gly Gln Gly Thr Lys Leu Glu Ile Lys
            100                 105                 110

<210> SEQ ID NO 39
<211> LENGTH: 330
<212> TYPE: DNA
<213> ORGANISM: Homo sapiens

<400> SEQUENCE: 39
gcacaagaca tccagatgac ccagtctcca ggcaccctgt ctttgtctcc aggggaaaga      60
gccaccctct cctgcagggc cagtgagagt cttaccagca cctacgtagc ctggtaccag     120
cacaaacctg gccaggctcc caggctcctc atccatgggg gatccaccag gccactggc     180
atcccagtca ggttcagtgg cagtgggtct gggacagact tcactcttac catcgccaca     240
ctggagccgg aagattttgc agtgtattac tgtcagcagt atggtagttc accgtacact     300
tttggccagg ggaccaagct ggagatcaaa                                      330

<210> SEQ ID NO 40
<211> LENGTH: 119
<212> TYPE: PRT
<213> ORGANISM: Homo sapiens

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Met Met Thr Trp Val Arg Gln Ala Pro Gly Lys Gly Leu Glu Trp Val
        35                  40                  45

Ser Ser Ile Ser Pro Ser Gly Gly Tyr Thr Ile Tyr Ala Asp Ser Ala
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ala Leu Ser Thr Gly Ser Phe Trp Asp Tyr Trp Gly Gln Gly
            100                 105                 110

Thr Leu Val Thr Val Ser Ser
        115

<210> SEQ ID NO 41
<211> LENGTH: 357
<212> TYPE: DNA
<213> ORGANISM: Homo sapiens

```
<400> SEQUENCE: 41
gaagttcaat tgttagagtc tggtggcggt cttgttcagc ctggtggttc tttacgtctt      60
tcttgcgctg cttccggatt cactttctct tattacatga tgacttgggt tcgccaagct     120
cctggtaaag gttggagtg ggtttcttct atctctcctt ctggtggcta tactatttat     180
gctgactccg ctaaaggtcg cttcactatc tctagagaca actctaagaa tactctctac     240
ttgcagatga acagcttaag ggctgaggac acggccgtgt attactgtgc gagagccttg     300
tctactggga gcttctggga ctactggggc cagggaaccc tggtcaccgt ctcaagc        357

<210> SEQ ID NO 42
<211> LENGTH: 110
<212> TYPE: PRT
<213> ORGANISM: Homo sapiens

<400> SEQUENCE: 42

Ala Gln Asp Ile Gln Met Thr Gln Ser Pro Gly Thr Leu Ser Leu Ser
  1               5                  10                  15

Pro Gly Glu Ser Gly Thr Leu Ser Cys Arg Ala Ser Glu Ser Val Ser
             20                  25                  30

Ser Arg His Phe Ala Trp Tyr Gln Gln Lys Pro Gly Gln Ala Pro Arg
         35                  40                  45

Leu Leu Ile Tyr Gly Ala Ser Ser Arg Pro Thr Gly Ile Pro Asp Arg
     50                  55                  60

Phe Ser Gly Ser Gly Ser Gly Thr Asp Phe Thr Leu Thr Leu Ser Arg
 65                  70                  75                  80

Leu Glu Pro Glu Asp Phe Ala Val Tyr Phe Cys Gln Tyr Tyr Gly Ser
                 85                  90                  95

Ser Pro Tyr Thr Phe Gly Gly Gly Thr Lys Val Glu Met Lys
            100                 105                 110

<210> SEQ ID NO 43
<211> LENGTH: 330
<212> TYPE: DNA
<213> ORGANISM: Homo sapiens

<400> SEQUENCE: 43
gcacaagaca tccagatgac ccagtctcca ggcaccctgt ctttgtctcc aggggagagc      60
ggcaccctct cctgtagggc cagtgagagt gttagtagca cacacttcgc ctggtaccag     120
cagaaacctg gccaggctcc caggctcctc atttatggtg catccagcag gcccactggc     180
atcccagaca ggttcagtgg cagtgggtct gggacagact tcactctcac cctcagcaga     240
ctggagcctg aggattttgc agtgtatttc tgtcagtact atggtagctc accgtacact     300
ttcggcggag ggaccaaggt ggagatgaaa                                       330

<210> SEQ ID NO 44
<211> LENGTH: 119
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Trp Tyr
             20                  25                  30

Lys Met Thr Trp Val Arg Gln Ala Pro Gly Lys Gly Leu Glu Trp Val
         35                  40                  45
```

```
Ser Ser Ile Ser Pro Ser Gly Gly Phe Thr Ser Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Asp Ile Arg His Ala Phe Asp Ile Trp Gly Gln Gly
             100                 105                 110

Thr Met Val Thr Val Ser Ser
            115
```

```
<210> SEQ ID NO 45
<211> LENGTH: 357
<212> TYPE: DNA
<213> ORGANISM: Homo sapiens

<400> SEQUENCE: 45
gaagttcaat tgttagagtc tggtggcggt cttgttcagc ctggtggttc tttacgtctt    60
tcttgcgctg cttccggatt cactttctct tggtacaaga tgacttgggt tcgccaagct   120
cctggtaaag gtttggagtg gtttcttct atctctcctt ctggtggctt tacttcttat    180
gctgactccg ttaaaggtcg cttcactatc tctagagaca actctaagaa tactctctac   240
ttgcagatga acagcttaag ggctgaggac acggccgtgt attactgtgc gagagacctc   300
gatatccggc atgcttttga tatctggggc caagggacaa tggtcaccgt ctcaagc      357
```

```
<210> SEQ ID NO 46
<211> LENGTH: 109
<212> TYPE: PRT
<213> ORGANISM: Homo sapiens

<400> SEQUENCE: 46

Ala Gln Asp Ile Gln Met Thr Gln Ser Pro Ser Ser Val Ser Ala Ser
 1               5                  10                  15

Val Gly Asp Arg Val Thr Ile Thr Cys Arg Ala Ser Gln Asp Val Ser
             20                  25                  30

Ile Trp Leu Ala Trp Tyr Gln Gln Lys Pro Gly Lys Ala Pro Lys Leu
         35                  40                  45

Leu Ile Phe Gly Ala Ser Arg Leu Gln Ser Gly Val Pro Ser Arg Phe
     50                  55                  60

Ser Gly Ser Arg Ser Gly Ala Asp Phe Thr Leu Thr Ile Asp Ser Val
 65                  70                  75                  80

Gln Pro Glu Asp Phe Ala Ser Tyr Tyr Cys Gln Gln Ala Asp Ser Phe
                 85                  90                  95

Pro Leu Thr Phe Gly Gly Gly Thr Lys Val Glu Ile Lys
            100                 105
```

```
<210> SEQ ID NO 47
<211> LENGTH: 327
<212> TYPE: DNA
<213> ORGANISM: Homo sapiens

<400> SEQUENCE: 47
gcacaagaca tccagatgac ccagtctccc tcttccgtgt ctgcatctgt gggagacaga    60
gtcaccatca cttgtcgggc gagtcaggat gttagcatct ggttagcctg gtatcagcag   120
aaaccgggga agcccctaa gctcctgatc tttggtgcgt cccgtttgca gagtggggtc    180
ccatcgaggt tcagcggcag tcgatctggg gcagatttca ctctcaccat cgacagcgtg   240
```

```
cagcctgaag attttgcatc ttactattgt cagcaggctg acagtttccc tctcactttc    300
ggcggaggga ccaaggtgga aatcaaa                                         327
```

<210> SEQ ID NO 48
<211> LENGTH: 126
<212> TYPE: PRT
<213> ORGANISM: Homo sapiens

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Asp Met Phe Trp Val Arg Gln Ala Pro Gly Lys Gly Leu Glu Trp Val
        35                  40                  45

Ser Trp Ile Ser Pro Ser Gly Gly Tyr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Ser Gly Leu Asp Tyr Tyr Asp Ser Ser Gly Tyr Leu Asp Ala
            100                 105                 110

Phe Asp Ile Trp Gly Gln Gly Thr Met Val Thr Val Ser Ser
        115                 120                 125
```

<210> SEQ ID NO 49
<211> LENGTH: 378
<212> TYPE: DNA
<213> ORGANISM: Homo sapiens

<400> SEQUENCE: 49

```
gaagttcaat tgttagagtc tggtggcggt cttgttcagc ctggtggttc tttacgtctt    60
tcttgcgctg cttccggatt cactttctct tggtacgata tgttttgggt tcgccaagct   120
cctggtaaag gtttggagtg gtttcttggg atctctcctt ctggtggcta tacgaagtat   180
gctgactccg ttaaaggtcg cttcactatc tctagagaca actctaagaa tactctctac   240
ttgcagatga acagcttaag ggctgaggac accgccatgt attactgtgc gagatcaggg   300
ttggattact atgatagtag tggttatctc gatgcttttg atatctgggg ccaagggaca   360
atggtcaccg tctcaagc                                                  378
```

<210> SEQ ID NO 50
<211> LENGTH: 110
<212> TYPE: PRT
<213> ORGANISM: Homo sapiens

<400> SEQUENCE: 50

```
Ala Gln Asp Ile Gln Met Thr Gln Ser Pro Ser Ser Leu Ser Ala Ser
1               5                   10                  15

Val Gly Asp Arg Val Ala Ile Thr Cys Arg Ala Ser Gln Ser Ile Asp
            20                  25                  30

Thr Tyr Leu Asn Trp Tyr Gln Gln Lys Pro Gly Lys Ala Pro Lys Leu
        35                  40                  45

Leu Ile Tyr Ala Ala Ser Lys Leu Glu Asp Gly Val Pro Ser Arg Phe
    50                  55                  60

Ser Gly Ser Gly Thr Gly Thr Asp Phe Thr Leu Thr Ile Arg Ser Leu
65                  70                  75                  80
```

Gln Pro Glu Asp Phe Ala Ser Tyr Phe Cys Gln Gln Ser Tyr Ser Ser
                85                   90                  95

Pro Gly Ile Thr Phe Gly Pro Gly Thr Lys Val Glu Ile Lys
            100                 105                 110

<210> SEQ ID NO 51
<211> LENGTH: 330
<212> TYPE: DNA
<213> ORGANISM: Homo sapiens

<400> SEQUENCE: 51
gcacaagaca tccagatgac ccagtctcca tcctccctgt ctgcatctgt gggagacaga     60
gtcgccatca cttgccgcgc aagtcagagc atcgacacct atttaaattg gtatcagcag    120
aaaccaggga aagcccctaa actcctgatc tatgctgcat ccaagttgga agacgggtc    180 ccatcaagat tcagtggcag tggaactggg acagatttca ctctcaccat cagaagtctg    240
caacctgaag attttgcaag ttatttctgt caacagagct actctagtcc agggatcact    300
ttcggccctg ggaccaaggt ggagatcaaa                                     330

<210> SEQ ID NO 52
<211> LENGTH: 125
<212> TYPE: PRT
<213> ORGANISM: Homo sapiens

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Met Met Gly Trp Val Arg Gln Ala Pro Gly Lys Gly Leu Glu Trp Val
        35                  40                  45

Ser Arg Ile Ser Pro Ser Gly Gly Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Trp Asn Tyr Ile Ser Tyr Tyr Tyr Tyr Leu
            100                 105                 110

Asp Val Trp Gly Lys Gly Thr Thr Val Thr Val Ser Ser
            115                 120                 125

<210> SEQ ID NO 53
<211> LENGTH: 375
<212> TYPE: DNA
<213> ORGANISM: Homo sapiens

<400> SEQUENCE: 53
gaagttcaat tgttagagtc tggtggcggt cttgttcagc ctggtggttc tttacgtctt     60
tcttgcgctg cttccggatt cactttctct cattacatga tgggttgggt tcgccaagct    120
cctggtaaag gtttggagtg gtttctcgt atctctcctt ctggtggcgg tactgtttat    180
gctgactccg ttaaaggtcg cttcactatc tctagagaca actctaagaa tactctctac    240
ttgcagatga acagcttaag ggctgaggac acggccgtgt attactgtgc gagaggtggt    300
aactggaact acatatccta ctactactac tacctggacg tctggggcaa agggaccacg    360
gtcaccgtct caagc                                                     375

<210> SEQ ID NO 54
<211> LENGTH: 113
<212> TYPE: PRT
<213> ORGANISM: Homo sapiens

<400> SEQUENCE: 54

Ala Gln Asp Ile Gln Met Thr Gln Ser Pro Leu Ser Leu Pro Val Thr
1               5                   10                  15

Pro Gly Glu Pro Ala Ser Ile Ser Cys Arg Ser Ser Gln Ser Leu Leu
            20                  25                  30

His Gly Asn Gly Tyr Asn Tyr Leu Asp Trp Tyr Leu Gln Arg Pro Gly
        35                  40                  45

Gln Ser Pro Gln Leu Leu Ile Tyr Ser Gly Ser Asn Arg Ala Ser Gly
    50                  55                  60

Val Pro Asp Arg Phe Ser Gly Ser Gly Ser Gly Thr Asp Phe Thr Leu
65                  70                  75                  80

Lys Ile Ser Arg Val Glu Ala Glu Asp Val Gly Val Tyr Tyr Cys Met
                85                  90                  95

Gln Ser Leu Gln Ser Arg Thr Phe Gly Gln Gly Thr Lys Val Glu Ile
            100                 105                 110

Lys

<210> SEQ ID NO 55
<211> LENGTH: 339
<212> TYPE: DNA
<213> ORGANISM: Homo sapiens

<400> SEQUENCE: 55
gcacaagaca tccagatgac ccagtctcca ctctccctgc ccgtcacccc tggagagccg      60
gcctccatct cctgcagatc tagtcagagc ctcctgcatg gtaatggata caactatttg     120
gattggtact tgcagaggcc agggcagtct ccacagctcc tgatctattc gggttctaat     180
cgggcctccg gggtccctga caggttcagt ggcagtgggt caggcacaga ctttacactg     240
aaaatcagca gagtggaggc tgaggatgtt ggggtttatt actgcatgca atctctacaa     300
agtcggacgt tcggccaagg gaccaaggtg gaaatcaaa                            339

<210> SEQ ID NO 56
<211> LENGTH: 121
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Lys Met Val Trp Val Arg Gln Ala Pro Gly Lys Gly Leu Glu Trp Val
        35                  40                  45

Ser Ser Ile Val Pro Ser Gly Gly Ile Thr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gln Gln Trp Leu Gly Arg Pro Tyr Phe Asp Tyr Trp Gly
            100                 105                 110

```
Gln Gly Thr Leu Val Thr Val Ser Ser
        115                 120

<210> SEQ ID NO 57
<211> LENGTH: 363
<212> TYPE: DNA
<213> ORGANISM: Homo sapiens

<400> SEQUENCE: 57
gaagttcaat tgttagagtc tggtggcggt cttgttcagc ctggtggttc tttacgtctt     60
tcttgcgctg cttccggatt cactttctct tggtacaaga tggtttgggt tcgccaagct    120
cctggtaaag gtttggagtg ggtttcttct atcgttcctt ctggtggcat tactatttat    180
gctgactccg ttaaaggtcg cttcactatc tctagagaca actctaagaa tactctctac    240
ttgcagatga acagcttaag ggctgaggac acggccgtat attactgtgc gagagtgcag    300
cagtggctgg acggcccta ctttgactac tggggccagg gaaccctggt caccgtctca    360
agc                                                                  363

<210> SEQ ID NO 58
<211> LENGTH: 110
<212> TYPE: PRT
<213> ORGANISM: Homo sapiens

<400> SEQUENCE: 58

Ala Gln Asp Ile Gln Met Thr Gln Ser Pro Gly Thr Leu Ser Leu Ser
1               5                   10                  15

Pro Gly Glu Arg Ala Thr Leu Ser Cys Arg Ala Thr Gln Ser Val Arg
            20                  25                  30

Lys Asn Phe Leu Ala Trp Tyr Gln Gln Lys Pro Gly Gln Ala Pro Arg
        35                  40                  45

Leu Leu Ile Tyr Asp Ala Ser Ser Arg Ala Thr Gly Ile Pro Asp Arg
    50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys Gln Gln Tyr Gly Asn
                85                  90                  95

Ser Pro Ile Ile Phe Gly Gln Gly Thr Arg Leu Glu Ile Lys
            100                 105                 110

<210> SEQ ID NO 59
<211> LENGTH: 330
<212> TYPE: DNA
<213> ORGANISM: Homo sapiens

<400> SEQUENCE: 59
gcacaagaca tccagatgac ccagtctcca ggcaccctgt ctttgtctcc aggcgaaaga     60
gccaccctct cctgcagggc cactcagagt gttagaaaga acttcttagc ctggtatcag    120
cagaaacctg gccaggctcc caggctcctc atctacgatg catccagcag ggccactggc    180
atcccagaca ggttcagtgg cagtgggtct gggacagact tcactctcac catcagcaga    240
ctggagcctg aagattttgc agtgtattac tgtcagcagt atggtaactc acctatcatc    300
ttcggccaag ggacacgact ggagattaaa                                     330

<210> SEQ ID NO 60
<211> LENGTH: 119
<212> TYPE: PRT
<213> ORGANISM: Homo sapiens
```

<400> SEQUENCE: 60

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ser Leu Arg Leu Ser Cys Ala Ala Ser Gly Phe Thr Phe Ser Trp Tyr
            20                  25                  30

Asp Met Trp Trp Val Arg Gln Ala Pro Gly Lys Gly Leu Glu Trp Val
              35                  40                  45

Ser Trp Ile Val Pro Ser Gly Gly Ile Thr Ala Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Ala Arg Gly Asn Tyr Gly Pro Ser Pro Phe Asp Tyr Trp Gly Gln Gly
                100                 105                 110

Thr Leu Val Thr Val Ser Ser
            115

<210> SEQ ID NO 61
<211> LENGTH: 357
<212> TYPE: DNA
<213> ORGANISM: Homo sapiens

<400> SEQUENCE: 61

```
gaagttcaat tgttagagtc tggtggcggt cttgttcagc ctggtggttc tttacgtctt      60
tcttgcgctg cttccggatt cactttctct tggtacgata tgtggtgggt tcgccaagct     120
cctggtaaag gtttggagtg ggtttcttgg atcgttcctt ctggtggcat tactgcttat     180
gctgactccg ttaaaggtcg cttcactatc tctagagaca actctaagaa tactctctac     240
ttgcagatga acagcttaag ggctgaggac acagccacat attactgtgc gagaggtaac     300
tacggcccat cgccgtttga ctactggggc cagggcaccc tggtcaccgt ctcaagc        357
```

<210> SEQ ID NO 62
<211> LENGTH: 110
<212> TYPE: PRT
<213> ORGANISM: Homo sapiens

<400> SEQUENCE: 62

Ala Gln Ser Ala Leu Thr Gln Pro Pro Ser Val Ser Ala Ala Pro Arg
 1                5                  10                  15

Gln Arg Val Thr Ile Ser Cys Ser Gly Ser Thr Ser Asn Ile Gly Asn
                 20                  25                  30

Asn Ala Val Thr Trp Tyr Gln Tyr Phe Pro Gly Lys Ala Pro Lys Leu
              35                  40                  45

Leu Ile Tyr Ser Asp Asn Gln Arg Pro Ser Gly Val Pro Asp Arg Phe
 50                      55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Arg Gly
                 85                  90                  95

Leu Ser Val Phe Gly Gly Gly Thr Lys Leu Thr Val Leu
                100                 105                 110

<210> SEQ ID NO 63
<211> LENGTH: 330
<212> TYPE: DNA

<213> ORGANISM: Homo sapiens

<400> SEQUENCE: 63

| gcacagagcg | ctttgactca | gccaccctcg | gtgtctgcag | ccccaggca | gagggtcacc | 60 |
| atctcctgtt | ctggaagcac | ttccaacatc | ggaaataatg | ctgtaacctg | gtaccagtat | 120 |
| ttcccaggaa | aggctcccaa | actcctcatc | tatagtgata | atcagcggcc | ctcaggggtc | 180 |
| cctgaccgat | tctctggctc | caagtctggc | acctcagcct | ccctggccat | cactgggctc | 240 |
| caggctgagg | atgaggctga | ttattactgc | cagtcgtatg | acagaggcct | gagtgtggtt | 300 |
| ttcggcggag | ggaccaagct | gaccgtccta | | | | 330 |

<210> SEQ ID NO 64
<211> LENGTH: 117
<212> TYPE: PRT
<213> ORGANISM: Homo sapiens

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ile Met His Trp Val Arg Gln Ala Pro Gly Lys Gly Leu Glu Trp Val
        35                  40                  45

Ser Gly Ile Val Pro Ser Gly Gly Leu Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Glu Ile Phe Gly Gln Phe Asp Tyr Trp Gly Gln Gly Thr Leu
            100                 105                 110

Val Thr Val Ser Ser
        115

<210> SEQ ID NO 65
<211> LENGTH: 351
<212> TYPE: DNA
<213> ORGANISM: Homo sapiens

<400> SEQUENCE: 65

| gaagttgaat | tgttagagtc | tggtggcggt | cttgttcagc | ctggtggttc | tttacgtctt | 60 |
| tcttgcgctg | cttccggatt | cactttctct | aagtacatta | tgcattgggt | tcgccaagct | 120 |
| cctggtaaag | gtttggagtg | ggtttctggt | atcgttcctt | ctggtggcct | tactgagtat | 180 |
| gctgactccg | ttaaaggtcg | cttcactatc | tctagagaca | actctaagaa | tactctctac | 240 |
| ttgcagatga | acagcttaag | ggctgaggac | acagccacat | attactgtgc | gaaagagatt | 300 |
| tttggacaat | ttgactactg | gggccaggga | accctggtca | ccgtctcaag | c | 351 |

<210> SEQ ID NO 66
<211> LENGTH: 109
<212> TYPE: PRT
<213> ORGANISM: Homo sapiens

<400> SEQUENCE: 66

Ala Gln Asp Ile Gln Met Thr Gln Ser Pro Ser Ser Leu Ser Ala Ser
1               5                   10                  15

Val Gly Asp Arg Val Thr Ile Ile Cys Arg Ala Asn Glu Arg Ile Asn

```
            20                  25                  30
Thr Tyr Leu Asn Trp Tyr Gln Gln Lys Pro Gly Lys Ala Pro Lys Leu
        35                  40                  45

Leu Ile Ser Gly Thr Ser Ser Leu Glu Ser Gly Val Pro Ser Arg Phe
    50                  55                  60

Ser Gly Ser Gly Ser Gly Thr Glu Phe Thr Leu Ser Ile Ser Ser Leu
65                  70                  75                  80

Gln Pro Glu Asp Phe Ala Ser Tyr Tyr Cys Gln Gln Ser Tyr Ser Ser
                85                  90                  95

Pro Tyr Thr Phe Gly Gln Gly Thr Asn Leu Glu Ile Arg
            100                 105
```

<210> SEQ ID NO 67
<211> LENGTH: 327
<212> TYPE: DNA
<213> ORGANISM: Homo sapiens

<400> SEQUENCE: 67

```
gcacaagaca tccagatgac ccagtctcca tcctccctgt ctgcatctgt aggagacaga    60
gtcaccatca tttgccgggc aaatgagcgc ataaacacct atttaaactg gtatcagcag   120
aagccaggaa aagcccctaa gttgttgatt tctggtacat ccagtttgga aagtggggtc   180
ccatcaaggt tcagtggcag tggatctgga acagaattca ctctcagtat cagcagtctg   240
caacctgaag attttgcatc ttactactgt caacagagtt acagttcccc gtacactttt   300
ggccagggga ccaacctgga gatcaga                                       327
```

<210> SEQ ID NO 68
<211> LENGTH: 120
<212> TYPE: PRT
<213> ORGANISM: Homo sapiens

<400> SEQUENCE: 68

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Glu Thr Gly Trp Val Arg Gln Ala Pro Gly Lys Gly Leu Glu Trp Val
        35                  40                  45

Ser Gly Ile Ser Pro Ser Gly Gly Tyr Thr Gln Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Val Gly Ala Thr Lys Ile Phe Asp Tyr Trp Gly Gln
            100                 105                 110

Gly Thr Leu Val Thr Val Ser Ser
        115                 120
```

<210> SEQ ID NO 69
<211> LENGTH: 360
<212> TYPE: DNA
<213> ORGANISM: Homo sapiens

<400> SEQUENCE: 69

```
gaagttcaat tgttagagtc tggtggcggt cttgttcagc ctggtggttc tttacgtctt    60
tcttgcgctg cttccggatt cactttctct tggtacgaga cgggttgggt tcgccaagct   120
```

```
cctggtaaag gtttggagtg ggtttctggt atctctcctt ctggtggcta tactcagtat      180
gctgactccg ttaaaggtcg cttcactatc tctagagaca actctaagaa tactctctac      240
ttgcagatga acagcttaag ggctgaggac acggccgtgt attactgtgc gagatcgggg      300
gtgggagcta ctaagatttt tgactactgg ggccaggaa  ccctggtcac cgtctcaagc      360

<210> SEQ ID NO 70
<211> LENGTH: 109
<212> TYPE: PRT
<213> ORGANISM: Homo sapiens

<400> SEQUENCE: 70

Ala Gln Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Ser Ile Gly
            20                  25                  30

Thr Tyr Leu Asn Trp Tyr Gln Gln Lys Pro Gly Thr Ala Pro Lys Val
        35                  40                  45

Leu Ile Tyr Ala Ala Ser Ser Leu Gln Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ser Thr Tyr Cys Gln Gln Ser Tyr Asn Thr
                85                  90                  95

Pro Arg Thr Phe Gly Gln Gly Thr Lys Leu Glu Ile Lys
            100                 105

<210> SEQ ID NO 71
<211> LENGTH: 327
<212> TYPE: DNA
<213> ORGANISM: Homo sapiens

<400> SEQUENCE: 71
gcacaagaca tccagatgac ccagtctcca tcctccctgt ctgcatctgt aggagacaga       60
gtcaccatca cttgccgggc aagtcagagc attggcacct atttaaattg gtatcagcag      120
aaaccaggga cagcccctaa ggtcctgatc tatgctgcat ccagtttgca aagtggggtc      180
ccatcaaggt tcagtggcag tggatctggg acagatttca ctctcaccat cagcagtctg      240
caacctgaag attttgcaac ttactactgt caacagagtt acaataccc  tcgcactttt      300 ggccagggga ccaaactgga gatcaaa                                           327

<210> SEQ ID NO 72
<211> LENGTH: 122
<212> TYPE: PRT
<213> ORGANISM: Homo sapiens

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met His Trp Val Arg Gln Ala Pro Gly Lys Gly Leu Glu Trp Val
        35                  40                  45

Ser Arg Ile Ser Pro Ser Gly Gly Tyr Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Thr Arg Gly Arg Tyr Thr Ser Gly Trp His Glu Tyr Phe Asp Pro Trp
            100                 105                 110

Gly Gln Gly Thr Leu Val Thr Val Ser Ser
        115                 120
```

<210> SEQ ID NO 73
<211> LENGTH: 366
<212> TYPE: DNA
<213> ORGANISM: Homo sapiens

<400> SEQUENCE: 73

```
gaagttcaat tgttagagtc tggtggcggt cttgttcagc ctggtggttc tttacgtctt    60
tcttgcgctg cttccggatt cactttctct tattacgata tgcattgggt tcgccaagct   120
cctggtaaag gtttggagtg gtttctcgt atctctcctt ctggtggcta tacttggtat    180
gctgactccg ttaaaggtcg cttcactatc tctagagaca actctaagaa tactctctac   240
ttgcagatga acagcttaag ggctgaggac acagccgtgt attactgtac gagaggaagg   300
tataccagcg gctggcatga gtacttcgac ccctggggcc agggcaccct ggtcaccgtc   360
tcaagc                                                              366
```

<210> SEQ ID NO 74
<211> LENGTH: 17
<212> TYPE: PRT
<213> ORGANISM: Homo sapiens

<400> SEQUENCE: 74

```
Lys Ser Ser Gln Ser Val Leu Tyr Ser Ser Asn Asn Lys Asn Tyr Leu
1               5                   10                  15

Ala
```

<210> SEQ ID NO 75
<211> LENGTH: 7
<212> TYPE: PRT
<213> ORGANISM: Homo sapiens

<400> SEQUENCE: 75

```
Trp Ala Ser Thr Arg Glu Ser
1               5
```

<210> SEQ ID NO 76
<211> LENGTH: 9
<212> TYPE: PRT
<213> ORGANISM: Homo sapiens

<400> SEQUENCE: 76

```
Gln Gln Tyr Tyr Ser Thr Pro Arg Thr
1               5
```

<210> SEQ ID NO 77
<211> LENGTH: 5
<212> TYPE: PRT
<213> ORGANISM: Homo sapiens

<400> SEQUENCE: 77

```
Gly Tyr Met Met Val
1               5
```

<210> SEQ ID NO 78

```
<211> LENGTH: 17
<212> TYPE: PRT
<213> ORGANISM: Homo sapiens

<400> SEQUENCE: 78

Arg Ile Ser Pro Ser Gly Gly Gln Thr Gly Tyr Ala Asp Ser Val Lys
1               5                   10                  15
Gly

<210> SEQ ID NO 79
<211> LENGTH: 11
<212> TYPE: PRT
<213> ORGANISM: Homo sapiens

<400> SEQUENCE: 79

Glu Glu Gly Gly Ser Tyr Gly Ala Phe Asp Ile
1               5                   10

<210> SEQ ID NO 80
<211> LENGTH: 11
<212> TYPE: PRT
<213> ORGANISM: Homo sapiens

<400> SEQUENCE: 80

Arg Ala Ser Gln Ser Ile Ser Ser Tyr Leu Asn
1               5                   10

<210> SEQ ID NO 81
<211> LENGTH: 7
<212> TYPE: PRT
<213> ORGANISM: Homo sapiens

<400> SEQUENCE: 81

Ala Ala Ser Ser Leu Gln Ser
1               5

<210> SEQ ID NO 82
<211> LENGTH: 9
<212> TYPE: PRT
<213> ORGANISM: Homo sapiens

<400> SEQUENCE: 82

Gln Gln Ser Tyr Ser Thr Pro Arg Thr
1               5

<210> SEQ ID NO 83
<211> LENGTH: 5
<212> TYPE: PRT
<213> ORGANISM: Homo sapiens

<400> SEQUENCE: 83

Trp Tyr Asp Met Ser
1               5

<210> SEQ ID NO 84
<211> LENGTH: 17
<212> TYPE: PRT
<213> ORGANISM: Homo sapiens

<400> SEQUENCE: 84

Arg Ile Ser Pro Ser Gly Gly Tyr Thr Met Tyr Ala Asp Ser Val Lys
1               5                   10                  15
Gly
```

```
<210> SEQ ID NO 85
<211> LENGTH: 14
<212> TYPE: PRT
<213> ORGANISM: Homo sapiens

<400> SEQUENCE: 85

Leu Glu Val Gly Ala Thr Ser Gly Gly Thr Ala Phe Asp Ile
1               5                   10

<210> SEQ ID NO 86
<211> LENGTH: 12
<212> TYPE: PRT
<213> ORGANISM: Homo sapiens

<400> SEQUENCE: 86

Arg Ala Ser Gln Ser Val Asn Ser Arg Asn Leu Ala
1               5                   10

<210> SEQ ID NO 87
<211> LENGTH: 7
<212> TYPE: PRT
<213> ORGANISM: Homo sapiens

<400> SEQUENCE: 87

Gly Ala Ser Thr Arg Ala Thr
1               5

<210> SEQ ID NO 88
<211> LENGTH: 8
<212> TYPE: PRT
<213> ORGANISM: Homo sapiens

<400> SEQUENCE: 88

Gln Gln Tyr Asn Ser Tyr Phe Thr
1               5

<210> SEQ ID NO 89
<211> LENGTH: 5
<212> TYPE: PRT
<213> ORGANISM: Homo sapiens

<400> SEQUENCE: 89

Trp Tyr Ser Met Leu
1               5

<210> SEQ ID NO 90
<211> LENGTH: 17
<212> TYPE: PRT
<213> ORGANISM: Homo sapiens

<400> SEQUENCE: 90

Tyr Ile Ser Pro Ser Gly Gly Phe Thr Asn Tyr Ala Asp Ser Val Lys
1               5                   10                  15

Gly

<210> SEQ ID NO 91
<211> LENGTH: 11
<212> TYPE: PRT
<213> ORGANISM: Homo sapiens

<400> SEQUENCE: 91

Trp Asp Tyr Asn Ser Gly Trp Tyr Tyr Asp His
1               5                   10

<210> SEQ ID NO 92
```

```
<211> LENGTH: 12
<212> TYPE: PRT
<213> ORGANISM: Homo sapiens

<400> SEQUENCE: 92

Arg Ala Ser Gln Ser Val Ser Ser Thr Tyr Leu Ala
1               5                   10

<210> SEQ ID NO 93
<211> LENGTH: 7
<212> TYPE: PRT
<213> ORGANISM: Homo sapiens

<400> SEQUENCE: 93

Glu Ala Ser Lys Arg Ala Thr
1               5

<210> SEQ ID NO 94
<211> LENGTH: 11
<212> TYPE: PRT
<213> ORGANISM: Homo sapiens

<400> SEQUENCE: 94

Gln His Arg His Asn Trp Pro Pro Gln Trp Thr
1               5                   10

<210> SEQ ID NO 95
<211> LENGTH: 5
<212> TYPE: PRT
<213> ORGANISM: Homo sapiens

<400> SEQUENCE: 95

Trp Tyr Asp Met Thr
1               5

<210> SEQ ID NO 96
<211> LENGTH: 17
<212> TYPE: PRT
<213> ORGANISM: Homo sapiens

<400> SEQUENCE: 96

Ser Ile Ser Pro Ser Gly Gly Tyr Thr Lys Tyr Ala Asp Ser Val Lys
1               5                   10                  15

Gly

<210> SEQ ID NO 97
<211> LENGTH: 8
<212> TYPE: PRT
<213> ORGANISM: Homo sapiens

<400> SEQUENCE: 97

Glu Phe Tyr Asp Tyr Leu Asp Val
1               5

<210> SEQ ID NO 98
<211> LENGTH: 12
<212> TYPE: PRT
<213> ORGANISM: Homo sapiens

<400> SEQUENCE: 98

Arg Ala Ser Gln Ser Val Arg Ser Asn Phe Leu Ala
1               5                   10

<210> SEQ ID NO 99
<211> LENGTH: 7
```

```
<212> TYPE: PRT
<213> ORGANISM: Homo sapiens

<400> SEQUENCE: 99

Gly Ala Ser Arg Arg Ala Ser
1               5

<210> SEQ ID NO 100
<211> LENGTH: 9
<212> TYPE: PRT
<213> ORGANISM: Homo sapiens

<400> SEQUENCE: 100

Gln Gln Tyr Gly Ser Ser Pro Asn Thr
1               5

<210> SEQ ID NO 101
<211> LENGTH: 5
<212> TYPE: PRT
<213> ORGANISM: Homo sapiens

<400> SEQUENCE: 101

Arg Tyr Gln Met Asn
1               5

<210> SEQ ID NO 102
<211> LENGTH: 17
<212> TYPE: PRT
<213> ORGANISM: Homo sapiens

<400> SEQUENCE: 102

Ser Ile Ser Pro Ser Gly Gly His Thr His Tyr Ala Asp Ser Val Lys
1               5                   10                  15

Gly

<210> SEQ ID NO 103
<211> LENGTH: 12
<212> TYPE: PRT
<213> ORGANISM: Homo sapiens

<400> SEQUENCE: 103

Asp Gly Arg Gln Gly Lys Ile Ser Thr Val Asp His
1               5                   10

<210> SEQ ID NO 104
<211> LENGTH: 20
<212> TYPE: DNA
<213> ORGANISM: Artificial
<220> FEATURE:
<223> OTHER INFORMATION: synthetic oligonucleotide

<400> SEQUENCE: 104
gggggacgat cgtcgggggg                                               20

<210> SEQ ID NO 105
<211> LENGTH: 20
<212> TYPE: DNA
<213> ORGANISM: Artificial
<220> FEATURE:
<223> OTHER INFORMATION: synthetic oligonucleotide

<400> SEQUENCE: 105
gggggagcat gctgggggc                                                20

<210> SEQ ID NO 106
```

```
<211> LENGTH: 21
<212> TYPE: DNA
<213> ORGANISM: Artificial
<220> FEATURE:
<223> OTHER INFORMATION: synthetic oligonucleotide

<400> SEQUENCE: 106
ggtcgttcca ttttactcca c                                              21

<210> SEQ ID NO 107
<211> LENGTH: 24
<212> TYPE: DNA
<213> ORGANISM: Artificial
<220> FEATURE:
<223> OTHER INFORMATION: synthetic oligonucleotide

<400> SEQUENCE: 107
tcgtcgtttt gtcgttttgt cgtt                                           24

<210> SEQ ID NO 108
<211> LENGTH: 77
<212> TYPE: PRT
<213> ORGANISM: Homo sapiens

<400> SEQUENCE: 108
```

Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

```
<210> SEQ ID NO 109
<211> LENGTH: 69
<212> TYPE: PRT
<213> ORGANISM: Homo sapiens

<400> SEQUENCE: 109
```

Pro Lys Arg Pro Pro Ser Ala Phe Phe Leu Phe Cys Ser Glu Tyr Arg
1               5                   10                  15

Pro Lys Ile Lys Gly Glu His Pro Gly Leu Ser Ile Gly Asp Val Ala
            20                  25                  30

Lys Lys Leu Gly Glu Met Trp Asn Asn Thr Ala Ala Asp Asp Lys Gln
        35                  40                  45

Pro Tyr Glu Lys Lys Ala Ala Lys Leu Lys Glu Lys Tyr Glu Lys Asp
    50                  55                  60

Ile Ala Ala Tyr Arg
65

```
<210> SEQ ID NO 110
<211> LENGTH: 351
<212> TYPE: DNA
<213> ORGANISM: Artificial
<220> FEATURE:
<223> OTHER INFORMATION: human heavy chain variable region with three
      silent mutations

<400> SEQUENCE: 110
gaagttcaat tgttagagtc tggtggcggt cttgttcagc ctggtggttc tttacgtctt    60
```

```
tcttgcgctg cttccggatt cactttctct tggtatgata tgacttgggt tcgccaagct      120
cctggtaaag gtttggagtg ggtttcttcc atctctcctt ctggtggcta tactaagtat      180
gctgactccg ttaaaggtcg cttcactatc tctcgagaca actctaagaa tactctctac      240
ttgcaaatga acagcttaag ggctgaggac acagccgtgt attactgtac cacagaattc      300
tacgattacc tggacgtctg gggcaaaggg accacggtca ccgtctcaag c               351
```

HIGH AFFINITY ANTIBODIES AGAINST HMGB1 AND METHODS OF USE THEREOF

CROSS REFERENCE TO RELATED APPLICATIONS

This application is a national phase filing of Application No. PCT/US2006/061258, which was filed with the Patent Corporation Treaty on Nov. 27, 2006, and claims the benefit under 35 U.S.C. §119(e) of United States Provisional Application Numbers 60/739,938, filed Nov. 28, 2005; 60/765,746, filed Feb. 7, 2006; 60/799,639, filed May 12, 2006; 60/822,044, filed Aug. 10, 2006; 60/822,041, filed Aug. 10, 2006; and is a continuation in part and claims the benefit under 35 U.S.C. §120 of U.S. patent application Ser. No.: 11/254,679, filed Oct. 21, 2005, which claims priority under 35 U.S.C. §119(e) to U.S. Provisional Application Nos.: 60/620,726, filed Oct. 22, 2004; 60/651,512 filed Feb. 10, 2005; 60/658,572 filed Mar. 7, 2005; 60/662,944, filed Mar. 18, 2005; and 60/713,712, filed Sept. 6, 2005; each of the above listed applications are hereby incorporated by reference herein in their entirety for all purposes.

1. BACKGROUND OF THE INVENTION

Inflammation is often induced by proinflammatory cytokines, such as tumor necrosis factor (TNF), interleukin (IL)-1α, IL-1β, IL-6, platelet-activating factor (PAF), macrophage migration inhibitory factor (MIF), and other compounds. These proinflammatory cytokines are produced by several different cell types, most importantly immune cells (for example, monocytes, macrophages and neutrophils), but also non-immune cells such as fibroblasts, osteoblasts, smooth muscle cells, epithelial cells, and neurons. These proinflammatory cytokines contribute to various disorders during the early stages of an inflammatory cytokine cascade.

Inflammatory cytokine cascades contribute to deleterious characteristics, including inflammation and apoptosis, of numerous disorders. Included are chronic and acute disorders characterized by both localized and systemic reactions, including, without limitation, diseases involving the gastrointestinal tract and associated tissues (such as appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, coeliac disease, hepatitis, Crohn's disease, enteritis, and Whipple's disease); systemic or local inflammatory diseases and conditions (such as asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, and sarcoidosis); diseases involving the urogenital system and associated tissues (such as septic abortion, epididymitis, vaginitis, prostatitis, and urethritis); diseases involving the respiratory system and associated tissues (such as bronchitis, emphysema, rhinitis, cystic fibrosis, pneumonitis, COPD, adult respiratory distress syndrome, pneumoultramicroscopicsilico-volcanoconiosis, alvealitis, bronchiolitis, pharyngitis, pleurisy, and sinusitis); diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts); dermatological diseases and conditions of the skin (such as psoriasis, burns, dermatitis, dermatomyositis, sunburn, urticaria warts, and wheals); diseases involving the cardiovascular system and associated tissues (such as vasulitis, angiitis, endocarditis, arteritis, atherosclerosis, thrombophlebitis, pericarditis, congestive heart failure, myocarditis, myocardial ischemia, periarteritis nodosa, restenosis and rheumatic fever); diseases involving the central or peripheral nervous system and associated tissues (such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis); diseases of the bones, joints, muscles and connective tissues (such as the various arthritides and arthralgias, osteomyelitis, fasciitis, Paget's disease, gout, periodontal disease, rheumatoid arthritis, and synovitis); other autoimmune and inflammatory disorders (such as myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, and Retier's syndrome); as well as various cancers, tumors and proliferative disorders (such as Hodgkins disease); and, in any case the inflammatory or immune host response to any primary disease.

The early proinflammatory cytokines (e.g., TNF, IL-1, etc.) mediate inflammation, and induce the late release of high mobility group protein 1 (HMG1) (also known as HMG-1, HMG1, and HMGB1), a protein that accumulates in serum and mediates delayed lethality and further induction of early proinflammatory cytokines.

HMG1 was first identified as the founding member of a family of DNA-binding proteins termed high mobility group (HMG) that are critical for DNA structure and stability. It was identified nearly 40 years ago as a ubiquitously expressed nuclear protein that binds double-stranded DNA without sequence specificity.

HMG1 binding bends DNA to promote formation and stability of nucleoprotein complexes that facilitates gene transcription of, for example, glucocorticoid receptors and RAG recombinase. The HMG1 molecule has three domains: two DNA binding motifs termed HMG A and HMG B boxes, and an acidic carboxyl terminus. The two HMG boxes are highly conserved 80 amino acid, L-shaped domains. HMG boxes are also expressed in other transcription factors including the RNA polymerase I transcription factor human upstream-binding factor and lymphoid-specific factor.

Recently, it has been found that the HMG A box serves as a competitive inhibitor of HMG proinflammatory action, and the HMG B box has the predominant proinflammatory activity of HMG (See, e.g., US20040005316). HMG1 has been demonstrated to be a long-searched-for nuclear danger signal passively released by necrotic, as opposed to apoptotic cells that will induce inflammation. It has also been shown that HMG1 can be actively secreted by stimulated macrophages or monocytes in a process requiring acetylation of the molecule, which enables translocation from the nucleus to secretory lysosomes and results in the secretion of an acetylated form of HMG1. See, PCT/IB2003/005718. Thus, HMG1 passively released from necrotic cells and HMGB1 actively secreted by inflammatory cells are molecularly different.

Further, HMG1 has been implicated as a cytokine mediator of delayed lethality in endotoxernia. See, e.g., U.S. Pat. Nos. 6,468,533 and 6,448,223. More specifically, it is been demonstrated that bacterial endotoxin (lipopolysaccharide (LPS)) activates monocytes/macrophages to release HMG1 as a late response to activation, resulting in elevated serum HMG1 levels that are toxic. Antibodies against HMG1 have been shown to prevent lethality of endotoxin even when antibody administration is delayed until after the early cytokine response. Like other proinflammatory cytokines, HMG1 is a potent activator of monocytes. Intratracheal application of HMG1 causes acute lung injury, and anti-HMG1 antibodies protect against endotoxin-induced lung edema. In addition, serum HMG1 levels are elevated in critically ill patients with sepsis or hemorrhagic shock, and levels are significantly higher in non-survivors as compared to survivors.

Extracellular HMG1 acts as a potent mediator of the inflammatory cascade by signaling via the Receptor for Advanced Glycated End-products (RAGE) and via members of the Toll-like receptor (TLR) family. See, e.g., U.S. patent publication no. US20040053841.

High mobility group protein 2 (HMG2) (also known as HMGB2 and HMG-2) is a close relative of HMG1 that likely originated from gene duplication. It is present in many cell types and shares many if not all of the biochemical properties of HMG1 (Bustin, 1999, *Mol. Cell. Biol.* 19, 5237-46 and Thomas et al., 2001, *Trends Biochem. Sci.* 26, 167-74). Although HMG2 is less abundant and has a more restricted distribution than HMG1 in adult mouse tissues, it is relatively abundant in the lymphoid organs, testis and lung where it may also play a role as a mediator of inflammation. Like HMG1, HMG2 is also a significant target antigen of autoantibodies (e.g., perinuclear anti-neutrophil cytoplasmic antibodies) in a number of autoimmune diseases including, systemic rheumatic diseases (Uesugi et al., 1998, *J Rheumatol.* 25:703-9), ulcerative colitis (Sobajima et al., 1998, *Clin Exp Immunol.* 111:402-7) and juvenile idiopathic arthritis (Wittemann et al., 1990, *Arthritis Rheum.* 33:1378-83; Rosenberg et al., 2000, *J Rheumatol.* 27, 2489-93).

Given the fact that antibodies that bind to HMG1 and polypeptide fragments thereof (e.g., HMG A and HMG B box) have been shown modulate the activity of HMG1 (e.g., proinflammatory activity), and the fact that modulating HMG1 activity in humans may have profound therapeutic uses for many diseases and disorders, there is a need in the art to identify antibodies that specifically bind HMG1 and polypeptide fragments thereof that have high affinity for HMG1 and low immunogenicity. Similarly, molecules that modulate the activity of HMG2 (e.g., antibodies that specifically bind HMG2 and polypeptide fragments) may also be useful therapeutics for a number of diseases and disorders.

2. SUMMARY OF THE INVENTION

The invention is based in part on the discovery that HMG1 synergizes with molecules having pathogen-associated molecular patterns (e.g. LPS, bacterial nucleic acids) to induce signaling and cytokine secretion via pattern-recognition receptors/molecules (e.g., Toll-Like-Receptors (TLRs)). Without wishing to be bound by any particular theory, HMG1 can bind to a molecule comprising a pathogen-associated molecular pattern, such molecules are referred to herein as "PAMPs", forming an immunostimulatory complex which augments PAMP signaling. In particular, HMG1 can function as a chaperone which brings a PAMP to the appropriate pattern-recognition receptors/molecules and thus enhance signaling. For example, it has been discovered that HMG1 binds to and forms a high affinity complex with CpG DNA, which stimulates cytokine production via a TLR9/MyD88 and RAGE dependent pathway. Taken together, these data provide a novel mechanism by which HMGB1, a secreted nuclear DNA binding protein, can bind to and confer potent immunostimulatory activity to DNA through a RAGE dependent mechanism which can contribute to the pathogenesis of immune disorders including but not limited to systemic autoimmune disorders.

Accordingly, the present invention provides methods of stimulating pattern-recognition receptors/molecules by co-administering HMG1 or a biologically functional fragment thereof in combination with one or more molecule having a pathogen-associated molecular pattern. The present invention also provides methods of inhibiting the interaction of HMG1 and/or an HMG1:PAMP complex with RAGE by administering antagonists of RAGE. In addition, the present invention provides methods of inhibiting pattern-recognition receptors/molecules by administering antagonists of HMG1 which can prevent and/or disrupt HMG1 binding to a PAMP and/or the chaperone activity of HMG1. Such therapies are useful for the treatment of cancers, infectious diseases, asthma and allergy.

The present invention is also based in part on the discovery of high affinity antibodies that specifically bind HMG1 (also referred herein as "HMGB1") and antigenic fragments thereof. Furthermore, the present invention is also based on the discovery that the high affinity antibodies of the invention can block the synergistic effect of HMG1 on signaling through pattern-recognition receptors/molecules. The high affinity antibodies of the present invention and pharmaceutical compositions comprising the same are useful for many purposes, for example, as therapeutics against a wide range of infectious and inflammatory diseases and disorders such as sepsis, rheumatoid arthritis, peritonitis, Crohn's disease, lupus, reperfusion injury, septicemia, endotoxic shock, cystic fibrosis, endocarditis, psoriasis, arthritis (e.g., psoriatic arthritis), anaphylactic shock, organ ischemia, reperfusion injury, spinal cord injury and allograft rejection. In addition, the high affinity antibodies of the present invention are useful for diagnostic applications.

In one embodiment of the present invention, the high affinity antibodies of the invention specifically bind a polypeptide comprising, or alternatively consisting of (or consisting essentially of) an HMG1 polypeptide of a human or other animal, e.g., mammals and invertebrates. In a specific embodiment, the high affinity antibodies of the present invention specifically bind a polypeptide comprising or alternatively consisting of a human HMG1 polypeptide (SEQ ID NO:1 or SEQ ID NO:2). Full-length HMG1 polypeptides of human and other animals are well known in the art (see, e.g., US20040005316; U.S. Pat. No. 6,468,533 and U.S. Pat. No. 6,448,223).

```
Human HMGB1 amino acid sequence
(GenBank Acc. No. NP_002119)
MGKGDPKKPRGKMSSYAFFVQTCREEHKKKHPDAS      (SEQ ID NO: 1)
VNFSEFSKKCSERWKTMSAKEKGKFEDMAKADKAR
YEREMKTYIPPKGETKKKFKDPNAPKRPPSAFFLF
CSEYRPKIKGEHPGLSIGDVAKKLGEMWNNTAADD
KQPYEKKAAKLKEKYEKDIAAYRAKGKPDAAKKGV
VKAEKSKKKKEEEEDEEDEEDEEEEEDEEDEDEEE
DDDDE Human HMGB1 amino acid sequence
(GenBank ACC. NO. AAA64970)
MGKGDPKKPTGKMSSYAFFVQTCREEHKKKHPDA
SVNFSKKCSERWKTMSAKEGKFEDMAKADKARYE
REMKTYIPPKGETKKKFKDPNAPKRLPSAFFLFC
SEYRPKIKGEHPGLSIGDVAKKLGEMWNNTAADD
KQPYEKKAAKLKEKYEKDIAAYRAKGKPDAAKKG
VVKAEKSKKKKEEEEDEEDEEDEEEEEDEEDEED      (SEQ ID NO: 2)
EEDDDDE
```

In another embodiment of the present invention, the high affinity antibodies of the invention specifically bind a polypeptide comprising, or alternatively consisting of (or consisting essentially of) an HMG2 (also referred to herein as "HMGB2") polypeptide of a human or other animal, e.g., mammals and invertebrates. In still another embodiment, the high affinity antibodies of the present invention specifically bind a polypeptide comprising or alternatively consisting of a human HMG2 polypeptide (SEQ ID NO:21). Full-length HMG2 polypeptides of human and other animals are well known in the art. See, e.g., Majumdar et al., 1991, *Nucleic Acids Res.* 19:6643; Shirakawa et al., 1992, *J Biol Chem* 267:6641-6645.

```
Human HMGB2 amino acid sequence
(GenBank Acc. No. AAA58659)
MGKGDPNKPRGKMSSYAFFVQTCREEHKKKHPDS     (SEQ ID NO: 21)
SVNFAEFSKKCSERWKTMSAKEKSKFEDMAKSDK
ARYDREMKNYVPPKGDKKGKKKDPNAPKRPPSAF
FLFCSEHRPKIKSEHPGLSIGDTAKKLGEMWSEQ
SAKDKQPYEQKAAKLKEKYEKDIAAYRAKGKSEA
GKKGPGRPTGSKKKNEPEDEEEEEEEDEDEEEE
DEDEE
```

In another embodiment of the present invention, the high affinity antibodies of the present invention specifically bind a polypeptide comprising, or alternatively consisting of (or consisting essentially of) either a HMG1 A box or HMG1 B box of a mammal (or other animals), preferably of a human HMG1 polypeptide. The amino acid sequences of HMG1 A box and HMG1 B box polypeptides of humans and other animals are highly conserved and are well known in the art (see, e.g., US20040005316; U.S. Pat. No. 6,468,533; U.S. Pat. No. 6,448,223, and US20040053841).

```
Human HMGB1 A box
PTGKMSSYAFFVQTCREEHKKKHPDASVNFSEFS    (SEQ ID NO: 3)
KKCSERWKTMSAKEKGKFEDMAKADKARYEREMK
TYIPPKGET Human HMGB1 B box
FKDPNAPKRLPSAFFLFCSEYRPKIKGEHPGLSI    (SEQ ID NO: 4)
GDVAKKLGEMWNNTAADDKQPYEKKAAKLKEKYE
KDIAAY
```

In still another embodiment of the present invention, the high affinity antibodies of the present invention specifically bind a polypeptide comprising, or alternatively consisting of (or consisting essentially of) either a HMG2 A box or HMG2 B box of a mammal (or other animals), preferably of a human HMG2 polypeptide. The amino acid sequences of HMG box polypeptides of humans and other animals are highly conserved and are well known in the art. See, e.g., Jantzuen et al., 1990, *Nature* 344:830-6; Kolodrubetz 1990, *Nucleic Acids Res.* 18:5565; Laudet et al., 1993, *Nucleic Acids Res.* 21:2493-501 and Thomas et al., 2001, *Trends Biochem Sci.* 26:167-74.

```
Human HMGB2 A box
PRGKMSSYAFFVQTCREEHKKKHPDSSVNFAEFS    (SEQ ID NO: 22)
KKCSERWKTMSAKEKSKFEDMAKSDKARYDREMK
NYVPPKGDK Human HMGB2 B box
KKDPNAPKRPPSAFFLFCSEHRPKIKSEHPGLS     (SEQ ID NO: 23)
IGDTAKKLGEMWSEQSAKDKQPYEQKAAKLKEKY
EKDIAAY
```

Also encompassed by the present invention are antibodies which specifically bind to an epitope comprising, or alternatively consisting of (or consisting essentially of) amino acid residues derived from both the A box and B box of HMG1 and/or HMG2. An epitopic derived from amino acid residues derived from both the A box B box may be a linear polypeptide derived from the junction of the A and B boxes or may result from the three dimensional confirmation of a polypeptide comprising amino acid residues from both the A and B boxes.

In another embodiment of the present invention, the high affinity antibodies of the present invention specifically bind an antigenic HMGB1 polypeptide fragment comprising, or alternatively consisting of (or consisting essentially of) a polypeptide fragment of human HMGB1 (or other animals).

In another embodiment of the present invention, the high affinity antibodies of the present invention specifically bind an antigenic HMGB2 polypeptide fragment comprising, or alternatively consisting of (or consisting essentially of) a polypeptide fragment of human HMGB2 (or other animals).

It is specifically contemplated that the high affinity antibodies of the present invention may specifically bind acetylated and/or non-acetylated HMG1 and antigenic fragments thereof. It is also specifically contemplated that the high affinity antibodies of the invention may be able to distinguish between the two forms. It is also contemplated that the high affinity antibodies of the present invention may specifically bind acetylated and/or non-acetylated HMG2 and antigenic fragments thereof. It is also specifically contemplated that the high affinity antibodies of the invention may be able to distinguish between the two forms.

In one embodiment, the high affinity antibodies of the present invention bind HMG1 and block the interaction of HMG1 with a PAMP. In another embodiment, the high affinity antibodies of the present invention bind HMG1 and block the interaction of a HMG1:PAMP complex with a pattern-recognition receptor/molecule (also referred to herein as "PRMs"). In another embodiment, the high affinity antibodies of the present invention bind HMG1 and block the interaction of a HMG1 with a pattern-recognition receptor/molecule (also referred to herein as "PRMs"). In still other embodiments, the high affinity antibodies of the present invention bind HMG1 and block the interaction of a HMG1:PAMP complex with RAGE.

In a specific embodiment of the present invention, antibodies that specifically bind HMG1 and antigenic fragments thereof are humanized or human antibodies. In another specific embodiment of the present invention, antibodies that specifically bind HMG2 and antigenic fragments thereof are humanized or human antibodies.

Another embodiment of present invention are antibodies that specifically bind HMG1 and antigenic fragments thereof with a dissociation constant or $K_d$ ($k_{off}/k_{on}$) of less than $10^{-5}$ M, or of less than $10^{-6}$ M, or of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than $10^{-13}$ M.

Still another embodiment of present invention are antibodies that specifically bind HMG2 and antigenic fragments thereof with a dissociation constant or $K_d$ ($k_{off}/k_{on}$) of less than $10^{-5}$ M, or of less than $10^{-6}$ M, or of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than $10^{-13}$ M.

In another embodiment, the antibody of the invention binds to HMG1 and/or antigenic fragments thereof with a $K_{off}$ of less than $1 \times 10^{-3}$ s$^{-1}$, or less than $3 \times 10^{-3}$ s$^{-1}$. In other embodiments, the antibody binds to HMG1 and antigenic fragments thereof with a $K_{off}$ of less than $10^{-3}$ s$^{-1}$, less than $5 \times 10^{-3}$ s$^{-1}$, less than $10^{-4}$ s$^{-1}$, less than $5 \times 10^{-4}$ s$^{-1}$, less than $10^{-5}$ s$^{-1}$ less than $5 \times 10^{-5}$ s$^{-1}$, less than $10^{-6}$ s$^{-1}$, less than $5 \times 10^{-6}$ s$^{-1}$, less than $10^{-7}$ s$^{-1}$, less than $5 \times 10^{-7}$ s$^{-1}$, less than $10^{-8}$ s$^{-1}$, less than $5 \times 10^{-8}$ s$^{-1}$, less than $10^{-9}$ s$^{1}$, less than $5 \times 10^{-9}$ s$^{-1}$, or less than $10^{-10}$ s$^{-1}$.

In yet another embodiment, the antibody of the invention binds to HMG2 and/or antigenic fragments thereof with a $K_{off}$ of less than $1\times10^{-3}$ s$^{-1}$, or less than $3\times10^{-3}$ s$^{-1}$. In other embodiments, the antibody binds to HMG2 and antigenic fragments thereof with a $K_{off}$ of less than $10^{-3}$ s$^{-1}$, less than $5\times10^{-3}$ s$^{-1}$, less than $10^{-4}$ s$^{-1}$, less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$, less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-10}$ s$^{-1}$.

In another embodiment, the antibody of the invention binds to HMG1 and/or antigenic fragments thereof with an association rate constant or $k_{on}$ rate of at least $10^5$ M$^{-1}$s$^{-1}$, at least $5\times10^5$ M$^{-1}$s$^{-1}$, at least $10^6$M$^{-1}$s$^{-1}$, at least $5\times10^6$ M$^{-1}$s$^{-1}$, at least $10^7$ M$^{-1}$s$^{-1}$, at least $5\times10^7$ M$^{-1}$s$^{-1}$, or at least $10^8$ M$^{-1}$s$^{-1}$, or at least $10^9$ M$^{-1}$s$^{-1}$.

In another embodiment, the antibody of the invention binds to HMG2 and/or antigenic fragments thereof with an association rate constant or $k_{on}$ rate of at least $10^5$ M$^{-1}$s$^{-1}$, at least $5\times10^5$ M$^{-1}$s$^{-1}$, at least $10^6$ M$^{-1}$s$^{-1}$, at least $5\times10^6$ M$^{-1}$s$^{-1}$, at least $10^7$ M$^{-1}$s$^{-1}$, at least $5\times10^7$ M$^{-1}$s$^{-1}$, or at least $10^8$ M$^{-1}$s$^{-1}$, or at least $10^9$ M$^{-1}$s$^{-1}$.

It is contemplated that the high affinity antibodies of the invention may specifically bind to HMG1 and not bind to HMG2 or may specifically bind to HMG2 and not bind to HMG1. It is further contemplated that the high affinity antibodies of the invention may specifically bind to both HMG1 and to HMG2 (e.g., an antibody that specifically recognized an epitope that is present in both HMG1 and HMG2). It is contemplated that the high affinities antibodies of the invention may specifically bind either HMG1 or HMG2 and cross-react with HMG2 or HMG1, respectively. It is further contemplated that the high affinity antibodies of the invention bind HMG1 and HMG2 with either the same or different binding affinities.

The high affinity antibodies of the invention include, but are not limited to, synthetic antibodies, monoclonal antibodies, recombinantly produced antibodies, intrabodies, multi-specific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv) (including bi-specific sdFvs), and anti-idiotypic (anti-Id) antibodies, and epitope-binding fragments of any of the above.

An additional nonexclusive embodiment of the present invention includes high affinity antibodies of the invention that have certain preferred biochemical characteristics such as a particular isoelectric point (pI) or melting temperature (Tm).

In one embodiment, the high affinity antibodies of the present invention have a pI ranging from 5.5 to 9.5.

In one embodiment, the high affinity antibodies of the present invention have a Tm ranging from about 65° C. to about 120° C.

Specific embodiments of the invention also include particular antibodies (and fragments thereof) that specifically bind HMG1 with high affinity which have been deposited with the American Type Culture Collection (10801 University Boulevard, Manassas, Va. 20110-2209) and assigned ATCC Deposit Nos. PTA-6142 (Deposited Aug. 4, 2004), PTA-6143 (Deposited Aug. 4, 2004), PTA-6259 (Deposited Oct. 19, 2004) and PTA-6258 (Deposited Oct. 19, 2004) (also referred to herein as "S2", "S6", "S16", and "G4", respectively). These deposits will be maintained under the terms of the Budapest Treaty on the International Recognition of the Deposit of Microorganisms for the Purposes of Patent Procedure. Since the strain referred to is being maintained under the terms of the Budapest Treaty, it will be made available to a patent office signatory to the Budapest Treaty.

Other specific embodiments of the invention also include particular antibodies (and fragments thereof) that specifically bind HMG1 with high affinity and comprise at least one of the variable regions disclosed herein (see, e.g., FIG. 2A-J and SEQ ID NOS.: 5-20, 24-27, and 30-73). Antibodies having at least one, at least two, at least three, at least four at least five or at least 6 of the CDRs of the antibodies disclosed herein are specific embodiments of the invention (see, e.g., FIG. 2A-J CDRs underlined and SEQ ID NOS: 74-103). Antibodies having at least one, at least two, at least three, at least four, at least five, or all six of the CDRs of the deposited antibodies are specific embodiments of the invention. Isolated polynucleotides that encode these antibodies (and fragments thereof) are also contemplated embodiments of the invention.

Further, any antibody that specifically binds the same epitope (e.g., epitopes within the HMG1 peptides 91-169 or 150-183) as the anti-HMG1 antibodies disclosed herein are included within the invention. In a specific embodiment, an antibody that specifically binds the same epitope as the deposited antibodies are included within the invention. It is specifically contemplated that these antibodies will bind the same epitope as the deposited antibodies with at least equal affinity, or better affinity, or less affinity. Isolated polynucleotides that encode these antibodies (and fragments thereof) are also specific embodiments of the invention.

Isolated polynucleotides that encode any of the high affinity antibodies of the invention are included as embodiments of the invention.

In other embodiments, the present invention also provides RAGE antagonists (referred to herein as "RAGE antagonists of the invention" or simply as "RAGE antagonists"). In certain embodiments, RAGE antagonists of the invention inhibit the interaction of HMG1 and/or an HMG1:PAMP complex with RAGE. In certain embodiments RAGE antagonists of the invention inhibit HMG1 mediated enhancement of TLR signaling stimulated by one or more TLR ligands. In certain embodiments, RAGE antagonists of the invention inhibit the interaction of a HMG1:PAMP complex with RAGE. In other embodiments, RAGE antagonists of the invention inhibit the internalization of an HMG1-PAMP. It is contemplated that RAGE antagonists of the invention may bind directly to RAGE and/or bind to HMG1 and/or a TLR and/or HMG1:PAMP complex and/or a RAGE/HMG1/TLR complex.

In still other embodiments, the present invention provides methods of inhibiting the interaction of HMG1 and/or an HMG1:PAMP complex with RAGE by administering RAGE antagonists.

In one embodiment, the high affinity antibodies of the present invention are RAGE antagonists. Other RAGE antagonists contemplated include, but are not limited to, soluble RAGE (e.g., a certain RAGE fragments, RAGE-Fc fusion proteins, etc) and HMG1 antagonists (e.g., HMG1 A-box).

In other embodiments, the invention is directed to compositions, e.g., pharmaceutical compositions, comprising the high affinity antibodies of the present invention in a pharmaceutically acceptable excipient. In still other embodiments, the invention is directed to compositions, e.g., pharmaceutical compositions, comprising the RAGE antagonists of the present invention in a pharmaceutically acceptable excipient.

In a specific embodiment, compositions comprise high affinity antibodies of the invention that specifically bind to an A box of HMG1 (e.g., an epitope within SEQ ID NOS: 3). In another specific embodiment, compositions comprise high affinity antibodies of the invention that specifically bind to a B box of HMG1 (e.g., an epitope within SEQ ID NOS: 4, 28, 29). In still another specific embodiment, compositions comprise high affinity antibodies of the invention that specifically bind to an epitope derived from both the A box and B box of HMG1 and/or HMG2. It is also contemplated that compositions of the invention may comprise a combination of high affinity antibodies of the invention, for example a combination of antibodies that specifically bind to an A box and antibodies that specifically bind a B box.

Compositions of the invention can comprise the high affinity antibodies of the present invention alone or in combination with other active therapeutic molecules and/or adjuvants such as steroids, other anti-inflammatory molecules, cytotoxic drugs, or other antibody therapeutics. More specifically, the compositions of the invention can comprise an antagonist of an early sepsis mediator. The antagonist of an early sepsis mediator is in one embodiment, an antagonist of a cytokine selected from the group consisting of TNF, IL-1α, IL-1β, MIF and IL-6.

The compositions of the invention may be utilized alone or in combination with other active therapeutic strategies against cancer and related conditions including but not limited to, surgery, radiation therapy and chemotherapy. In certain embodiments, the compositions of the invention may be useful in increasing the sensitivity of tumor cells to radiation in radiotherapy and/or in potentiating and/or enhancing damage to tumors by chemotherapeutic agents. The compositions of the invention may also be useful for sensitizing multidrug-resistant tumor cells.

In another embodiment of the present invention, the compositions described herein can inhibit a condition mediated or characterized by activation of an inflammatory cytokine cascade including both acute and chronic inflammatory conditions.

In still another embodiment of the present invention, the compositions described herein are more protective (by at least 10% or at least 15%, or at least 20%, or at least 30%, or at least 40%, or at least 50%, or at least 60%, or at least 70%, or at least 80%, or at least 90%) than a control composition in an animal CLP sepsis model (e.g., mouse or piglet CLP model).

In yet another embodiment of the present invention, the compositions described herein are more protective (by at least 10% or at least 15%, or at least 20%, or at least 30%, or at least 40%, or at least 50%, or at least 60%, or at least 70%, or at least 80%, or at least 90%) than a control composition in an animal arthritis model (e.g., rat AIA, mouse passive or active CIA models).

In still another embodiment of the present invention, the compositions described herein reduce bone loss and/or cartilage damage (by at least 10% or at least 15%, or at least 20%, or at least 30%, or at least 40%, or at least 50%, or at least 60%, or at least 70%, or at least 80%, or at least 90%) more than a control composition in an animal arthritis model (e.g., rat AIA, mouse passive or active CIA models).

In still another embodiment of the present invention, the compositions described herein reduce bone loss and/or cartilage damage (by at least 10% or at least 15%, or at least 20%, or at least 30%, or at least 40%, or at least 50%, or at least 60%, or at least 70%, or at least 80%, or at least 90%) more than a control composition in humans.

In another embodiment of the present invention, the compositions described herein are more protective (by at least 10% or at least 15%, or at least 20%, or at least 30%, or at least 40%, or at least 50%, or at least 60%, or at least 70%, or at least 80%, or at least 90%) than Renbrel® (with or without methotrexate) in a rodent arthritis model.

In still another embodiment of the present invention, the compositions described herein are more protective (by at least 10% or at least 15%, or at least 20%, or at least 30%, or at least 40%, or at least 50%, or at least 60%, or at least 70%, or at least 80%, or at least 90%) than Enbrel® (with or without methotrexate) in humans.

In yet another embodiment of the present invention, the compositions described herein are more protective (by at least 10% or at least 15%, or at least 20%, or at least 30%, or at least 40%, or at least 50%, or at least 60%, or at least 70%, or at least 80%, or at least 90%) than a control composition in a mouse peritonitis model.

In another embodiment, the compositions described herein reduce hyperostosis (by at least 10% or at least 15%, or at least 20%, or at least 30%, or at least 40%, or at least 50%, or at least 60%, or at least 70%, or at least 80%, or at least 90%) more than a control composition in an animal arthritis model (e.g., rat ATA, mouse passive or active CIA models).

In still another embodiment of the present invention, the compositions described herein reduce hyperostosis (by at least 10% or at least 15%, or at least 20%, or at least 30%, or at least 40%, or at least 50%, or at least 60%, or at least 70%, or at least 80%, or at least 90%) more than a control composition in humans.

Other contemplated embodiments of the present invention include methods of treating or preventing arthritis, e.g., rheumatoid arthritis, osteoclast-mediated diseases, or other inflammatory diseases of the joints comprising administering an antibody composition described herein.

In another embodiment, the present invention includes methods of treating or preventing arthritis, e.g., rheumatoid arthritis, osteoclast-mediated diseases, or other inflammatory diseases comprising administering any antibody (or antibody composition) that specifically binds HMG1 or antigenic fragment thereof (e.g., HMG B box) irregardless of the binding affinity of the antibody.

In another embodiment, the present invention includes methods of treating or preventing arthritis, e.g., rheumatoid arthritis, osteoclast-mediated diseases, or other inflammatory diseases comprising administering any antibody (or antibody composition) that specifically binds HMG2 or antigenic fragment thereof (e.g., HMG B box) irregardless of the binding affinity of the antibody.

In another embodiment, the present invention includes methods of treating or preventing arthritis, e.g., rheumatoid arthritis, osteoclast-mediated diseases, or other inflammatory diseases comprising administering a combination of antibodies (or antibody composition) that specifically bind HMG1 and/or HMG2 or antigenic fragment thereof (e.g., HMG B box) irregardless of the binding affinity of the antibody.

In another embodiment, the present invention includes methods of treating or preventing diseases associated with abnormal bone deposition, e.g., ankylosing spondylitis, undifferentiated spondylarthopathy, juvenile spondyloarthritis, or other diseases associated with hyperostosis comprising administering any antibody (or antibody composition) that specifically binds HMG1 or antigenic fragment thereof (e.g., HMG B box) irregardless of the binding affinity of the antibody.

In another embodiment, the present invention includes methods of treating or preventing the present invention includes methods of treating or preventing diseases associated with abnormal bone deposition, e.g., ankylosing spondylitis, undifferentiated spondylarthopathy, juvenile spondyloarthritis, or other diseases associated with hyperostosis comprising administering any antibody (or antibody composition) that specifically binds HMG2 or antigenic fragment thereof (e.g., HMG B box) irregardless of the binding affinity of the antibody.

In another embodiment, the present invention includes methods of treating or preventing the present invention includes methods of treating or preventing diseases associated with abnormal bone deposition, e.g., ankylosing spondylitis, undifferentiated spondylarthopathy, juvenile spondyloarthritis, or other diseases associated with hyperostosis comprising administering a combination of antibodies (or antibody composition) that specifically bind HMG1 and/or HMG2 or antigenic fragment thereof (e.g., HMG B box) irregardless of the binding affinity of the antibody.

In still another embodiment of the present invention, the compositions described herein ameliorate the severity of spinal cord injury (SCI) (by at least 10%, or at least 15%, or at least 20%, or at least 30%, or at least 40%, or at least 50%, or at least 60%, or at least 70%, or at least 80%, or at least 90%) more than a control composition in a human or a rodent SCI model.

In other specific embodiments, the invention is directed to methods of administering and using compositions and antibodies of the invention to treat and prevent a wide range of inflammatory conditions including both chronic and acute conditions, such as appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, restenosis, COPD adult respiratory distress syndrome, meningitis, encephalitis, multiple sclerosis, cerebral infaretion, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Retier's syndrome, and Hodgkins disease.

In other specific embodiments, the invention is directed to methods of administering and using compositions and antibodies of the invention to treat and prevent diseases associated with hyperostosis.

In other specific embodiments, the invention is directed to methods of administering and using compositions and antibodies of the invention to treat and prevent diseases associated with abnormal bone deposition, such as ankylosing spondylitis, undifferentiated spondylarthopathy, juvenile spondyloarthritis, reactive arthritis, and enteropathic arthritis.

In other specific embodiments, the invention is directed to methods of administering and using compositions and antibodies of the invention to treat and prevent conditions associated with abnormal bone metabolism, such as spina bifida, Paget's disease, Paget's disease of the breast, fibrous dysplasia, McCune-Albright syndrome, cleidiocranial dysplasia, Ellis-van Creveld syndrome, Russel-Silver syndrome, Ollier disease, Maffucci syndrome, Langer-Giedion syndrome, Freiberg's disease, Sever's disease, Scheuermann's disease, Camurati-Englemann syndrome, Idiopathic osteolysis, pyenodysotosis, osteogenesis imperfecta, Marfan's syndrome, hyperparathyroidism, rickets, cherubism, florid osseous dysplasia, osteomalacia, Oosteodystrophy, fibrous osteodystrophy, otosclerosis, Fanconi's syndrome, fibrodysplasia ossificans progressiva, osteosclerosis, osteopetrosis, Perthes disease, scoliosis, skeletal fluorosis, craniaometaphyseal dysplasia, exostosis, osteochondromatosis.

In other specific embodiments, the invention is directed to methods of administering and using compositions and antibodies of the invention to treat and prevent conditions associated with cancers of the bone, such as osteoma, Ewing's sareoma, chrondosareoma, and osteosareoma.

In other specific embodiments, the invention is directed to methods of administering and using compositions and antibodies of the invention to treat and prevent conditions associated with osteoblast dysfunction, such as hypertrophic osteoarthropathy, Solente-Gole syndrome, van Buchem disease and autosomal dominant osteosclerosis.

The present invention is also directed to a method of inhibiting release of a proinflammatory cytokine from a mammalian cell. The method comprises treating the cell with an antibody or antibody composition of the present invention in an amount sufficient to inhibit release of the proinflammatory cytokine from the cell. In these embodiments, the cell is any cell capable of releasing a proinflammatory cytokine including but not limited to, peripheral blood monocytes and macrophages. In addition, the proinflammatory cytokine may be selected from the group consisting of TNF, IL-1α, IL-1β, MIF and IL-6. In a specific embodiment, the cell is a macrophage and the proinflammatory cytokine is selected from the group consisting of TNF, IL-1α, IL-1β, MIF and IL-6. In one embodiment, the methods are used to treat a cell in a patient suffering from, or at risk for, a condition characterized by activation of the inflammatory cytokine cascade. Specific conditions are enumerated herein.

In related embodiments, the present invention is directed to a method of treating a condition in a patient characterized by activation of an inflammatory cytokine cascade. The method comprises administering to the patient an antibody or an antibody composition of the present invention. Specific conditions have already been enumerated.

3. BRIEF DESCRIPTION OF THE DRAWINGS

FIG. 1. Alignment of human HMG1 and HMG2.

FIG. 2. The Nucleotide and Corresponding Amino acid sequence of the variable regions of the heavy ($V_H$) and the light chains ($V_L$) of the Human anti-HMG1 antibodies of the invention. Underlined: CDRs (Kabat definition). A) S2 $V_L$ (SEQ ID NO.: 5-6); B) S2 $V_H$(SEQ ID NO.: 7-8); C) S6 $V_L$ (SEQ ID NO.: 9-10); D) S6 $V_H$ (SEQ ID NO.: 11-12); E) S16 $V_L$ (SEQ ID NO.: 13-14); F) S16 $V_H$(SEQ ID NO.: 15-16); G) G4 $V_L$ (SEQ ID NO.: 17-18); H) G4 $V_H$(SEQ ID NO.: 19-20); I) E11 $V_L$ (SEQ ID NO.: 24-25); and J) E11 $V_H$ (SEQ ID NO.: 26-27). Panel K depicts the predicted RNA splicing sites in the heavy chain variable region of G4 and S6. Panel L is the alignment of the wildtype nucleic acid sequence encoding the heavy chain variable region of G4 (SEQ ID NO.: 20) and the mutated sequence containing three silent nucleotide changes to remove one donor and two acceptor splicing sites (SEQ ID NO.: 110). SEQ ID NOS. refer to the amino acid and nucleotide sequences, see Table 4 for more detail.

FIG. 3. Physical Characteristics of Human anti-HMB 1 Antibodies A) Isoelectric focusing (IEF) analysis of a panel of human anti-HMB1 antibodies indicates that there is a wide range of pI values (e.g., ~7.77 to ~9.24) for the different human anti-HMG1 antibodies. B) Differential scanning calorimetry (DSC) analysis of a panel of human anti-HMG1 antibodies indicates that there is a wide range of Tm values (e.g., ~66° C. to ~90° C.) for the different human anti-HMG1 antibodies. C) Graphical representation of the IEF and DSC analysis indicates that there is not a direct correlation between pI and Tm values.

FIG. 4. Binding Kinetics and Specificity of Human anti-HMG1 Antibodies. Panel A) The binding curves from an HMG1 capture ELISA for several of the human anti-HMG1 antibodies demonstrating that the antibodies have differing affinities for E. coli produced recombinant HMG1. Panel B) The binding curves from an HMG1 capture ELISA for several human anti-HMG1 antibodies comparing the capture of recombinant HMG1 (left) and native nuclear HMG1 (right) indicate that S16 and G4 bind both forms of HMG1 while S2, S6 and S10 bind better to recombinant HMG1 than to native nuclear HMG1. Panel C) The binding curves from an HMG1 capture ELISA for several human anti-HMG1 antibodies comparing the capture of native nuclear, necrotic and activated HMG1 indicate that S6 and to a lesser extent G4 bind with differing affinities to the various forms while S16 does not. Panel D) The binding curves from capture ELISA assays performed for several human anti-HMG1 antibodies comparing two different capture formats, immobilized antibody (squares) and immobilized HMG1 (triangles), indicate that E11 and to a lesser extent S17 have a higher affinity for soluble HMG1 while G2, G4, G9 and G12 showed little difference in binding to immobilized or soluble HMG1. Panel E) ELISA data showing the relative binding affinity of several human anti-HMG1 antibodies for HMG1 and HMG2 indicated that most of the antibodies tested (G2, G4, G9, G12, S3, G20, G34, G35, S2, S6, S10, S14 and S17) are specific for HMG1 while S12 and S16 exhibit some binding to both HMG1 and HMG2 and E11 appears to have a higher binding affinity for HMG2 in this assay. The data from these assays and others not shown are summarized in Table 1. Panel F) Early passage HUVECs were either untreated (left panels) or treated with 100 ng/ml LPS (middle panels). Four hours later, cells were briefly fixed with 1% paraformaldehyde and anti-HMGB1 mAb, S6 (upper panels) or G4 (lower panels) or isotype control (not shown) was added. The detection was goat anti-human IgG-FITC. Cell nuclei were stained using DAPI staining (right panels). Panel G) ELISA binding of G4, S6 and the isotype control (R347) to joint lysate from adjuvant induced arthritis rats (black bars), sera from septic peritonitis mice (grey bars) and recombinant HMGB (speckled bars) are plotted in the top panel. Western blot analysis of immunoprecipitated material from joint lysate (bottom left) or sera from sepsis patients (bottom right) using S16 (lane 2), S6 (lane 3) or G4 (lane 4) shows that S6 does not immunoprecipitate HMGB1 from joint lysates and brings down a smaller form of HMGB1 from sepsis sera. Lane 5 is Thymus-HMGB1 alone and Lane 1 is Magic Mark Protein standards.

FIG. 5. HMG1 B Box Epitope Mapping Studies. The binding curves from HMG1 B Box peptide ELISAs for several human anti-HMG1 antibodies are shown. The curves indicate that S12, S16 and G4 bind to HMG1 peptide 91-169 (Panel A). S12 also binds to HMG1 peptide 150-183 (Panel B). The remaining antibodies tested (S2, S6, S10, G2 and G9) do not bind either of the HMG1 B Box peptides tested in this assay. Panel C depicts the domains of HMGB1 with the amino acid residue numbers for each domain indicated above (top panel) as well as the binding of G4 (left panel) and S16 (right panel) to a number of smaller peptides spanning the HMGB1 protein. G4 shows some binding to the B-box peptide 91-108 and 108-138 and stronger binding to the C-terminal tail peptide 188-216, while S16 binds the B-box peptide 91-108 and to a lesser extent peptides 166-183 and 179-186.

FIG. 6. Many Human anti-HMG1 Antibodies Inhibit HMG1 Stimulated Cytokine Release From Human PBMCs. Representative dose response curves of recombinant HMG1 stimulated IL-1B, IL-6 and TNF-a release inhibition activity for several human anti-HMG1 antibodies (G9, S14, G20, S2, S6 and S17) are shown in Panel A. The results were plotted both as pg/ml of cytokine released (top graphs) and as percent inhibition (bottom graphs). Dose response curves of recombinant HMG1 stimulated IL-6 release inhibition for several additional human anti-HMG1 antibodies (G4, S6, S16 and S6+S16) and for a RAGE-Fc fusion protein are shown in Panel B. Representative dose response curves of native activated HMG1 stimulated IL-6 cytokine release inhibition for E11, S13, S16, S17, G4, G9, S6, RAGE-Fc and A box fusion proteins are shown in Panel C. The $IC_{50}$ values calculated from these data and other data not shown are summarized in Table 1.

Figure 7:
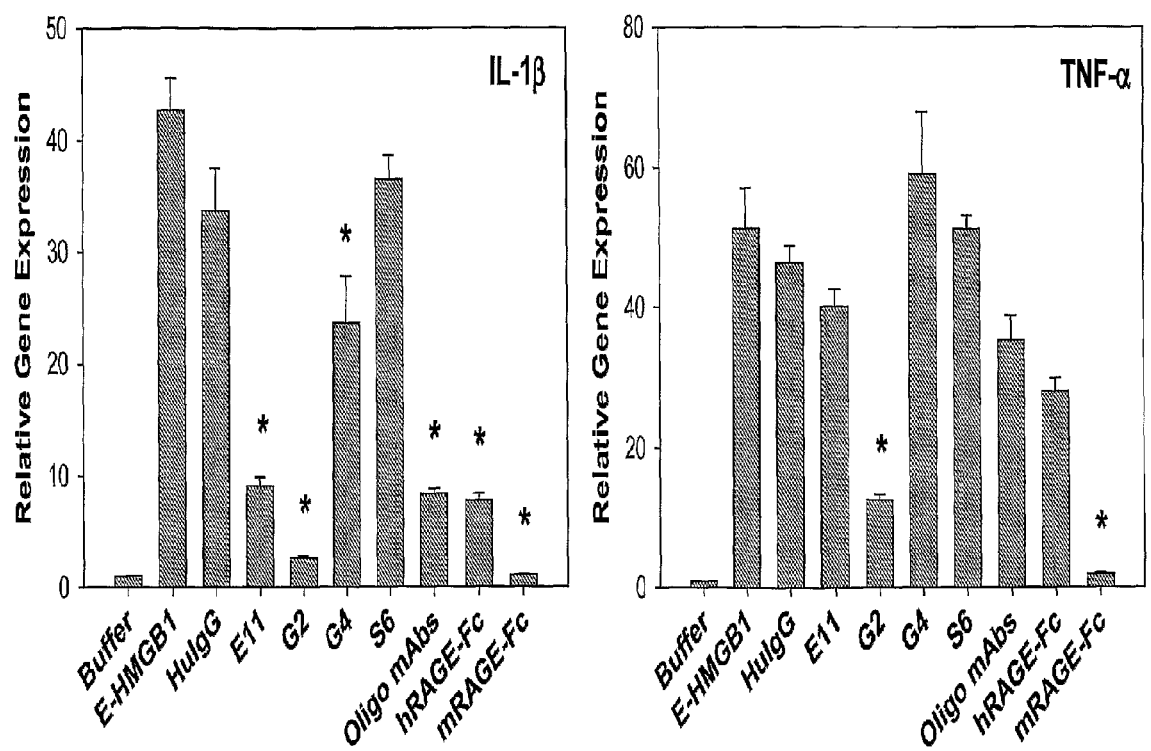

FIG. 7. Several Human anti-HMG1 Antibodies Inhibit HMG1 Stimulated Cytokine Gene Expression In Mouse Macrophages (mMØ). The relative gene expression of IL-1β (left) or TNF-a (right) are shown for mouse macrophages treated with buffer, recombinant HMG1 (E-HMGB1) alone, and the combination of E-HMGB1 plus a human isotype control (HuIgG), human anti-HMG1 antibodies (E11, G2, G4, S6 and oligoclonal) as well as mouse and human RAGE-Fc fusion proteins. E11, G2, G4 and oligoclonal as well as both RAGE-Fc fusion proteins robustly inhibited IL-1β expression. G2 and the mouse RAGE-Fc fusion protein robustly inhibited TNF-a expression. These data and other data not shown are summarized in Table 1.

Figure 8:
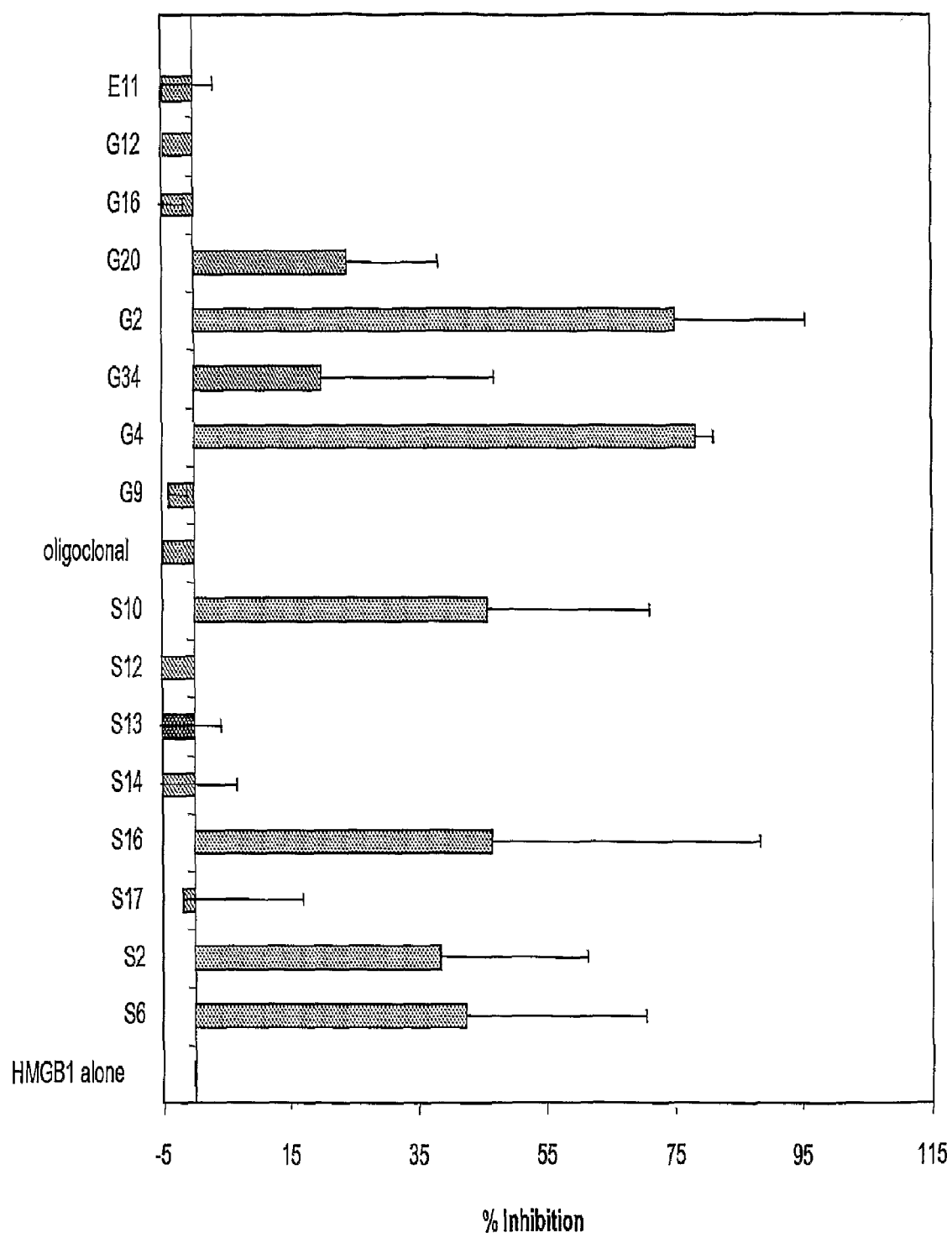

FIG. 8. A Subset of Human anti-HMG1 Antibodies Block the Binding of recombinant HMG1 to RAGE. An ELISA based binding assay was used to measure the binding of HMG1 to a RAGE-Ig fusion. The percent inhibition for a number of human anti-HMG1 antibodies is shown. G2, G4, S10, S16, S2 and S6 show significant ability to block the binding of HMG1 to RAGE while E11, G12, G16, G20, G34, G9, oligoclonal, S12, S14 and S17 do not at the concentrations tested. These data and other data not shown are summarized in Table 1.

Figure 9:
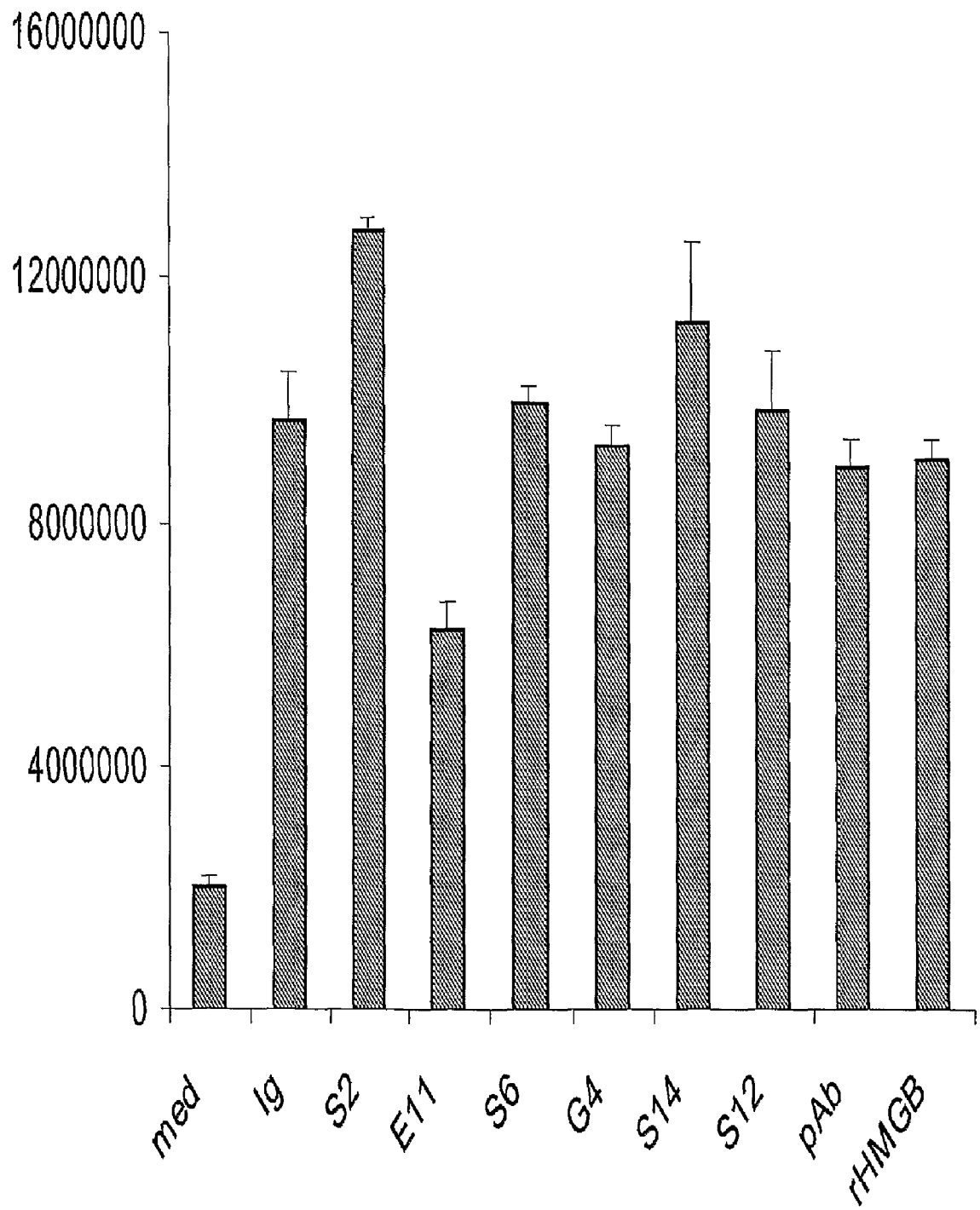

FIG. 9. TLR4 Activation Is Partially Blocked by E11. HMG1 induced TLR4 activation was measured using a cell based luciferase reporter system. The total luciferase activity for cells treated with media alone, recombinant HMG1 (rHMGB) alone and the combination of rHMG1 plus S2, E11, S6, G4, S14 or polyclonal antibody is shown. E11 showed significant ability to block HMG1 induced TLR4 activation. These data and other data not shown are summarized in Table 1.

Figure 10:
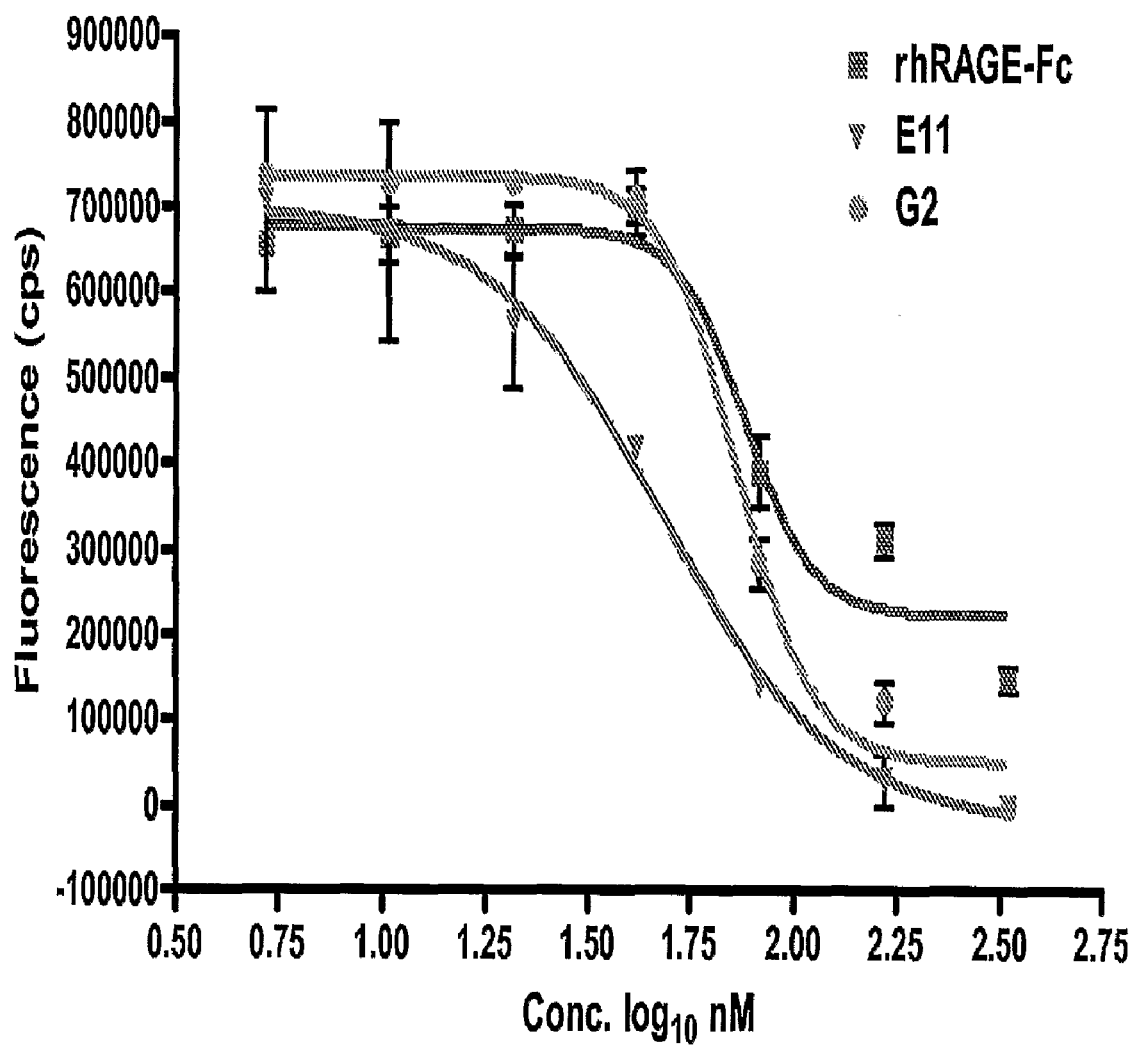

FIG. 10. Inhibition of Recombinant HMG1 Binding to Thp-1 Cells. Representative dose response curves showing inhibition of recombinant HMG1 binding to Thp-1 cells by E11, G2 and a RAGE-Fc fusion protein are shown. The $IC_{50}$ values calculated from these data and other data not shown are summarized in Table 1.

FIG. 11. Human Anti-HMG1 Antibodies Are Protective in a Mouse CLP Model of Sepsis. Show are representative survival curves from the mouse CLP model of sepsis comparing treatment with either human anti-HMG1 antibodies or a human isotype control antibody (R3-47). G4 (Panels A and B), S16 (Panels A and D), S6 (Panel C), E11 and the oligoclonal (both Panel D) anti-HMG1 antibodies are able to improve survival by up to 60%.

FIG. 12. HMG1 Levels are Upregulated in Several Models of Inflammatory Disease. The level of HMG1 present in fore paws harvested at day 10 from untreated passive CIA mice was seen to increase by at least 10 fold over that present in normal mice (panel A). The relative gene expression level of HMGB1, RAGE, TLR2, TLR4 and TLR9 was seen to rise in the hind paws (right) while only HMGB1, RAGE and TLR2 were seen to increase in the fore paws (left) of joints from untreated active CIA mice (both Panel B). The relative gene expression level of IL-1b, IL-6 and TNF-a was seen to rise in both the hind (plot) and fore paws (plot) of joints from untreated active CIA mice (both Panel C). The rise in HMGB1 levels in the ankle joints of AIA rats (upper right) correlates with both the increase in paw inflammation score (upper left) and the decrease in relative weight (lower left)(all Panel D). The levels of HMBG1, IL-1B and TNF-a present in the serum of animals challenged with *S. aureus* are seen to rise (Panel E) with HMGB1 levels increasing constantly from 2 hr post challenge, TNF-a showing an early peak at 2 hours which drops to near baseline by about 7 hours and a second peak at about 12 hours while IL-6 peaking at about 2 hours and then increasing slowly. H MGB1 levels in BAL fluid from ALT mice increase to over 16 ng/ml within 50 hr post LPS administration with the most dramatic rise starting at about 26 hrs (left) correlating with the maximum increase in the total number of cells seen in BAL fluid (right) (both Panel F). Panel G shows the levels of HMBG1 (top left) and IL-6 (bottom left) present in ankle joints of AIA rats after treatment with PBS, human isotype control (HuIgG), the anti-HMG1 antibody G4, the HMG1 A-box-Fc fusion protein, methotrexate (MTX), MTX+HuIgG, MTX+Renbrel, and MTX+G4. Also shown are the levels of TNF-a (top right) present in the ankle joints of AIA rats after treatment with HuIgG G4, or MTX+HuIgG. G4 alone and MTX+HuIgG or MTX+Renbrel show a reduction in the levels of HMG1, IL-6 and TNF-a, however, the combination of MTX+G4 shows the most striking reduction. These data correlate with the reduction seen in the paw inflammation scores for the various treatments (see FIG. 16B).

FIG. 13. Human Anti-HMG1 Antibodies Are Protective in a Passive CIA Mouse Model of Arthritis. Panel A shows the paw inflammation scores over time for passive CIA mice treated with MTX and Renbrel (top left), the human anti-HMG1 antibodies S6 (top right) and G16 (bottom left) and the HMG1 A-Box-Fc fusion protein (lower right). Both the MTX/Renbrel combination and the S6 antibody reduced clinical scores with S6 having a more dramatic effect in this model. Plots of the bone (upper left), cartilage (upper right) and inflammation (lower left) scores obtained by histological examination for both fore and hind paws (panel B) or fore paws alone (panel C) are shown. Panel D shows the body weight index over time for mice treated with MTX and Renbrel (top left), the human anti-HMG1 antibodies S6 (top right) and G16 (bottom left) and the HMG1 A-Box-Fc fusion protein (lower right). As was seen for the clinical scores, both the MTX/Renbrel combination and S6 show protection with S6 showing better efficacy.

FIG. 14. Human Anti-HMG1 Antibodies Are Protective in a Passive CIA Mouse Model of Arthritis. Experiment 2 (Panel A) the paw inflammation scores over time for passive CIA mice treated with PBS, Renbrel or G4 (right) and for treatment with PBS, G4 or an isotype control antibody (left). Experiment 3 (Panel B)) the paw inflammation scores over time for passive CIA mice treated with PBS, G4 or an isotype control antibody. The clinical scores for normal mice were also tracked and plotted for both studies. Both experiments demonstrate that the G4 human anti-HMG1 antibody is able to protect against inflammation in this model. In Experiment 2, G4 demonstrated better efficacy than Renbrel.

FIG. 15. Human Anti-HMG1 Antibodies Are Protective in an Active CTA Mouse Model of Arthritis. The paw inflammation scores over time for active CIA mice treated with PBS, an isotype control antibody or G4 (left graph) and for active CIA mice treated with PBS or Renbrel (right graph) are shown in panel A. The relative body weight plotted over time for the isotype control and G4 antibody treatment groups is shown in panel B. Also plotted on all panels are the scores for PBS treated and normal mice. The G4 human anti-HMG1 antibody showed better protection against both inflammation and weight loss in this model than Renbrel.

FIG. 16. Human Anti-HMG1 Antibodies Are Protective in an AIA Rat Model of Arthritis. Paw inflammation scores were plotted over time for MA rats treated with PBS, an isotype control antibody or G4 (left) and for CIA mice treated with PBS or Renbrel (right) (both Panel A, also see Panel B) demonstrated that the G4 anti-HMG1 antibody is able to reduce paw inflammation scores by about 35% over the PBS control while Renbrel alone only reduced paw inflammation by 25% over the PBS control in this model (Panel A). The paw inflammation scores were plotted over time for AIA rats treat with combinations of methotrexate and a second reagent (isotype control, G4 or Renbrel) (Panel 16B) demonstrated that combination of MTX and G4 was even more effective than both G4 alone and the MTX/Renbrel combination. Treatment with MTX and G4 reduced the paw inflammation scores to near normal (Panel B). Also shown are the paw inflammation scores for treatment with an HMG1 A-box-Fc fusion protein which was less effective than G4 alone. Micro CT analysis reveals prominent hyperostosis in AIA rats treated with isotype IgG (Panel C, middle) compared to normal control (Panel C, left), evidenced as thick radiating projections of subperiosteal cortical bone and cortex thickening (Panel C, middle). Hyperostosis is inhibited with treatment of G4 (Panel C, right). Severity of hyperostosis, inflammation and joint damage was scored (Panel D, top, lower left and lower right, respectively) for each of the three groups. Histological examination of inflammatory changes in the AIA rats treated with Isotype IgG (Panel E, middle) versus the control (Panel E, left) rats showed marked edema and dilation of the tibal-talar joint space. In addition, an increased recruitment of inflammatory cells was seen in the AIA rats versus control rats. Treatment with G4 (Panel E, right) alleviated the edema and dilation of the joint space as well as limited the recruitment of inflammatory cells to the joint compared to the isotype control (Panel E, middle). The paw inflammation scores of animals treated with higher doses of Renbrel provided protection that was comparable to that seen for G4 treatment alone and the combination of G4 and high dose Renbrel showed a greater reduction then either treatment alone (Panel F).

Figure 17:
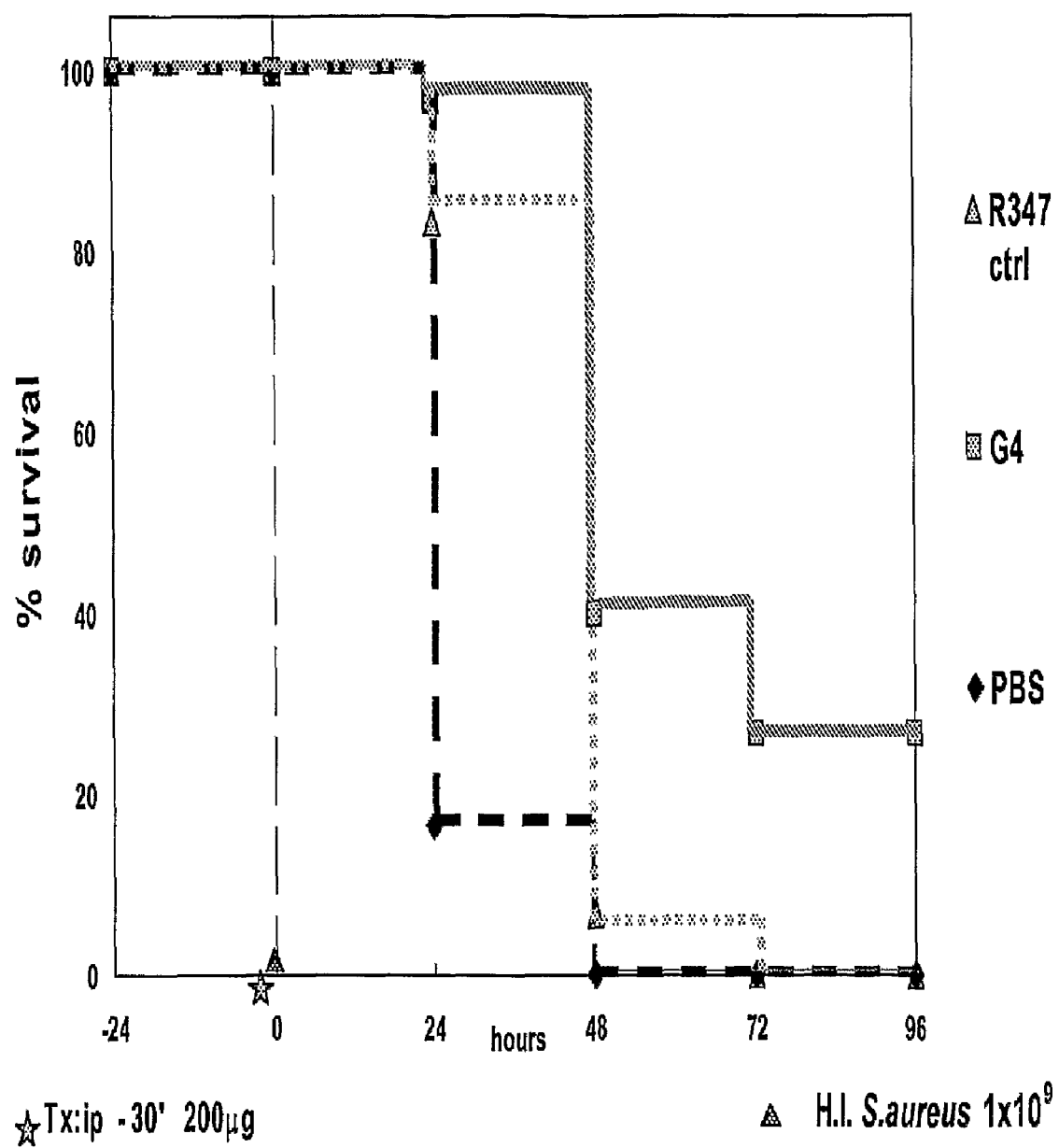

FIG. 17. Human Anti-HMG1 Antibodies Are Protective in a Mouse Model of Peritonitis. The percent survival over a 96 hour time course in mice challenged with heat inactivated *S. aureus* to induce peritonitis shows that G4 improves survival by nearly 30% over mice treated with either PBS or an isotype control (R347) (Panel A). Antibody was administered at time −30 minutes (star) *S. aureus* challenge was administered at time 0 minutes (triangle).

Figure 18:
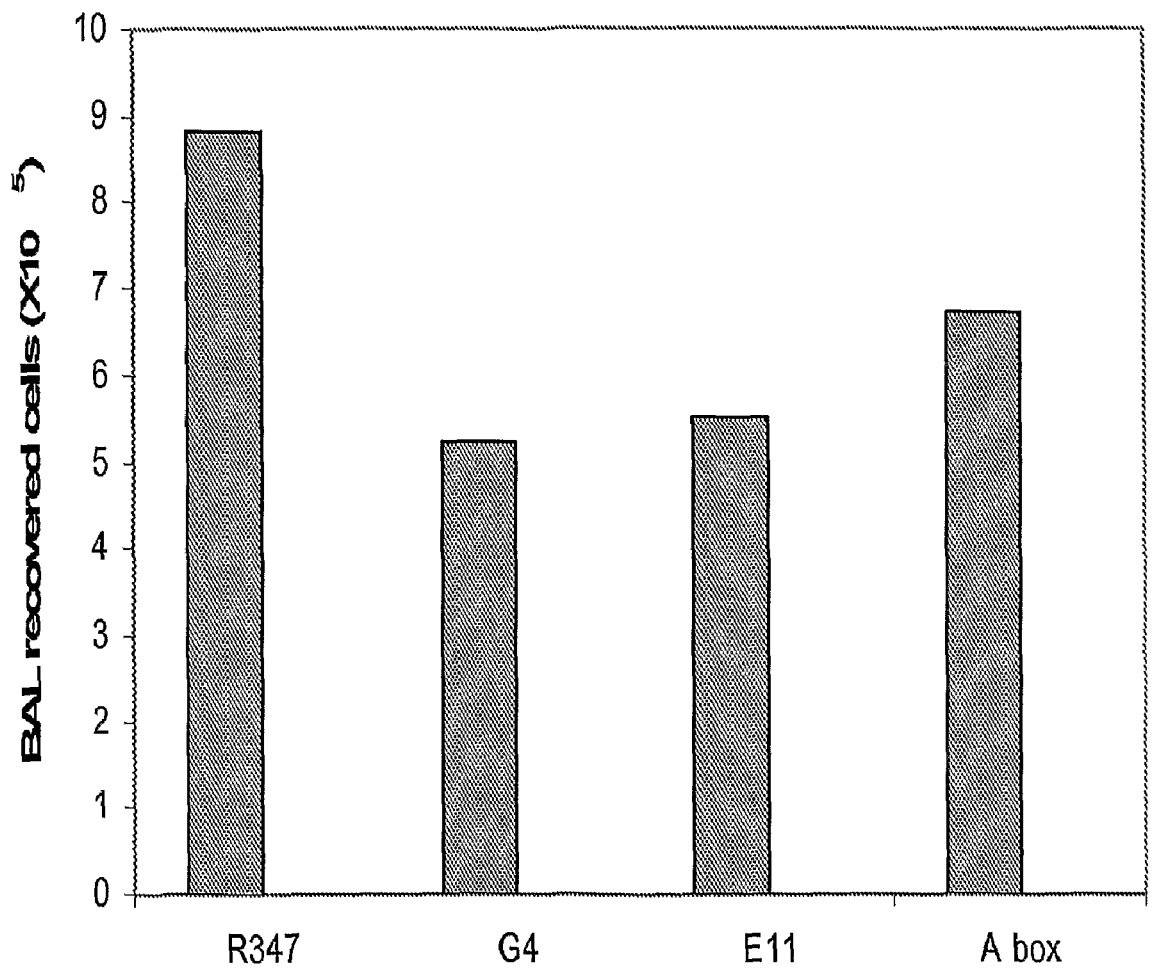

FIG. 18. Human Anti-HMG1 Antibodies Are Protective in a Mouse Model of Acute Lung Injury (ALI). Total cells recovered in BAL fluid from ALI mice treated with either G4 or E11 were reduced nearly 40% as compared to mice treated with either an isotype control antibody (R347). Treatment with an HMG1 A-box-Fc fusion protein only reduced total cells recovered by 23%.

FIG. 19. HMG1 Staining Patterns in Human Brain Tissue of Multiple Sclerosis (MS) Specimens A) background staining of an MS Plaque with Activated Microglia using 1 μg/ml Isotype Control, B) specific HMGB1 staining of the cytoplasm of the microglia and the interstitia of an MS Plaque with Activated Microglia using 1 μg/ml G16, and C) the reduced staining seen in an MS Plaque-with demyelination, few activated microglia and numerous lymphocytes using 1 μg/ml G16.

Figure 20:
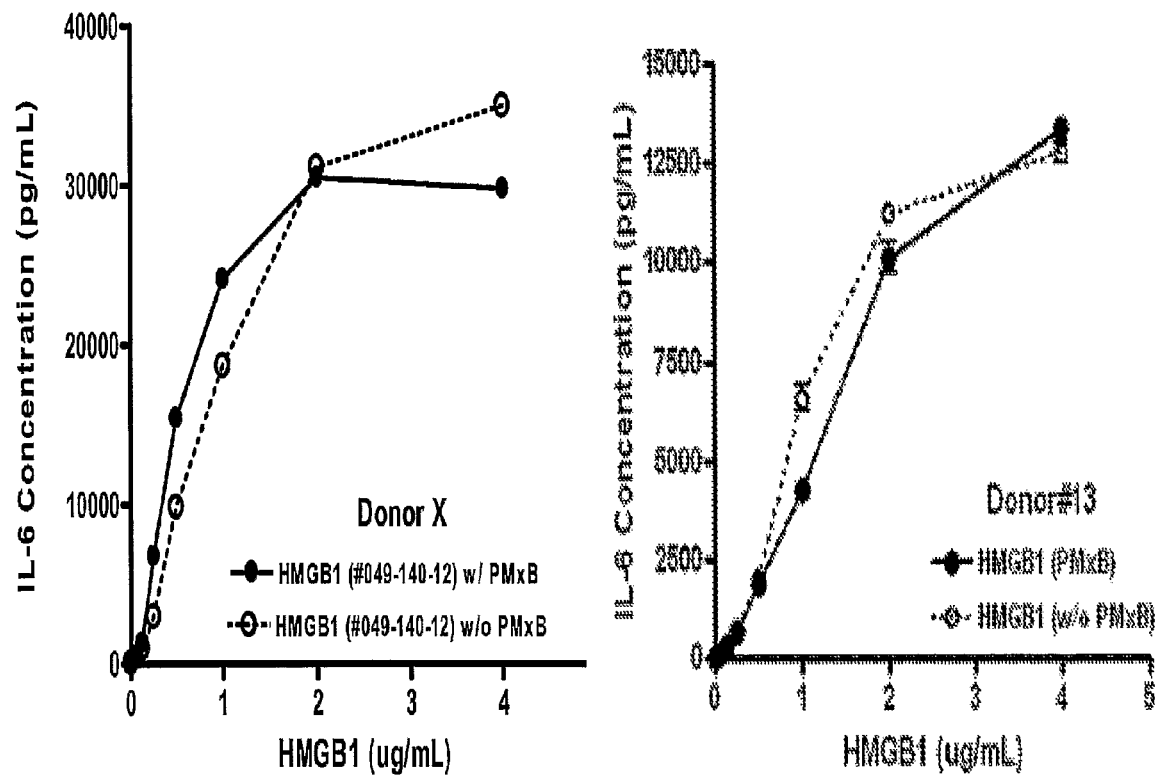

FIG. 20. Recombinant HMG1 (rHMG1) containing trace amounts of endotoxin stimulated IL-6 cytokine release to the same level in the presence (solid line) or absence (dotted line) of Polymyxin B (PMxB). The same result was seen for donor X (left panel) and donor 13 (right panel).

Figure 21:
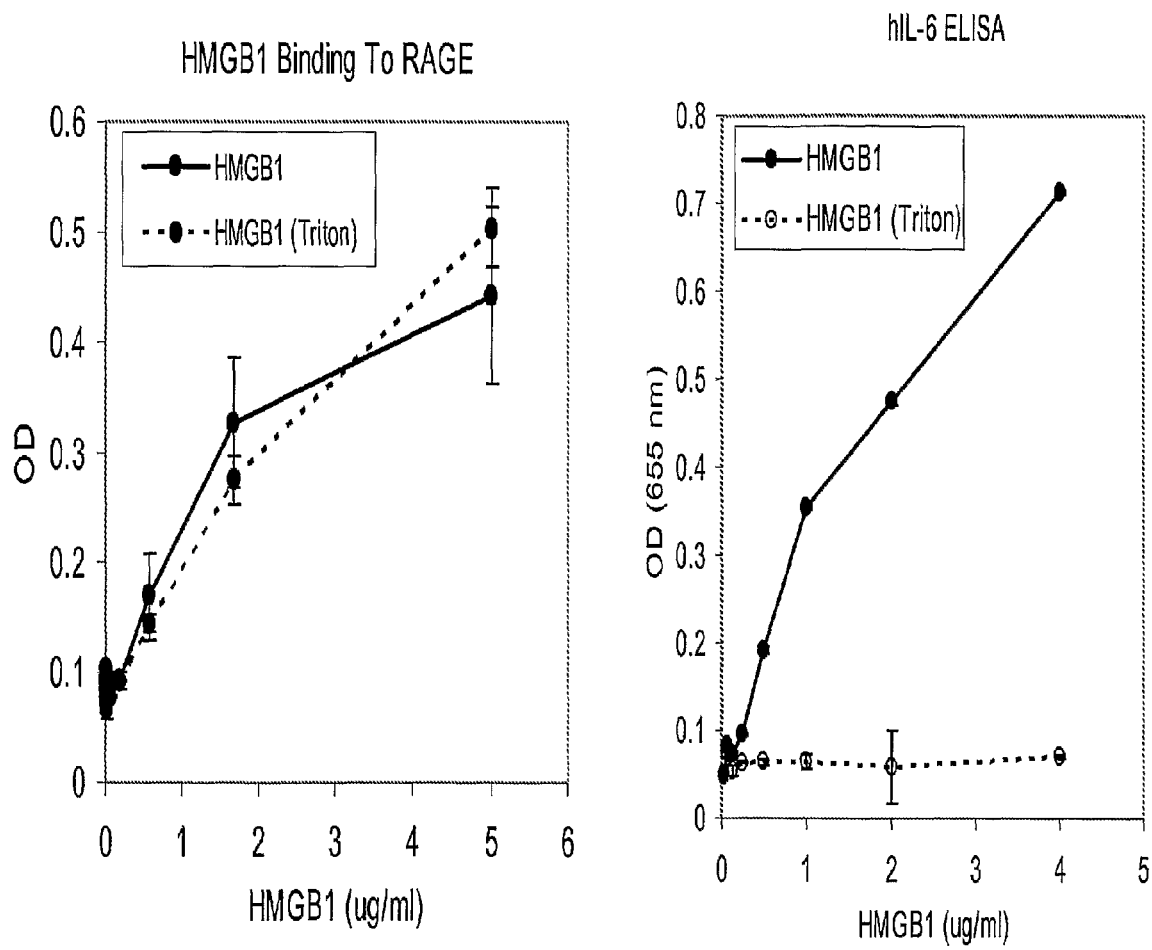

FIG. 21. Triton Extracted HMG1 Does Not Stimulated Cytokine Release. rHMG1 (solid line) and Triton extracted rHMG1 (dotted line) bind RAGE to the same degree (loft panel) only rHMG stimulated IL-6 release (right panel).

Figure 22:
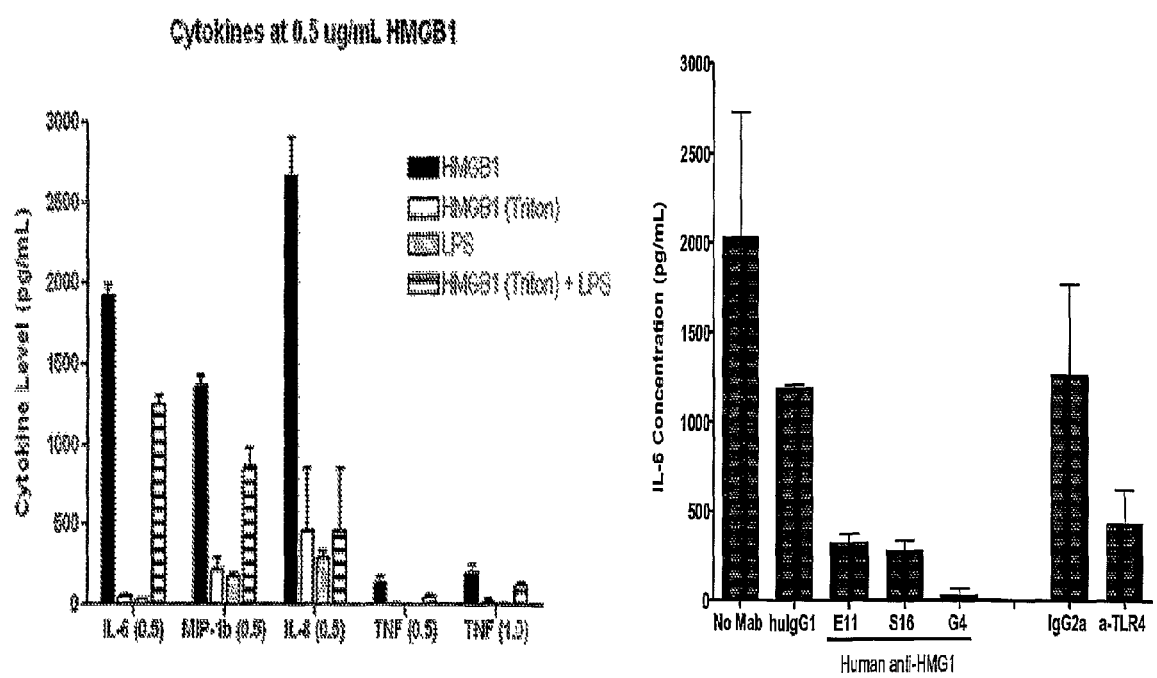

FIG. 22. Synergy Between HMG1 and the TLR4 Ligand LPS. Left Panel) Treatment of human PBMCs with rHMG1 (black bars) stimulated the release of several cytokines (IL-6, MIP-1b, IL-8 and TNF), while cells treated with Triton extracted HMG1 (white bars) showed no stimulation. However, cells treated with Triton extracted HMG1 in combination with a suboptimal concentration of LPS (striped bars) showed cytokine release that was nearly the same as seen for HMG1 treatment while treatment suboptimal concentration of LPS alone (speckled bars) showed no stimulation of cytokine release. Right Panel) Human PBMCs treated with Triton extracted HMGB1+LPS in combination with either an anti-TLR4 antibody or anti-HMG1 antibodies E11, S16 or G4 show a reduction in IL-6 release to near background levels while cells treated with isotype control antibodies (R3, IgG2a) do not.

FIG. 23. Triton Extracted HMG1 Does Not Stimulate Intracellular Cytokine Production But Can Increase Cytokine mRNA Levels. A) Cells treated with rHMG1 have increased intracellular levels of IL-6 (top row) and TNF-a (bottom row) compared to untreated cells as determined by flow cytometry of stained cells (compare left and right panels), while cells treated with Triton extracted rHMG1 have much reduced levels of intracellular of IL-6 and TNF-a (compare left and middle panels). B) Cells treated with LPS, rHMG1 or Tx-HMGB1 all show an increase in TNF-a, IL1-β and IL-6 mRNA levels.

Figure 24:
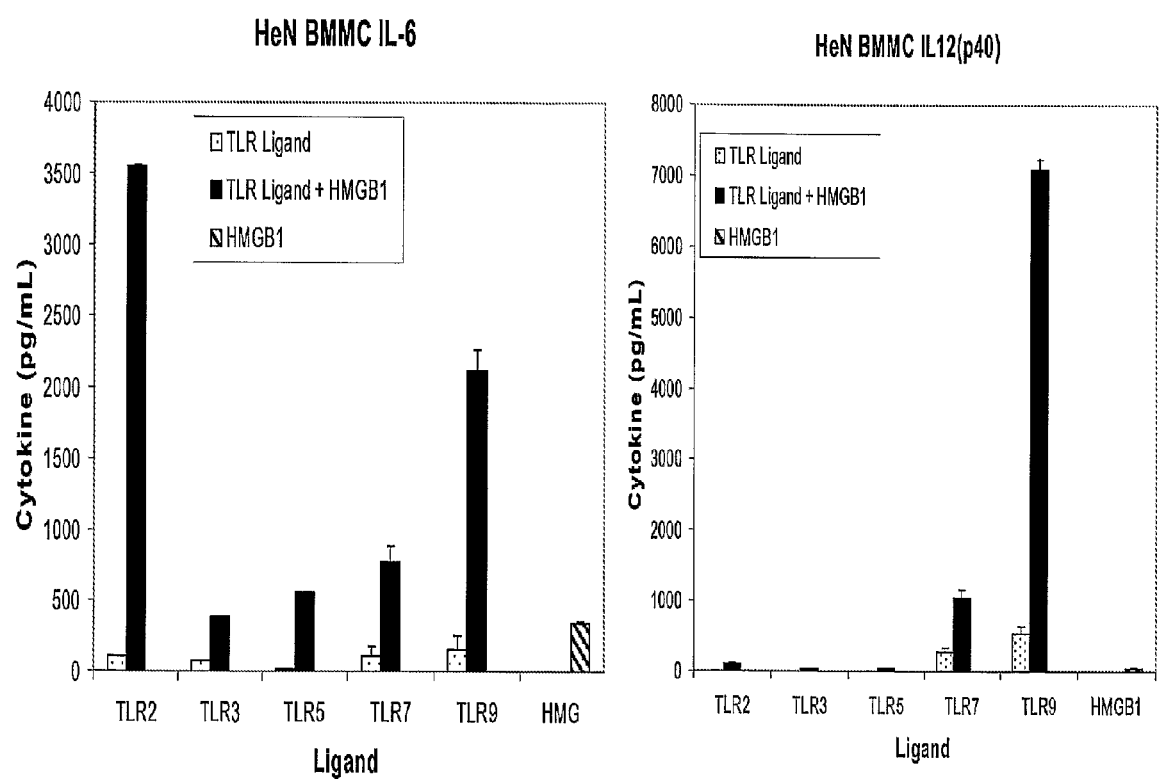

FIG. 24. Synergy Between HMG1 and Other TLR Ligands. Cells treated with rHMGB1 in combination with suboptimal concentrations of the following TLR ligands: TLR2-PAM3-CSK4, TLR3-Poly (I:C), TLR5-Flagelin, TLR7-Imiquinod and TLR9-CpG (black bars) showed enhanced IL-6 release, much greater than that induced by either HMG1 (striped bars) or TLR ligands (specked bars) alone, for each ligand examined (left panel). A similar response was seen for IL-12 release with the most dramatic enhancement seen for the TLR7 and TLR9 ligands (right panel).

Figure 25:
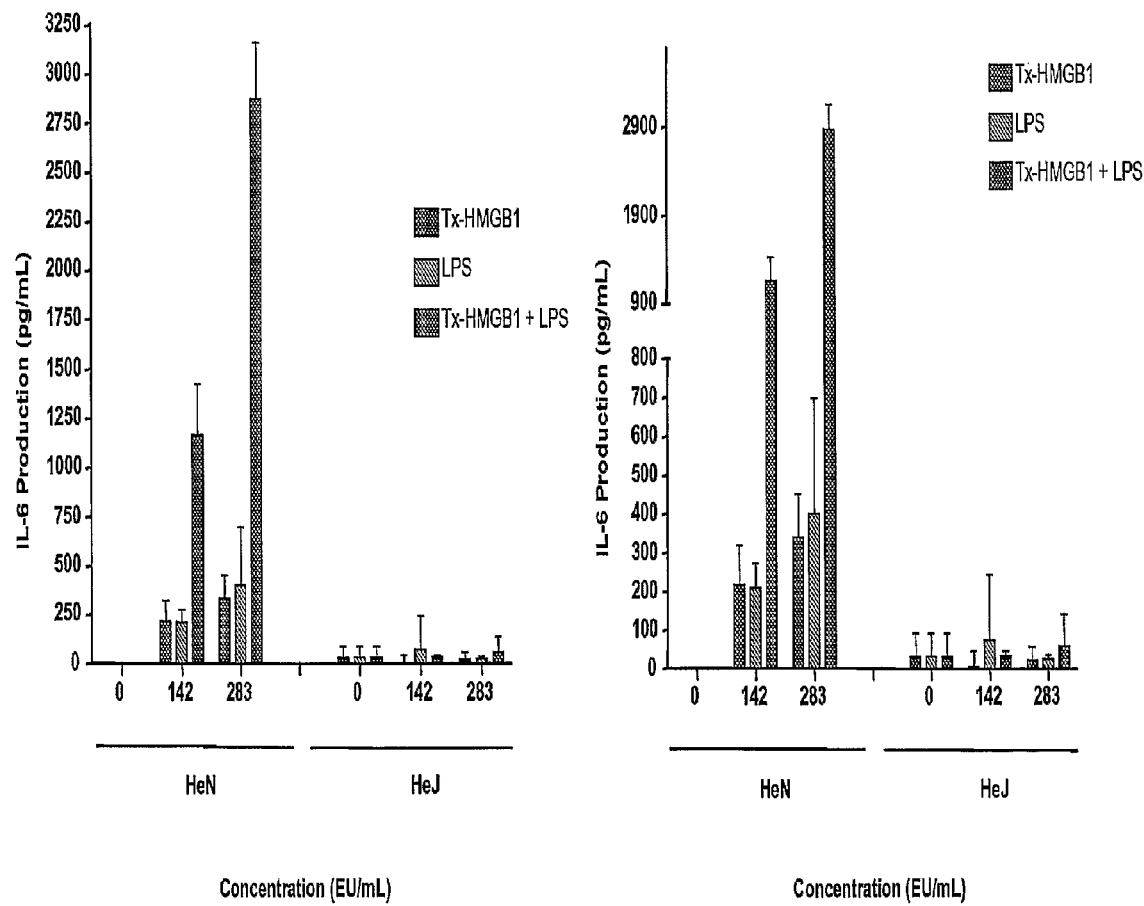

FIG. 25. Synergistic Activity of Tx-HMGB1 Not Seen In Cells Defective in TLR4 Activity. Tx-HMGB1 in combination with LPS has a synergistic effect on IL-6 production in normal mouse bone marrow cells. No enhancement of LPS signaling is seen in bone marrow cells from HeJ (TLR4 defective) mice. The results of two separate experiments are shown (right and left panels). The concentration of LPS used is indicated along the bottom.

Figure 26:
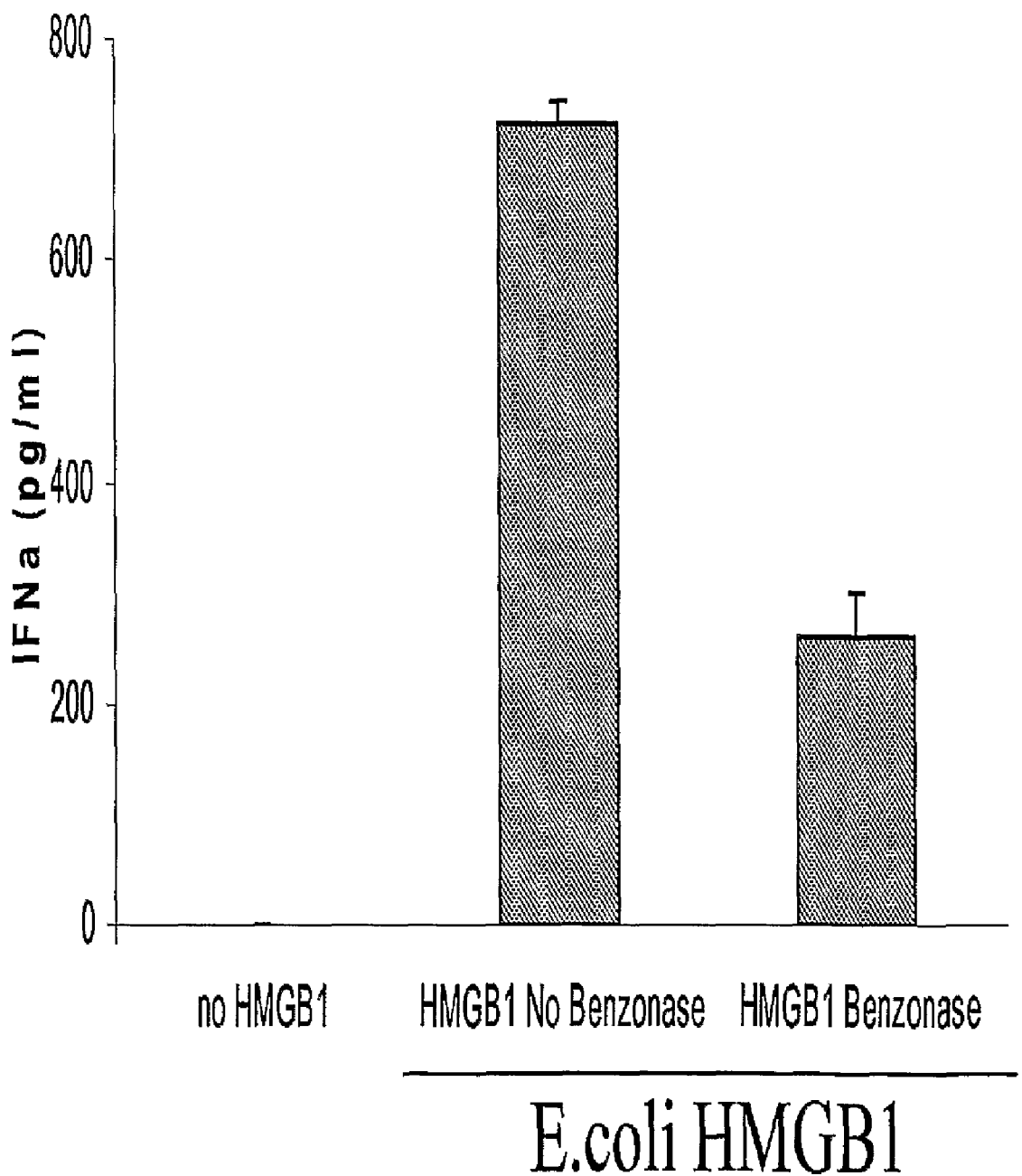

FIG. 26. Recombinantly Produced HMG1 (rHMG1) Contains Trace Amounts Of Bacterial DNA Which Enhances TLR Signaling. IFN-α release is stimulated by rHMG1 and this release is reduced by pretreatment with benzonase to remove contaminating DNA.

Figure 27:
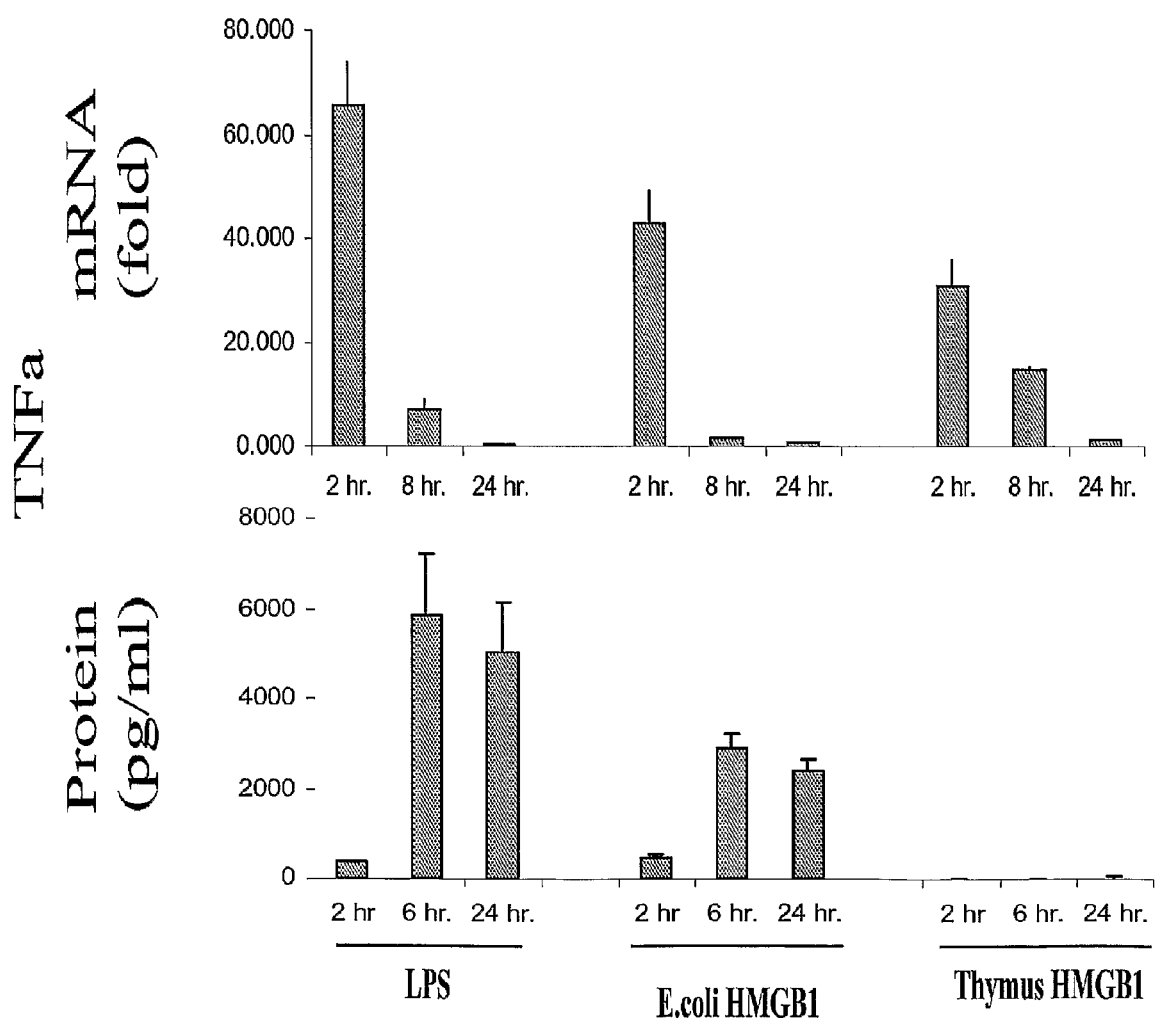

FIG. 27. The TRL4 Ligand LPS As Well As Both rHMG1 And Native HMG1 Induce TNF-a mRNA But Only rHMG1 Induces TNF-a Protein Release. At 2 hours LPS, rHMG1 and native HMG1 purified from bovine thymus showed about a 66 fold, 43 fold and 30 fold induction in TNF-a mRNA levels, respectively (top panel). rHMG1 was seen to induce about a 10 fold increase in TNF-a present in the supernate of mouse macrophages while native HMG1 purified from thymus showed no induction (bottom panel).

Figure 28:
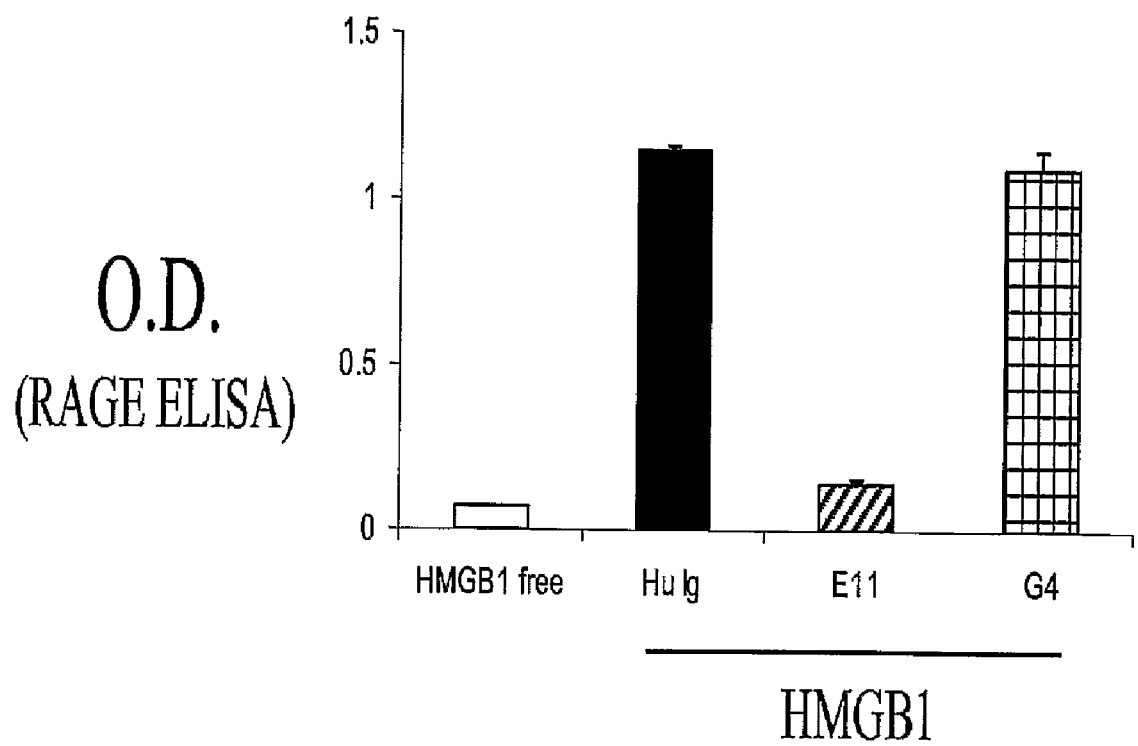

FIG. 28. The Human anti-HMG1 Antibody E11 Blocks the Binding of Native (thymus) HMG1 to RAGE. An ELISA based binding assay was used to measure the binding of native HMG1 isolated from bovine thymus to a RAGE-Ig fusion. E11 shows significant ability to block the binding of native HMG1 to RAGE while G4 did not at the concentrations tested. These data and other binding data are summarized in Table 1.

Figure 29:
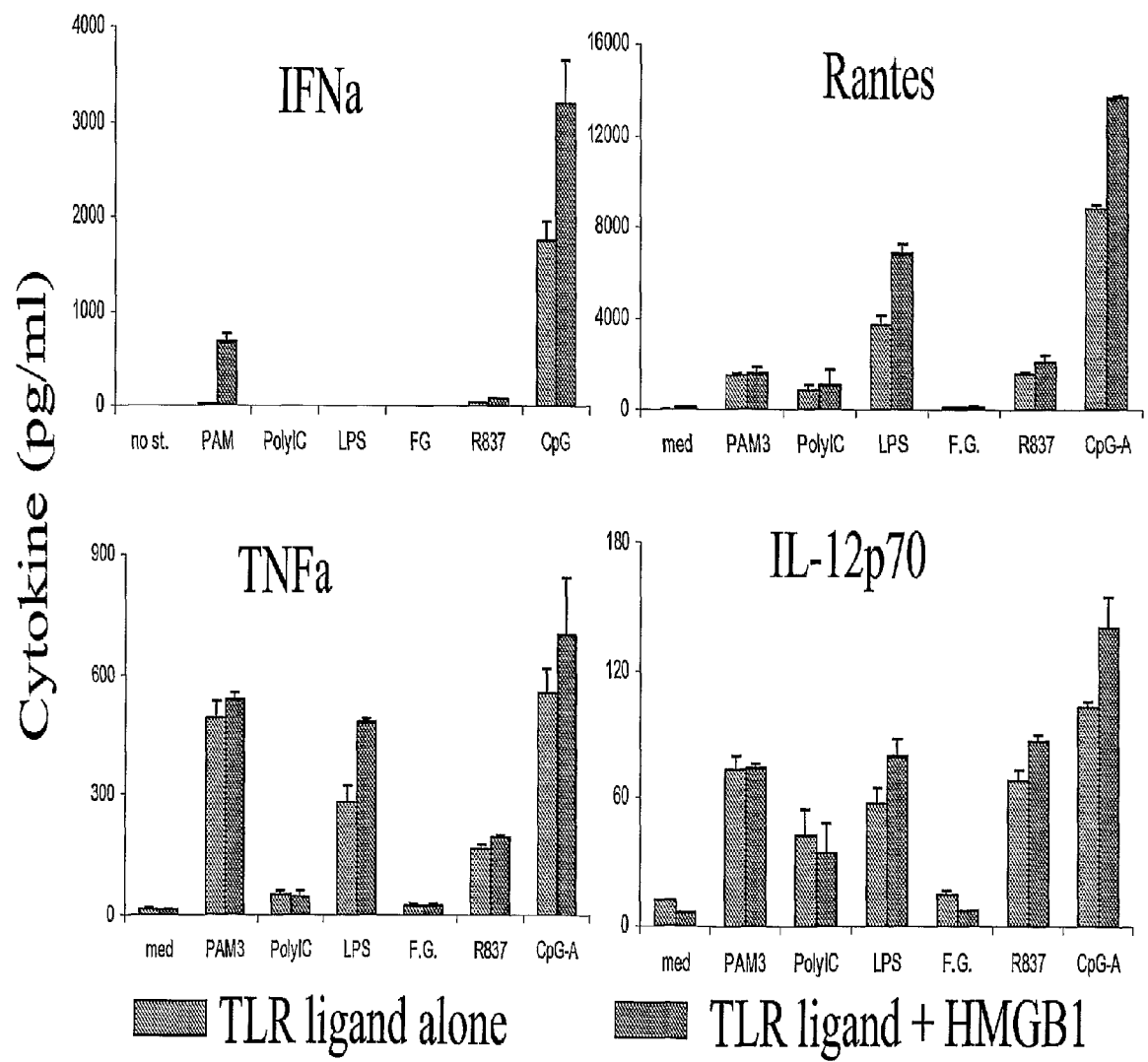

FIG. 29. Native HMG1 enhances Signaling Via TLR2, 4, 7 and 9. The release of IFN-a (upper left), Rantes (upper right), IL-6 (lower left) and IL-12p70 (lower right) induced by the TLR7 ligand R837 and the TLR9 ligand CpG was enhanced by thymus HMG1. The release of Rantes, IL-6 and IL-12p70 induced by the TLR4 ligand LPS and the release of IFN-a and TNF-a induced by the TLR2 ligand PAM3 were also enhanced by thymus HMG1. Light bars indicate ligand alone, Dark bars indicate ligand+HMG1.

Figure 30:
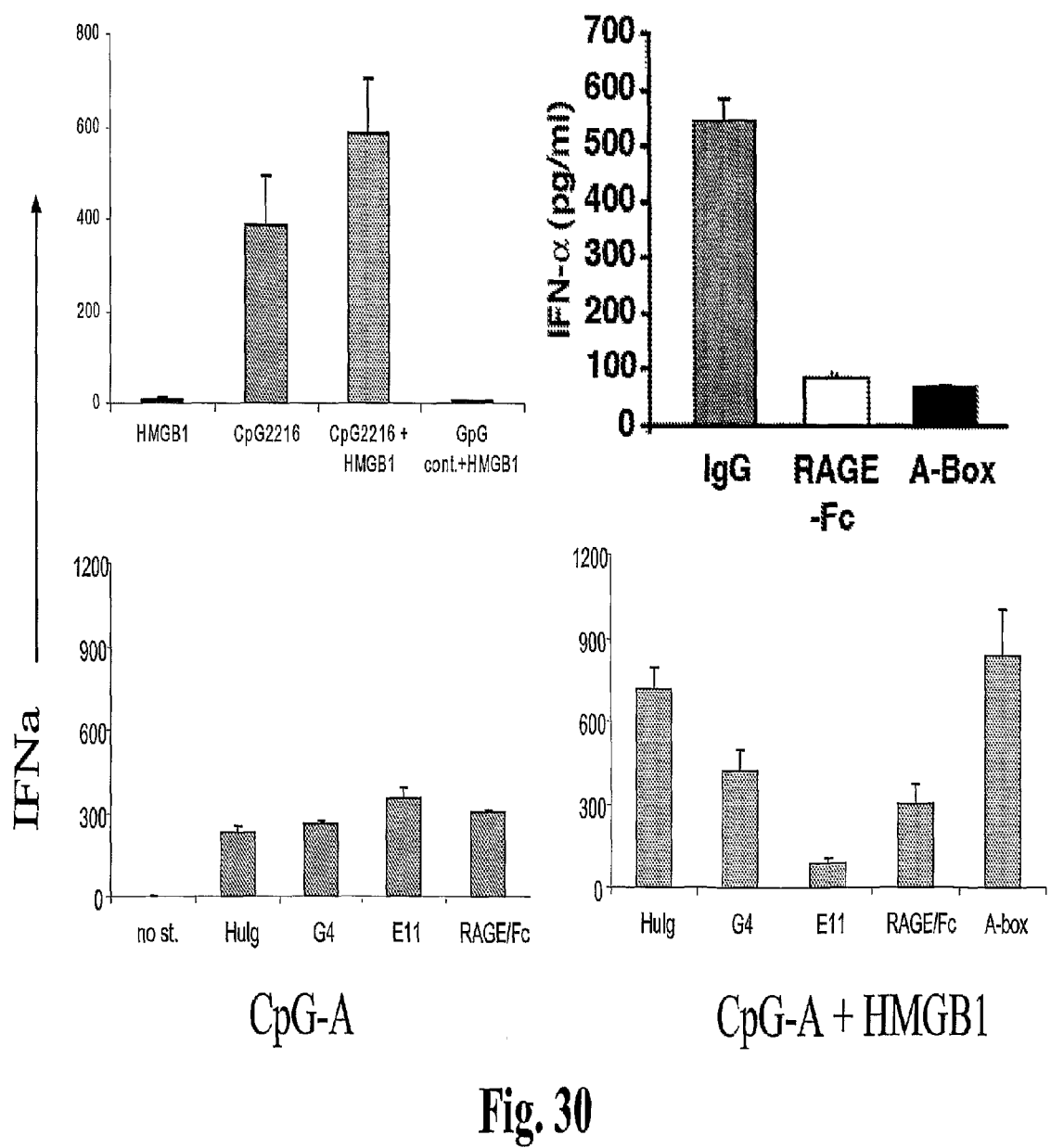

FIG. 30. The release of IFN-a from mouse bone marrow cells treated with CpG alone was not blocked by the anti-HMG1 antibodies E11, G4 or by a human isotype control (bottom left panel) while the release of IFN-a from cells treated with CpG in combination with thymus HMG1 was blocked by the anti-HMG1 antibody E11 but not by anti-HMG1 antibody G4 or by an isotype control antibody (bottom right panel). In subsequent experiments under optimized conditions, both RAGE-FC and the A-box are seen to inhibit IFN-a release from cells treated with CpG in combination with thymus HMG1 (top right panel). Control experiments demonstrate that neither thymus HMG1 or non stimulatory CpG alone or in combination stimulate IFN-a release and confirm that the IFN-a release simulated by CpG2216 is enhanced by thymus HMG1 (top left panel).

Figure 31:
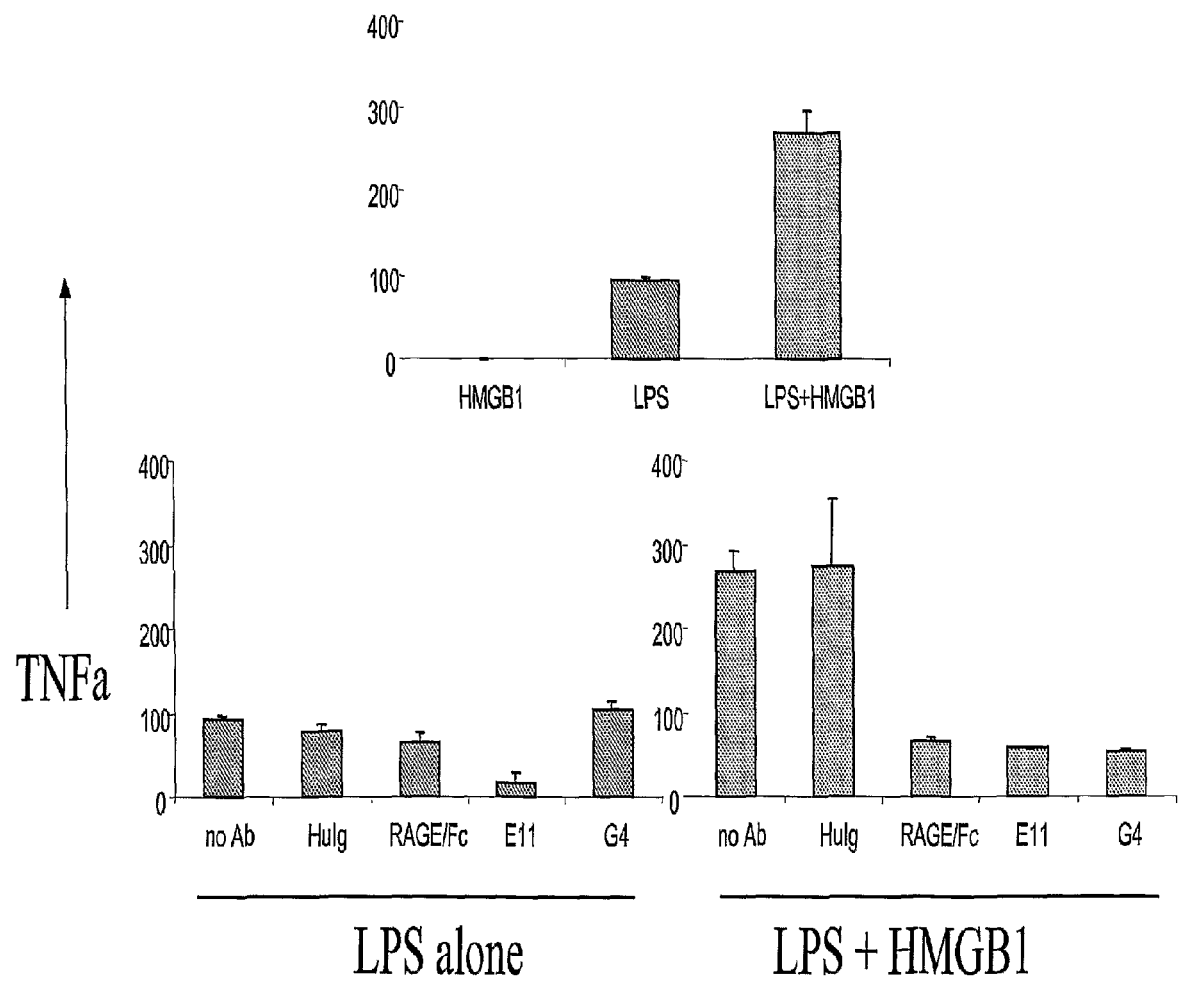

FIG. 31. The release of TNF-a stimulated by LPS is enhanced by HMGB1 (top panel). E11, G4 and Rage/Fc inhibits the release of TNF-a induced by LPS+HMG1 (bottom right). E11 also inhibits signaling by LPS alone (bottom left).

FIG. 32. HMGB1 Enhancement of TLR Signaling is Altered in RAGE Knockout Cells. Panel A) HMGB1 enhanced release of INF-a via TLR2, 7 and 9 signaling was reduced in cells derived from RAGE knock out mice (top panels). HMGB1 enhanced release of TNF-a via TLR2, 4 and 9 signaling was nearly unchanged or enhanced in cells derived from RAGE knock out mice (bottom panels). Panel B) Total bone marrow cells isolated from wild type (closed symbols) or RAGE deficient bone marrow cells (open symbols) were stimulated with increasing concentrations of CpG-A (ODN 2336) alone (squares) or CPG-A/HMGB1 complex (circles, top left) or CPG-A/B-box complex (circles, top right), HMGB enhanced INF-a release was seen to be reduced by up to 70% in RAGE deficient bone marrow cells. INF-a release stimulated by CPG-A alone and enhance release stimulated by HMGB1/CPG-A complexes was not detectible in cells isolated from TLR9 or MyD88 deficient cells (bottom panel).

Figure 33:
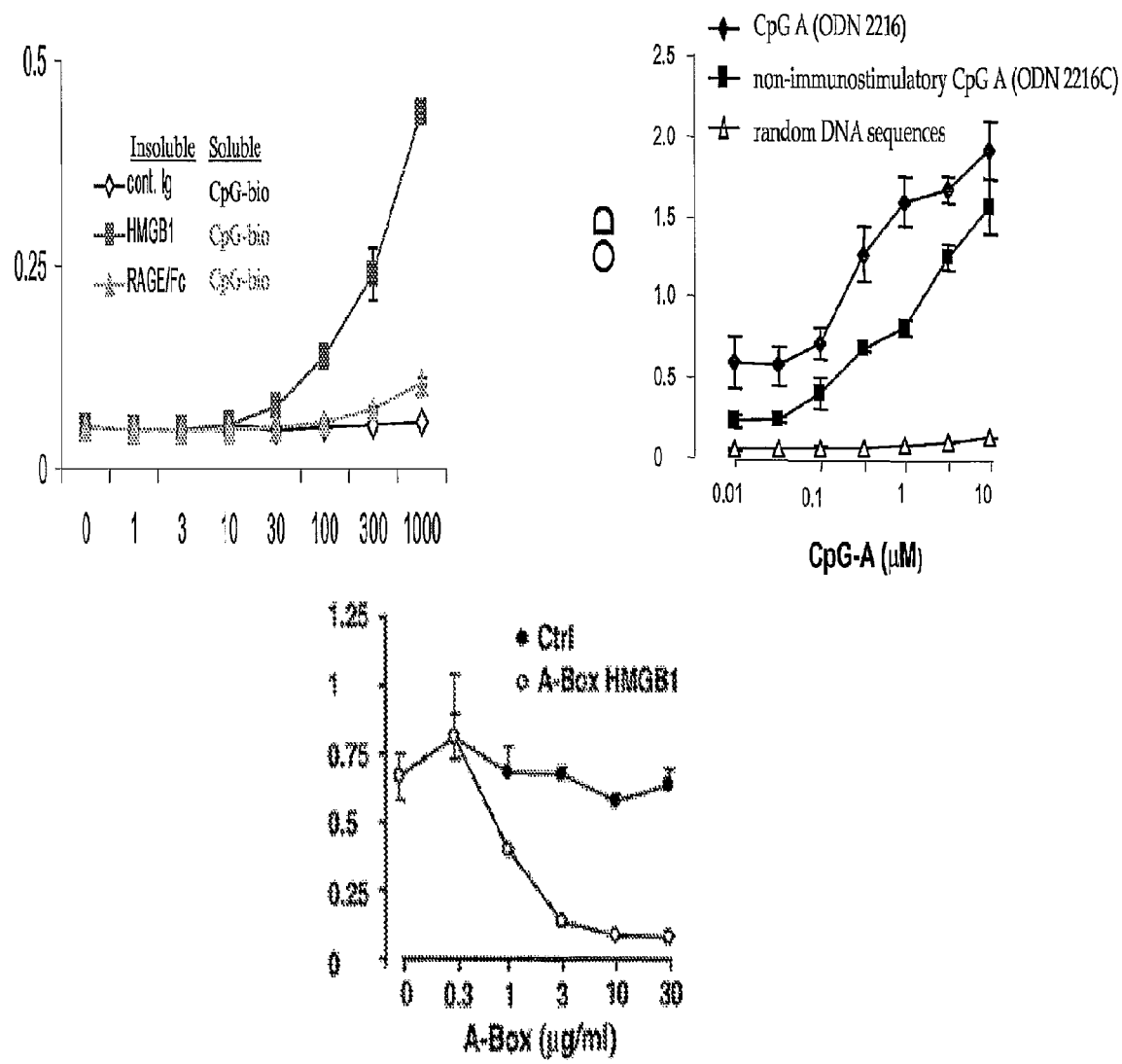

FIG. 33. HMGB1/CpG/RAGE binding. Top Left, Soluble CpG binds directly to immobilized HMBG1 (square) but not to an immobilized control IgG (diamond) or immobilized RAGE/Fc fusion (triangle) by ELISA. Top Right, HMGB1 binds to both CpG-A stimulatory (closed diamonds) and non-stimulatory (closed squares) sequences but not to random DNA sequences (open triangles). Bottom, A-box peptides (open circles) inhibit the interaction of CpG and HMGB1 while control peptides do not (closed circles).

FIG. 34. HMGB1/CpG complexes synergistically stimulate immune responses. Panel A. pDCs isolated from total bone marrow cells of B6 mice were stimulated with CpG-A ODN2216 alone (open circles), or in combination with 1 μg/ml of HMGB1 (filled squares) or 3 μg/ml of HMGB1 (filled triangles) for 24 hr and IFN-α and TNF-α protein measured in the supernatant by ELISA (left and right panels, respectively). Panel B. Cells were stimulated with A Box HMGB1, B box HMGB1 or CpG alone as non-complex proteins or stimulated with the complex of either A box/CpG or B box CpG and IFN-a production measured by ELISA. IFN-α production was seen to increase from cells stimulated with CpG-A complexed with B box HMGB1.

Figure 35:
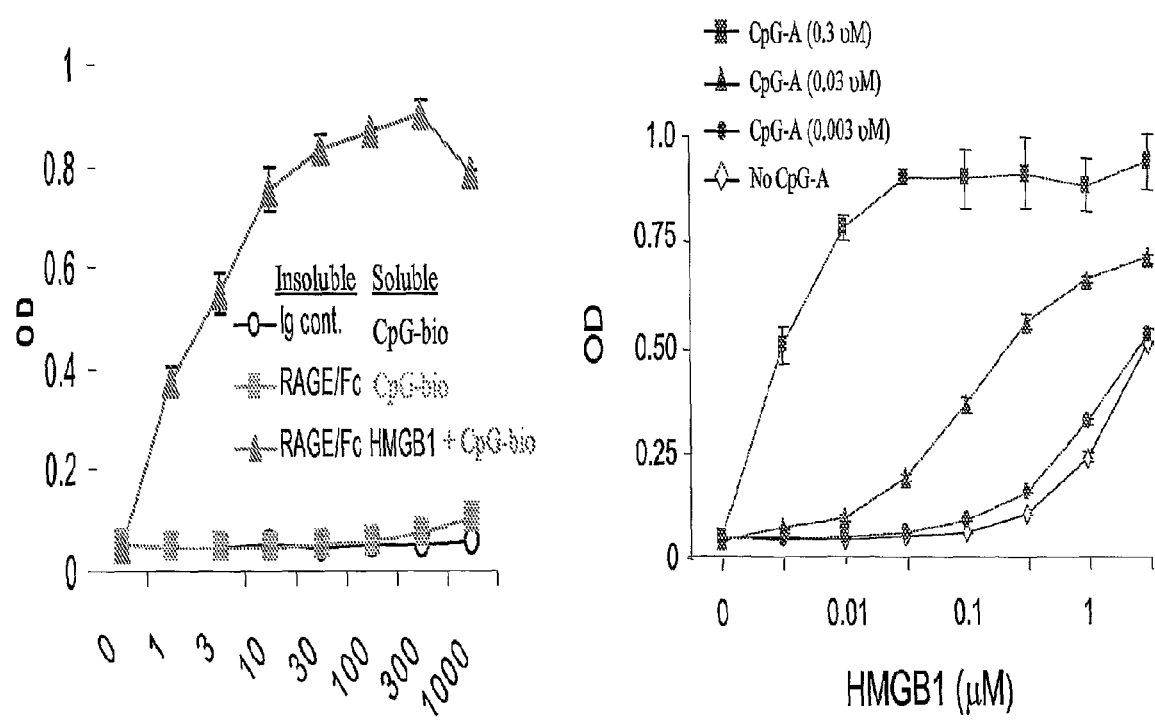

FIG. 35. HMGB1/CpG complexes bind RAGE. Left Panel, Soluble CpG alone does not bind directly to immobilized control IgG (open circle) or immobilized RAGE/Fc fusion (closed square) but a soluble complex of HMGB1 and CpG does bind RAGE/Fc fusion (closed triangle) by ELISA. Right Panel, The binding of HMGB1 to RAGE-Fc (open diamonds) was greatly enhanced in the presence of 0.003 μM CpG-A (filled circles), 0.03 μM CpG-A (filled triangles) or 0.3 μM CpG-A (filled squares).

Figure 36:
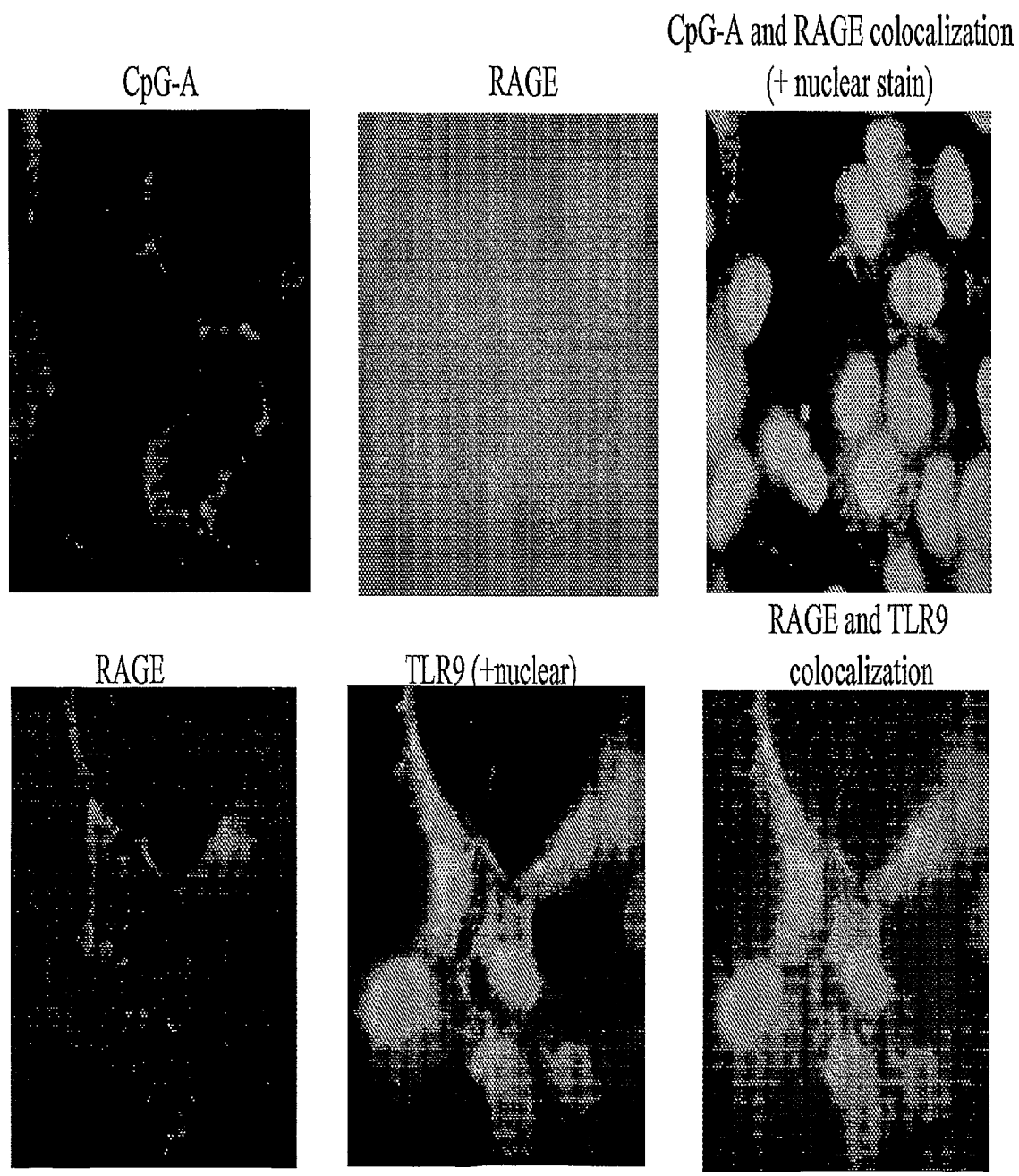

FIG. 36. Staining of CpG-A (top left), RAGE (top middle and bottom left), TLR9 and nuclear (bottom middle) and the merge showing that CpG-A and RAGE colocalize (top right) as do TLR9 and RAGE (bottom right) in HEK293 cells stably expressing TLR9 and transfected with RAGE stimulated with HMGB1 and CpG-A simultaneously.

Figure 37:
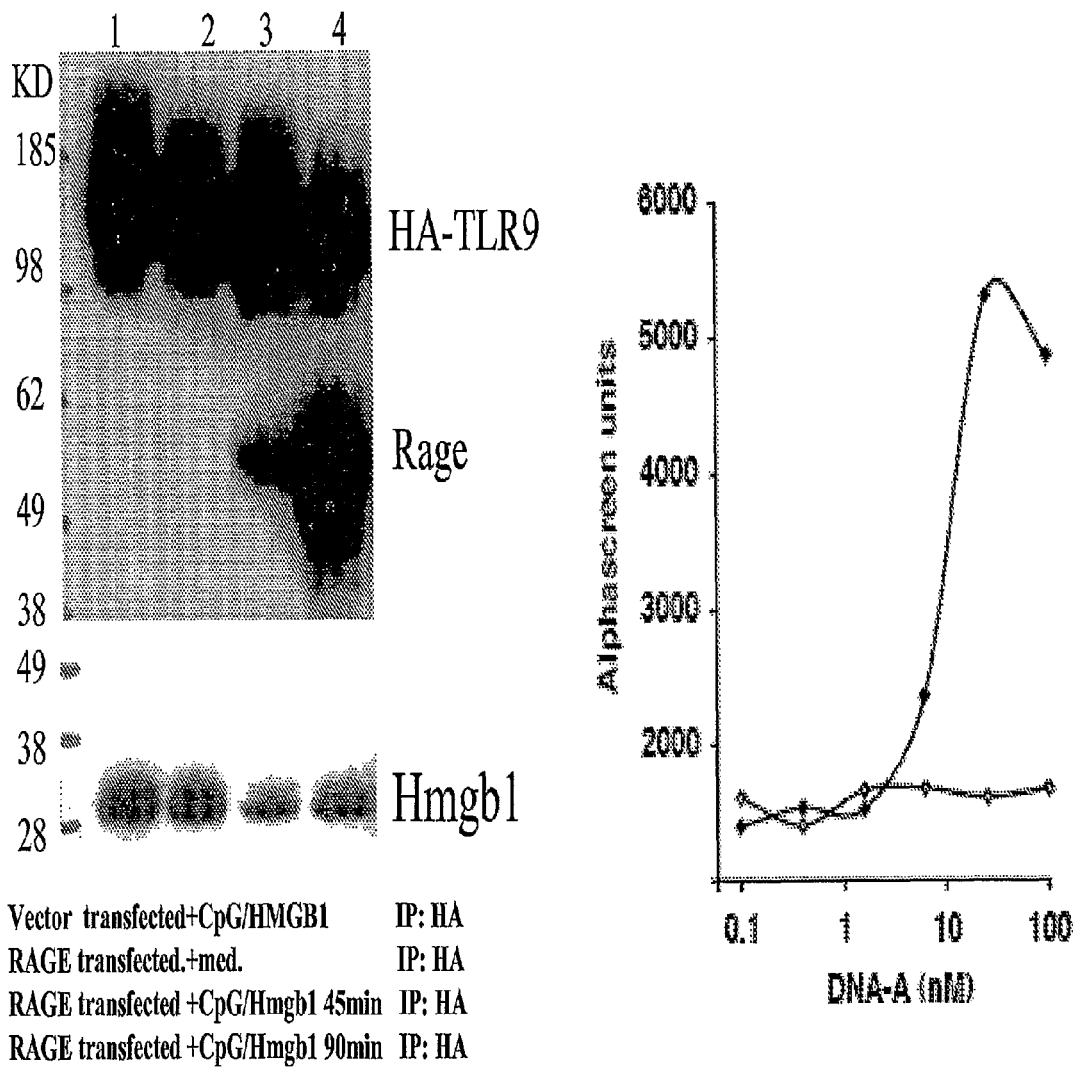

FIG. 37. HMGB1/CpG complex recruits RAGE and TLR9. Left Panel, Rage immunoprecipitates with TLR9 from cells stimulated with HMGB1 and CpG simultaneously for 45 minutes (lanes 3) the amount of RAGE associated with TLR9 increases after 90 minutes of simulation (lane 4). No co-precipitation is seen from cells treated with media alone (lane 2) or in cells transfected with vector alone (lane 1). Right Panel, RAGE-FC and TLR9-Fc coupled to Alphascreen acceptor and donor beads, respectively interact when incubated with increasing concentrations of CpG-A (closed circles) but not CpG-B (open circles) beads.

Figure 38:
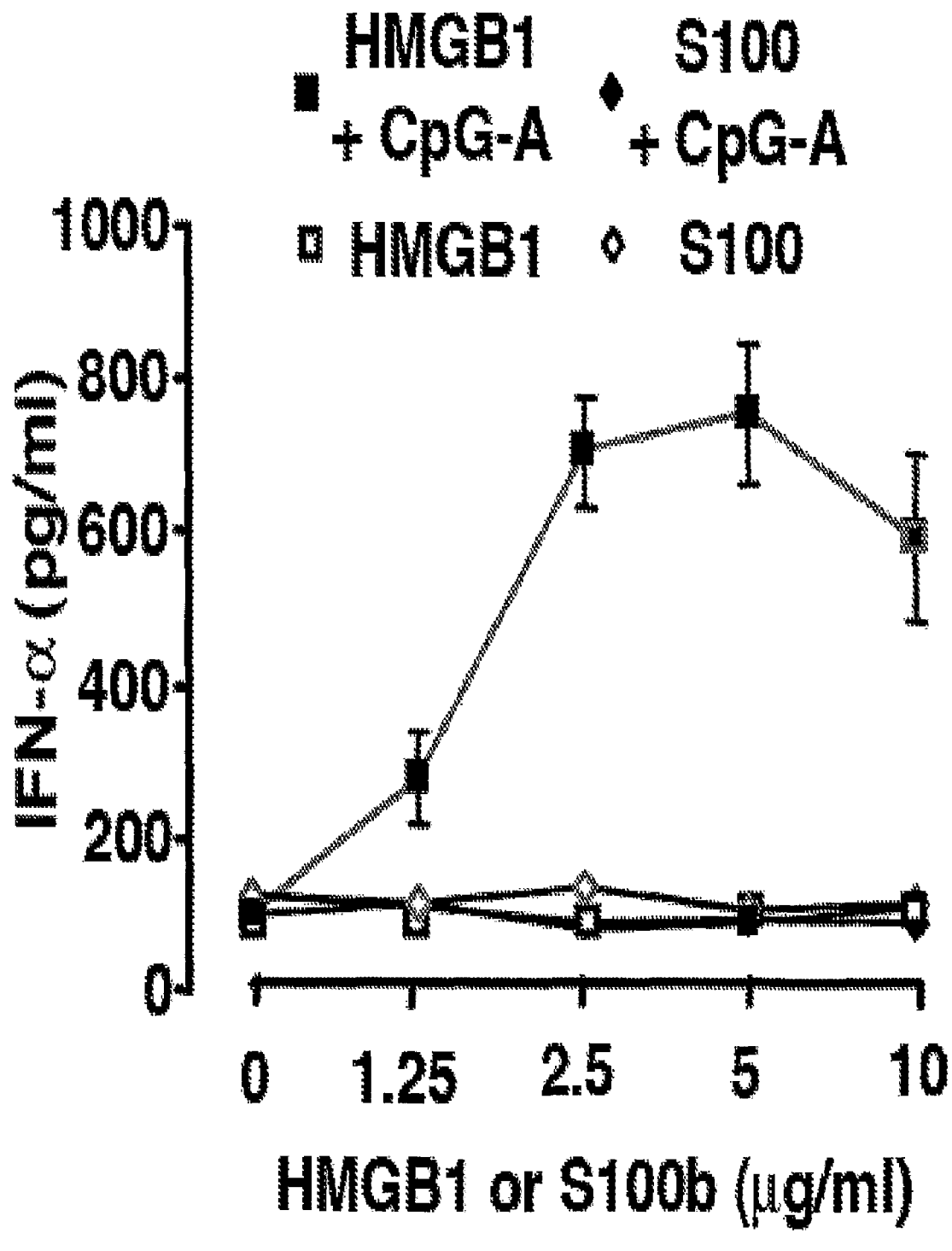

FIG. 38. IFN induction by HMGB1 alone (closed circles), HMGB1+CpG DNA (closed squares), S100 alone (open circle), S100+CpG DNA (open squares).

Figure 39:
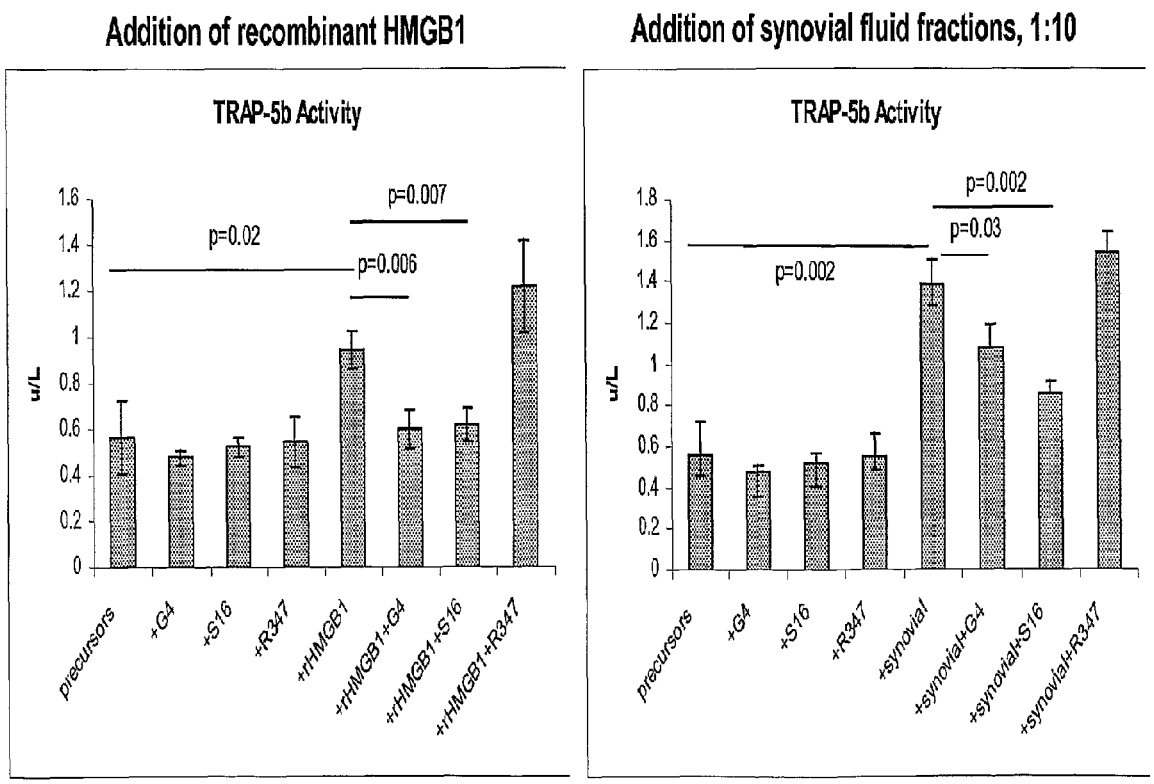

FIG. 39. Anti-HMBG1 Antibodies Reduce HMGB-1 induction of TRAP-5b Production in Osteoclast Precursor Cultures. Osteoclast precursor cells stimulated with recombinant HMGB (left panel) or synovial fluid fractions containing HMGB1 (right panel) show an increase in TRAP-5b activity. Treatment with either source of HMGB1 in combination with either the G4 or S16 anti-HMGB1 antibody but not an isotype control antibody did not result in a similar increase in TRAP-5b activity. Treatment with antibody alone had no effect.

4. BRIEF DESCRIPTION OF THE TABLES

Table 1—Antibody Characteristics and Deposit Info
Table 2—Families of Conservative Amino Acid Substitutions
Table 3—TLR Ligands
Table 4—Legend for Sequence Listing
Table 5—Legend for Passive CIA mouse model treatment protocol
Table 6—Legend for AIA Rat model treatment protocol
Table 7—Legend for Peritonitis model treatment protocol

5. DETAILED DESCRIPTION OF THE INVENTION

The present invention is based in part on the discovery that HMG1 synergizes with molecules having pathogen-associated molecular patterns (e.g. LPS, bacterial nucleic acids) to induce signaling and cytokine secretion via pattern-recognition receptors/molecules (e.g., Toll-Like-Receptors (TLRs)). HMG1 acts as a potent mediator of the inflammatory cascade by signaling via members of the Toll-like receptor (TLR) family of pattern-recognition receptors/molecules (PRMs). See, e.g., U.S. patent publication no. US20040053841. PRMs (e.g., TLRs) recognize general features of microorganisms, such as cell-wall lipids, peptidoglycans and stretches of guanine oligonucleotides. The structures recognized are called pathogen-associated molecular patterns and collectively the molecules comprising or alternatively consisting of pathogen-associated molecular patterns are referred to herein as PAMP(s). The stimulation of different PRMs (e.g., TLRs) leads to the activation of numerous signaling pathways which can result in activation of the inflammatory cascade, stimulation of innate immunity and the development of antigen-specific acquired immunity. PRMs (e.g., TLRs) and their ligands are well known in the art (see, e.g., Medzhitov and Janeway, 2002, *Science*, 296:298-300; Akira et al., 2004, *Nat. Rev. Immunol.* 4:499-511).

Without wishing to be bound by any particular theory, HMG1 appears to act in synergy with PAMPs such as TLR ligands (e.g., LPS, dsRNA, PolyI:C, imiquinod, CpG) and may act as an enhancer of the activity of these molecules and other proinflammatory factors. In particular, the present invention is based on the discovery that HMG1 can bind directly to PAMPS such as TLR ligands (e.g., CpG) and act as a chaperone enhancing the delivery of the PAMP to its receptor (see Examples 13, 14 and 15, infra). For example, HMG1 may bind an extracellular PAMP and chaperone it to its intracellular receptor, this may occur via interaction with one or more receptors including, but not limited to, a PRM, an HMG1 receptor (e.g., RAGE), or a combination of receptors. Alternatively (or in combination) HMG1 may bind a PAMP present intracellularly (e.g. viral nucleic acids present during infection) and enhance the binding and/or delivery of the PAMP to its intracellular receptor.

In particular, it has been discovered that HMG1 binds to and forms a high affinity complex with CpG DNA which stimulates cytokine production via a TLR9/MyD88 and RAGE dependent pathway (see Example 15, infra). TLR9 is expressed by a number of different cell types, most notably pDCs which, account for the majority of IFNα produced after TLR9 activation (Ronnblom, L., et al., 2003, *Autoimmunity*

36, 463-472; Assclin-Paturel, C. & Trinchieri, G., 2005, *J. Exp. Med.* 202, 461-465). Furthermore, studies have shown that HMGB1 is secreted by both pDCs and myeloid dendritic cells following stimulation with CpG ODNs and regulates the production of IFN-α in an autocrine manner. Type I interferons (e.g., IFN-α) are believed to play a central role in the pathogenesis of a number of autoimmune disorders including systemic lupus erythematosus (SLE) and Sjoegrens disease (Jego, G. et al. 2003, *Immunity* 19, 225-234; Blanco, P. et al., 2001, *Science* 294, 1540-1543; Crow, M. K., 2005, *Curr. Rheumatol. Rep.* 7, 463-468; Gottenberg, J. E. et al., 2006, *Proc. Natl. Acad. Sci. U.S.A.* 103, 2770-2775; Bennett, L. et al. 2003, *J. Exp. Med.* 197, 711-723). Studies have shown that HMGB1 is secreted by both pDCs and myeloid dendritic cells following stimulation with CpG ODNs and regulates the production of IFN-α in an autocrine manner. In addition, HMGB1 has recently been reported to be expressed in lesions of individuals with cutaneous lupus (Popovic, K. et al., 2005, *Arthritis Rheum.* 52, 3639-3645). Together, these data provide a novel mechanism by which HMGB1 can contribute to immune dysregulation in disorders such as SLE.

Without wishing to be bound by any particular theory, the enhancement of PAMP signaling mediated by HMGB can be by at least 2 different mechanisms. For cell surface PRMs co-crosslinking of the HMGB receptor (e.g., RAGE) with a PRM by the PAMP-HMGB complex forms heteroreceptor complexes that signal markedly more effectively than PRM alone ("co-stimulation"). Inhibition of formation of the PAMP-HMGB complex or inhibition of the complex binding to the HMGB receptor and/or the PRM can block this enhanced signaling. For intracellular PRMs, heteroreceptor complexes are formed by the PAMP-HMGB complex but this is after internalization of HMGB-PAMP complex through the HMGB receptor (e.g., RAGE). This intracellular heteroreceptor complex again signals much more effectively than the homotypic receptor. Alternatively (or in combination), by virtue of the internalization of the HMGB-PAMP complex through the HMGB cell surface receptor (e.g., RAGE), the PAMP is delivered more effectively to the intracellular compartment containing the appropriate PRM such that overall signaling through the PRM is significantly enhanced. Again inhibition of formation of this PAMP-HMGB complex blocks the enhanced signaling. Ligand induced activation of PRMs (e.g., TLRs) may be determined by various procedures well known in the art. Specific methods useful for studying HMG1 mediated enhancement of PRM signaling are disclosed herein (see Examples 13, 14 and 15, infra).

Accordingly, the present invention provides methods of stimulating pattern-recognition receptors/molecules by co-administering HMG1 or a biologically functional fragment thereof in combination with one or more molecule having a pathogen-associated molecular pattern. The present invention also provides methods of inhibiting the interaction of HMG1 and/or an HMG1:PAMP complex with RAGE. In addition, the present invention provides methods of inhibiting pattern-recognition receptors/molecules by administering antagonists of HMG1 which can prevent and/or disrupt HMG1 binding to a PAMP and/or the chaperone activity of HMG1.

In addition, the present invention provides methods for inhibiting HMG1 mediated enhancement of TLR signaling stimulated by one or more TLR ligands by administering antagonists of HMG1. Furthermore, the present invention also provides methods of inhibiting the interaction of HMG1 and/or an HMG1:PAMP complex with RAGE and/or inhibiting RAGE mediated signaling of HMG1 by administering antagonists of RAGE. Such therapies are useful for the treatment of cancers, infectious diseases, asthma, allergy and autoimmune diseases and conditions including, but not limited to SLE and rheumatoid arthritis.

The present invention also provides methods of screening for molecules which prevent/antagonize/inhibit one or more of the following: HMGB1 and/or HMGB1/PAMP complexes binding to RAGE, HMGB1 binding to a PAMP (e.g., LPS, CpG), HMGB1 binding to one or more pattern recognition receptor/molecules (also referred to herein as "PRMs") (e.g., Toll-like receptor, TLR2 and TLR4)), internalization of HMGB1 and/or HMGB1/PAMP complexes, HMGB1 binding to a cell surface (e.g., a THP-1 cell), HMG1-mediated release of proinflammatory cytokines, RAGE-mediated internalization of HMGB1 and/or HMGB1/PAMP complexes, intracellular localization of a RAGE molecule with a TLR and/or HMG1 PAMP complex, RAGE-mediated signaling of HMGB1 and/or HMGB1/PAMP complexes; RAGE-mediated release of proinflammatory cytokines; HMG1-mediated inflammation, HMG1-mediated sepsis, HMG1-mediated inflammation (e.g., of joints), and HMG1-mediated arthritis. These activities may be assayed by the methods disclosed herein, or one of many known methods in the art. See, e.g., US20040005316, U.S. Pat. No. 6,468,533 and U.S. Pat. No. 6,448,223, and Section entitled "Examples" infra. Molecules which prevent/antagonize/inhibit one or more activity of HMGB1 are collectively referred to as "HMGB1 antagonists" and like terms. Molecules which prevent/antagonize/inhibit one or more activity of RAGE are collectively referred to as "RAGE antagonists" and like terms. As demonstrated herein, (see, Example 14, infra) HMGB1 and RAGE can interact physically and can modulate the same pathway, accordingly, it will be understood by one of skill in the art that a single molecule may function as an antagonist of both RAGE and HMGB1. HMGB1 and/or RAGE antagonists and compositions comprising the same are useful for many purposes, for example, as therapeutics against a wide range of infectious, chronic and acute inflammatory diseases and disorders.

The present invention is based in part of the discovery of antibodies that specifically bind HMG1 (also referred to herein as "HMGB1") and antigenic fragments thereof which exhibit certain biochemical, binding, and functional characteristics. The antibodies that specifically bind HMG1 are specifically referred to herein as "high affinity antibodies of the invention," "high affinity antibodies" and are also encompassed by the more expansive terms "antibodies of the invention," "anti-HMG1 antibodies" and simply "HMG antibodies," as well as like terms. As described above, HMG1 and HMG2 share a high degree of homology and may have similar and/or overlapping biologically functions. Accordingly, the methods and molecules disclosed herein may be useful for targeting (e.g., antagonizing) HMG1 and or HMG2. In particular, the present invention is also based in part by the discovery of antibodies that bind both HMG1 and HMG2.

Furthermore, the present invention is also based on the discovery that the high affinity antibodies of the invention can block the synergistic effect of HMG1 on signaling through pattern-recognition receptors/molecules. It is likely that different epitopes on HMGB are involved in the interaction with the different PAMPs. Thus antibodies which bind to different regions of HMGB would be expected to selectively interfere with various PAMP-HMGB interactions. In one embodiment, the high affinity antibodies of the present invention bind HMG1 and block the interaction of HMG1 with PAMP. Non-limiting examples of PAMPs are, lipopolysaccharide (LPS) from the gram-negative cell wall, peptidoglycan, lipoteichoic acids from the gram-positive cell wall, flagellin, pilin, mannose rich glycans, bacterial and viral nucleic acids, N-formylmethionine found in bacterial proteins, double-stranded RNA from viruses, phosphorylcholine and other lipids common to microbial membranes and glucans such as lipoteichoic acids, glycolipids, and zymosan from fungal cell walls.

It is contemplated that an antibody can be derived that selectively blocks the association of an HMGB-PAMP complex with a PRM and that such an antibody would selectively inhibit the inflammatory response to that PRM. In one embodiment, the high affinity antibodies of the present invention bind HMG1 and block the interaction of a HMG1:PAMP complex with a pattern-recognition receptor. In another embodiment, the high affinity antibodies of the present invention bind HMG1 and block the interaction of a HMO 1 with a pattern-recognition receptor/molecule. Non-limiting examples of pattern-recognition receptors are the endocytic pattern-recognition receptors (e.g., mannose receptors, scavenger receptors) signaling pattern-recognition receptors (e.g., the toll-like receptors (TLRs), CD14, nucleotide-binding oligomerization domain (NOD) proteins) and secreted pattern recognition receptors (e.g., mannan-binding lectin, C-reactive protein). Exemplary TLRs and their respective ligands are listed in Table 3.

The biochemical characteristics of the antibodies of the invention include but are not limited to, isoelectric point (pI) and melting temperature ($T_m$). The binding characteristics of the antibodies of the invention include, but are not limited to, binding specificity, dissociation constant ($K_d$), epitope, ability to distinguish between various forms and/or preparations of HMG1 (e.g., recombinant, native, acetylated) and ability to bind soluble and/or immobilized antigen. The functional characteristics of the antibodies of the present invention include, but are not limited to, inhibition of HMG1-induced cytokine release, inhibition of HMG1 binding to one or more receptor, inhibition of HMG1 binding to the cell surface and protection in one or more model of inflammatory disease (e.g., sepsis, arthritis, acute lung injury, peritonitis).

The antibodies of the invention and compositions comprising the same are useful for many purposes, for example, as therapeutics against a wide range of infectious, chronic and acute inflammatory diseases and disorders including, but not limited to, sepsis, rheumatoid arthritis, peritonitis, Crohn's disease, reperfusion injury, septicemia, endotoxic shock, cystic fibrosis, endocarditis, psoriasis, arthritis (e.g., psoriatic arthritis), anaphylactic shock, organ ischemia, reperfusion injury, spinal cord injury and allograft rejection.

In addition, the high affinity antibodies of the present invention are useful for diagnostic applications. Antibodies of the present invention may be used, for example, but not limited to, to purify, detect, and target the HMG1 and/or HMG2 polypeptides of the present invention, including both in vitro and in vivo diagnostic and therapeutic methods. For example, the antibodies have use in immunoassays for qualitatively and quantitatively measuring levels of the HMG1 and/or HMG2 polypeptides of the present invention in biological samples. See, e.g., Harlow et al., Antibodies: A Laboratory Manual, (Cold Spring Harbor Laboratory Press, 2nd ed. 1988).

5.1 HMG1 and/or RAGE Antagonists of the Invention

The present invention provides molecules and methods of screening for molecules which prevent/antagonize/inhibit one or more activity of HMGB1. Activities of HMGB1 include but are not limited to the following: HMGB1 and/or HMGB1/PAMP complexes binding to RAGE, HMGB1 binding to a PAMP (e.g., LPS, CpG), HMGB1 binding to one or more pattern recognition receptor/molecules (also referred to herein as "PRMs") (e.g., Toll-like receptor, TLR2 and TLR4)), internalization of HMGB1 and/or HMGB1/PAMP complexes, HMGB1 and/or HMGB1/PAMP-mediated internalization of RAGE and/or intracellular localization of a HMG1:PAMP complex with a TLR or intracellular localization of a PAGE molecule with a TLR, HMG1:PAMP complex-mediated intracellular binding of a RAGE polypeptide to a TLR, HMG1:PAMP complex-mediated intracellular binding of a HMG1:PAMP complex to a TLR, HMGB1 mediated targeting of a TLR ligand to an intracellular TLR, HMGB1 binding to a cell surface (e.g., a THP-1 cell), HMG1-mediated release of proinflammatory cytokines, HMG1-mediated inflammation, HMG1-mediated sepsis, HMG1-mediated inflammation (e.g., of joints), and HMG1-mediated arthritis. These activities may be assayed by one or many known methods in the art. See, e.g., US20040005316, U.S. Pat. No. 6,468,533 and U.S. Pat. No. 6,448,223, and Section entitled "Examples" infra.

The present invention provides molecules and methods of screening for molecules which prevent/antagonize/inhibit one or more activity of RAGE. Activities of RAGE include but are not limited to the following: RAGE binding to HMGB1 and/or HMGB1/PAMP complexes, RAGE-mediated internalization of HMGB1 and/or HMGB1/PAMP complexes, intracellular localization of a RAGE molecule with a TLR and/or HMG1:PAMP complex, RAGE-mediated signaling of HMGB1 and/or HMGB1/PAMP complexes and RAGE-mediated release of proinflammatory cytokines.

HMGB1 antagonists may function directly by binding to HMGB1. For example, an antibody specifically binding to HMGB1 may prevent HMBG1 from binding a PAMP. Alternatively, or in combination, HMGB1 antagonists may function indirectly, for example, by down regulating HMGB1 expression or binding to and preventing the interaction of a receptor of HMGB1. RAGE antagonists may function directly by binding to RAGE. Alternatively, or in combination, RAGE antagonists may function indirectly, for example, by down regulating RAGE expression or binding to and preventing the interaction of a ligand of RAGE. As described above, a single molecule may function as an antagonist of both RAGE and HMGB1. For example, and not by way of limitation, a molecules (e.g., an anti-HMGB1 antibody including, but not limited to, those disclosed herein; a soluble RAGE polypeptide including, but not limited to those disclosed in PCT publications WO 00/192892; WO 05/051995; WO 06/012415) which binds HMGB1 and prevents binding to RAGE will function as both an antagonist of RAGE and HMGB1.

In certain aspects, the present invention provides polypeptides, small molecules, peptidomimetics and other agents that bind to HMGB11 and function as antagonists of HMGB1. In other aspects, the present invention provides agents that effectively antagonize HMGB1 by reducing or downregulating HMGB1 expression; such HMGB1 antagonists include but are not limited to nucleic acid agents, such as siRNAs, antisense molecules, and ribozymes. In still other aspects, the present invention provides agents that modulate the downstream targets of HMGB activity (e.g., TLRs, RAGE).

In one embodiment, the present invention provides inhibitory oligonucleotides and small molecules which are antagonists of HMGB1 mediated enhancement of RAGE signaling stimulated by one or more proinflammatory factors (e.g., TLR ligands). Examples of inhibitory oligonucleotides and small molecules include, but are not limited to, CPG 7909 (also known as PF-3512676 or ProMune™) and Actilon, (CPG 10101). Other examples are known in the art, (see, for example U.S. patent publications US20050239733 and 20050119273) and methods to identify such molecules have been described (see, for example, U.S. patent publication US20050181422).

In one embodiment, the present invention provides antibodies which are antagonists of HMGB1. In a specific embodiment, antibodies which are antagonists of HMGB1 specifically bind HMGB1. In another embodiment, the present invention provides antibodies which are antagonists of RAGE. In a specific embodiment, antibodies which are antagonists of RAGE specifically bind RAGE.

In another embodiment, the present invention provides soluble RAGE peptides which are antagonists of HMGB1. Soluble RAGE polypeptides will generally comprise a functional portion of the extracellular domain of RAGE. A soluble RAGE polypeptide may be fused to additional polypeptides, such as Fc domains or scrum albumin (HSA). A soluble RAGE polypeptide may also modified so as to improve pharmacokinetics, e.g., by covalent attachment to one or more polyalkylene glycol moieties, particularly polyethylene glycol (PEG). Methods for generating soluble RAGE polypeptide are known in the art (see, e.g., U.S. patent application Ser. No. 11/186,422).

In another embodiment, the present invention provides HMGB1 antagonists which are nucleic acid compounds. Examples of categories of nucleic acid compounds include antisense nucleic acids, RNAi constructs, and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100, or no more than 50 nucleotides of the HMGB1 nucleic acid sequence. In certain embodiments, the region of complementarity will be at least 8 nucleotides, and optionally at least 10 or at least 15 nucleotides. A region of complementarity may fall within an intron, a coding sequence or a noncoding sequence of the target transcript, such as the coding sequence portion. Generally, a nucleic acid compound will have a length of about 8 to about 500 nucleotides or base pairs in length, and optionally the length will be about 14 to about 50 nucleotides. A nucleic acid may be a DNA (particularly for use as an antisense), RNA, or RNA:DNA hybrid. Any one strand may include a mixture of DNA and RNA, as well as modified forms that cannot readily be classified as either DNA or RNA. Likewise, a double stranded compound may be DNA:DNA, DNA:RNA or RNA:RNA, and any one strand may also include a mixture of DNA and RNA, as well as modified forms that cannot readily be classified as either DNA or RNA. A nucleic acid compound, may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will generally have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA, or any other variation. The duplex portion of double stranded or single stranded "hairpin" RNAi construct will generally have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90% or more when contacted with cells under physiological conditions and at a concentration where a nonsense or sense control has little or no effect. Contemplated concentrations for testing the effect of nucleic acid compounds are 1, 5 and 10 micromolar. Nucleic acid compounds may also be tested for effects on, for example, angiogenesis.

In certain aspects, the disclosure provides isolated nucleic acid compounds known in the art as aptamers. Aptamers are macromolecules composed of nucleic acid (e.g., RNA, DNA) that bind tightly to a specific molecular target (e.g., HMGB1, A Box or B Box of HMGB1 and/or HMGB1 polypeptides as described herein). A particular aptamer may be described by a linear nucleotide sequence and an aptamer is typically about 15-60 nucleotides in length. The chain of nucleotides in an aptamer form intramolecular interactions that fold the molecule into a complex three-dimensional shape, and this three-dimensional shape allows the aptamer to bind tightly to the surface of its target molecule. Given the extraordinary diversity of molecular shapes that exist within the universe of all possible nucleotide sequences, aptamers may be obtained for a wide array of molecular targets, including proteins and Small molecules. In addition to high specificity, aptamers have very high affinities for their targets (e.g., affinities in the picomolar to low nanomolar range for proteins). Aptamers are chemically stable and can be boiled or frozen without loss of activity. Because they are synthetic molecules, they are amenable to a variety of modifications, which can optimize their function for particular applications. For in vivo applications, aptamers can be modified to dramatically reduce their sensitivity to degradation by enzymes in the blood. In addition, modification of aptamers can also be used to alter their biodistribution or plasma residence time.

Selection of apatmers that can bind HMGB1 or a fragment there of (e.g., A box, B box or a fragment thereof) can be achieved through methods known in the art. For example, aptamers can be selected using the SELEX (Systematic Evolution of Ligands by Exponential Enrichment) method (Tuerk, C., and Gold, L., *Science* 249:505-510 (1990)). In the SELEX method, a large library of nucleic acid molecules (e.g., 10's different molecules) is produced and/or screened with the target molecule (e.g., HMGB1, A Box or B Box of HMGB1 and/or HMGB1 polypeptides as described herein). The target molecule is allowed to incubate with the library of nucleotide sequences for a period of time. Several methods can then be used to physically isolate the aptamer target molecules from the unbound molecules in the mixture and the unbound molecules can be discarded. The aptamers with the highest affinity for the target molecule can then be purified away from the target molecule and amplified enzymatically to produce a new library of molecules that is substantially enriched for aptamers that can bind the target molecule. The enriched library can then be used to initiate a new cycle of selection, partitioning, and amplification. After 5-15 cycles of this selection, partitioning and amplification process, the library is reduced to a small number of aptamers that bind tightly to the target molecule. Individual molecules in the mixture can then be isolated, their nucleotide sequences determined, and their properties with respect to binding affinity and specificity measured and compared. Isolated aptamers can then be further refined to eliminate any nucleotides that do not contribute to target binding and/or aptamer structure (i.e., aptamers truncated to their core binding domain). See Jayasena, S. D. *Clin. Chem.* 45:1628-1650 (1999) for review of aptamer technology.

In certain embodiments, the aptamers of the invention have the binding specificity and/or functional activity described herein for the anti-HMGB1 antibodies. Thus, for example, in certain embodiments, the present invention is drawn to aptamers that have the same or similar binding specificity as described herein for the anti-HMGB1 antibodies (e.g., binding specificity, agonistic or antagonistic activity). In particular embodiments, the aptamers of the invention can bind to an HMGB1 polypeptide and inhibit one or more activity of the HMGB1 polypeptide as described herein.

The present invention also provides methods for screening for HMGB1 antagonists. In one embodiment, the invention provides a method for screening for a compound that inhibits or diminishes the specific binding of HMGB1 to an interacting molecule (e.g., a PAMP, RAGE, etc), the method comprising combining a first composition, comprising a candidate compound, with a second composition comprising a interacting molecule that specifically binds to HMGB1 in an in vitro binding assay; and detecting an inhibition or diminution in specific binding of the interacting molecule to HMGB1. In certain embodiments, the interacting molecule is RAGE. In other embodiments, the interacting molecule is a TLR ligand. In a specific embodiment, the interacting molecule is a polynucleotide. In another specific embodiment, the interacting molecule is CpG.

In another embodiment, the invention provides a method for screening for a compound that inhibits or diminishes the specific binding of an HMGB1/PAMP complex to RAGE, the method comprising combining a first composition, comprising a candidate compound, with a second composition comprising RAGE in an in vitro binding assay; and detecting an inhibition or diminution in specific binding of RAGE to the HMGB1/PAMP complex. In a specific embodiment, the PAMP is a TLR ligand. The TLR ligand may be a ligand of a TLR selected from the group consisting of TLR1, TLR2, TLR3, TLR4, TLR5, TLR6, TLR7, TLR8 and TLR9. In another specific embodiment, the PAMP is CpG.

In one embodiment, the invention provides a method for screening for a compound that inhibits or diminishes HMGB1 mediated enhancement of TLR signaling, the method comprising stimulating a cell which can be stimulated by one or more TLR ligand and shows an HMGB1 mediated enhancement of TLR signaling, with a TLR ligand in the presence of HMGB1 in combination with a composition, comprising a candidate compound, and detecting an inhibition or diminution in HMGB1 mediated enhancement of TLR signaling in the cell. In certain embodiments, the TLR signaling is stimulated by one or more TLR ligands. In certain embodiments, the TLR signaling is signaling through a TLR selected from the group consisting of TLR1, TLR2, TLR3, TLR4, TLR5, TLR6, TLR7, TLR8 and TLR9.

In another embodiment, the invention provides a method for screening for a compound that inhibits or diminishes the internalization of HMGB1 and/or a HMGB1/PAMP complex, the method comprising stimulating a cell, which can internalize HMGB1 and/or a HMGB1/PAMP complex, with HMGB1 and/or a HMGB1/PAMP complex in combination with a composition, comprising a candidate compound, and detecting an inhibition or diminution in internalization of HMGB1 and/or the HMGB1/PAMP complex. In specific embodiments, the HMGB1/PAMP complex is a complex of HMGB1 and a TLR ligand. In another specific embodiment, the HMGB1/PAMP complex is a complex of HMGB1 and a TLR ligand selected from the group consisting of TLR3, TLR7 and TLR9. In still another specific embodiment, the HMGB1/PAMP complex is a complex of HMGB1 and CpG.

5.2 Antibodies of the Invention

High affinity antibodies or fragments thereof that "specifically bind to HMG1 and antigenic fragments thereof" as used herein refers to, for example, high affinity antibodies or fragments thereof that specifically bind to an HMG1 polypeptide or a fragment of an HMG1 polypeptide (e.g., HMG1 A box and HMG1 B Box) or an epitope of an HMG1 polypeptide (as determined by immunoassays well known in the art for assaying specific antibody-antigen binding) and do not specifically bind to other polypeptides. In one embodiment, high affinity antibodies or fragments that specifically bind to an HMG1 polypeptide or fragment thereof do not non-specifically cross-react with other antigens (e.g., binding cannot be competed away with a non-HMG1 protein, e.g., BSA). The present invention also encompasses high affinity antibodies or fragments thereof that specifically bind to an HMG2 polypeptide or fragment of an HMG2 polypeptide (e.g. HMG2 A box and HMG2 B Box) or an antigenic fragment of an HMG2 polypeptide.

It will be recognized by one skilled in the art that HMG1 and HMG2 while being distinct proteins do have regions of homology (see, FIG. 1). Accordingly, it is contemplated that high affinity antibodies or fragments thereof may specifically bind to HMG1 and antigenic fragments thereof and not bind to HMG2 or antigenic fragments thereof. It is further contemplated that high affinity antibodies or fragments thereof may specifically bind to HMG2 and antigenic fragments thereof and not bind to HMG1 or antigenic fragments thereof. It is further contemplated that the high affinity antibodies of the invention may specifically bind an epitope that is common to both HMG1 and to HMG2. A common epitope may be identical in both HMG1 and HMG2, in such a case the amino acid sequence comprising the epitope is identical in HMG1 and HMG2. Accordingly, the high affinity antibodies of the invention may specifically bind to both HMG1 and to HMG2 (e.g., an antibody that specifically recognized a identical epitope that is present in both HMG1 and HMG2). Alternatively, a common epitope may be similar in both HMG1 and HMG2. For example, a similar epitope may share significant homology (e.g., 60%-99% identity) and/or adopt a similar three dimensional conformation between HMG1 and HMG2 such that a high affinity antibody of the present invention will cross-react with the shared epitope. Accordingly, the high affinities antibodies of the invention may specifically bind either HMG1 or HMG2 and cross-react with HMG2 or HMG1, respectively. A high affinity antibody of the present invention may have differing affinities for a similar epitope present on HMG1 and HMG2. Accordingly, it is further contemplated that the high affinity antibodies of the invention bind HMG1 and HMG2 with either the same or different binding affinities. In a specific embodiment, high affinity antibodies or fragments thereof specifically bind HMG1 and/or HMG2 over other antigens.

In one embodiment, the high affinity antibodies of the present invention specifically bind a polypeptide comprising, or alternatively consisting of (or consisting essentially of) an A box of HMG1 and/or HMG2 (e.g., SEQ ID NOS. 3 and 22, respectively).

In another embodiment, the high affinity antibodies of the present invention specifically bind a polypeptide comprising, or alternatively consisting of (or consisting essentially of) a B box of HMG1 and/or HMG2 (e.g., SEQ ID NOS. 4 and 23, respectively).

Also encompassed by the present invention are antibodies which specifically bind to an epitope comprising, or alternatively consisting of (or consisting essentially of) amino acid residues derived from both the A box and B box of HMG1 and/or HMG2. An epitope derived from amino acid residues derived from both the A box B box may be a linear polypeptide derived from the junction of the A and B boxes or may result from the three dimensional confirmation of a polypeptide comprising amino acid residues from both the A and B boxes.

The present invention also specifically encompasses antibodies with multiple specificities (e.g., an antibody with specificity for two or more discrete antigens (reviewed in Cao et al, 2003, *Adv Drug Deliv Rev* 55:171; Hudson et al., 2003, *Nat Med* 1:129)). For example, bispecific antibodies contain two different binding specificities fused together. In the simplest case a bispecific antibody would bind to two adjacent epitopes on a single target antigen, such an antibody would not cross-react with other antigens (as described supra). Alternatively, bispecific antibodies can bind to two different antigens, Such an antibody specifically binds to two different molecules (e.g., HMG1 and HMG2) but not to other unrelated molecules (e.g., BSA). In addition, an antibody that specifically binds HMG1 and/or HMG2 may cross-react with related HMG proteins.

The term HMG1 and/or HMG2 "fragments" described herein include an HMG1 and/or HMG2 peptide or polypeptide comprising, or alternatively consisting of (or consisting essentially of) an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of HMG1 and/or HMG2 polypeptide (e.g., human HMG1 and/or HMG2).

The term HMG1 and/or HMG2 "fragments" described herein also specifically include polypeptides comprising, or alternatively consisting of (or consisting essentially of) an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, or at least contiguous 80 amino acid residues of an HMG A (e.g., a human HMG1 and/or HMG2 A box) box or an HMG B (e.g., a human HMG1 and/or HMG2 B box) box.

"High affinity antibodies" (also referred to herein as "high affinity antibodies of the invention," "high affinity antibodies," and are also encompassed by the more expansive terms "antibodies of the invention" and simply "HMG antibodies") of the invention include, but are not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdfv) (including bi-specific sdFvs), and anti-idiotypic (anti-Id) antibodies, and epitope-binding fragments of any of the above. The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO91/00360; WO 92/05793; Tutt, et al., J. Immunol. 147:60-69 (1991); U.S. Pat. Nos. 4,474,893; 4,714,681; 4,925,648; 5,573,920; 5,601, 819; Kostelny et al., J. Immunol. 148:1547-1553 (1992).

Antibody-like and antibody-domain fusion proteins which bind HMGB1 are also contemplated as antibodies of the present invention. An antibody-like molecule is any molecule that has been generated with a desired binding property, see, e.g., PCT Publication Nos. WO 04/044011; WO 04/058821; WO 04/003019 and WO 03/002609. Antibody-domain fusion proteins may incorporate one or more antibody domains such as the Fc domain or the variable domain. For example, the heterologous polypeptides may be fused or conjugated to a Fab fragment, Fd fragment, Fv fragment, F(ab)$_2$ fragment, a VH domain, a VL domain, a VH CDR, a VL CDR, or fragment thereof. A large number of antibody-domain molecules are known in the art including, but not limited to, diabodies (dsFv)$_2$ (Bera et al., 1998, J. *Mol. Biol.* 281:475-83); minibodies (homodimers of scFv-CH3 fusion proteins)(Pessi et al., 1993, *Nature* 362:367-9), tetravalent di-diabody (Lu et al., 2003 *J. Immunol. Methods* 279:219-32), tetravalent bi-specific antibodies called Bs(scFv)$_4$-IgG (Zuo et al., 2000, *Protein Eng.* 13:361-367). Fc domain fusions combine the Fc region of an immunoglobulin with a fusion partner which in general can be an protein, including, but not limited to, a ligand, an enzyme, the ligand portion of a receptor, an adhesion protein, or some other protein or domain. See, e.g., Chamow et al., 1996, *Trends Biotechnol* 14:52-60; Ashkenazi et al., 1997, *Curr Opin Immunol* 9:195-200; Heidaran et al., 1995, FASEB J. 9:140-5. Methods for fusing or conjugating polypeptides to antibody portions are well known in the art. See, e.g., U.S. Pat. Nos. 5,336,603, 5,622,929, 5,359,046, 5,349,053, 5,447,851, and 5,112,946; European Patent Nos. EP 307,434 and EP 367,166; PCT Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al, 1992, Proc. Natl. Acad. Sci. USA 89:11337-11341.

An antibody which can bind an intracellular epitope, (e.g., an intrabody) is useful for binding to and disrupting/inhibiting one or more activity of intracellular HMGB1 (e.g., nuclear and/or cytoplasmic HMGB1). An intrabody comprises at least a portion of an antibody (e.g. an scFv) that is capable of specifically binding an antigen and which has been manipulated so that it can be expressed intracellularly. Generally, an intrabody does not contain sequences coding for its secretion. Such antibodies will bind antigen intracellularly. When combined with methods for expression and/or targeting to precise intracellular locations inside mammalian cells intrabodies are particularly useful for intracellular targets.

Generation of intrabodies is well-known to the skilled artisan and is described, for example, in U.S. Pat. Nos. 6,004, 940; 6,072,036; 5,965,371. Further, the construction of intrabodies is discussed in Ohage and Steipe, 1999, *J. Mol. Biol.* 291:1119-1128; Ohage et al., 1999, *J. Mol. Biol.* 291:1129-1134; and Wirtz and Steipe, 1999, *Protein Science* 8:2245-2250; Stocks, M. R. *Drug Disc. Today* Vol 9, No. 22 Nov. 2004. Recombinant molecular biological techniques may also be used in the generation of intrabodies.

In one embodiment, intrabodies of the invention retain at least about 75% of the binding effectiveness of the complete antibody (i.e., having the entire constant domain as well as the variable regions) to the antigen. In one embodiment, the intrabody retains at least 85%, at least 90%, or at least 95% of the binding effectiveness of the complete antibody.

Specific localization sequences can be attached to the intrabody polypeptide to direct the intrabody to a specific location. Intrabodies can be localized, for example, to the following intracellular locations: endoplasmic reticulum (Munro et al., 1987, *Cell* 48:899-907; Hangejorden et al., 1991, *J. Biol. Chem.* 266:6015); nucleus (Lanford et al., 1986, *Cell* 46:575; Stanton et al., 1986, *PNAS* 83:1772; Harlow et al., 1985, *Mol. Cell. Biol.* 5:1605; Pap et al., 2002, *Exp. Cell Res.* 265:288-93); nucleolar region (Seomi et al., 1990, *J. Virology* 64:1803; Kubota et al., 1989, *Biochem. Biophys. Res. Comm.* 162:963; Siomi et al., 1998, *Cell* 55:197); endosomal compartment (Bakke et al., 1990, *Cell* 63:707-716); mitochondrial matrix (Pugsley, A. P., 1989, "Protein Targeting", Academic Press, Inc.); Golgi apparatus (Tang et al., 1992, *J. Bio. Chem.* 267: 10122-6); liposomes (Letourneur et al., 1992, *Cell* 69:1183); peroxisome (Pap et al., 2002, *Exp. Cell Res.* 265:288-93); bans Golgi network (Pap et al., 2002, *Exp. Cell Res.* 265:288-93); and plasma membrane (Marehildon et al., 1984, *PNAS* 81:7679-82; Henderson et al., 1987, *PNAS* 89:339-43; Rhee et al., 1987, *J. Virol.* 61:1045-53; Schultzetal., 1984, *J. Virol.* 133:431-7; Otsuyama et al., 1985, *Jpn. J. Can. Res.* 76: 1132-5; Ratner et al., 1985, *Nature* 313:277-84).

Recombinantly expressed intrabody may be administered to a patient to mediate a prophylactic or therapeutic effect. To direct the intrabody intracellularly the intrabody polypeptide is associated with a "membrane permeable sequence". Membrane permeable sequences are polypeptides capable of penetrating through the cell membrane from outside of the cell to the interior of the cell. When linked to another polypeptide, membrane I permeable sequences can also direct the translocation of that polypeptide across the cell membrane as well. Useful membrane permeable sequence include the hydrophobic; region of a signal peptide (sec, e.g., Hawiger, 1999, *Curr. Opin. Chem. Biol.* 3:89-94; Hawiger, 1997, *Curr. Opin. Immunol.* 9:189-94; U.S. Pat. Nos. 5,807,746 and 6,043,339). The sequence of a membrane permeable sequence can be based on the hydrophobic region of any signal peptide. The signal peptides can be selected, e.g., from the SIGPEP database (see e.g., von; Heijne, 1987, *Prot. Seq. Data Anal.* 1:41-2; von Heijne and Abrahmsen, 1989, FEBS Lett.; 224:439-46). When a specific cell type is to be targeted for insertion of an intrabody; polypeptide, the membrane permeable sequence is preferably based on a signal peptide endogenous to that cell type. In another embodiment, the membrane permeable sequence is a viral protein (e.g., Herpes Virus Protein VP22) or fragment thereof (see e.g., Phelan et al., 1998, Nat. Biotechnol. 16:440-3). A membrane permeable sequence with the appropriate properties for a particular intrabody and/or a particular target cell type can be determined empirically by assessing the ability of each membrane permeable sequence to direct the translocation of the intrabody across the cell membrane.

Multispecific antibodies have binding specificities for at least two different antigens. While such molecules normally will only bind two antigens (i.e. bispecific antibodies, BsAbs), antibodies with additional specificities such as trispecific antibodies are encompassed by the instant invention. Examples of BsAbs include without limitation those with one arm directed against an HMG1 and/or HMG2 epitope and the other arm directed against any other antigen. Methods for making bispecific antibodies are known in the art. Traditional production of full-length bispecific antibodies is based on the coexpression of two immunoglobulin heavy chain-light chain pairs, where the two chains have different specificities (Millstein et al., 1983, *Nature*, 305:537-539). Because of the random assortment of immunoglobulin heavy and light chains, these hybridomas (quadromas) produce a potential mixture of different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Trauncker et al., 1991, *EMBO J.*, 10:3655-3659. A more directed approach is the generation of a Di-diabody a tetravalent bispecific antibody. Methods for producing a Di-diabody are known in the art (see e.g., Lu et al., 2003, J Immunol Methods 279:219-32; Marvin et al., 2005, Acta Pharmacolical Sinica 26:649).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when, the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm (e.g., an HMG1 and/or HMG2 epitope such as the A-box, B-box), and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., 1986, *Methods in Enzymology*, 121:210. According to another approach described in WO96/27011, a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089) Heteroconjugate antibodies may be made using any convenient cross-linking methods. Suitable cross-linking agents are well known in the art, and are disclosed in U.S. Pat. No. 4,676,980, along with a number of cross-linking techniques.

Antibodies with more than two valencies incorporating at least one hinge modification of the invention are contemplated. For example, trispecific antibodies can be prepared. See, e.g., Tutt et al. J. Immunol. 147: 60 (1991).

Other antibodies specifically contemplated are "oligoclonal" antibodies. As used herein, the term "oligoclonal" antibodies" refers to a predetermined mixture of distinct monoclonal antibodies. Methods for generating oligoclonal antibodies are known in the art. See, e.g., "Examples Section", example 1, PCT publication WO 95/20401; U.S. Pat. Nos. 5,789,208 and 6,335,163. In certain embodiments, oligoclonal antibodies consist of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule (e.g., HMG1). Those skilled in the art will know or can determine what type of antibody or mixture of antibodies is applicable for an intended purpose and desired need. In particular, antibodies of the present invention include immunoglobulin molecules and immunologically active portions of immunoglobulin molecules, i.e., molecules that contain an antigen binding site that specifically binds to an HMG1 antigen (e.g., one or more complementarity determining regions (CDRs) of an anti-HMG1 antibody). It is also specifically contemplated that the antibodies of the present invention include immunoglobulin molecules and immunologically active portions of immunoglobulin molecules, i.e., molecules that contain an antigen binding site that specifically binds to an HMG2 antigen (e.g., one or more complementarity determining regions (CDRs) of an anti-HMG2 antibody). The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins may have both a heavy and light chain. An array of IgG, IgE, IgM, IgD, IgA, and IgY heavy chains may be paired with a light chain of the kappa or lambda forms.

The antibodies of the invention also encompass immunoglobulin molecules and immunologically active fragments of immunoglobulin molecules, i.e., molecules that contain an antigen binding site, these fragments may or may not be fused to another immunoglobulin domain including but not limited to, an Fc region or fragment thereof. As outlined herein, the terms "antibody" and "antibodies" include the antibodies which specifically bind HMG1 and/or HMG2 described herein, full length antibodies and Fc variants thereof comprising Fc regions, or fragments thereof, comprising at least one novel amino acid residue described herein fused to an immunologically active fragment of an immunoglobulin or to other proteins as described herein. Such variant Fc fusions include but are not limited to, scFv-Fc fusions, variable region (e.g., VL and VH)-Fc fusions, scFv-scFv-Fc fusions. Immunoglobulin molecules can be of any type (e.g., IgG, IgE, IgM, IgD, IgA and IgY), class (e.g., IgG1, IgG2, IgG3, IgG4, IgA1 and IgA2) or subclass.

Antibodies of the present invention also encompass antibodies that have half-lives (e.g., serum half-lives) in a mammal, (e.g., a human), of greater than 5 days, greater than 10 days, greater than 15 days, greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention in a mammal, (e.g., a human), results in a higher serum titer of said antibodies or antibody fragments in the mammal, and thus, reduces the frequency of the administration of said antibodies or antibody fragments and/or reduces the concentration of said antibodies or antibody fragments to be administered. Antibodies having increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S. Patent Publication No. 2003/0190311 and discussed in more detail below).

In one embodiment, the antibodies of the invention may comprise modifications/substations and/or novel amino acids within their Fc domains such as, for example, those disclosed in Ghetie et al., 1997, Nat. Biotech. 15:637-40; Duncan et al, 1988, Nature 332:563-564; Lund et al., 1991, J. Immunol. 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al., 2000, J Immunol 164:4178-4184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; U.S. patent application Ser. No. 10/370,749 and PCT Publications WO 94/2935; WO 99/58572; WO 00/42072; WO 02/060919, WO 04/029207. Other modifications/substitutions of the Fc domain will be readily apparent to one skilled in the art.

Antibodies of the invention comprising modifications/substations and/or novel amino acid residues in their Fc regions can be generated by numerous methods well known to one skilled in the art. Non-limiting examples include, isolating antibody coding regions (e.g., from hybridoma) and making one or more desired substitutions in the Fc region of the isolated antibody coding region. Alternatively, the variable regions of an antibody of the invention may be subcloned into a vector encoding an Fc region comprising one or modifications/substations and/or novel amino acid residues.

Antibodies of the invention may also be modified to alter glycosylation, again to alter one or more functional properties of the antibody.

In one embodiment, the glycosylation of the antibodies of the invention is modified. For example, an aglycosylated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714, 350 and 6,350,861.

Additionally or alternatively, an antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176, 195; PCT Publications WO 03/035835; WO 99/54342.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from binding an HMG1 and/or HMG2 polypeptide or fragment thereof and/or generating a desired response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids. See below, Section 5.5 entitled "Antibody Derivitives and Conjugates."

Antibodies of the present invention may also be described or specified in terms of their cross-reactivity. Antibodies that do not bind any other analog, ortholog, or homolog of a polypeptide of the present invention are included. Antibodies that bind polypeptides (and polypeptide fragments) with at least 95%, at least 90%, at least 85%, at least 80%, at least 75%, at least 70%, at least 65%, at least 60%, at least 55%, and at least 50% identity (as calculated using methods known in the art and described herein) to a human HMG1 polypeptide (e.g., a human HMG1 A box or B box) of the present invention are also included in the present invention. In specific embodiments, antibodies of the present invention cross-react with murine, rat and/or rabbit homologs of human HMG1 proteins and the corresponding epitopes thereof. Also encompassed by the present invention are antibodies that bind polypeptides (and polypeptide fragments) with at least 95%, at least 90%, at least 85%, at least 80%, at least 75%, at least 70%, at least 65%, at least 60%, at least 55%, and at least 50% identity (as calculated using methods known in the art and described herein) to a human HMG2 polypeptide (e.g., a human HMG2 A box or B box). It is further contemplated that antibodies that bind to a human HMG2 polypeptide or fragment thereof may cross-react with murine, rat and/or rabbit homologs of human HMG1 proteins and the corresponding epitopes thereof.

Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to an HMG1 and/or HMG2 polypeptide of the present invention are also included in the present invention.

In one embodiment, antibodies or fragments thereof that specifically bind to an HMG1 polypeptide or fragment thereof prevent/antagonize/inhibit one or more of the following: HMGB1 binding to RAGE, HMGB1 binding to one or more pattern recognition receptor/molecules (also referred to herein as "PRMs") (e.g., Toll-like receptor, TLR2 and TLR4)), HMGB1 binding to a PAMP (e.g., LPS, CpG), HMGB1 binding to a cell surface (e.g., a THP-1 cell), HMG1-mediated release of proinflammatory cytokines, HMG1-mediated inflammation, HMG1-mediated sepsis, HMG1-mediated inflammation (e.g., of joints), and HMG1-mediated arthritis. These activities may be assayed by one or many known methods in the art. See, e.g., U.S.20040005316, U.S. Pat. No. 6,468,533 and U.S. Pat. No. 6,448,223, and Section 6 entitled "Examples" infra.

The term "inhibitory concentration 50%" (abbreviated as "$IC_{50}$") represents the concentration of an inhibitor (e.g., an antibody of the invention) that is required for 50% inhibition of a given activity of the molecule the inhibitor targets (e.g., HMG1). It will be understood by one in the art that a lower $IC_{50}$ value corresponds to a more potent inhibitor. In one embodiment, the antibodies of the invention inhibit HMG1-mediated release of proinflammatory cytokines with an $IC_{50}$ of less than 5000 ng/ml, or of less than 4000 ng/ml, or of less than 3000 ng/ml, or of less than 2000 ng/ml, or of less than 1000 ng/ml, or of less than 500 ng/ml, or of less than 250 ng/ml, or of less than 100 ng/ml, or of less than 50 ng/ml, or of less than 10 ng/ml, or of less than 5 ng/ml. In another embodiment, the antibodies of the invention inhibit HMG1-mediated release of proinflammatory cytokines with an $IC_{50}$ of less than 1000 nM, or of less than 500 nM, or of less than 250 nM, or of less than 100 nM, or of less than 50 nM, or of less than 25 nM, or of less than 10 nM, or of less than 5 nM, or of less than 0.25 nM, or of less than 0.1 nM, or of less than 0.01 nM.

In one embodiment, the antibodies of the invention prevent/antagonize/inhibit the binding of HMG1 to RAGE, but does not substantially affect the binding of HMG1 to one or more PRMs (e.g., Toll-like receptors, TLR2 and TLR4) and/or the binding of HMG1 to one or more PAMP (e.g., LPS, CpG). In another embodiment, the antibodies of the invention prevent/antagonize/inhibit the binding of HMG1 to one or more PRMs (e.g., Toll-like receptors, TLR2 and TLR4) and/or the binding of HMG1 to one or more PAMP (e.g., LPS, CpG), but does not substantially affect the binding of HMG1 to RAGE. In still another embodiment, the antibodies of the invention prevent/antagonize/inhibit the binding of HMG1 to RAGE and inhibit the binding of HMG1 to one or more PRMs (e.g., Toll-like receptors, TLR2 and TLR4) and/or the binding of HMG1 to one or more PAMP (e.g., LPS, CpG). These activities may be assayed by one or many known methods in the art. See, e.g., US20040005316, U.S. Pat. No. 6,468,533 and U.S. Pat. No. 6,448,223, and the section entitled "Examples" infra.

In a specific embodiment, the antibodies of the invention inhibit the binding of HMG1 to RAGE by at least about 10%, or by at least about 20%, or by at least about 30%, or by at least about 40%, or by at least about 50%, or by at least about 60%, or by at least about 70%, or by at least about 80%, or by at least about 90%, or by about 100%. In another specific embodiment, the antibodies of the invention inhibit the binding of HMG1 to one or more PRMs (e.g., Toll-like receptors, TLR2 and TLR4) by at least 10%, or by at least 20%, or by at least 30%, or by at least 40%, or by at least 50%, or by at least 60%, or by at least 70%, or by at least 80%, or by at least 90%, or by 100%. In a specific embodiment, the antibodies of the invention inhibit the binding of HMG1 to one or more PAMP (e.g., LPS, CpG) by at least about 10%, or by at least about 20%, or by at least about 30%, or by at least about 40%, or by at least about 50%, or by at least about 60%, or by at least about 70%, or by at least about 80%, or by at least about 90%, or by about 100%. In another specific embodiment, the antibodies of the invention inhibit the binding of HMG1 to RAGE by at least 10%, or by at least 20%, or by at least 30%, or by at least 40%, or by at least 50%, or by at least 60%, or by at least 70%, or by at least 80%, or by at least 90%, or by 100%. In another specific embodiment, the antibodies of the invention inhibit the binding of HMG1 to one or more PRMs (e.g., Toll-like receptors., TLR2 and TLR4) by at least 10%, or by at least 20%, or by at least 30%, or by at least 40%, or by at least 50%, or by at least 60%, or by at least 70%, or by at least 80%, or by at least 90%, or by 100%. In still another a specific embodiment, the antibodies of the invention inhibit the binding of HMG1 to one or more PAMP (e.g., LPS, CpG) by at least 10%, or by at least 20%, or by at least 30%, or by at least 40%, or by at least 50%, or by at least 60%, or by at least 70%, or by at least 80%, or by at least 90%, or by 100%.

In one embodiment, antibodies of the invention inhibit the HMG1 mediated enhancement of one or more proinflammatory factors. In specific embodiments, the proinflammatory factors are PAMPs including, but not limited to, TLR ligands (e.g., LPS, dsRNA, Poly (I:C), imiquinod, R-848, CpG, PAM3-CSK4, Flagellin, zymosan, peptidoglycan, lipoteicholic acids, etc.). In another embodiment, antibodies of the invention inhibit the HMG1 mediated enhancement of pattern-recognition receptor signaling stimulated by one or more PAMP. In a specific embodiment, antibodies of the invention inhibit the HMG1 mediated enhancement of TLR signaling stimulated by one or more TLR ligands. In additional specific embodiments, TLR signaling is mediated by one or more TLR including, but not limited to, TLR1, TLR2, TLR3, TLR4, TLR5, TLR6, TLR7, TLR8, TLR9 and heterodimers of TLRs, such as, TLR6:TLR2 and TLR2:TLR1. Specific methods to determine the affect of antibodies on HMG1 mediated enhancement of one or more proinflammatory factors, TLR ligands in particular, are disclosed herein (see Examples 13 and 14, infra).

As demonstrated herein, antibodies may discriminate between the same polypeptide isolated from different sources. Without wishing to be bound by any particular theory, a polypeptide of similar or identical amino acid sequence isolated from different sources may be distinguished by a number of differences including but not limited to, posttranslational modifications (e.g., phosphorylation, acetylation, methylation, glycosylation, etc.), alterations in overall structure (e.g., changes in disulfide bonding and/or folding) and differences in any other molecules that the polypeptide may be associated with (e.g., salts, additional subunits such as polynucleotides and/or other polypeptides). In one embodiment, the antibodies of the invention specifically bind HMG1 recombinantly produced in E. coli with the same or higher affinity than native HMG1 (e.g., isolated from a mammalian cell or tissue). In another embodiment, the antibodies of the invention bind native HMG1 (e.g., isolated from a mammalian cell or tissue) with the same or higher affinity than recombinant HMG1 produced in E. coli. In still another embodiment, the antibodies of the invention will bind one or more forms of native HMG1 including, but not limited to, nuclear HMG1 (e.g., isolated from cells by freeze thaw), released HMG1 (e.g., isolated from the supernatant of necrotic cells) and activated HMG1 (e.g., isolated from stimulated cells, such as LPS stimulated cells). In yet another embodiment, the antibodies of the invention will not bind one or more forms of native HMG1 including, but not limited to, nuclear HMG1 (e.g., isolated from cells by freeze thaw), released HMG1 (e.g., isolated from the sup ematant of necrotic cells) and activated HMG1 (e.g., isolated from stimulated cells, such as LPS stimulated cells). Specific methods for obtaining native and recombinant HMG1 are disclosed herein (see Example 2, infra).

In one embodiment, the antibodies of the invention specifically bind to soluble HMG1 and/or HMG2. In another embodiment, the antibodies of the invention specifically bind to immobilized HMG1 and/or HMG2. In still another embodiment, the antibodies of the invention specifically bind to both soluble and insoluble HMG1 and/or HMG2.

As described above, HMG1 and HMG2 are known polynucleotide (i.e. DNA and RNA) binding proteins. In one embodiment, the antibodies of the invention bind to HMG1 and/or HMG2 wherein said HMG1 and/or HMG2 is bound to a polynucleotide molecule. In another embodiment, the antibodies of the invention prevent/antagonize/inhibit one or more of the following: HMGB1 binding to RAGE, HMGB1 binding to one or more PRM (e.g., a Toll-like receptor, TLR2 and TLR4) or PAMP (e.g., LPS), HMGB1 binding to a cell surface (e.g., a THP-1 cell), HMG1-mediated release of proinflammatory cytokines, HMG1-mediated inflammation, HMG1-mediated sepsis, HMG1-mediated inflammation (e.g., of joints), and HMG 1-mediated arthritis, wherein said HMG1 is bound to a polynucleotide. In specific embodiments, the polynucleotide molecule is one that promotes an inflammatory response (e.g., a polynucleotide derived from a microorganism or a necrotic cell).

In a specific embodiment, the antibodies of the invention bind acetylated HMG1 with a higher affinity than non-acetylated HMG1. In another specific embodiment, the antibodies of the invention bind non-acetylated. HMG1 with a higher affinity than acetylated HMG1. In still another specific embodiment, the antibodies of the invention prevent bind both acetylated and non-acetylated HMG1 with substantially the same affinity.

In another embodiment, the high affinity antibodies of the invention specifically bind a polypeptide comprising, or alternatively consisting of (or consisting essentially of) an HMG1 polypeptide or an antigenic fragment thereof of a human or other animal, e.g., mammals and invertebrates. In a specific embodiment, the high affinity antibodies of the present invention specifically bind a polypeptide comprising, or alternatively consisting of (or consisting essentially of) a human HMG1 polypeptide (SEQ ID NO:1 or 2). HMG1 polypeptides of human and other animals are well known in the art (see, e.g., US20040005316, U.S. Pat. No. 6,468,533 and U.S. Pat. No. 6,448,223).

In a embodiment, the high affinity antibodies of the invention specifically bind a polypeptide comprising, or alternatively consisting of (or consisting essentially of) an HMG1 polypeptide having at least 60% identity, or at least 70% identity, or at least 80% identity, at least 85% identity, at least 90% identity, at least 95% identity, or at least at least 97% identity, or at least 99% identity, or 100% identity to the human HMG1 polypeptide of SEQ ID NO: 1 or 2.

In another embodiment, the high affinity antibodies of the present invention specifically bind a polypeptide comprising, or alternatively consisting of (or consisting essentially of) a polypeptide having at least 60% identity, or at least 70% identity, or at least 80% identity, or at least 85% identity, or at least 90% identity, or at least 95% identity, or at least at least 97% identity, or at least 99% identity, or 100% identity to the human HMG1 A box polypeptide of SEQ ID NO:3.

In yet another embodiment, the high affinity antibodies of the present invention specifically bind a polypeptide comprising, or alternatively consisting of (or consisting essentially of) a polypeptide having at least 60% identity, or at least 70% identity, or at least 80% identity, or at least 85% identity, or at least 90% identity, or at least 95% identity, or at least at least 97% identity, or at least 99% identity, or 100% identity to the human HMG1 B box polypeptide of SEQ ID NO:4 and/or SEQ ID NO: 28 and/or SEQ ID NO:29.

In another embodiment, the high affinity antibodies of the invention specifically bind a polypeptide comprising, or alternatively consisting of (or consisting essentially of) an HMG2 polypeptide or an antigenic fragment thereof of a human or other animal, e.g., mammals and invertebrates. In a specific embodiment, the high affinity antibodies of the present invention specifically bind a polypeptide comprising, or alternatively consisting of (or consisting essentially of) a human HMG2 polypeptide (SEQ ID NO:21). HMG2 polypeptides of human and other animals are well known in the art. See, e.g., Jantzen et al., 1990, *Nature* 344:830-6; Kolodrubetz 1990, *Nucleic Acids Res.* 18:5565; Laudet et al., 1993, *Nucleic Acids Res.* 21:2493-501 and Thomas et al., 2001, *Trends Biochem Sci.* 26:167-74.

In one embodiment, the high affinity antibodies of the invention specifically bind a polypeptide comprising, or alternatively consisting of (or consisting essentially of) an HMG2 polypeptide having at least 60% identity, or at least 70% identity, or at least 80% identity, at least 85% identity, at least 90% identity, at least 95% identity, or at least at least 97% identity, or at least 99% identity, or 100% identity to the human HMG2 polypeptide of SEQ ID NO:21.

In another embodiment, the high affinity antibodies of the present invention specifically bind a polypeptide comprising, or alternatively consisting of (or consisting essentially of) a polypeptide having at least 60% identity, or at least 70% identity, or at least 80% identity, or at least 85% identity, or at least 90% identity, or at least 95% identity, or at least at least 97% identity, or at least 99% identity, or 100% identity to the human HMG2 A box polypeptide of SEQ ID NO:22.

In yet another embodiment, the high affinity antibodies of the present invention specifically bind a polypeptide comprising, or alternatively consisting of (or consisting essentially of) a polypeptide having at least 60% identity, or at least 70% identity, or at least 80% identity, or at least 85% identity, or at least 90% identity, or at least 95% identity, or at least at least 97% identity, or at least 99% identity, or 100% identity to the human HMG2 B box polypeptide of SEQ ID NO:23.

The percent identity of two amino acid sequences (or two nucleic acid sequences) can be determined, for example, by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=# of identical positions/total # of positions×100). The actual comparison of the two sequences can be accomplished by well-known methods, for example, using a mathematical algorithm. A specific, non-limiting example of such a mathematical algorithm is described in Karlin et al., Proc. Natl. Acad. Sci. USA, 90:5873-5877 (1993). Such an algorithm is incorporated into the BLASTN and BLASTX programs (version 2.2) as described in Schaffer et al., Nucleic Acids Res., 29:2994-3005 (2001). When utilizing BLAST and Gapped BLAST programs, the default parameters of the respective programs (e.g., BLASTN) can be used. See http://www.ncbi.nlm.nih.gov, as available on Apr. 10, 2002. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Another, non-limiting example of a mathematical algorithm utilized for the comparison of sequences is the algorithm of Myers and Miller, CABIOS (1989). Such an algorithm is incorporated into the ALIGN program (version 2.0), which is part of the GCG (Accelrys) sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, Comput. Appl. Biosci., 10: 3-5 (1994); and FASTA described in Pearson and Lipman, Proc. Natl. Acad. Sci. USA, 85: 2444-8 (1988).

In another embodiment, the percent identity between two amino acid sequences can be accomplished using the GAP program in the GCG software package (available at http://www.accelrys.com, as available on Aug. 31, 2001) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package (available at http://www.cgc.com), using a gap weight of 50 and a length weight of 3.

Another embodiment of present invention are antibodies that specifically bind HMG1 and antigenic fragments thereof with a dissociation constant or $K_d$ ($k_{off}/k_{on}$) of less than $10^{-5}$ M, or of less than $10^{-6}$ M, or of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than $10^{-13}$ M, or of less than $5\times10^{-13}$M, or of less than $10^{-14}$M, less than $5\times10^{-14}$M, or of less than $10^{-15}$M, or of less than $5\times10^{-15}$M. In still another embodiment, an antibody of the invention that specifically binds HMG1 and antigenic fragments thereof has a dissociation constant or $K_d$ ($k_{off}/k_{on}$) of between about $10^{-7}$M and about $10^{-8}$M, between about $10^{-8}$M and about $10^{-9}$M, between about $10^{-9}$M and about $10^{-10}$M, between about $10^{-11}$M and about $10^{-11}$M, between about $10^{-11}$M and about $10^{-12}$M, between about $10^{-12}$M and about $10^{-13}$M, between about $10^{-13}$M and about $10^{-14}$M. In still another embodiment, an antibody of the invention that specifically binds HMG1 and antigenic fragments thereof has a dissociation constant or $K_d$ ($k_{off}/k_{on}$) of between $10^{-7}$M and $10^{-8}$M, between $10^{-8}$M and $10^{-9}$M, between $10^{-9}$M and $10^{-10}$M, between $10^{-10}$M and $10^{-11}$M, between $10^{-11}$M and $10^{-12}$M, between $10^{-12}$M and $10^{-13}$M, between $10^{-13}$M and $10^{-14}$M.

Another embodiment of present invention are antibodies that specifically bind HMG2 and antigenic fragments thereof with a dissociation constant or $K_d$ ($k_{off}/k_{on}$) of less than $10^{-5}$ M, or of less than $10^{-6}$ M, or of less than $10^{-7}$ M, or of less than $10^{-8}$ M, or of less than $10^{-9}$ M, or of less than $10^{-10}$ M, or of less than $10^{11}$ M, or of less than $10^{-12}$ M, or of less than $10^{-13}$ M, or of less than $5 \times 10^{-13}$M, or of less than $10^{-14}$M, less than $5 \times 10^{-14}$M, or of less than $10^{-15}$M, or of less than $5 \times 10^{-15}$M. In still another embodiment, an antibody of the invention that specifically binds HMG2 and antigenic fragments thereof has a dissociation constant or $K_d$ ($k_{off}/k_{on}$) of between about $10^{-7}$M and about $10^{-8}$M, between about $10^{-8}$M and about $10^{-9}$M, between about $10^{-9}$M and about $10^{-10}$M, between about $10^{10}$M and about $10^{-11}$M, between about $10^{-11}$M and about $10^{-12}$M, between about $10^{-12}$M and about $10^{-13}$M, between about $10^{-13}$M and about $10^{-14}$M. In still another embodiment, an antibody of the invention that specifically binds HMG2 and antigenic fragments thereof has a dissociation constant or $K_d$ ($k_{off}/k_{on}$) of between $10^{-7}$M and $10^{-8}$M, between $10^{-8}$M and $10^{-9}$M, between $10^{-9}$M and $10^{-10}$M, between $10^{-10}$M and $10^{-11}$M, between $10^{-11}$M and $10^{-12}$M, between $10^{-12}$M and $10$-$13$M, between $10^{-13}$M and $10^{-14}$M.

It is well known in the art that the equilibrium dissociation constant ($K_d$) is defined as $k_{off}/k_{on}$. It is generally understood that a binding molecule (e.g., and antibody) with a low $K_d$ (i.e., high affinity) is preferable to a binding molecule (e.g., and antibody) with a high $K_d$ (i.e., low affinity). However, in some instances the value of the $k_{on}$ or $k_{off}$ may be more relevant than the value of the $K_d$. One skilled in the art can determine which kinetic parameter is most important for a given antibody application. In certain embodiments, the antibodies of the invention have a lower $K_d$ for one antigen than for others.

In another embodiment, the antibody binds to HMG1 and antigenic fragments thereof with a $k_{off}$ of less than $1 \times 10^{-3}$ s$^{-1}$, or of less than $3 \times 10^{-3}$ s$^{-1}$. In other embodiments, the antibody binds to HMG1 and antigenic fragments thereof with a $k_{off}$ of less than $10^{-3}$ s$^{-1}$, less than $5 \times 10^{-3}$ s$^{-1}$, less than $10^{-4}$ s$^{-1}$, less than $5 \times 10^{-4}$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$, less than $10^{-7}$ s$^{-1}$, less than $5 \times 10^{-7}$ s$^{-1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$, or less than $10^{-10}$ s$^{-1}$.

In another embodiment, the antibody binds to HMG2 and antigenic fragments thereof with a $k_{off}$ of less than $1 \times 10^{-3}$ s$^{-1}$, or of less than $3 \times 10^{-3}$ s$^{-1}$. In other embodiments, the antibody binds to HMG2 and antigenic fragments thereof with a $K_{off}$ of less than $10^{-3}$ s$^{-1}$, less than $5 \times 10^{-3}$ s$^{-1}$, less than $10^{-4}$ s$^{-1}$, less than $5 \times 10^{-4}$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$, less than $10^{-7}$ s$^{-1}$, less than $5 \times 10^{-7}$ s$^{1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$, or less than $10^{-10}$ s$^{-1}$.

In another embodiment, the antibody of the invention binds to HMG1 and/or antigenic fragments thereof with an association rate constant or $k_{on}$ rate of at least $10^5$ M$^{-1}$s$^{-1}$, at least $5 \times 10^5$ M$^{-1}$s$^{-1}$, at least $10^6$ M$^{-1}$s$^{-1}$, at least $5 \times 10^6$ M$^{-1}$s$^{-1}$, at least $10^7$ M$^{-1}$s$^{-1}$, at least $5 \times 10^7$ M$^{-1}$s$^{-1}$, or at least $10^8$ M$^{-1}$s$^{-1}$, or at least $10^9$ M$^{-1}$s$^{-1}$.

In another embodiment, the antibody of the invention binds to HMG2 and/or antigenic fragments thereof with an association rate constant or $k_{on}$ rate of at least $10^5$ M$^{-1}$ s$^{-1}$, at least $5 \times 10^5$ M$^{-1}$s$^{-1}$, at least $10^6$ M$^{-1}$s$^{-1}$, at least $5 \times 10^6$ M$^{-1}$s$^{-1}$, at least $10^7$ M$^{-1}$s$^{-1}$, at least $5 \times 10^7$ M$^{-1}$s$^{-1}$, or at least $10^8$ M$^{-1}$s$^{-1}$, or at least $10^9$ M$^{-1}$s$^{-1}$.

Antibodies like all polypeptides have an Isoelectric Point (pI), which is generally defined as the pH at which a polypeptide carries no net charge. It is known in the art that protein solubility is typically lowest when the pH of the solution is equal to the isoelectric point (pI) of the protein. As used herein the pI value is defined as the pI of the predominant charge form. The pI of a protein may be determined by a variety of methods including but not limited to, isoelectric focusing and various computer algorithms (see, e.g., Bjellqvist et al., 1993, *Electrophoresis* 14:1023). In addition, the thermal melting temperatures (Tm) of the Fab domain of an antibody, can be a good indicator of the thermal stability of an antibody and may further provide an indication of the shelf-life. A lower Tm indicates more aggregation/less stability, whereas a higher Tm indicates less aggregation/more stability. Thus, in certain embodiments antibodies having higher Tm are preferable. Tm of a protein domain (e.g., a Fab domain) can be measured using any standard method known in the art, for example, by differential scanning calorimetry (see, e.g., Vermeer et al., 2000, *Biophys. J.* 78:394-404; Vermeer et al., 2000, *Biophys. J.* 79: 2150-2154).

Accordingly, an additional nonexclusive embodiment of the present invention includes high affinity antibodies of the invention that have certain preferred biochemical characteristics such as a particular isoelectric point (pI) or melting temperature (Tm).

More specifically, in one embodiment, the high affinity antibodies of the present invention have a pI ranging from 5.5 to 9.5. In still another specific embodiment, the high affinity antibodies of the present invention have a pI that ranges from about 5.5 to about 6.0, or about 6.0 to about 6.5, or about 6.5 to about 7.0, or about 7.0 to about 7.5, or about 7.5 to about 8.0, or about 8.0 to about 8.5, or about 8.5 to about 9.0, or about 9.0 to about 9.5. In other specific embodiments, the high affinity antibodies of the present invention have a pI that ranges from 5.5-6.0, or 6.0 to 6.5, or 6.5 to 7.0, or 7.0-7.5, or 7.5-8.0, or 8.0-8.5, or 8.5-9.0, or 9.0-9.5. Even more specifically, the high affinity antibodies of the present invention have a pI of at least 5.5, or at least 6.0, or at least 6.3, or at least 6.5, or at least 6.7, or at least 6.9, or at least 7.1, or at least 7.3, or at least 7.5, or at least 7.7, or at least 7.9, or at least 8.1, or at least 8.3, or at least 8.5, or at least 8.7, or at least 8.9, or at least 9.1, or at least 9.3, or at least 9.5. In other specific embodiments, the high affinity antibodies of the present invention have a pI of at least about 5.5, or at least about 6.0, or at least about 6.3, or at least about 6.5, or at least about 6.7, or at least about 6.9, or at least about 7.1, or at least about 7.3, or at least about 7.5, or at least about 7.7, or at least about 7.9, or at least about 8.1, or at least about 8.3, or at least about 8.5, or at least about 8.7, or at least about 8.9, or at least about 9.1, or at least about 9.3, or at least about 9.5.

It is possible to optimize solubility by altering the number and location of ionizable residues in the antibody to adjust the pI. For example the pI of a polypeptide can be manipulated by making the appropriate amino acid substitutions (e.g., by substituting a charged amino acid such as a lysine, for an uncharged residue such as alanine). Without wishing to be bound by any particular theory, amino acid substitutions of an antibody that result in changes of the pI of said antibody may improve solubility and/or the stability of the antibody. One skilled in the art would understand which amino acid substitutions would be most appropriate for a particular antibody to achieve a desired pI. In one embodiment, a substitution is generated in an antibody of the invention to alter the pI. It is specifically contemplated that the substitution(s) of the Fe region that result in altered binding to FcγR (described supra) may also result in a change in the pI. In another embodiment, substitution(s) of the Fc region are specifically chosen to effect both the desired alteration in FcγR binding and any desired change in pI.

In one embodiment, the high affinity antibodies of the present invention have a Tm ranging from 65° C. to 120° C. In specific embodiments, the high affinity antibodies of the present invention have a Tm ranging from about 75° C. to about 120° C., or about 75° C. to about 85° C., or about 85° C. to about 95° C., or about 95° C. to about 105° C., or about 105° C. to about 115° C., or about 115° C. to about 120° C. In other specific embodiments, the high affinity antibodies of the present invention have a Tm ranging from 75° C. to 120° C., or 75° C. to 85° C., or 85° C. to 95° C., or 95° C. to 105° C., or 105° C. to 115° C., or 115° C. to 120° C. In still other specific embodiments, the high affinity antibodies of the present invention have a Tm of at least about 65° C., or at least about 70° C., or at least about 75° C., or at least about 80° C., or at least about 85° C., or at least about 90° C., or at least about 95° C., or at least about 100° C., or at least about 105° C., or at least about 110° C., or at least about 115° C., or at least about 120° C. In yet other specific embodiments, the high affinity antibodies of the present invention have a Tm of at least 65° C., or at least 70° C., or at least 75° C., or at least 80° C., or at least 85° C., or at least 90° C., or at least 95° C., or at least 100° C., or at least 105° C., or at least 110° C., or at least 115° C., or at least 120° C.

In a specific embodiment, the high affinity antibodies of the invention or fragments thereof are human or humanized antibodies.

In one embodiment, the invention also includes particular antibodies (and fragments thereof) that specifically bind HMG1 with high affinity. In particular are the anti-HMG1 antibodies referred to here as "S2", "S6", "S16" and "G4" which have been deposited with the American Type Culture Collection (ATCC, 10801 University Boulevard, Manassas, Va. 20110-2209) and assigned ATCC Deposit Nos. PTA-6142, PTA-6143, PTA-6259 and PTA-6258, respectively. These deposits will be maintained under the terms of the Budapest Treaty on the International Recognition of the Deposit of Microorganisms for the Purposes of Patent Procedure. Since the strain referred to is being maintained under the terms of the Budapest Treaty, it will be made available to a patent office signatory to the Budapest Treaty.

In another embodiment, the invention includes antibodies that specifically bind HMG1 and/or HMG2 which comprise one or more of the variable regions disclosed herein (see FIG. 2A-J, SEQ ID NOS.: 5-20, 24-27 and 30-73).

The present invention also encompasses variants of G2, G4, G9, G12, G16, G20, G34, G35, S2, S6, S10, S12, S14, S16, S17 and E11 (see FIG. 2A-J, SEQ ID NOS.: 5-20, 24-27 and 30-73) comprising one or more amino acid residue substitutions in the variable light ($V_L$) domain and/or variable heavy ($V_H$) domain. The present invention also encompasses variants of G2, G4, G9, G12, G16, G20, G34, G35, S2, S6, S10, S12, S14, S16, S17 and E11 (see FIG. 2A-J, SEQ ID NOS.: 5-20, 24-27 and 30-73) with one or more additional amino acid residue substitutions in one or more $V_L$ CDRs and/or one or more $V_H$ CDRs. The antibody generated by introducing substitutions in the $V_H$ domain, $V_H$ CDRs, $V_L$ domain and/or $V_L$ CDRs of G2, G4, G9, G12, G16, G20, G34, G35, S2, S6, S10, S12, S14, S16, S17 and E11 (see FIG. 2A-J, SEQ ID NOS.: 5-20, 24-27 and 30-73) can be tested in vitro and in vivo, for example, for its ability to bind to HMG1 and/or HMG2 (by, e.g., immunoassays including, but not limited to ELISAs and BIAcore), or for its ability to inhibit HMG1-induced cytokine release, prevent, treat, manage or ameliorate inflammatory disease or one or more symptoms thereof.

It will be understood that the complementarity determining regions (CDRs) residue numbers referred to herein are those of Kabat et al. (1991, NIH Publication 91-3242, National Technical Information Service, Springfield, Va.). Specifically, residues 24-34 (CDR1), 50-56 (CDR2) and 89-97 (CDR3) in the light chain variable domain and 31-35 (CDR1), 50-65 (CDR2) and 95-102 (CDR3) in the heavy chain variable domain. Note that CDRs vary considerably from antibody to antibody (and by definition will not exhibit homology with the Kabat consensus sequences). Maximal alignment of framework residues frequently requires the insertion of "spacer" residues in the numbering system, to be used for the Fv region. It will be understood that the CDRs referred to herein are those of Kabat et al. supra. In addition, the identity of certain individual residues at any given Kabat site number may vary from antibody chain to antibody chain due to interspecies or allelic divergence.

In other embodiments, the invention includes antibodies having least one, at least two, at least three, at least four, at least five, or at least six of the CDRs disclosed herein (see, e.g., FIG. 2A-J, CDRs indicated by underline). In still other embodiments, the present invention encompasses an antibody that specifically binds HMG1 and/or HMG2 comprising a $V_H$ CDR having the amino acid sequence of any of the $V_H$ CDRs listed in Table 4 and/or derived from the heavy chain variable region of any of the antibody heavy chain variable regions listed in Table 4. In another specific embodiment, the present invention encompasses an antibody that specifically binds HMG1 and/or HMG2 comprising a $V_L$ CDR having the amino acid sequence of any of the $V_L$ CDRs listed in Table 4 and/or derived from the light chain variable region of any of the antibody light chain variable regions listed in Table 4.

The present invention encompasses antibodies that specifically bind to HMG1 and/or HMG2, comprising derivatives of the $V_H$ domains, $V_H$ CDRs, $V_L$ domains, or $V_L$ CDRs described herein that specifically bind to HMG1 and/or HMG2. Standard techniques known to those of skill in the art can be used to introduce mutations (e.g., additions, deletions, and/or substitutions) in the nucleotide sequence encoding an antibody of the invention, including, for example, site-directed mutagenesis and PCR-mediated mutagenesis are routinely used to generate amino acid substitutions. In one embodiment, the $V_H$ and/or $V_L$ CDRs derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions in the relative to the original $V_H$ and/or $V_L$ CDRs. In another embodiment, the $V_H$ and/or $V_L$ CDRs derivatives have conservative amino acid substitutions (e.g. supra) are made at one or more predicted non-essential amino acid residues (i.e., amino acid residues which are not critical for the antibody to specifically bind to HMG1 and/or HMG2). Alternatively, mutations can be introduced randomly along all or part of the $V_H$ and/or $V_L$ CDR coding sequence, such as by saturation mutagenesis, and the resultant mutants can be screened for biological activity to identify mutants that retain activity. Following mutagenesis, the encoded antibody can be expressed and the activity of the antibody can be determined.

The present invention also encompasses antibodies that specifically bind to HMG1 and/or HMG2 or a fragment thereof, said antibodies comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of G2, G4, G9, G12, G16, G20, G34, G35, S2, S6, S10, S12, S14, S16, S17 and E11 (see FIG. 2A-J, SEQ ID NOS.: 5-20, 24-27 and 30-73). The present invention also encompasses antibodies that specifically bind to HMG1 and/or HMG2 or a fragment thereof, said antibodies comprising an amino acid sequence of a variable heavy chain and/or variable light chain that is at least about 45%, at least about 50%, at least about 55%, at least about 60%, at least about 65%, at least about 70%, at least about 75%, at least about 80%, at least about 85%, at least about 90%, at least about 95%, or at least about 99% identical to the amino acid sequence of the variable heavy chain and/or light chain of G2, G4, G9, G12, G16, G20, G34, G35, S2, S6, S10, S12, S14, S16, S17 and E11 (see FIG. 2A-J, SEQ ID NOS.: 5-20, 24-27 and 30-73).

The present invention further encompasses antibodies that specifically bind to HMG1 and/or HMG2 or a fragment thereof, said antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of G2, G4, G9, G12, G16, G20, G34, G35, S2, S6, S10, S12, S14, S16, S17 and E11 (see FIG. 2A-J, SEQ ID NOS.: 5-20, 24-27 and 30-73). The present invention further encompasses antibodies that specifically bind to HMG1 and/or HMG2 or a fragment thereof, said antibodies or antibody fragments comprising an amino acid sequence of one or more CDRs that is at least about 45%, at least about 50%, at least about 55%, at least about 60%, at least about 65%, at least about 70%, at least about 75%, at least about 80%, at least about 85%, at least about 90%, at least about 95%, or at least about 99% identical to the amino acid sequence of one or more CDRs of G2, G4, G9, G12, G16, G20, G34, G35, S2, S6, S10, S12, S14, S16, S17 and E11 (see FIG. 2A-J, SEQ ID NOS.: 5-20, 24-27 and 30-73). The determination of percent identity of two amino acid sequences can be determined by any method known to one skilled in the art, including BLAST protein searches.

The present invention also encompasses antibodies that specifically bind to HMG1 and/or HMG2 or fragments thereof, where said antibodies are encoded by a nucleotide sequence that hybridizes to the nucleotide sequence of G2, G4, G9, G12, G16, G20, G34, G35, S2, S6, S10, S12, S14, S16, S17 and E11 (see FIG. 2A-J, SEQ ID NOS.: 5-20, 24-27 and 30-73) under stringent conditions. In another embodiment, the invention encompasses antibodies that specifically bind to HMG1 and/or HMG2 or a fragment thereof, said antibodies comprising one or more CDRs encoded by a nucleotide sequence that hybridizes under stringent conditions to the nucleotide sequence of one or more CDRs of G2, G4, G9, G12, G16, G20, G34, G35, S2, S6, S10, S12, S14, S16, S17 and E11 (see FIG. 2A-J, SEQ ID NOS.: 5-20, 24-27 and 30-73). Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

Antibodies having at least one, at least two, at least three, at least four, at least five, or all six of the CDRs of the deposited antibodies are specific embodiments of the invention. Isolated polynucleotides that encode these antibodies (and fragments thereof) are also specific embodiments of the invention. The binding and functional characteristics for "S2", "S4", "S16" and "G4" as well as several other specific anti-HMG1 antibodies of the invention are listed in Table 1.

TABLE 1

Characteristics and Deposit Information for anti-HMG1 antibodies[a]

| IgG | ATCC # | $K_d$ (nM)[b] | Competes for HMG1 Binding[b] | PI[c] | Tm[d] | Binds Native HMG1[e] | | | Binds to HMG2[e] | In vitro Inhibition of HMG1[f] | | | |
|---|---|---|---|---|---|---|---|---|---|---|---|---|---|
| | | | | | | Nuclear | Released | Activated | | Rage Binding | mMØ activation | TLR4 Activation | Thp-1 Binding |
| G2 | | 101 | | 7.78 | 67.1 | − | − | | − | + | + | − | 73.30 |
| G4 | PTA-6258 | 30 | G9, S2, S6 | 8.12 | 72.1 | ++ | ++ | ++ | − | + | +/− | − | |
| G9 | | 125 | | 9.01 | 77.9 | | | | − | − | | | |
| G12 | | 73 | | 8.6 | 78.8 | | | | − | − | | | |
| G16 | | 22 | | | | | | | − | | | | |
| G20 | | 114 | | 7.8 | 71.2 | − | − | | − | +/− | − | + | |
| G34 | | 67 | S2 | ~8.7 | ~75 | | | | − | +\− | | | |
| G35 | | 242 | | 8.61 | 69 | | | | − | | | | |
| S2 | PTA-6142 | 36 | G4, G9, S6 | 8.53 | 79.2 | | | | − | + | − | | |
| S6 | PTA-6143 | 39 | G4, G9, S2 | 8.81 | 76.3 | − | + | − | − | + | − | − | |
| S10 | | 54 | | 8.76 | 75.3 | | | | − | + | | | |
| S12 | | n.d. | | 8.73 | 66.9 | | | | + | − | | − | |
| S14 | | 205 | | 8.62 | 70.7 | | | | − | − | | | |
| S16 | PTA-6259 | 23 | | 8.11 | 71.4 | ++ | ++ | ++ | + | + | − | − | |
| S17 | | 331 | | 8.7 | 90.0 | − | − | | − | − | − | +/− | |
| E11 | | n.d. | | 8.92 | 66.3 | + | +/− | | + | + | + | + | 48.10 |

TABLE 1-continued

Characteristics and Deposit Information for anti-HMG1 antibodies[a]

| | IC$_{50}$[g] | | | | | IC$_{50}$ nm IL-6 Native | in vivo[h] | | | | | | Inhibition of Synergy |
|---|---|---|---|---|---|---|---|---|---|---|---|---|---|
| IgG | IL-12 | IL-1β | TNF-α | IL-6 | NO | HMGB | CLP | CIA passive | CIA active | AIA | S. aureus | ALI | (PAMP/Cytokine)[i] |
| G2 | 1262 | 5029 | 1347 | 0.9941 | | − | 60% | 0% | | | | | |
| G4 | 715 | 5015 | 5510 | 0.8997 | | − | 60% | 36% | 34% | 30%[j] | 27% | 40% | LPS/IL-6 |
| G9 | | 211.4 | 247.7 | 0.246 | | − | | | | | | | |
| G12 | 2788 | 5908 | 796.5 | 1.119 | | | | | | | | | |
| G16 | | | | 1.061 | 21974 | | | | | | | | |
| G20 | | 400.4 | 598.2 | 0.6521 | 20380 | − | | | | | | | |
| G34 | | | | 0.8580 | | | | | | | | | |
| G35 | | | | 0.5635 | | | | | | | | | |
| S2 | | 220 | 64.16 | 0.1628 | | | 15% | | | | | | |
| S6 | | 23.15 | 18.24 | 0.1739 | 4152 | − | 35-50% | 60% | | | | | |
| S10 | 1132 | 2593 | 874.7 | 0.3235 | | | | | | | | | |
| S12 | | | | 1.669 | | | | | | | | | |
| S14 | | 67.78 | 66.18 | 0.1914 | | | | | | | | | |
| S16 | 1237 | 6051 | 1441 | 0.5597 | | 38.89 | 60-75% | 0% | | 0% | | | LPS/IL-6 |
| S17 | | 80.89 | | 0.1623 | 41745 | 11.47 | | | | | | | |
| E11 | | | | 1.221 | 101321 | 1.733 | 35% | | 0% | | 8% | 37% | CpG/IFN-a, LPS/IL-6 |

[a]No value indicates that the assay was not performed or value not determined.
[b]via BIAcore analysis using recombinant HMG1 (Example 1), note: the K$_d$ for E11 and S12 have not yet been determined by BIAcore.
[c]via isoelectric focusing gel electrophoresis (see Example 1)
[d]via differential scanning calorimetry (see Example 1)
[e]Relative binding determined by ELISA studies (see Example 2)
[f]Relative inhibition indicated for rage binding, mMØ and TLR4, IC$_{50}$ (nM) indicated for Thp-1 binding (see Examples 4 & 14)
[g]Determined by cytokine release inhibition analysis using recombinant HMG1 (see Example 3) IC$_{50}$ values for IL-6 are listed as nM the rest are listed as ng/ml
[h]Percent protection is calculated by subtracting the isotype control (see Examples 5-11).
[i]Inhibition of the enhancement of PAMP stimulation by HMG1, the PAMP used and cytokine assayed for are indicated (see, Examples 13-14)
[j]G4 also reduced hyperostosis in the rat AIA model Another embodiment of the present invention includes the introduction of conservative amino acid substitutions in any portion of an anti-HMG1 antibody of interest, described supra (see table 1). It is well known in the art that "conservative amino acid substitution" refers to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in Table 2.

TABLE 2

Families of Conservative Amino Acid Substitutions

| Family | Amino Acids |
|---|---|
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

The term "conservative amino acid substitution" also refers to the use of amino acid analogs or variants. Guidance concerning how to make phenotypically silent amino acid substitutions is provided in Bowie et al., "Deciphering the Message in Protein Sequences: Tolerance to Amino Acid Substitutions," (1990, Science 247:1306-1310).

5.3 Methods of Generating and Screening Antibodies of the Invention

High affinity antibodies or fragments that specifically bind to an HMG1 polypeptide can be identified, for example, by immunoassays, BIAcore, or other techniques known to those of skill in the art.

Antibodies that selectively bind an HMGB1-PAMP complex may block the interaction of an HMGB1-PAMP complex with a PRM thereby selectively inhibiting the HMGB1 enhanced inflammatory response to that PAMP. Without wishing to be bound by any particular theory it is contemplated that anti-HMG1 antibodies which recognize HMGB1-PAMP complexes may be raised by immunizing animals with HMGB1 combined with an adjuvant comprising one or more PAMP (e.g. Freund's adjuvant) and screening for those antibodies which bind only to HMGB1-PAMP complexes. Alternatively, anti-HMG1 antibodies, which recognize HMGB1-PAMP complexes, may be isolated from an antibody library (e.g., a phage display or expression library) by panning with an HMGB1-PAMP complex.

Antibodies that bind HMGB1 and block the formation of one or more HMGB1-PAMP complex may prevent HMGB1 mediated synergy of signaling by that PAMP. Without wishing to be bound by any particular theory antibodies which block the formation of an HMGB1-PAMP complex may be isolated from an antibody library (e.g., a phage display or expression library) by panning with an exceptionally pure HMGB1 antigen which is NOT bound to a PAMP and screening for those antibodies which block the formation of an HMGB11-PAMP complex. It is contemplated that antibodies raised by immunizing animals are unlikely to efficiently block the binding of HMGB1 to a PAMP as the animals are likely to raise an antibodies only to HMGB1 already complexed to a PAMP present in the adjuvant or to HMGB1 complexed to cellular nucleic acids or other biological molecules.

The antibodies of the present invention may be generated by any suitable method known in the art. Polyclonal antibodies to an antigen-of-interest can be produced by various procedures well known in the art. For example, an HMG1 polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

A "monoclonal antibody" may comprise, or alternatively consist of, two proteins, i.e., a heavy and a light chain.

Methods for producing and screening for specific antibodies using hybridoma technology are routine and well known in the art. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

The antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., *J. Immunol. Methods* 184:177-186 (1995); Kettleborough et al., *Eur. J. Immunol.* 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including manmnalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., *AJRI* 34:26-34 (1995); and Better et al., Science 240:1041-1043 (1988).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., *PNAS* 90:7995-7999 (1993); and Skerra et al., Science 240:1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, Science 229:1202 (1985); Oi et al., *BioTechniques* 4:214 (1986); Gillies et al., (1989) *J. Immunol. Methods* 125:191-202; U.S. Pat. Nos. 5,807,715; 4,816,567; and 4,816397. Humanized antibodies are antibody molecules from non-human species antibody that bind the desired antigen having one or more complementarity determining regions (CDRs) from the non-human species and a framework region from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988)). Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899-903 (1988)).

Further, antibodies to the polypeptides of the invention can, in turn, be utilized to generate anti-idiotype antibodies that "mimic" polypeptides of the invention using techniques well known to those skilled in the art (See, e.g., Greenspan & Bona, *FASEB J.* 7(5):437-444; (1989) and Nissinoff, *J. Immunol.* 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

If the antibody is used therapeutically in in vivo applications, the antibody is preferably modified to make it less immunogenic in the individual. For example, if the individual is human the antibody is preferably "humanized."; where the complementarity determining region(s) of the antibody is transplanted into a human antibody (for example, as described in Jones et al., *Nature* 321:522-525, 1986; and Tempest et al., *Biotechnology* 9:266-273, 1991).

Phage display technology can also be utilized to select antibody genes with binding activities towards the polypeptide either from repertoires of PCR amplified v-genes of lymphocytes from humans screened for possessing anti-B box antibodies or from naive libraries (McCafferty et al., *Nature* 348:552-554, 1990; and Marks, et al., *Biotechnology* 10:779-783, 1992). The affinity of these antibodies can also be improved by chain shuffling (Clackson et al., *Nature* 352: 624-628, 1991).

The choice of polypeptide to be used for the generation can be readily determined by one skilled in the art. Polypeptides may be chosen such that the antibody generated will not significantly cross-react or specifically bind to another member of the HMG protein family. Alternatively, polypeptides which share a large degree of homology between two or more members of the HMG protein family may be used for the generation of an antibody that can specifically bind (i.e., cross-react) with multiple members of the HMG protein family (e.g., HMG1 and HMG2).

5.4 Polynucleotides Encoding Antibodies

The invention further provides polynucleotides comprising a nucleotide sequence encoding a high affinity antibody of the invention and fragments thereof. The invention also encompasses polynucleotides that hybridize under stringent or lower stringency hybridization conditions, e.g., as defined herein, to polynucleotides that encode an antibody that specifically binds to an HMG1 and/or HMG2 polypeptide of the invention (e.g. SEQ ID NO: 1 or 2 or fragments thereof). In a particular embodiment, a polynucleotide of the invention encodes an antibody that binds to a polypeptide having the amino acid sequence of SEQ ID NO:1 or 2. In another embodiment, a polynucleotide of the invention encodes an antibody which binds specifically to a polypeptide having the amino acid sequence of SEQ ID NO:3. In another preferred embodiment, a polynucleotide of the invention encodes an antibody which binds specifically to a polypeptide having the amino acid sequence of SEQ ID NO:4. In another embodiment, a polynucleotide of the invention encodes an antibody which binds a polypeptide having the amino acid sequence of SEQ ID NO:21. In still another embodiment, a polynucleotide of the invention encodes an antibody which binds a polypeptide having the amino acid sequence of SEQ ID NO:22. In yet another embodiment, a polynucleotide of the invention encodes an antibody which binds a polypeptide having the amino acid sequence of SEQ ID NO:23. In still other embodiments, a polynucleotide of the invention encodes an antibody which binds a polypeptide having the amino acid sequence of SEQ ID NO:28 and/or 29.

By "stringent hybridization conditions" is intended overnight incubation at 42.degree. C. in a solution comprising: 50% formamide, 5.times.SSC (750 mM NaCl, 75 mM trisodium cirate), 50 mM sodium phosphate (pH 7.6), 5.times. Denhardt's solution, 10% dextran sulfate, and 20 µg/ml denatured, sheared salmon sperm DNA, followed by washing the filters in 0.1.times.SSC at about 65.degree. C.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably polyA+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY), to generate antibodies having a different amino acid sequence, for example to create amino acid substitutions, deletions, and/or insertions.

In a specific embodiment, the amino acid sequence of the heavy and/or light chain variable domains of the antibodies of the invention may be inspected to identify the sequences of the complementarity determining regions (CDRs) by methods that are well known in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention.

Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

5.5 Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, 3T3, PerC6 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)). Also see, e.g., U.S. Pat. Nos. 5,827,739, 5,879,936, 5,981,216, and 5658759.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera* frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad. Sci. USA* 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, NS0, Per.C6 and in particular, breast cancer cell lines such as, for example, BT483, Hs578T, HTB2, BT20 and T47D, and normal mammary gland cell lines such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Proc Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 Clinical Pharmacy 12:488-505; Wu and Wu, Biotherapy 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); May, 1993, *TIB TECH* 11(5):155-215); and hygro, which confers resistance to hygromycin (Santerre et al., *Gene* 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., *J. Mol. Biol.* 150:1 (1981).

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature* 322:562 (1986); Kohler, *Proc. Natl. Acad. Sci. USA* 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Moreover, the antibodies or fragments thereof of the present invention can be fused to marker sequences, such as a peptide to facilitate purification. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

5.6 Antibody Conjugates and Derivatives

The antibodies of the invention include derivatives that are modified (e.g., by the covalent attachment of any type of molecule to the antibody). For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Antibodies or fragments thereof with increased in. vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Further, antibodies can be conjugated to albumin in order to make the antibody or antibody fragment more stable in vivo or have a longer half life in vivo. The techniques are well known in the art, see e.g., International Publication Nos. WO 93/15199, WO 93/15200, and WO 0177137; and European Patent No. EP 413, 622. The present invention encompasses the use of antibodies or fragments thereof conjugated or fused to one or more moieties, including but not limited to, peptides, polypeptides, proteins, fusion proteins, nucleic acid molecules, small molecules, mimetic agents, synthetic drugs, inorganic molecules, and organic molecules.

In one embodiment, the present invention encompasses the use of antibodies or fragments thereof recombinantly fused or chemically conjugated (including both covalent and non-covalent conjugations) to a heterologous protein or polypeptide (or fragment thereof, specifically to a polypeptide of at least 10, at least 20, at least 30, at least 40, at least 50, at least 60, at least 70, at least 80, at least 90 or at least 100 amino acids) to generate fusion proteins. In another embodiment, the present invention encompasses the use of antibodies or fragments thereof recombinantly fused or chemically conjugated (including both covalent and non-covalent conjugations) to a heterologous protein or polypeptide (or fragment thereof, specifically to a polypeptide of at least about 10, at least about 20, at least about 30, at least about 40, at least about 50, at least about 60, at least about 70, at least about 80, at least about 90 or at least about 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452.

The present invention further includes formulations comprising heterologous proteins, peptides or polypeptides fused or conjugated to antibody fragments. For example, the heterologous polypeptides may be fused or conjugated to a Fab fragment, Fd fragment, Fv fragment, F(ab)$_2$ fragment, a VH domain, a VL domain, a VH CDR, a VL CDR, or fragment thereof. Methods for fusing or conjugating polypeptides to antibody portions are well known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins, e.g., of antibodies that specifically bind HMG1 and/or HMG2 or fragments thereof (e.g., supra), may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16(2): 76-82; Hansson, et al., 1999, J. Mol. Biol. 287:265-76; and Lorenzo and Blasco, 1998, Biotechniques 24(2): 308-313. Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to a C/CLP may be recombined with one or more components, motifs, sections, parts, domains, fragments, etc. of one or more heterologous molecules.

Moreover, the antibodies of the invention or fragments thereof can be fused to marker sequences, such as a peptide to facilitate purification. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographics, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin; and examples of suitable radioactive material include but are not limited to, $^{125}$I, $^{131}$I, $^{111}$In or $^{99}$Tc, in addition positron emitting metals using various positron emission tomographies, nonradioactive paramagnetic metal ions, and molecules that are radiolabelled or conjugated to specific radioisotopes can be conjugated to the antibodies of the invention.

Further, an antibody of the invention or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum(II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). A more extensive list of therapeutic moieties can be found in PCT publications WO 03/075957/

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567-1574 (1994)), VEGI (See, International Publication No. WO 99/23105), CD40 Ligand, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Mareel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", *Immunol. Rev.* 62:119-58 (1982).

The antibodies of the invention can be conjugated to other polypeptides. Methods for fusing or conjugating antibodies to polypeptide moieties are known in the art. See, e.g., U.S. Pat. Nos. 5,336,603; 5,622,929; 5,359,046; 5,349,053; 5,447, 851, and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vil et al., 1992, PNAS USA 89:11337. The fusion of an antibody to a moiety does not necessarily need to be direct, but may occur through linker sequences. Such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171

Alternatively, an antibody can be conjugated to a second antibody to form an antibody heteroconjugate as described by Segal in U.S. Pat. No. 4,676,980.

An antibody, with or without a therapeutic moiety conjugated to it, administered alone or in combination with cytotoxic factor(s) and/or cytokine(s) can be used as a therapeutic.

5.7 Assays for Antibody Binding and Activity

The antibodies of the invention may be assayed for specific (i.e., immunospecific) binding by any method known in the art. The immunoassays which can be used, include but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCt, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4.degree. C., adding protein A and/or protein G sepharose beads to the cell lysate, incubating for about an hour or more at 4.degree. C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity and other binding properties (e.g., off-rate of an antibody-antigen interaction) of an antibody to an antigen may be determined by a variety of in vitro assay methods well known in the art including for example, equilibrium methods (e.g., enzyme-linked immunoabsorbent assay (ELISA; or radioimmunoassay (RIA)), or kinetics (e.g., BIACORE® analysis), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody. Other specific methods are disclosed herein, see Examples 2-4, infra.

The antibodies of the invention may be assayed for biological activity by any method known in the art.

The protocols and formulations of the invention are preferably tested in vitro, and then in vivo, for the desired therapeutic or prophylactic activity, prior to use in humans. For example, in vitro assays which can be used to determine whether administration of a specific therapeutic protocol formulation or combination therapy of the invention is indicated, include in vitro cell culture assays in which a patient tissue sample is grown in culture, and exposed to or otherwise contacted with a formulation of the invention, and the effect of such a formulation upon the tissue sample is observed. The tissue sample can be obtained by biopsy from the patient. This test allows the identification of the therapeutically most effective prophylactic or therapeutic agent(s) for each individual patient. In various specific embodiments, in vitro assays can be carried out with representative cells of cell types involved in an autoimmune disorder, an inflammatory disorder, a disorder associated with aberrant expression and/or activity of HMG1 and/or HMG2, to determine if a formulation of the invention has a desired effect upon such cell types. For example, a lower level of HMG1 and/or HMG2 and/or proinflammatory cytokines produced by the contacted cells indicates that the composition of the invention may be effective to treat the condition in the patient. Alternatively, instead of culturing cells from a patient, a formulation of the invention may be screened using cells which can be stimulated by HMG1 and/or HMG2 such as for example peripheral blood mononuclear cells (PBMCs), THP-1 cells or Macrophages (MØs). Many assays standard in the art can be used to assess cytokine production including ELISA assays, realtime PCR and other methods well known in the art. Specific methods are also disclosed herein (see Examples 2 and 6, infra).

Prophylactic or therapeutic agents can be tested in suitable animal model systems prior to testing in humans, including but not limited to in rats, mice, chicken, cows, monkeys, rabbits, hamsters, etc.

The principle animal models for known in the art and widely used are known and described in the art as described above. In addition, specific animal models for sepsis (see Example 5), peritonitis (see Example 10) and arthritis (see Examples 7-9) are disclosed herein.

Further, any assays known to those skilled in the art can be used to evaluate the prophylactic and/or therapeutic utility of the combinatorial therapies disclosed herein for treatment or prevention of inflammatory disease.

5.8 Antibodies, Antibody Compositions of the Invention and Therapeutic and/or Prophylactic Administration Thereof The present invention encompasses anti-HMG1 antibodies as disclosed herein and is also directed to antibody compositions referred to herein as "antibody compositions of the invention," "compositions of the invention" or more simply as "compositions". In certain embodiments, the compositions of the invention comprise an antibody of the invention in a pharmaceutically acceptable excipient. As used herein, the term "pharmaceutically-acceptable carrier" means a chemical composition with which an antibody of the invention may be combined and which, following the combination, can be used to administer the antibody of the invention to a subject. These antibody compositions are also referred to herein as "pharmaceutical compositions". In other embodiments, the compositions of the present invention.

The present further includes methods for treating a condition characterized by activation of the inflammatory cytokine cascade, including both acute and chronic inflammatory conditions, comprising administering a therapeutically effective amount of an antibody or pharmaceutical composition of the invention. Chronic inflammatory conditions are characterized by an inflammatory response of prolonged duration—weeks, months, or even indefinitely which results in tissue damage that is often permanent. Chronic inflammatory conditions include but are not limited to, arthritis (e.g. rheumatoid arthritis), inflammatory bowel disease (e.g., ulcerative colitis and Crohn's disease), and cholecystitis. Acute inflammatory conditions are usually characterized by a sudden onset of symptoms including, increased vascular permeability, oedema, systemic fever often resulting in tissue necrosis and may result in death. Acute inflammatory conditions include but are not limited to, sepsis (e.g., due to microbial infection), hypersensitivity reactions, tissue necrosis and appendicitis. The condition can be one where the inflammatory cytokine cascade causes a systemic reaction, such as with endotoxic shock. Alternatively, the condition can be mediated by a localized inflammatory cytokine cascade, as in rheumatoid arthritis. In one embodiment, compositions of the invention comprise high affinity antibodies that specifically bind to an A box of HMG1 (e.g., an epitope within SEQ ID NO: 3). In another embodiment, compositions comprise high affinity antibodies of the invention that specifically bind to a B box of HMG1 (e.g., an epitope within SEQ ID NOS: 4, 28, 29). In still another embodiment, compositions of the invention comprise high affinity antibodies that specifically bind to an A box of HMG2 (e.g., an epitope within SEQ ID NOS: 22). In another embodiment, compositions comprise high affinity antibodies of the invention that specifically bind to a B box of HMG2 (e.g., an epitope within SEQ ID NOS: 23).

As described above, HMG1 signaling is mediated, at least in part, via the RAGE and likely via members of the PRM and PAMP family of proteins. Both the A box and B box likely play a role in receptor binding and signaling. Without wishing to be bound by any particular theory it is therefore contemplated that a combination of antibodies (or other antagonists) which specifically bind the A box and antibodies (or other antagonists) which specifically bind the B box would effectively block HMG1 binding to RAGE and/or PRM and/or PAMP proteins. Accordingly, compositions of the invention may comprise a combination of high affinity antibodies of the invention (or other HMGB1 antibodies or antagonists), for example, but not by way of limitation, a combination of antibodies that specifically bind to an HMG1 A box and antibodies that specifically bind a HMG1 B box, or a combination of antibodies that specifically bind to an HMG2 A box and antibodies that specifically bind a HMG2 B box. In a specific embodiment, compositions comprise high affinity antibodies of the invention that specifically bind to an epitope derived from both the A box and B box of HMG1 (e.g., an epitope which spans the junction between the A and B box).

Compositions of the invention can comprise the high affinity antibodies of the present invention alone or in combination with other active therapeutic molecules and/or adjuvants such as steroids, other anti-inflammatory molecules, or other antibody therapeutics. More specifically, the compositions of the invention can comprise an antagonist of an early sepsis mediator. The antagonist of an early sepsis mediator is in one embodiment, an antagonist of a cytokine selected from the group consisting of TNF, IL-1α, IL-1β, MIF and IL-6. In a specific embodiment, the antagonist of an early sepsis mediator is an antibody to TNF or MIF, or an IL-1 receptor antagonist.

The compositions of the invention may be utilized alone or in combination with other active therapeutic strategies against cancer and related conditions including but not limited to, surgery, radiation therapy and chemotherapy. In certain embodiments, the compositions of the invention may be useful in increasing the sensitivity of tumor cells to radiation in radiotherapy and/or in potentiating and/or enhancing damage to tumors by chemotherapeutic agents. The compositions of the invention may also be useful for sensitizing multidrug-resistant tumor cells.

In one embodiment the pharmaceutical compositions of the invention are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with monoclonal antibodies, even trace amounts of harmful and dangerous endotoxin must be removed. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

When used for in vivo administration, the compositions described herein should be sterile. This is readily accomplished, for example, by filtration through sterile filtration membranes or by other means well known in the art. Sterile compositions for injection can be formulated according to conventional pharmaceutical practice as described in Remington's Pharmaceutical Sciences (180' ed, Mack Publishing Company, Easton, Pa., 1990). Compositions comprising antibodies, such as those disclosed herein, ordinarily will be stored in lyophilized form or in solution. It is contemplated that sterile compositions comprising antibodies of the invention are placed into a container having a sterile access port, for example, an intravenous solution bag or vial having an adapter that allows retrieval of the formulation, such as a stopper pierceable by a hypodermic injection needle.

In one embodiment of the present invention, the compositions described herein can inhibit a condition mediated or characterized by activation of an inflammatory cytokine cascade including both acute and chronic inflammatory conditions. In a specific embodiment, the compositions described herein are useful for the treatment of an acute inflammatory condition (e.g., sepsis). In another specific embodiment, the compositions described herein are useful for the treatment of a chronic inflammatory condition (e.g., rheumatoid arthritis). In yet another embodiment, the compositions described herein are useful for the treatment of both acute and chronic inflammatory conditions.

It is contemplated that the compositions of the invention will be protective when administered to a subject having an inflammatory condition mediated or characterized by activation of an inflammatory cytokine cascade. The protection conferred by a composition of the invention may be measured by methods well known in the art. Methods used to determine how protective a composition of the invention is will vary depending on the condition being treated and/or prevented and the measurements be examined. For example, in a rodent model of arthritis a comparison of the paw inflammation scores of animals treated with a composition of the invention and animals treated with an appropriate control composition may be used to determine how protective a composition of the invention is. In a CLP model of sepsis a comparison of the survival of animals treated with a composition of the invention and animals treated with an appropriate control composition may be used to determine protection conferred by antibody treatment. Generally, treatment with a composition of the invention will be compared to certain control treatments. For example, a control treatment may comprise a control antibody or may comprise only excipient. In some cases the control may be the standard of care (or an appropriate surrogate molecule) for treatment of a disease such as for example methotrexate or anti-TNFs (e.g., Enbrel, Humira) for treatment of arthritis. In some cases the control may be a negative control (e.g., PBS). When the control represents the standard of care the composition of the invention may be administered either alone or in combination with the standard of care treatment and the level of protection for each group compared. The choice of control will depend on factors including condition being treated and/or prevented and the measurements be examined and can be readily determined by one of skill in the art. Specific examples of methods to determine the protection conferred by a composition of the invention are provided herein (see Examples 7-11, infra)

In another embodiment of the present invention, the compositions described herein are more protective (by at least 10% or at least 15%, or at least 20%, or at least 30%, or at least 40%, or at least 50%, or at least 60%, or at least 70%, or at least 80%, or at least 90%) than a control composition, in an animal CLP sepsis model. In a specific embodiment, the compositions described herein are more protective (by at least 10% or at least 15%, or at least 20%, or at least 30%, or at least 40%, or at least 50%, or at least 60%, or at least 70%, or at least 80%, or at least 90%) than a control composition, in an animal CLP sepsis model selected from the group comprising, a mouse CLP model and a piglet CLP model. In another specific embodiment, the animal CLP model is the mouse CLP model.

In still another embodiment of the present invention, the compositions described herein are more protective (by at least 10% or at least 15%, or at least 20%, or at least 30%, or at least 40%, or at least 50%, or at least 60%, or at least 70%, or at least 80%, or at least 90%) than a control composition, in a mouse collagen-induced arthritis model. In a specific embodiment, the mouse collagen-induced arthritis model is the passive collagen-induced arthritis model. In another specific embodiment, the mouse collagen-induced arthritis model is the active collagen-induced arthritis model.

In yet another embodiment of the present invention, the compositions described herein are more protective (by at least 10% or at least 15%, or at least 20%, or at least 30%, or at least 40%, or at least 50%, or at least 60%, or at least 70%, or at least 80%, or at least 90%) than Renbrel® (with or without methotrexate) in a mouse collagen-induced arthritis model. In a specific embodiment, the mouse collagen-induced arthritis model is the passive collagen-induced arthritis model. In another specific embodiment, the mouse collagen-induced arthritis model is the active collagen-induced arthritis model.

In still another embodiment of the present invention, the compositions described herein reduce bone loss and/or cartilage damage (by at least 10% or at least 15%, or at least 20%, or at least 30%, or at least 40%, or at least 50%, or at least 60%, or at least 70%, or at least 80%, or at least 90%) more than a control composition in a mouse collagen-induced arthritis model. In a specific embodiment, the mouse collagen-induced arthritis model is the passive collagen-induced arthritis model. In another specific embodiment, the mouse collagen-induced arthritis model is the active collagen-induced arthritis model.

In other embodiments, the compositions described herein are more protective (by at least 10% or at least 15%, or at least 20%, or at least 30%, or at least 40%, or at least 50%, or at least 60%, or at least 70%, or at least 80%, or at least 90%) than a control composition in a rat adjuvant-induced arthritis model.

In still other embodiments of the present invention, the compositions described herein are more protective (by at least 10% or at least 15%, or at least 20%, or at least 30%, or at least 40%, or at least 50%, or at least 60%, or at least 70%, or at least 80%, or at least 90%) than Renbrel® (with or without methotrexate) in a rat adjuvant-induced arthritis model.

In yet other embodiments of the present invention, the compositions described herein reduce bone loss and/or cartilage damage (by at least 10% or at least 15%, or at least 20%, or at least 30%, or at least 40%, or at least 50%, or at least 60%, or at least 70%, or at least 80%, or at least 90%) more than a control composition in a rat adjuvant-induced arthritis model.

In another embodiment of the present invention, the compositions described herein are more protective (by at least 10% or at least 15%, or at least 20%, or at least 30%, or at least 40%, or at least 50%, or at least 60%, or at least 70%, or at least 80%, or at least 90%) than Enbrel® (with or without methotrexate) in humans.

In yet another embodiment of the present invention, the compositions described herein are more protective (by at least 10% or at least 15%, or at least 20%, or at least 30%, or at least 40%, or at least 50%, or at least 60%, or at least 70%, or at least 80%, or at least 90%) than a control composition in a mouse peritonitis model.

In still another embodiment of the present invention, the compositions described herein ameliorate the severity of spinal cord injury (SCI) (by at least 10%, or at least 15%, or at least 20%, or at least 30%, or at least 40%, or at least 50%, or at least 60%, or at least 70%, or at least 80%, or at least 90%) more than a control composition in a human or in a rodent SCI model.

In still another embodiment of the present invention, the compositions described herein ameliorate the severity of acute lung injury (ALI) (by at least 10%, or at least 15%, or at least 20%, or at least 30%, or at least 40%, or at least 50%, or at least 60%, or at least 70%, or at least 80%, or at least 90%) more than a control composition in a human or in a rodent ALI model.

In another embodiment, the compositions described herein reduce hyperostosis (by at least 10% or at least 15%, or at least 20%, or at least 30%, or at least 40%, or at least 50%, or at least 60%, or at least 70%, or at least 80%, or at least 90%) more than a control composition in an animal arthritis model (e.g., rat AIA, mouse passive or active CIA models).

In still another embodiment of the present invention, the compositions described herein reduce hyperostosis (by at least 10% or at least 15%, or at least 20%, or at least 30%, or at least 40%, or at least 50%, or at least 60%, or at least 70%, or at least 80%, or at least 90%) more than a control composition in humans.

The present invention is also directed to a method of inhibiting release of a proinflammatory cytokine from a mammalian cell. The method comprises treating the cell with an antibody or antibody composition of the present invention in an amount sufficient to inhibit release of the proinflammatory cytokine from the cell. In these embodiments, the cell is preferably a macrophage. In certain embodiments, the proinflammatory cytokine is selected from the group consisting of TNF, IL-1α, IL-1β, MIF and IL-6. In other embodiments, the cell is a macrophage and the proinflammatory cytokine is selected from the group consisting of TNF, IL-1α, IL-1β, MIF and IL-6. In still other embodiments, the cell is a PBMC and the proinflammatory cytokine is selected from the group consisting of INF, IL-1α, IL-1β, MIF and IL-6. In one embodiment the methods treat a cell in a patient suffering from, or at risk for, a condition characterized by activation of the inflammatory cytokine cascade. Specific conditions are enumerated herein.

The present invention is also directed to a method of the inhibiting release of HMG1 and/or HMG2 from a mammalian cell. The method comprises treating the cell with an antibody or antibody composition of the present invention in an amount sufficient to inhibit release of HMG1 and/or HMG2 from the cell. The methods preferably treat a cell in a patient suffering from, or at risk for, a condition characterized by activation of the inflammatory cytokine cascade. Preferred conditions are enumerated herein.

Methods to determine the inhibition of cytokines, HMG1 and/or HMG2 release can be determined by numerous methods well known in the art such as those described above and disclosed herein (see Examples 2-11, infra).

As used herein, a "therapeutically effective amount," an "amount sufficient" and like terms refers to that amount of the therapeutic agent, e.g., an HMG1 antibody composition of the invention, sufficient to treat or manage a disease or disorder mediated by HMG1 and/or HMG2. A therapeutically effective amount may refer to the amount of therapeutic agent sufficient to delay or minimize the onset of the disease, e.g., delay or minimize the severity of a disease. A therapeutically effective amount may also refer to the amount of the therapeutic agent that provides a therapeutic benefit in the treatment or management of an inflammatory disorder. Further, a therapeutically effective amount with respect to a pharmaceutical composition of the invention means that amount of therapeutic agent alone, or in combination with other therapies, that provides a therapeutic benefit in the treatment or management a disease, e.g., an inflammatory disease.

The present invention further provides methods of preventing, managing, treating or ameliorating an inflammatory disorder or one or more symptoms thereof, said methods comprising administering to a subject in need thereof an antibody composition of the invention and/or one or more therapies. Any agent or therapy which is known to be useful, or which has been used or is currently being used for the prevention, management, treatment or amelioration of an inflammatory disorder or one or more symptoms thereof can be used in combination with an antibody composition of the invention. Examples of such agents include, but are not limited to, immunomodulatory agents, an anti-angiogenic agents, anti-inflammatory agents and TNF-.alpha. antagonists.

Nonlimiting examples of conditions which can be usefully treated using the antibody compositions, i.e., pharmaceutical compositions of the present invention include those conditions enumerated in the background section of this specification and below. Preferably, the condition is appendicitis, peptic, gastric or duodenal ulcers, peritonitis, pancreatitis, ulcerative, pseudomembranous, acute or ischemic colitis, diverticulitis, epiglotftitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, COPD, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid. cysts, burns, dermatitis, dermatomyositis, sunburn, urticaria, warts, wheals, vasulitis, angiitis, endocarditis, arteritis, atherosclerosis, restenosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infaretion, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Beehcets's syndrome, allograft rejection, graft-versus-host disease, Berger's disease, Type I diabetes, ankylosing spondylitis, Retier's syndrome, or Hodgkins disease. In more preferred embodiments, the condition is appendicitis, peptic, gastric or duodenal ulcers, peritonitis, pancreatitis, ulcerative, pseudomembranous, acute or ischemic colitis, hepatitis, Crohn's discasc, asthma, allergy, anaphylactic shock, organ ischemia, reperfilsion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infaretion, cerebral embolism, spinal cord injury, paralysis, allograft rejection or graft-versus-host disease.

In one embodiment, the invention is directed. to methods of administering and using compositions and antibodies or the invention to treat and/or prevent a condition selected from the group consisting of appendicitis, peptic, gastric and duodenal ulcers, peritonitis, pancreatitis, ulcerative, pseudomembranous, acute and ischemic colitis, hepatitis, Crohn's disease, asthma, allergy, anaphylactic shock, rheumatoid arthritis, lupus, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infaretion, cerebral embolism, spinal cord injury, paralysis, allograft rejection and graft-versus-host disease. In certain embodiments, the condition is endotoxic shock or allograft rejection. Where the condition is allograft rejection, the composition may advantageously also include an immunosuppressant that is used. to inhibit allograft rejection, such as cyclosporin. In certain other embodiments, the condition is lupus.

A specific embodiment of the invention is directed to methods of administering and using compositions and antibodies of the invention to treat and/or prevent sepsis, lupus and arthritis (e.g., RA, psoriatic arthritis, juvenile rheumatoid arthritis). In addition, a specific preferred, embodiment of the invention is directed to methods of administering and, using compositions and antibodies of the invention to treat and prevent psoriasis.

In another embodiment, the present invention includes methods of treating or preventing diseases associated with abnormal bone deposition, e.g., ankylosing spondylitis, undifferentiated spondylarthopathy, juvenile spondyloarthritis, or other diseases associated with hyperostosis comprising administering any antibody (or antibody composition) that specifically binds HMG1 or antigenic fragment thereof (e.g., HMG B box) irregardless of the binding affinity of the antibody.

In another embodiment, the present invention includes methods of treating or preventing the present invention includes methods of treating or preventing diseases associated with abnormal bone deposition, e.g., ankylosing spondylitis, undifferentiated spondylarthopathy, juvenile spondyloarthritis, or other diseases associated with hyperostosis comprising administering any antibody (or antibody composition) that specifically binds HMG2 or antigenic fragment thereof (e.g., HMG B box) irregardless of the binding affinity of the antibody.

In another embodiment, the present invention includes methods of treating or preventing the present invention includes methods of treating or preventing diseases associated with abnormal bone deposition, e.g., ankylosing spondylitis, undifferentiated spondylarthopathy, juvenile spondyloarthritis, or other diseases associated with hyperostosis comprising administering a combination of antibodies (or antibody composition) that specifically bind HMG1 and/or HMG2 or antigenic fragment thereof (e.g., HMG B box) irregardless of the binding affinity of the antibody.

Another specific preferred embodiment of the invention is directed to methods of administering and using compositions and antibodies of the invention to treat and prevent restenosis, vascular diseases, and cardiovascular disease.

Yet another specific preferred embodiment of the invention is directed to methods of administering and using compositions and antibodies of the invention to treat and prevent tissue damage and to promote tissue repair and regeneration.

In another embodiment, the composition of the present invention may be administered orally, parenterally, i.e. including subcutaneous injections, intravenous, intramuscular, intrasternal injection or infusion techniques, by inhalation spray, or rectally, in dosage unit formulations containing conventional non-toxic pharmaceutically acceptable carriers, adjuvants and vehicles.

In yet another embodiment, in accordance with the method of the present invention, said composition can be administered separately at different times during the course of therapy or concurrently in divided or single combination forms. The present invention is therefore to be understood as embracing all such regimes of simultaneous or alternating treatment and the term "administering" is to be interpreted accordingly.

In still another embodiment, the prophylactic or therapeutic agents used in combination with a HMGB1 inhibitor of the present invention can be administered concomitantly or sequentially to a subject. The prophylactic or therapeutic agents used in combination with a HMGB1 inhibitor of the present invention can also be cyclically administered. Cycling therapy involves the administration of a first prophylactic or therapeutic agent for a period of time, followed by the administration of a second prophylactic or therapeutic agent for a period of time and repeating this sequential administration, i.e., the cycle, in order to reduce the development of resistance to one of the agents, to avoid or reduce the side effects of one of the agents, and/or to improve the efficacy of the treatment.

In one embodiment, the antibodies of the invention are used in combination with antibodies that bind one or more PRM (e.g., TLR2, TLR4, TLR9). In a specific embodiment, the antibodies that bind one or more PRM (e.g., TLR2, TLR4, TLR9) inhibit signaling of the PRM. In another specific embodiment, the antibodies that bind one or more PRM (e.g., TLR2, TLR4, TLR9) inhibit ligand binding.

As discussed supra, any agent or therapy which is known to be useful, or which has been used or is currently being used for the prevention, management, treatment or amelioration of an inflammatory disorder or one or more symptoms thereof can be used in combination with an antibody composition of the invention. Specific examples of immunomodulatory agents which can be administered in combination with an antibody composition of the invention to a subject with an inflammatory disorder include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), anti-T cell receptor antibodies (e.g., anti-CD4 antibodies (e.g., cM-T412 (Boeringer), IDEC-CE9.1™ (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson)) anti-CD20 antibodies (e.g., Rituxan (IDEC & Genentech, U.S. and International Patent Publications US2004/0202658, WO00/67796) and derivatives there of, HuMax-CD20 (GenMab and Medarex, U.S. Patent Publication 2004/0167319)), anti-CD19 antibodies (see, e.g., U.S. and international Patent Publications US20020041847, US20030133930 and WO 05/012493), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilcx)), anti-CD2 antibodies (e.g., MEDI-507 (MedImmune, Inc., International Publication Nos. WO 02/098370 and WO 02/069904), anti-CD11a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-.alpha. antibodies, anti-IL-.beta. antibodies, anti-IL-6 antibodies, anti-IL-8 antibodies (e.g., ABX-IL-8 (Abgenix)), and anti-IL-12 antibodies)); anti-CD22 antibodies (e.g., non-ligand blocking antibodies such as Epratuzumab (Immunomedics) and ligand blocking antibodies (e.g., U.S. Patent Publications 2004/0001828 and 2003/0202975)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-.alpha. receptor or a fragment thereof, the extracellular domain of an IL-1.beta. receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, TNF-.alpha., TNF-.beta., interferon (IFN)-.alpha., IFN-.beta., IFN-.gamma., and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-.alpha. antibodies, and anti-IFN-.gamma. antibodies).

Non-limiting examples of anti-angiogenic agents which can be administered in combination with an antibody composition of the invention to a subject with an inflammatory disorder include Vitaxin® (MedImmune) or other anti-alpha v beta3 antibodies (e.g., CNTO95 (Centocor)), endostatin, angiostatin, apomigren, anti-angiogenic antithrombin III, the 29 kDa N-terminal and a 40 kDa C-terminal proteolytic fragments of fibronectin, a uPA receptor antagonist, the 16 kDa proteolytic fragment of prolactin, the 7.8 kDa proteolytic fragment of platelet factor-4, the anti-angiogenic 24 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, RGD and NGR containing peptides, the small anti-angiogenic peptides of laminin, fibronectin, procollagen and EGF, acid fibroblast growth factor (aFGF) antagonists, basic fibroblast growth factor (bFGF) antagonists, vascular endothelial growth factor (VEGF) antagonists, VEGF receptor (VEGFR) antagonists (e.g., anti-VEGFR antibodies), and Avastin®.

Non-limiting examples of TNF-.alpha. antagonists which can be administered in combination with an antibody composition of the invention to a subject with an inflammatory disorder include proteins, polypeptides, peptides, fusion proteins, antibodies (e.g., human, humanized, chimeric, monoclonal, polyclonal, Fvs, ScFvs, Fab fragments, F(ab).sub.2 fragments, and antigen-binding fragments thereof) such as antibodies that immunospecifically bind to TNF-.alpha., nucleic acid molecules (e.g., antisense molecules or triple helices), organic molecules, inorganic molecules, and small molecules that blocks, reduces, inhibits or neutralizes the function, activity and/or expression of TNF-.alpha. In various embodiments, a TNF-.alpha. antagonist reduces the function, activity and/or expression of TNF-.alpha. by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS). Examples of antibodies that immunospecifically bind to TNF-.alpha. include, but are not limited to, infliximab (REMICADE™; Centacor), D2E7 (Abbott Laboratories/Knoll Pharmaceuticals Co., Mt. Olive, N.J.), CDP571 which is also known as HUMICADE™ and CDP-870 (both of Celltech/Pharmacia, Slough, U.K.), and TN3-19.12 (Williams et al., 1994, Proc. Natl. Acad. Sci. USA 91: 2762-2766; Thorbecke et al., 1992, Proc. Natl. Acad. Sci. USA 89:7375-7379). The present invention also encompasses the use of antibodies that immunospecifically bind to TNF-.alpha. disclosed in the following U.S. patents in the compositions and methods of the invention: U.S. Pat. Nos. 5,136,021; 5,147,638; 5,223,395; 5,231,024; 5,334,380; 5,360,716; 5,426,181; 5,436,154; 5,610,279; 5,644,034; 5,656,272; 5,658,746; 5,698,195; 5,736,138; 5,741,488; 5,808,029; 5,919,452; 5,958,412; 5,959,087; 5,968,741; 5,994,510; 6,036,978; 6,114,517; and 6,171,787. Examples of soluble TNF-.alpha. receptors include, but are not limited to, sTNF-R1 (Amgen), etanercept (ENBREL™; Immunex) and its rat homolog RENBREL™, soluble inhibitors of TNF-.alpha. derived from TNFrI, TNFrII (Kohno et al., 1990, Proc. Natl. Acad. Sci. USA 87:8331-8335), and TNF-.alpha. Inh (Seckinger et al, 1990, Proc. Natl. Acad. Sci. USA 87:5188-5192).

Other TNF-.alpha. antagonists encompassed by the invention include, but are not limited to, IL-10, which is known to block TNF-.alpha. production via interferon .gamma.-activated macrophages (Oswald et al. 1992, Proc. Natl. Acad. Sci. USA 89:8676-8680), TNFR-IgG (Ashkenazi et al., 1991, Proc. Natl. Acad. Sci. USA 88:10535-10539), the murine product TBP-1 (Scrono/Ycda), the vaccine CytoTAb (Protherics), antisense molecule104838 (ISIS), the peptide RDP-58 (SangStat), thalidomide (Celgene), CDC-801 (Celgene), DPC-333 (Dupont), VX-745 (Vertex), AGIX-4207 (AtheroGenics), ITF-2357 (Italfarmaco), NPI-13021-31 (Nereus), SCIO-469 (Scios), TACE targeter (Immunix/AHP), CLX-120500 (Calyx), Thiazolopyrim (Dynavax), auranofin (Ridaura) (SmithKline Beecham Pharmaceuticals), quinacrine (mepacrine dichlorohydrate), tenidap (Enablex), Melanin (Large Scale Biological), Lenercept (Roche, Switzerland), Thalidomide, and anti-p38 MAPK agents by Uriach.

Non-limiting examples of anti-inflammatory agents which can be administered in combination with an antibody composition of the invention to a subject with an inflammatory disorder include non-steroidal anti-inflammatory drugs (NSATDs), steroidal anti-inflammatory drugs, beta-agonists, anticholingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketorolac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxygenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

In specific embodiments, patients with osteoarthritis are administered a prophylactically or therapeutically effective amount of an antibody composition of the invention in combination with other agents or therapies useful for osteoarthritis prevention, treatment, management or amelioration including but not limited to: analgesics (non-limiting examples are acetaminophen, in a dose up to 4000 mg/d; phenacetin; and tramadol, in a daily dose in the range of 200 to 300 mg); NSAIDs (non-limiting examples include but not limited to, aspirin, diflunisal, diclofenac, etodolac, fenamates, fenoprofen, flurbiprofen, ibuprofen, indomethacin, ketoprofen, methylsalicylate, nebumetone, naproxin, oxaprazin, phenylbutazone, piroxicam, sulindac, and tolmetin. Low dose NSAIDs are preferred, e.g., ibuprofen at 1200 mg/d, naproxen at 500 mg/d. A gastroprotective agent, e.g., misoprostol, famotidine or omeprazole, is preferred to use concurrently with a NSAID); nonacetylated salicylates including but not limited to salsalate; cyclooxygenase (Cox)-2-specific inhibitors (CSIs), including but not limited to, celecoxib and rofecoxib; intra- or periarticular injection of a depot glucocorticoid preparation; intra-articular injection of hyaluronic acid; capsaicin cream; copious irrigation of the osteroarthritis knee to flush out fibrin, cartilage shards and other debris; and joint replacement surgery. The antibody compositions of the invention can also be used in combination with other nonpharmacologic measures in prevention, treatment, management and amelioration of osteoarthritis including but not limited to: reduction of joint loading (non-limiting examples are correction of poor posture, support for excessive lumbar lordosis, avoid excessive loading of the involved joint, avoid prolonged standing, kneeling and squatting); application of heat to the affected joint; aerobic exercise and other physical therapies.

In specific embodiments, patients with rheumatoid arthritis and/or other diseases associated with abnormal bone deposition are administered a prophylactically or therapeutically effective amount of an antibody composition of the invention in combination with other agents or therapies useful in prevention, treatment, management and amelioration of rheumatoid arthritis and/or other diseases associated with abnormal bone deposition including but not limited to: NSAIDs (non-limiting examples include but not limited to, aspirin, diflunisal, diclofenac, etodolac, fenamates, fenoprofen, flurbiprofen, ibuprofen, indomethacin, ketoprofen, methylsalicylate, nebumetone, naproxin, oxaprazin, phenylbutazone, piroxicam, sulindac, and tolmetin); analgesics (non-limiting examples are acetaminophen, phenacetin and tramadol); bisphosphonates including but not limited to etidronate, pamidronate, alendronate, risedronate, zoledronate, ibandronate; CSIs including but not limited to, celecoxib and rofecoxib; glucocorticoids (preferably low-dose oral glucocorticoids, e.g., <7.5 mg/d prednisone, or monthly pulses with high-dose glucocorticoids, or intraarticular glucocorticoids); disease-modifying antirheumatic drugs (DMARDs) including but not limited to, methotrexate (preferably given intermittent low dose, e.g., 7.5-30 mg once weekly), gold compounds (e.g., gold salts), D-penicillamine, the antimalarials (e.g., chloroquine), and sulfasalazine; TNF-.alpha. neutralizing agents including but not limited to, etanercept and infliximab; immunosuppressive and cytotoxic agents (examples include but not limited to, azathioprine, leflunomide, cyclosporine, and cyclophosphamide), and surgery (examples include but not limited to, arthroplasties, total joint replacement, reconstructive hand surgery, open or arthroscopic synovectomy, and early tenosynovectomy of the wrist). The antibody compositions of the invention may also be used in combination with other measures in prevention, treatment, management and amelioration of rheumatoid arthritis and/or other diseases associated with abnormal bone deposition including but not limited to: rest, splinting to reduce unwanted motion of inflamed/damaged joint, exercise, used of a variety of orthotic and assistive devices, and other physical therapies. The antibody compositions of the invention may also be used in combination with some nontraditional approaches in prevention, treatment, management and amelioration of rheumatoid arthritis and/or other diseases associated with abnormal bone deposition including but not limited to, diets (e.g., substituting omega-3 fatty acids such as eicosapentaenoic acid found in certain fish oils for dietary omega-6 essential fatty acids found in meat), vaccines, hormones and topical preparations.

In specific embodiments, patients with chronic obstructive pulmonary disease (COPD) are administered a prophylactically or therapeutically effective amount of an antibody composition of the invention alone or in combination with other agents or therapies useful in prevention, treatment, management and amelioration of COPD including, but not limited to: bronchodilators including but not limited to, short- and long-acting .beta..sub.2-adrenergic agonists (examples of short-acting .beta..sub.2 agonist include but not limited to, albuterol, pirbuterol, terbutaline, and metaproterenol; examples of long-acting .beta..sub.2 agonist include but not limited to, oral sustained-release albuterol and inhaled salmeterol), anticholinergics (examples include but not limited to ipratropium bromide), and theophylline and its derivatives (therapeutic range for theophylline is preferably 10-20 g/mL); glucocorticoids; exogenous .alpha..sub.1AT (e.g., .alpha..sub.1AT derived from pooled human plasma administered intravenously in a weekly dose of 60 mg/kg); oxygen; lung transplantation; lung volume reduction surgery; endrotracheal intubation, ventilation support; yearly influenza vaccine and pneumococcal vaccination with 23-valent polysaccharide; exercise; and smoking cessation.

In specific embodiments, patients with pulmonary fibrosis are administered a prophylactically or therapeutically effective amount of an antibody composition of the invention alone or in combination with an effective amount of one or more other agents useful for pulmonary fibrosis therapy including but not limited to: oxygen; corticosteroids (a non-limiting example is to administer daily prednisone beginning at 1-1.5 mg/kg/d (up to 100 mg/d) for six weeks and tapering slowly over 3-6 months to a minimum maintenance dose of 0.25 mg/kg/d); cytotoxic drugs (non-limiting examples are cyclophosphamide at 100-120 mg orally once daily, and azathioprine at 3 mg/kg up to 200 mg orally once daily); bronchodilators (non-limiting examples are short- and long-acting .beta..sub.2-adrenergic agonists, anticholinergics, and theophylline and its derivatives); and antihistamines (non-limiting examples are diphenhydramine and doxylamine).

In specific embodiment, patients with SCI are administered prophylactically or therapeutically effective amount of an antibody composition of the invention alone or in combination with an effective amount of one or more other agents useful for SCI therapy including but not limited to: glucocorticoid steroids (a non-limiting example is to administer methylprednisolone 30 mg/kg bolus over 15 minutes and an infusion of methylprednisolone at 5.4 mg/kg/h for 23 hours beginning 45 minutes after the bolus), neuroprotectors (e.g., minocyclin), regeneration therapies (e.g., stem cell treatments, hydrogels), weak electrical fields (e.g., extraspinal oscillating field stimulator implantable medical device).

In specific embodiments, patients with asthma are administered a prophylactically or therapeutically effective amount of an antibody composition of the invention alone or in combination with an effective amount of one or more other agents useful for asthma therapy including but not limited to: adrenergic stimulants (examples include but not limited to, catecholamines, e.g., epinephrine, isoproterenol, and isoetharine; resorcinols, e.g., metaproterenol, terbutaline, and fenoterol; and saligenins, e.g., salbutamol. Inhalation is the preferred route of administration for adrenergic stimulants); methylxanthines including but not limited to theophylline and its various salts; anticholinergics including but not limited to, atropine sulfate, atropine methylnitrate, and ipratropium bromide; glucocorticoids (examples including but not limited to systemic or oral steroids, and inhaled glucocorticoids); mast cell stabilizing agents (examples include but not limited to, cromolyn sodium and nedocromil sodium); leukotriene modifiers (examples include but not limited to, Zileuton, zafirlukast and montelukast); immunosuppressant agents (examples include but not limited to, methotrexate and gold salts); and mucolytic agents (examples include but not limited to acetylcysteine).

The invention provides methods of treatment, inhibition and prophylaxis by administration to a subject of an effective amount of a compound or pharmaceutical composition of the invention, preferably an antibody of the invention. In a preferred embodiment, the compound is substantially purified (e.g., substantially free from substances that limit its effect or produce undesired side effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, *J. Biol. Chem.* 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, 1987, CRC Crit. Ref Biomed. Eng. 14:201; Buchwald et al., 1980, *Surgery* 88:507; Saudek et al., 1989, *N. Engl. J. Med.* 321:574). In another embodiment, polymeric materials can be used (see Medical Applications of Controlled Release, Langer and Wise (eds.), CRC Press, Boca Raton, Fla. (1974); Controlled Drug Bioavailability, Drug Product Design and Performance, Smolen and Ball (eds.), Wiley, New York (1984); Ranger and Peppas, J., 1983, *Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, *Science* 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, *Proc. Natl. Acad. Sci. USA* 88:1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The excipient included with the polypeptide in these compositions is chosen based on the expected route of administration of the composition in therapeutic applications. The route of administration of the composition depends on the condition to be treated. For example, intravenous injection may be preferred for treatment of a systemic disorder such as endotoxic shock, and oral administration may be preferred to treat a gastrointestinal disorder such as a gastric ulcer. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Thus, depending on the condition, the antibody composition can be administered orally, parenterally, intranasally, vaginally, rectally, lingually, sublingually, bucally, intrabuccaly and transdermally to the patient.

Accordingly, compositions designed for oral, lingual, sublingual, buccal and intrabuccal administration can be made without undue experimentation by means well known in the art, for example, with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used.

The compositions of the present invention can easily be administered parenterally such as, for example, by intravenous, intramuscular, intrathecal or subcutaneous injection. Parenteral administration can be accomplished by incorporating the antibody compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120 C, dissolving the antibody composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

The antibody compositions described herein can also include an antagonist of an early sepsis mediator. As used herein, an early sepsis mediator is a proinflammatory cytokine that is released from cells soon (i.e., within 30-60 min.) after induction of an inflammatory cytokine cascade (e.g., exposure to LPS). Nonlimiting examples of these cytokines are TNF, IL-1α, IL-11β, IL-6, PAF, and MIF. Also included as early sepsis mediators are receptors for these cytokines (for example, tumor necrosis factor receptor type 1) and enzymes required for production of these cytokines, for example, interleukin-1β converting enzyme). Antagonists of any early sepsis mediator, now known or later discovered, can be useful for these embodiments by further inhibiting an inflammatory cytokine cascade.

Nonlimiting examples of antagonists of early sepsis mediators are antisense compounds that bind to the mRNA of the early sepsis mediator, preventing its expression (see, e.g., Ojwang et al., 1997, *Biochemistry* 36:6033-6045; Pampfer et al., 1995, *Biol. Reprod.* 52:1316-1326; U.S. Pat. No. 6,228, 642; Yahata et al., 1996, *Antisense Nucleic Acid Drug Dev.* 6:55-61; and Taylor et al., 1998, *Antisense Nucleic Acid Drug Dev.* 8:199-205), ribozymes that specifically cleave the mRNA of the early sepsis mediator (see, e.g., Leavitt et al., 2000, *Antisense Nucleic Acid Drug Dev.* 10: 409-414; Kisich et al., 1999; and Hendrix et al., 1996, *Biochem. J.* 314: 655-661), and antibodies that bind to the early sepsis mediator and inhibit their action (see, e.g., Kam and Targan, 2000, *Expert Opin. Pharmacother.* 1: 615-622; Nagahira et al., 1999, *J. Immunol Methods* 222, 83-92; Lavine et al., 1998, *J. Cereb. Blood Flow Metab.* 18: 52-58; and Holmes et al., 2000, *Hybridoma* 19: 363-367). Any antagonist of an early sepsis mediator, now known or later discovered, is envisioned as within the scope of the invention. The skilled artisan can determine the amount of early sepsis mediator to use in these compositions for inhibiting any particular inflammatory cytokine cascade without undue experimentation with routine dose-response studies.

5.9 Diagnostics and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder.

Antibodies of the invention can be used to assay protein levels in a biological sample using classical immunohistological methods known to those of skill in the art (e.g., see Jalkanen, et al., 1985, *J. Cell. Biol.* 101:976-985; Jalkanen, et al., 1987, *J. Cell. Biol.* 105:3087-3096). Other antibody-based methods useful for detecting protein gene expression include immunoassays, such as the enzyme linked immunosorbent assay (ELISA) and the radioimmunoassay (RIA).

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003).

One embodiment of the invention is the detection and diagnosis of a disease or disorder associated with aberrant expression of a polypeptide of interest in an animal, preferably a mammal and most preferably a human. In one embodiment, diagnosis comprises: (a) administering (for example, parenterally, subcutaneously, or intraperitoneally) to a subject an effective amount of a labeled molecule which specifically binds to the polypeptide of interest; (b) waiting for a time interval following the administering for permitting the labeled molecule to preferentially concentrate at sites in the subject where the polypeptide is expressed (and for unbound labeled molecule to be cleared to background level); (c) determining background level; and (d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

Also as described herein, antibodies of the invention may be used to treat, diagnose, or prognose an individual having sepsis, rheumatoid arthritis, peritonitis, Crohn's disease, reperfusion injury, septicemia, endotoxic shock, cystic fibrosis, endocarditis, psoriasis, psoriatic arthritis, arthritis, anaphylactic shock, organ ischemia, reperfusion injury, and allograft rejection.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

5.9 Pharmaceutical Compositions Comprising a Combination of an HMGB1 Polypeptide and a PAMP (e.g., TLR Ligand) and Methods of Use Thereof.

The present invention provides for a pharmaceutical composition comprising a therapeutically effective amount of a combination of an HMGB1 polypeptide and a PAMP (e.g., TLR ligand), and a pharmaceutically acceptable excipient. In another embodiment, the invention is a pharmaceutical composition comprising a therapeutically effective concentration of an HMGB1 polypeptide in combination with a PAMP, wherein said PAMP is present at a concentration sufficient to enhance the effect of said HMGB1 polypeptide.

The HMGB1 polypeptide can be a full length HMGB1, for example, a full length human HMGB1. In one embodiment, the full length human HMGB1 has the amino acid sequence of SEQ ID NO:3. The HMGB1 polypeptide can also be a fragment of full-length HMGB1. In one embodiment, the fragment of HMGB1 is an A box. In another embodiment, the fragment of HMGB1 is a B box. The fragment of full-length HMGB1 can additionally be a polypeptide comprising at least five contiguous amino acids, at least 10 contiguous amino acid, at least 20 contiguous amino acids or at least 25 contiguous amino acids. The fragment of full-length HMGB1 can additionally be a polypeptide consisting of 5-10 contiguous amino acids, 10-20 contiguous amino acids, or 15-25 contiguous amino acids.

In a specific embodiment, the PAMP is a TLR ligand. As used herein, a "TLR ligand" is a molecule that interacts with a TLR and is able to evoke signaling by the TLR under conditions that are suitable for such interaction and such signaling. TLR ligands include ligand that are now known or later discovered. In one embodiment a TLR ligand is a molecule that interacts with an extracellular domain of a TLR. In another embodiment, the TLR ligand is a natural ligand or a fragment thereof. A natural ligand is a TLR ligand that is found in nature. In another embodiment, the TLR ligand is a non-natural or synthetic ligand. The TLR ligand can be a ligand of any toll-like receptor including, for example, TLR1, TLR2, TLR3, TLR4, TLR5, TLR6, TLR7, TLR8, TLR9, TLR10 and TLR11.

Ligands for the various TLRs have been described in the literature and include, but are not limited to, the following:

TABLE 3

TLR Ligands

| TLR | Ligand |
|---|---|
| TLR1 | triacyl lipoproteins |
| TLR2 | lipoproteins, gram positive peptidoglycan, lipoteichoic acids, fungi, Amphotericin B, saturated fatty acids and Pam-3-Cys (S-[2,3-bis(palmitoyloxy)-(2RS)-propyl]-N-palmitoyl-R-Cys-S-Ser-Lys4-OH |
| TLR3 | double stranded RNA, polyinosinic-polycytidic acid (poly I:C) |
| TLR4 | lipopolysaccharide |
| TLR5 | flagellin |
| TLR6 | diacyl lipoproteins |
| TLR7 | single stranded RNA |
| TLR8 | Imidizaquinolines (such as resiquimod and imiquimod), GU-containing RNA |
| TLR9 | Bacterial DNA, synthetic CpG oligodeoxyribonucleotide |

PAMPs (e.g., TLR ligands) also specifically encompasses synthetic PAMPs including TLR agonists such as CPG 7909 (also known as PF-3512676 or ProMune™) and Actilon, (CPG 10101) currently under development by Coley Inc.

The pharmaceutical composition comprising an effective amount of a combination of an HMGB polypeptide and a PAMP can be utilized to treat any condition in which administration of an HMGB polypeptide or a PAMP is therapeutic or prophylactic including, but not limited to, cancers, infectious diseases, asthma and allergies.

In one embodiment, the invention is a method of increasing an immune response in a patient in need thereof comprising administering a pharmaceutical composition comprising an effective amount of a combination of an HMGB polypeptide and a PAMP. The use of HMGB1 itself for increasing an immune response have been described in International Patent Publication No. WO 2004/046338 and U.S. Patent Publication No. 2004/242481. Patients in need of immune response stimulation include, for example, patients suffering from cancer or an infectious disease. Cancers including, but are not limited to, cancer of the head, neck, eye, mouth, throat, esophagus, chest, bone, lung, colon, rectum, colorectal, or other gastrointestinal tract organs, stomach, spleen, renal, skeletal muscle, subcutaneous tissue, metastatic melanoma, endometrial, prostate, breast, ovaries, testicles or other reproductive organs, skin, thyroid, blood, lymph nodes, kidney, liver, pancreas, and brain or central nervous system. Infectious diseases include, but are not limited to, viral infectious diseases such as HIV-1, HIV-2, herpes simplex virus type 1, herpessimplex virus type 2, Ebola virus, Ebola virus, and hepatitis A, B, C, D, and E viruses, disease caused pathogenic bacteria such as *bacillus tumerculoses* and *bacillus anthracis*.

In another embodiment, the pharmaceutical composition comprising an effective amount of a combination of an HMGB polypeptide and a TLR ligand can be used with a vaccine. Examples of vaccines include hepatitis B, diphtheria, tetanus, pertussis, *hemophilus influenzae* type B, polio, measles, mumps, rubella, varicella, pneumococcal, hepatitis A, influenze, Japanese encephalitis, rotavirus, yellow fever, trypanosome cruzi and rabies. The vaccine may additionally comprise an adjuvant such as immunostimulatory oligonucleotides, imidazoquinolines, monophosphoryl lipid A and detoxified lipopolysaccharide (LPS).

In a further embodiment, the invention is a method for the treatment of tissue damage and/or to promote tissue repair and regeneration comprising administering a pharmaceutical composition comprising an effective amount of a combination of an HMGB polypeptide and a PAMP. The use of HMGB1 for the treatment of tissue damage and/or to promote tissue repair is described in International Patent Publication No. WO 2004/004763. In one embodiment, the tissue is cardiac tissue or skeletal tissue. The composition can be utilized for the treatment or repair and regeneration of necrotic tissue. Necrotic tissue can, for example, be the result of sepsis or multiple organ failure. Necrotic tissue can also occur in intestinal infaretion, acute pancreatitis and/or other trauma. In another embodiment, the invention is a method for the treatment of tissue damage caused by trauma or ischemia, such as, at burn sites or after myocardial infaretion.

In yet another embodiment, the invention is a method for affecting weight loss or treating obesity in a patient in need thereof comprising administering a pharmaceutical composition comprising an effective amount of a combination of an HMGB polypeptide and a PAMP.

TABLE 4

Legend for Sequence Listing

| SEQ ID NO: | DESCRIPTION[a] |
|---|---|
| 1 | Human HMG1 aa Acc. # NP-002119 |
| 2 | Human HMG1 aa Acc, # AAA64970 |
| 3 | Human HMG1 A box aa |
| 4 | Human HMG1 B box aa |
| 5 | Anti HMG1 antibody S2 $V_L$ aa |
| 6 | Anti HMG1 antibody S2 $V_L$ nt |
| 7 | Anti HMG1 antibody S2 $V_H$ aa |
| 8 | Anti HMG1 antibody S2 $V_H$ nt |
| 9 | Anti HMG1 antibody S6 $V_L$ aa |
| 10 | Anti HMG1 antibody S6 $V_L$ nt |
| 11 | Anti HMG1 antibody S6 $V_H$ aa |
| 12 | Anti HMG1 antibody S6 $V_H$ nt |
| 13 | Anti HMG1 antibody S16 $V_L$ aa |
| 14 | Anti HMG1 antibody S16 $V_L$ nt |
| 15 | Anti HMG1 antibody S16 $V_H$ na |
| 16 | Anti HMG1 antibody S16 $V_H$ nt |
| 17 | Anti HMG1 antibody G4 $V_L$ aa |
| 18 | Anti HMG1 antibody G4 $V_L$ nt |
| 19 | Anti HMG1 antibody G4 $V_H$ aa |
| 20 | Anti HMG1 antibody G4 $V_H$ nt |
| 21 | Human HMG2 aa |
| 22 | Human HMG2 A box aa |
| 23 | Human HMG2 B box aa |
| 24 | Anti HMG1 antibody E11 $V_L$ aa |

TABLE 4-continued

Legend for Sequence Listing

| SEQ ID NO: | DESCRIPTION[a] |
|---|---|
| 25 | Anti HMG1 antibody E11 $V_L$ nt |
| 26 | Anti HMG1 antibody E11 $V_H$ aa |
| 27 | Anti HMG1 antibody E11 $V_H$ nt |
| 28 | HMG1 B-box peptide aa 91-169 |
| 29 | HMG1 B-box peptide aa 150-183 |
| 30 | Anti HMG1 antibody G2 $V_L$ aa |
| 31 | Anti HMG1 antibody G2 $V_L$ nt |
| 32 | Anti HMG1 antibody G2 $V_H$ aa |
| 33 | Anti HMG1 antibody G2 $V_H$ nt |
| 34 | Anti HMG1 antibody G9 $V_L$ aa |
| 35 | Anti HMG1 antibody G9 $V_L$ nt |
| 36 | Anti HMG1 antibody G9 $V_H$ aa |
| 37 | Anti HMG1 antibody G9 $V_H$ nt |
| 38 | Anti HMG1 antibody G12 $V_L$ aa |
| 39 | Anti HMG1 antibody G12 $V_L$ nt |
| 40 | Anti HMG1 antibody G12 $V_H$ aa |
| 41 | Anti HMG1 antibody G12 $V_H$ nt |
| 42 | Anti HMG1 antibody G16 $V_L$ aa |
| 43 | Anti HMG1 antibody G16 $V_L$ nt |
| 44 | Anti HMG1 antibody G16 $V_H$ aa |
| 45 | Anti HMG1 antibody G16 $V_H$ nt |
| 46 | Anti HMG1 antibody G20 $V_L$ aa |
| 47 | Anti HMG1 antibody G20 $V_L$ nt |
| 48 | Anti HMG1 antibody G20 $V_H$ aa |
| 49 | Anti HMG1 antibody G20 $V_H$ nt |
| 50 | Anti HMG1 antibody G34 $V_L$ aa |
| 51 | Anti HMG1 antibody G34 $V_L$ nt |
| 52 | Anti HMG1 antibody G34 $V_H$ aa |
| 53 | Anti HMG1 antibody G34 $V_H$ nt |
| 54 | Anti HMG1 antibody G35 $V_L$ aa |
| 55 | Anti HMG1 antibody G35 $V_L$ nt |
| 56 | Anti HMG1 antibody G35 $V_H$ aa |
| 57 | Anti HMG1 antibody G35 $V_H$ nt |
| 58 | Anti HMG1 antibody S10 $V_L$ aa |
| 59 | Anti HMG1 antibody S10 $V_L$ nt |
| 60 | Anti HMG1 antibody S10 $V_H$ aa |
| 61 | Anti HMG1 antibody S10 $V_H$ nt |
| 62 | Anti HMG1 antibody S12 $V_L$ aa |
| 63 | Anti HMG1 antibody S12 $V_L$ nt |
| 64 | Anti HMG1 antibody S12 $V_H$ aa |
| 65 | Anti HMG1 antibody S12 $V_H$ nt |
| 66 | Anti HMG1 antibody S14 $V_L$ aa |
| 67 | Anti HMG1 antibody S14 $V_L$ nt |
| 68 | Anti HMG1 antibody S14 $V_H$ aa |
| 69 | Anti HMG1 antibody S14 $V_H$ nt |
| 70 | Anti HMG1 antibody S17 $V_L$ aa |
| 71 | Anti HMG1 antibody S17 $V_L$ nt |
| 72 | Anti HMG1 antibody S17 $V_H$ aa |
| 73 | Anti HMG1 antibody S17 $V_H$ nt |
| 74 | S2 $V_L$ CDR1 aa |
| 75 | S2 $V_L$ CDR2 aa |
| 76 | S2 $V_L$ CDR3 aa |
| 77 | S2 $V_H$ CDR1 aa |
| 78 | S2 $V_H$ CDR2 aa |
| 79 | S2 $V_H$ CDR3 aa |
| 80 | S6 $V_L$ CDR1 aa |
| 81 | S6 $V_L$ CDR2 aa |
| 82 | S6 $V_L$ CDR3 aa |
| 83 | S6 $V_H$ CDR1 aa |
| 84 | S6 $V_H$ CDR2 aa |
| 85 | S6 $V_H$ CDR3 aa |
| 86 | S16 $V_L$ CDR1 aa |
| 87 | S16 $V_L$ CDR2 aa |
| 88 | S16 $V_L$ CDR3 aa |
| 89 | S16 $V_H$ CDR1 aa |
| 90 | S16 $V_H$ CDR2 aa |
| 91 | S16 $V_H$ CDR3 aa |
| 92 | G4 $V_L$ CDR1 aa |
| 93 | G4 $V_L$ CDR2 aa |
| 94 | G4 $V_L$ CDR3 aa |
| 95 | G4 $V_H$ CDR1 aa |
| 96 | G4 $V_H$ CDR2 aa |
| 97 | G4 $V_H$ CDR3 aa |
| 98 | E11 $V_L$ CDR1 aa |
| 99 | E11 $V_L$ CDR2 aa |
| 100 | E11 $V_L$ CDR3 aa |
| 101 | E11 $V_H$ CDR1 aa |
| 102 | E11 $V_H$ CDR2 aa |
| 103 | E11 $V_H$ CDR3 aa |
| 104 | CpG-A sequence |
| 105 | Control ODN sequence |
| 106 | Random DNA ODNs |
| 107 | CpG-B sequence |
| 108 | A-box peptide (example 15) |
| 109 | B-box peptide (example 15) |
| 110 | Silent splice site mutated G4 $V_H$ nt |

[a]nucleotide sequences are designated "nt" amino acid sequences are designated "aa"

6. EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

6.1 Example 1

Development and Physical Characterization of Human Anti-HMG1 Antibodies

A large panel of human anti-HMG1 antibodies were isolated from a naïve human Fab phage display library by several rounds of panning against human HMG1 (SEQ ID NO: 1 and 2, also see FIG. 1). The clones were then sequenced to eliminate duplicate clones and the Fab fragments were subcloned into an expression vector for the production of full length IgG. The nucleotide and corresponding amino acid sequences of the variable regions of the light and heavy chains of several antibody clones (G2, G4, G9, G12, G16, G20, G34, G35, S2, S6, S10, S12, S14, S16, S17 and E11) are provided in the sequence listing (see Table 4 for specific SEQ ID NOS.). FIG. 2 represents the variable regions of the heavy and light chains of several antibody clones (S2, S6, S16 and G4) that have been deposited with the American Type Culture Collection (deposit numbers PTA-6142, PTA-6143, PTA-6259 and PTA-6258, respectively). Also shown in FIG. 2 are the variable regions heavy and light chains of the anti-HMG1 antibody E11. The CDRs for each antibody depicted in FIG. 2 are underlined and provided in the sequence listing (see Table 4 for specific SEQ ID NOS.). The resulting full length antibodies were purified and their physical characteristics were determined as described below. As summarized in Table 1, these analysis show that the human anti-HMG1 antibodies developed exhibit a wide range of characteristics.

The G4 antibody was found to have low expression levels. Examination of the nucleotide sequences encoding the heavy chain variable region of several human anti-HMBG1 antibodies, including G4, S6 and S16, revealed putative RNA splice sites. The predicted splice sites for G4 and S6 are shown in FIG. 2K. RT PCR analysis of heavy chain transcripts from transiently expressed G4, and S6 revealed several low molecular weight bands which corresponded to spliced messages (data not shown). Site directed mutagenesis was used to knock out the G4 splice sites introducing a silent mutation at each splice site with a score greater then 0.5. The three mutation introduced are boxed in the nucleotide alignment in FIG. 2L. The amino acid sequence of G4 is unchanged from that shown in FIG. 2H. Similar changes can be introduced into the nucleotide sequence encoding S6 or other anti-HMGB1 antibodies using similar criteria to increase expression by eliminating mRNA splice sites thus stabilizing the message.

6.1.1 Materials and Methods

Isolation of Hunan anti-HMG1 Antibodies: A human Fab phage display library (Dyax, Cambridge, Mass.) was screened by three rounds of panning as follows: Day 1. I) Coat an immunotube with full length HMGB-1 at 20 µg/ml in 0.1 M Carbonate buffer (pH 9.6). Leave it in 4° C. for overnight. Day 2. I) Using 100 fold of phage as library size. Add ⅕ volume of PEG 6000 (20%). Leave on ice for 1 h. Spin at 14000 rpm for 10 min. Resuspend in PBS (pH 7.4) to precipitate phage library. II) Both the antigen-coated immunotube and the phage are blocked with 2% milk/PBS. The immunotube is then rinsed with PBS 2×. and the phage are transferred to the immunotube and mixed by rotating for 30 min and then allow to incubate for an additional 1.5 hrs stationary. III) The immunotube is washed with PBST (PBS+ 0.1% Tween 20) 10-20 times then PBS 10-20 times and the phage are eluted with 1 ml of 100 mM triethylamine. Eluted phage are neutralized with 0.5 ml of 1 M Tris-Cl (pH 7.5). IV) 1 volume of eluted neutralized phage are mixed with 5 volumes of log phase TG1 and 4 volume of 2YT. Incubate at 37° C. for 30 min (water bath). The infected cells are harvested by centrifugation and resuspended in 2YT and plated on 2YT agar with carbenicillin and 2% glucose.

Expression of Human anti-HMG1 Oligoclonal and Monoclonal Antibodies: The plasmid was extracted from several pools of bacterium after $3^{rd}$ round panning. The Fab gene fragments were then excised from the plasmid and inserted into the IgG expression vector under the control of CMV promoter. The plasmid of IgG expression vector with Fab fragment was transient transfected into 293H cells and the oligoclonal antibodies were purified from grow medium by passing it through protein A column. Each pool of oligoclonal antibodies was tested for reactivity to HMG1. Those pools testing positive were further screen to identify individual positive clones.

Isoelectric Focusing Gel Electrophoresis: Isoelectric points were determined using a Pharmacia Biotech Multiphor 2 electrophoresis system with a multi temp 3 refrigerated bath recirculation unit and an EPS 3501 XL power supply. Pre-cast ampholine gels (Amersham Biosciences, pI range 2.5-10) were loaded with 5 µg of protein. Broad range pI marker standards (Amersham, pI range 3-10, 8 µL) were used to determine relative pI for the Mabs. Electrophoresis was performed at 1500 V, 50 mA for 105 minutes. The gel was fixed using a Sigma fixing solution (5×) diluted with purified water to 1×. Staining was performed overnight at room temperature using Simply Blue stain (Invitrogen). Destaining was carried out with a solution that consisted of 25% ethanol, 8% acetic acid and 67% purified water. Isoelectric points were determined using a Bio-Rad Densitometer relative to calibration curves of the standards.

Differential Scanning Calorimetry: Thermal melting temperatures ($T_m$) were measured with a VP-DSC (MicroCal, LLC) using a scan rate of 1.0° C./min and a temperature range of 25-120° C. A filter period of 8 seconds was used along with a 5 minute pre-scan thermostating. Samples were prepared by dialysis into 25 mM Histidine-HCl, pH 6 using Pierce dialysis cups (3.5 kD). Average Mab concentrations were 50 µg/mL as determined by $A_{280}$. Melting temperatures were determined following manufacturer procedures using Origin software supplied with the system. Briefly, multiple baselines were run with buffer in both the sample and reference cell to establish thermal equilibrium. After the baseline was subtracted from the sample thermogram, the data were concentration normalized and fitted using the deconvolution function.

6.1.2 Results

Figure 3A:
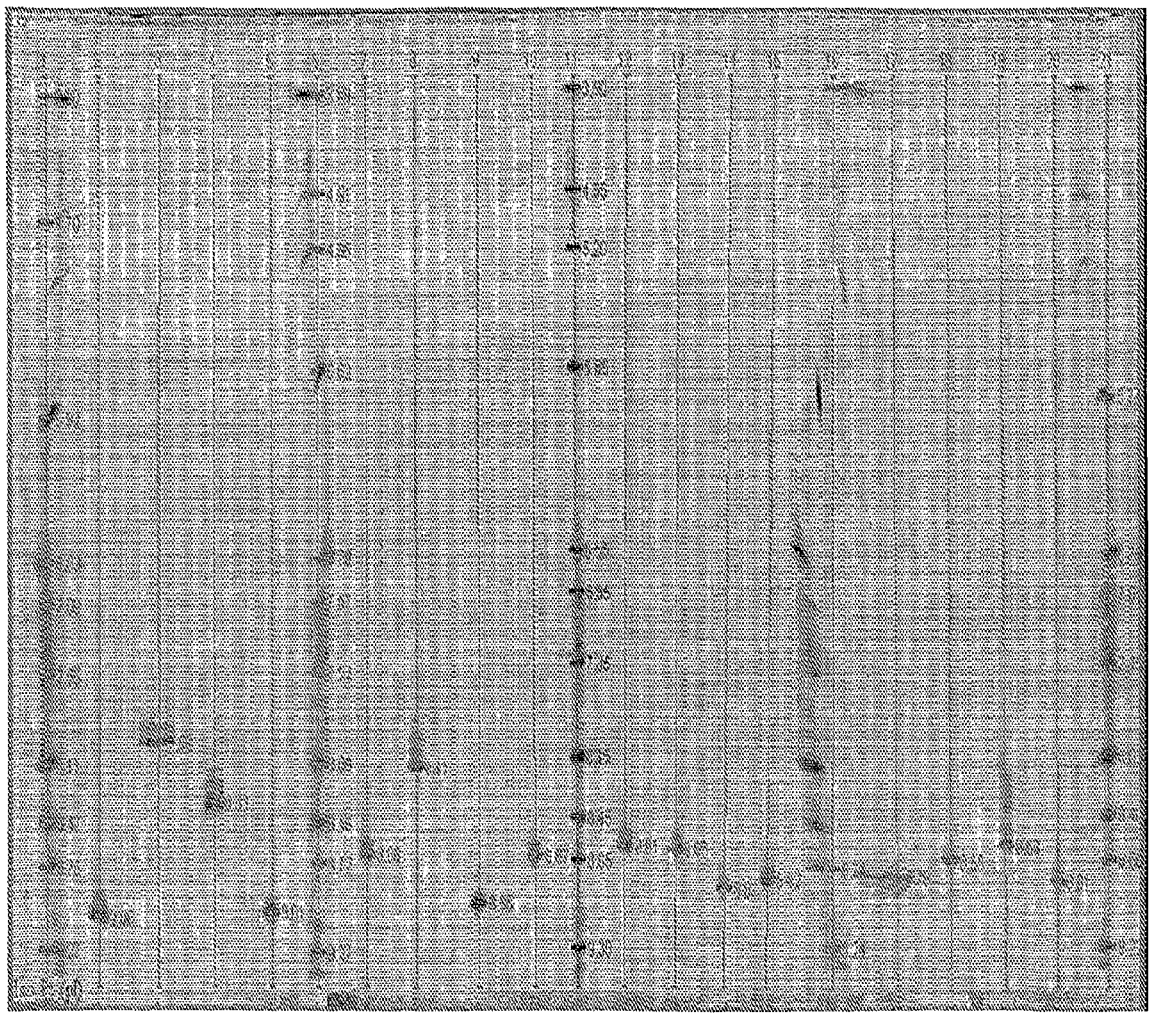
Figure 3B:
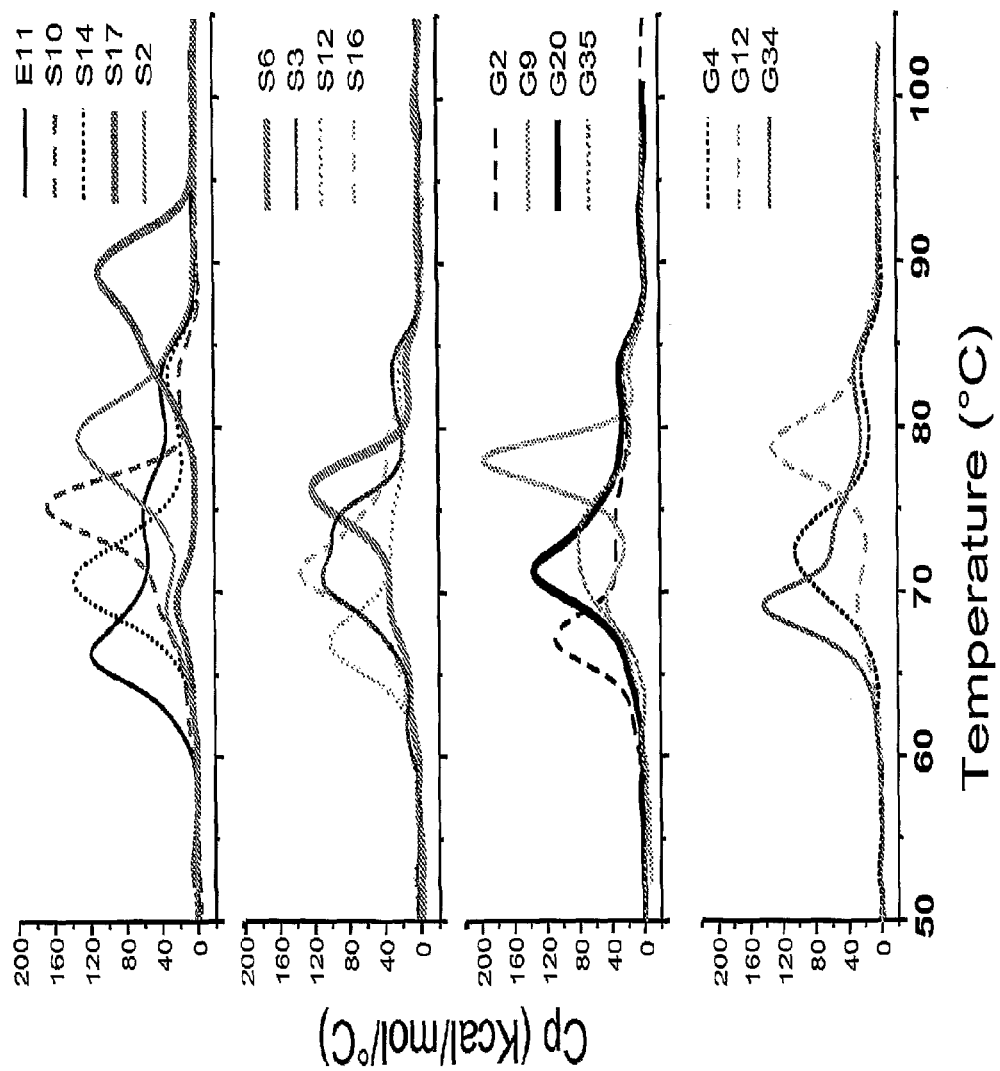
Figure 3C:
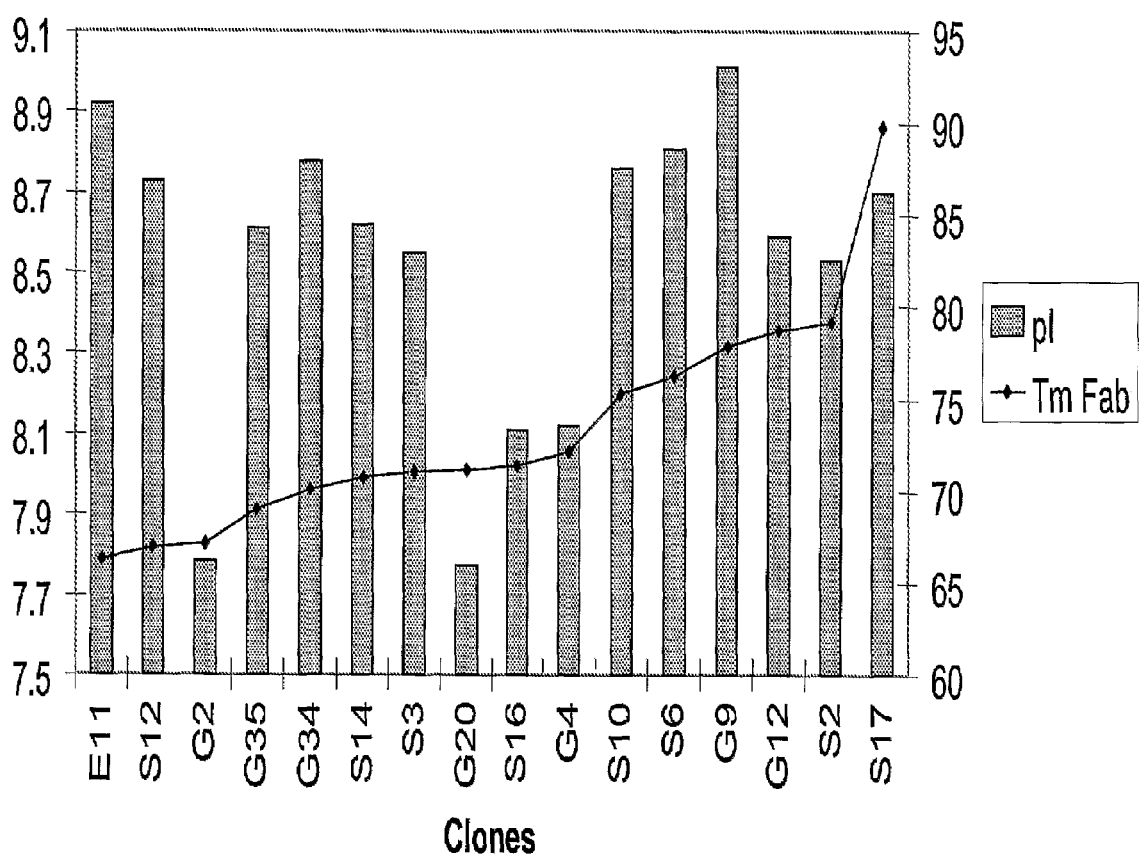

Over 35 individual Fab clones were isolated from a single phage display library, 18 of which were converted into full length IgG1 and purified from transient transfections. The subsequent analysis of these clones demonstrate that they have a wide range of characteristics. For example, they exhibit dissociation constants ($K_d$) between a high of about 330 nM to a low of just 22 nM (summarized in Table 1). The Tm values, which can give an indication of stability, range from a low of just about 70° C. to a high of about 90° C. (FIGS. 3B and 3C). pI values, which can give an indication of solubility of an antibody, also showed a wide range with the antibodies having pI values from 7.8-9.0 (FIGS. 3A and 3C). Antibodies with various characteristics have been screened in a number of in vitro and in vivo studies (see below) to determine the most desirable combination of characteristics. In addition, a large number of other clones are available for further screening.

6.2 Example 2

Kinetic Analysis of Human anti-HMG1 Antibodies

The binding kinetics and specificity of several human anti-HMG1 antibodies was examined using a variety of techniques. In addition, several peptides were used in epitope mapping studies. As summarized in Table 1, these analysis show that the human anti-HMG1 antibodies have differing binding kinetics and specificity. In addition, the data indicate that the anti-HMG1 antibodies bind to a variety of epitopes including the HMG1 B-Box and A-Box.

6.2.1 Materials and Methods

Production/Isolation of Recombinant HMG1: Recombinant HMG1 (rHMG1) is purified from *E. coli* as a calmodulin binding protein (CBP) fusion protein (CBP is fused to N-terminal end of HMGB1). *E. coli* expressing CBP-HMG1 are induced for 2-3 hours and the protein is release by microfluidization in 25 mM Tris-HCl, 150 mM NaCl, 2 mM $CaCl_2$, pH 8.0. The lysed cells are centrifuged at 125,000×g for 1 hour, the filtered supernatant is applied to a calmodulin column in the presence of $CaCl_2$. The column is washed with 2-2.5 column volumes of lysis buffer and then with a linear gradient to 50 mM Tris, 400 mM NaCl, 2 mM $CaCl_2$, pH 8.0 in 5 column volumes and the protein is eluted with 100 mM Tris, 400 mM NaCl, 5 mM EGTA, pH 8.0. A TritonX114 extraction is used to remove endotoxin. TX-114 is used. at a final concentration of 2% and is incubated. at 4 C for 30 minutes, moved. to 37° C. for 30 minutes and centrifuged to separate the phases. The protein is extracted twice.

Preparation of Four forms of a Native HMG1: Nuclear HMG1 is Prepared from 293H (ATCC number CRL-1573, human kidney, epithelial) cells grown in DMEM with 10% FBS according to protocol from ATCC. Cells were harvested at 80% confluence by the addition of Trypsin/EDTA for less than 1 min at RT. Cell were recovered at once in PBS by gentle flushing of the flask followed by centrifugation at 1100 rpm for 3 min. Cells were washed twice with PBS and transferred to 2 ml eppendorf tube at a final concentration about 2 to $5 \times 10^7$/ml in PBS and then frozen in liquid nitrogen for 2 minutes followed by a 5-10 minute thaw in water bath at RT. The freeze thaw process was repeated two more times. The lysed cells were centrifuged at 13,000 rpm and the supernatant was removed to a new sterile tube and stored at −70 to −80° C. The amount of supernatant used is based on cell concentration of supernatant prior to freeze thaw.

Released HMG1 is prepared from the conditioned media of necrotic 293H cells. 293H cells were grown in DMEM medium with 10% FBS for 10 days without changing the medium. The medium is harvested from the flask and centrifuged at 3000 rpm for 10 minutes, the supernatant was then passed through a 0.2 um filter and placed into a dialyze bag and dialyzed against concentration solution (PIERCE). The concentration solution was changed as needed until the volume of the media was reduced about ten fold. The concentrated medium was then dialyzed against PBS (pH 7.2). The concentration of HMGB1 present in the concentrated sample was determined by a sandwich ELISA (see below) using a purified HMGB1 as a standard.

Activated HMG1 is prepared from THP-1 (ATCC number TIB-202, human monocyte) cells grown in RPMI1640 (Cat# 03-0078DJ) with 10% FBS, 0.05 mM 2-mercaptoethanol according to protocol from ATCC. Cells were treated with LPS at a final concentration of 0.5 μg/ml overnight (14 to 16 hour) when they reached about $4 \times 10^5$ cells/ml. Cells were collected by centrifugation at 1,100 rpm×3 min and washed three times with PBS to completely remove media containing LPS and transferred to 2 ml eppendorf tube at a final concentration about 2 to $5 \times 10^7$/ml in PBS and then frozen in liquid nitrogen for 2 minutes followed by a 5-10 minute thaw in water bath at RT. The freeze thaw process was repeated two more times. The lysed cells were centrifuged at 13, 000 rpm and the supernatant was removed to a new sterile tube and stored at −70 to −80° C. The amount of supernatant used is based on cell concentration of supernatant prior to freeze thaw.

Calf Thymus HMG1: was prepared essentially as described in Walker, J. M., Goodwin, G. H., Johns, E. W., Wietzes, P. & Gaastra, W. A comparison of the amino-terminal sequences of two calf-thymus chromatin non-histone proteins. *Int. J. Pept. Protein Res.* 9, 220-223 (1977).

HMG1 Binding Affinity via BIAcore Analysis: All experiments were performed on a BIAcore 3000 instrument (BIAcore, Inc., Piscataway, N.J.). Briefly, each mAb was immobilized to a CM5 sensor chip using a standard amine coupling chemistry. Separately a reference (control) flow cell was also prepared. Two-fold, serial dilutions of HMG1 in instrument buffer were sequentially injected at a slow flow rate over the individual mAb and reference flow-cell surfaces. Following the binding and dissociation of HMG1, the mAbs surfaces were regenerated with a brief pulse of 1M NaCl-50 mM NaOH. At the end of each experiment, the binding curves were evaluated using a steady-state model available through the BIAevaluation software supplied by BIAcore, Inc. (Piscataway, N.J.). The $K_d$ values determined from these studies are listed in Table 1.

Figure 4A:
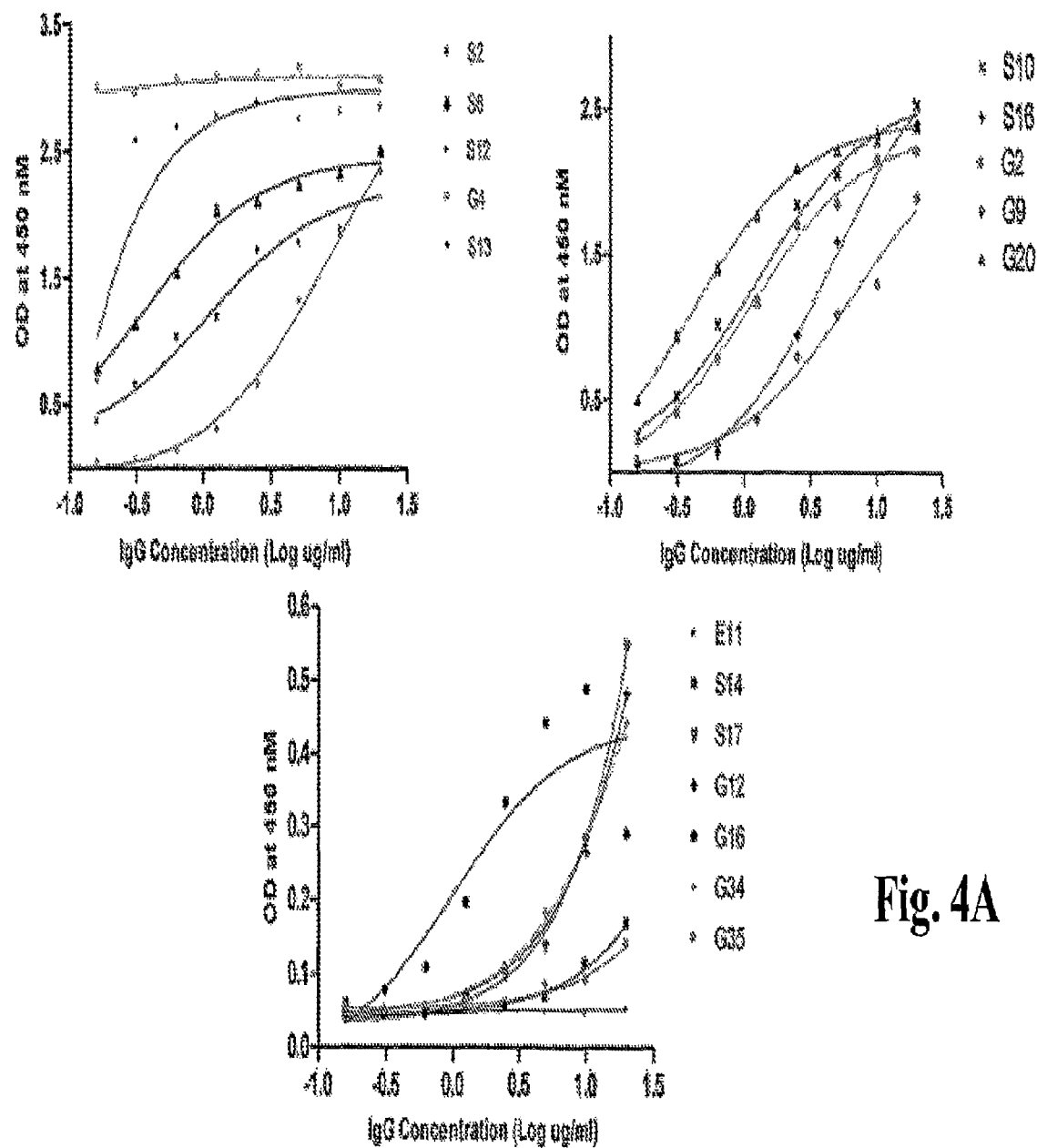

Direct ELISA (immobilized HMG1): Individual wells of a 96-well immunoplate (EIA/RIA plate, High binding, Costar) were coated with HMGB-1 at 5 μg/ml in PBS at 4° C. overnight. The plate was then blocked with 4% milk powder dissolved in PBS at 37° C. for 1 hour. The blocking solution was removed and replaced with human anti-HMG1 antibodies at various concentrations (see FIG. 4A). The plate was then washed (ELX-405 Plate washer, BIO-TEK) and secondary antibody (anti-human IgG-HRP, PIERCE) was added at a final concentration of 1:125,000 at 37° C. for 1 hour. HRP activity was detected with Sureblue HRP substrate (KPL). Plates were read at 450 nm using a Kinetic Microplate Reader (Molecular Devices). The data are summarized in Table 1 and representative binding curves are shown in FIGS. 4A and D.

Figure 4B:
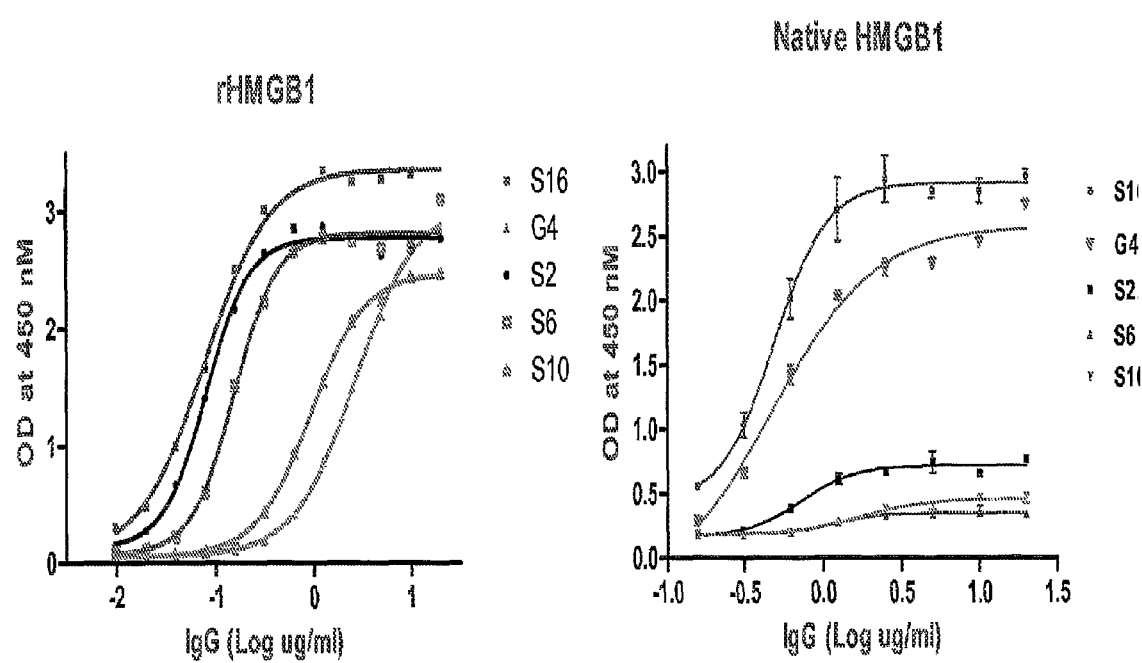
Figure 4C:
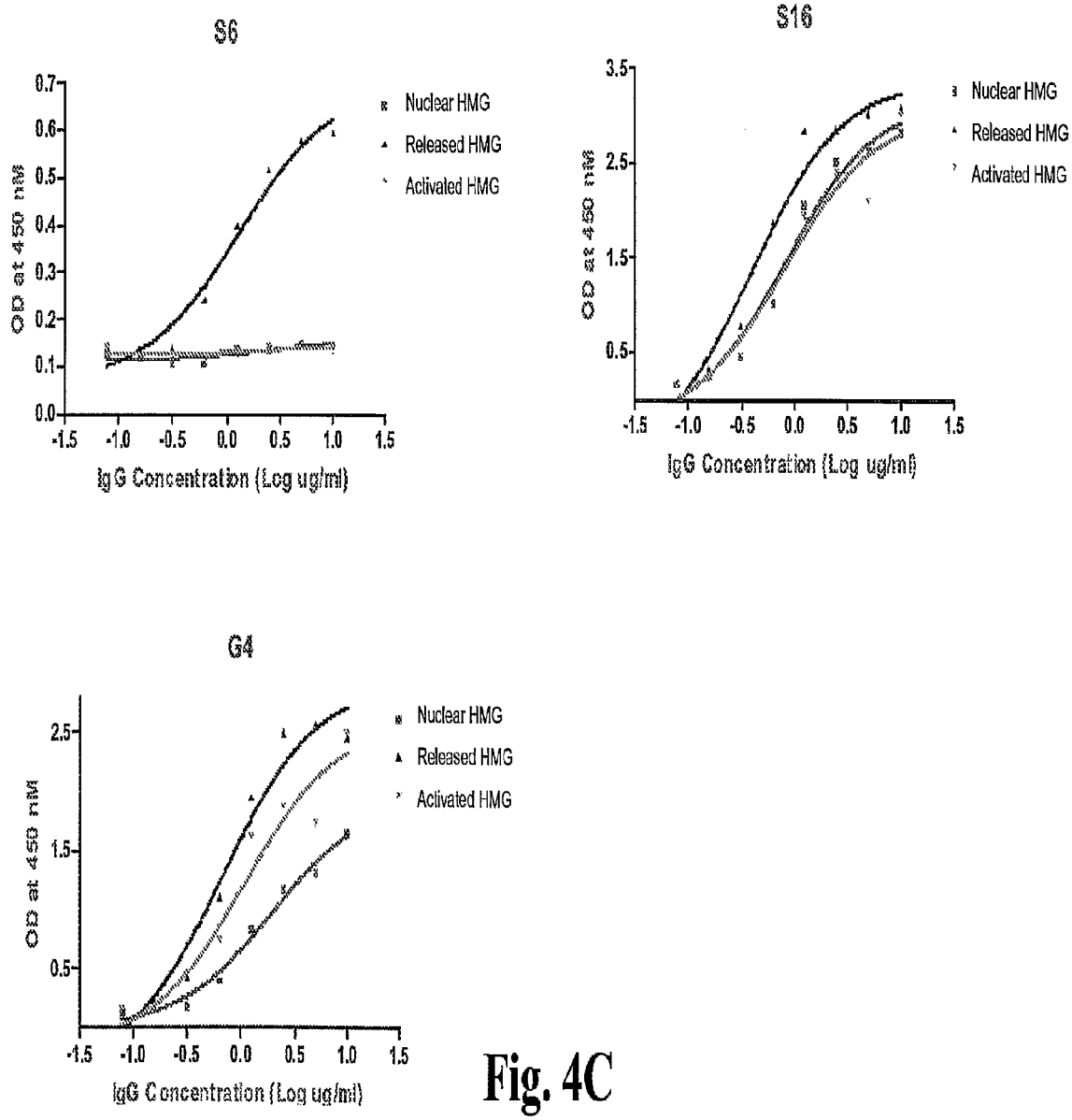
Figure 4D:
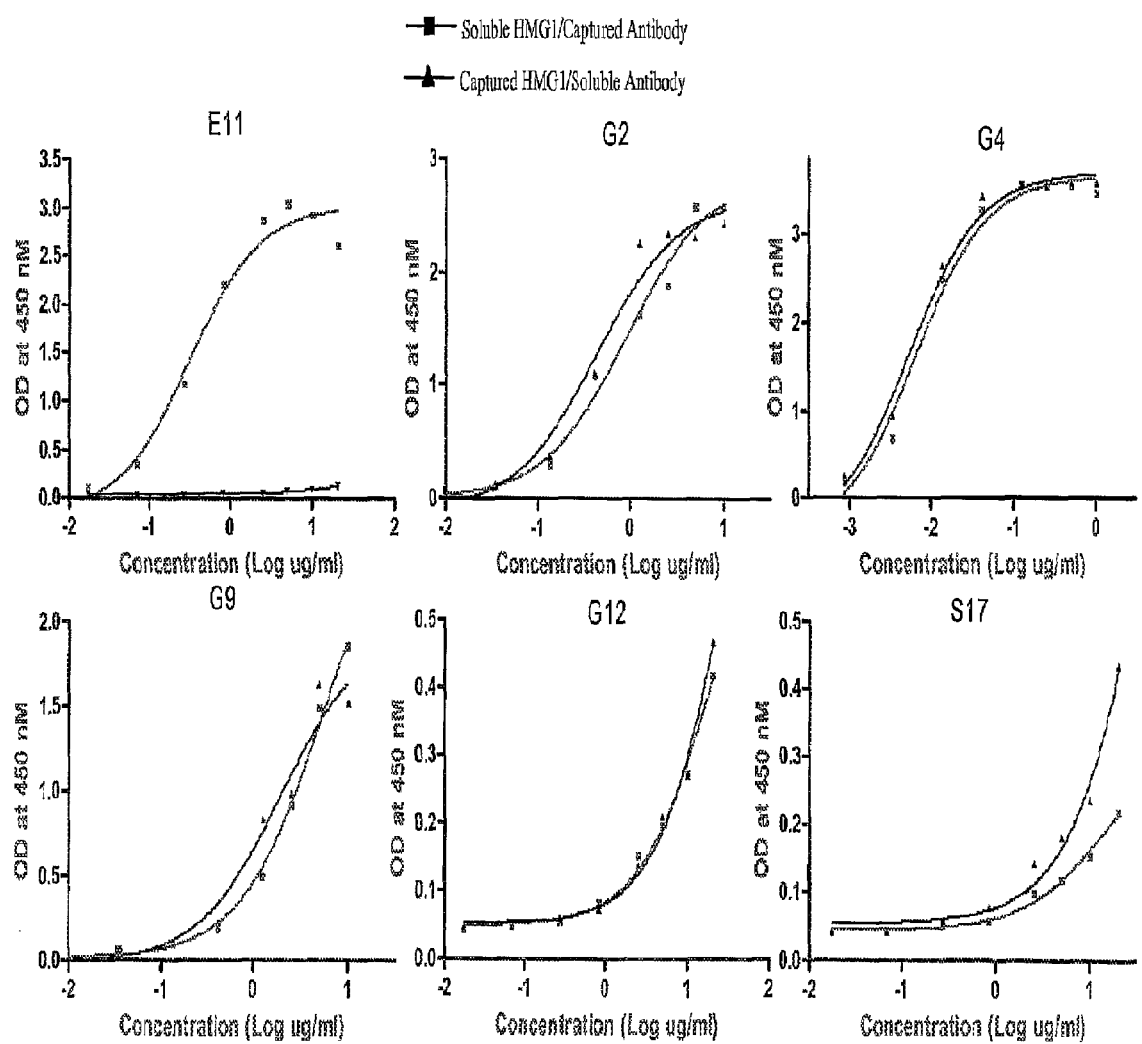

Sandwich ELISA (soluble HMG1): Immunoplates (EIA/RIA plate, High binding, Costar) were coated with anti human IgG Fc at 10 μg/ml in PBS (pH 7.2) and incubated at 4° C. overnight. The coating reagent was removed and the plates were rinsed briefly with PBS. The plates were then blocked with 4% milk for 1 hour at 37° C. and rinsed with PBS. The anti-HMG1 antibodies were diluted in 4% milk. For serial dilutions, the antibodies were used at a starting concentration of 20 μg/ml. The diluted anti-HMG1 antibodies were then added into plate and incubated for 1 hr at 37° C. The plate was then washed 10 times with PBST (PBS/0.1% tween 20) and incubate with antigen (HMGB1, 2 μg/ml; or 0.7 μg/ml for native HMGB1) in 4% milk and incubated at 37° C. for 1 h. The plate was then wash 10 times and incubated with mouse anti-HMGB1, 1 μg/ml in 4% milk at 37° C. for 1 h. The plate was washed 10 times and incubated with anti-mouse IgG-HRP at 1:1000 at 37° C. for 1 h. The plate was then washed and developed. HRP activity was detected with Sureblue HRP substrate (KPL). Plates were read at 450 nm using a Kinetic Microplate Reader (Molecular Devices). The data are summarized in Table 1 and representative binding curves are shown in FIGS. 4B-D.

Antibody HMG1 Binding Competition via BIAcore Analysis: All experiments were performed on a BIAcore 3000 instrument (BIAcore, Inc., Piscataway, N.J.). The HMGB-1 protein was immobilized onto a CM5 sensor using a standard amine coupling chemistry protocol, as described in the BIAcore Handbook (BIAcore, Inc., Piscataway, N.J.). Briefly, the CM5 surface subject to the NHS/EDC activation. After activation a HMGB-1 was injected over the surface at a concentration of 100 nM or 200 nM (in 10 mM NaOAc, pH4) to a surface density of between 1100 and 1200 RU's. Following this, unreacted sites on the sensor chip surface were "capped" with an injection of 1M ethanolamine. For reference purposes, a blank flow cell was also prepared, utilizing this same procedure that was used to immobilize HMGB-1, but without any ligand.

MAbs G2, G4, G9, S6 and Synagis were prepared at 1 uM and 2 uM. All mAb solutions were prepared in HBS-EP buffer (BIAcore, Inc., Piscataway, N.J.). Each cycle started with a 100 μL injection of the first mAb, injected at 1 μM, followed by a second 100 μL injection of a 1:1 mixture of two, 2× concentration mAbs, such that the final concentration of each component mAb in the mixture is equivalent to the first injection. Following each injection cycle, the HMGB-1 surfaces were regenerated with a 1 min pulse of 10 mM HCl.

Once the entire set had been collected, the maximum RU responses for each mAb after each injection cycle was recorded. These were then used to calculate an average response level for each mAb. This average binding response was then used to calculate the percent each mAb bound to the HMGB-1 surface following it's saturation with the first mAb. Taken together, these binding/blocking patterns were used to determine if the mAbs bound to sites which unrelated or related sites on HMGB-1. These data are summarized in Table 1.

Figure 4E:
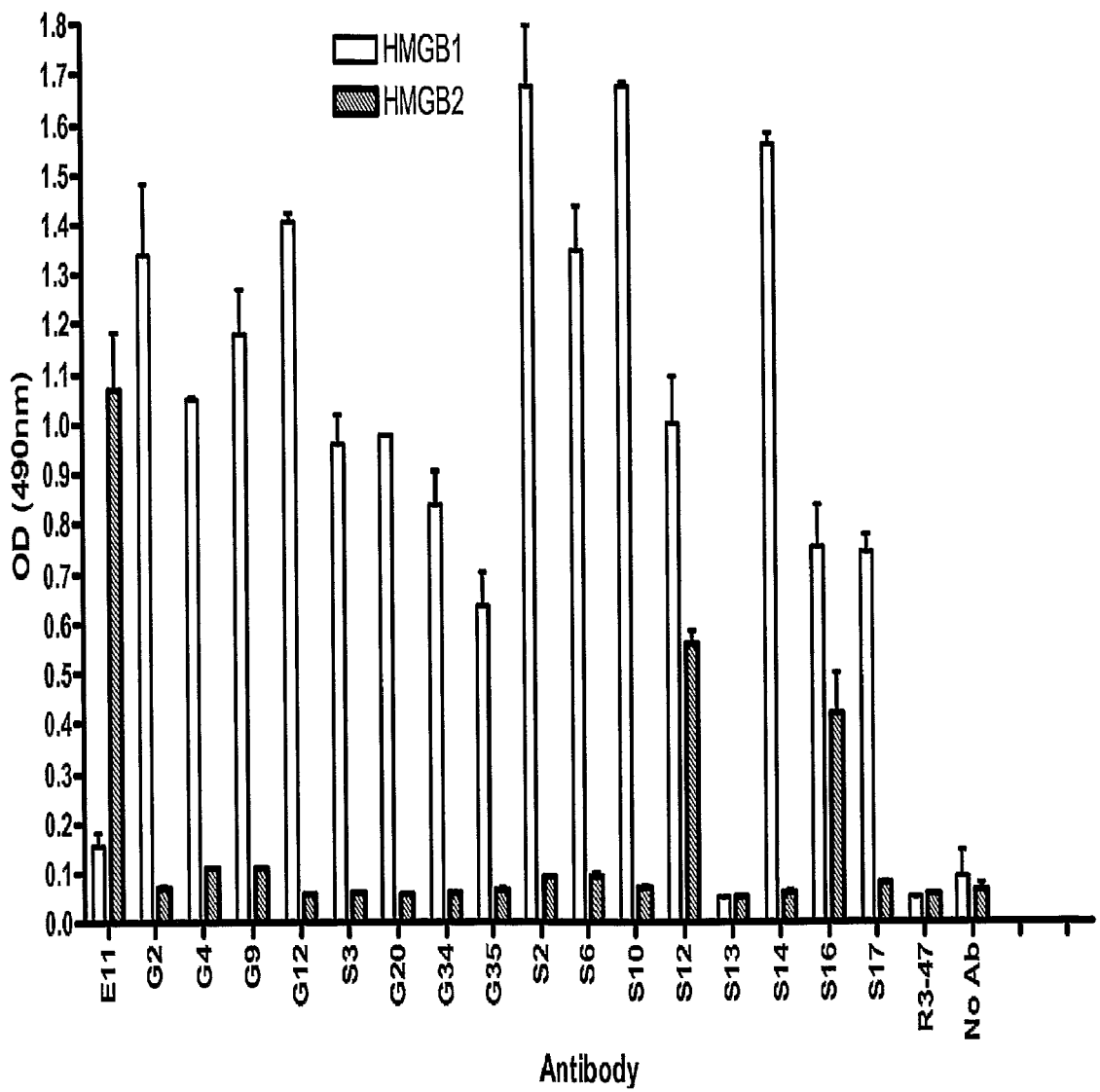

Binding to HMG1 vs. HMG2: Ultra high-binding ELISA plates (ThermoLab systems, #3855) were coated with either 5 ug/mL of Calf thymus HMGB1 or HMBG2 diluted in 10 mM Phosphate buffered saline (PBS), pH 7.2 and incubate overnight at 4 degrees. The plates were washed twice with Ca and Mg free PBS and 100 microliters of anti-HMGB1 antibody diluted in 10 mM PBS, pH 7.2+1% bovine serum albumin (BSA) to a final concentration of 10 ug/mL was added to each well and the plates were incubated 1 hour at room temperature. The wells were washed three times with 100 μl of PBS, pH 7.2. HRP labeled goat-anti-human IgG Kappa-chain (KPL, #14-10⁻¹⁰) and goat-anti-human IgG Lambda-chain (KPL, #14-10-11) were diluted in 10 mM PBS+1% BSA 1:1000 and 100 µl were added to each well and incubated for 1 hour at room temperature. The wells were then washed three times with 100 µl of PBS, pH 7.2. OPD substrate (Pierce chemical company, #34006) was prepared following the manufacturers instructions and, 100 µl of prepared substrate was added to each well and the plates incubated at room temperature in the dark for 20-30 minutes. The reaction was stopped with the addition of 100 µl of 2M $H_2SO_4$, and the plates read on a plate reader at a wavelength of 490 nm. The OD values for a number of antibodies are shown in FIG. 4E and summarized in Table 1.

HMG1 B Box and Peptide Mapping: Individual wells of a 96-well immunoplate (EIA/RIA plate, High binding, Costar) were coated with HMG1 B Box peptide amino acids 91-169 (FIG. 5A) or amino acids 150-183 (FIG. 5B) at 10 µg/ml in PBS at 4° C. overnight. The plate was then blocked with 4% milk powder dissolved in PBS at 37° C. for 1 hour. The blocking solution was removed and replaced with human anti-HMG1 antibodies at various concentrations (see FIGS. 5A-B). The plate was then washed (ELX-405 Plate washer, BIO-TEK) and secondary antibody (anti-human IgG-HRP, PIERCE) was added at a final concentration of 1:125,000 at 37° C. for 1 hour. HRP activity was detected with Sureblue HRP substrate (KPL). Plates were read at 450 nm using a Kinetic Microplate Reader (Molecular Devices). To obtain more detailed peptide mapping information, similar ELISA assays were performed using 16 biotinylated overlapping peptides spanning the HMGB1 protein from amino acid 1 to 215 as follows, maxisorp microtiter plate was coated with 2 µg/ml of NeutroAvidin (Pierce) overnight at 4° C. After washing and blocking with 1% BSA in PBS, the biotinylated peptides were individually added into the avidin coated wells and incubated for 30 min at room temperature. The serial diluted antibody G4, S16 and S6 at the initial concentration at 10 µg/ml were then transferred into the wells followed by adding mouse anti human IgG-HRP conjugate (Pierce). Detection was accomplished by adding 50 µl of tetramethylbenzidine (TMB) substrate (KPL) and the absorbance was read at 450 nm. The peptides used were amino acids: 46-63; 61-78; 76-93; 91-108; 106-123; 136-153; 151-168; 166-183; 179-185; 181-198; and 196-215.

HMGB1 Detection from Biological Samples: For detection of the HMGB1 from AIA joint homogenates and peritonitis sera, sandwich ELISA was performed. Goat anti-human Fc (Pierce) 14 µg/ml in PBS was coated on Immunlon IV microtiter plate over night at 4° C. After washing and blocking with 5% milk 1 hr at room temperature, G4 or S6 in blocking buffer (10 µg/ml) were added to each well of the blocked plate. The plate was washed 1 hour later and 25 µl of AIA homogenates containing 0.8 µg/ml of HMGB1 or peritonitis sera containing 7 µg/ml of HMGB1 in 0.5 M NaCl/blocking buffer were added to the wells at two fold serial dilutions. The unbound materials were removed by washing one hr after incubation. The bound HMGB1 was detected by a mouse anti-HMGB1 antibody at 2 µg/ml followed by an anti-mouse antibody conjugated with horseradish peroxidase. Mouse peritonitis sera was obtained by heart puncture 7 days after infection with heat killed *staphylococcus aureus*. Joint lysate was prepared from the whole paw of AIA rats as described in Example 6 below. Human sepsis sera were purchased from a commercial source.

Immunofluorescence: Intracytoplasmic (ic) HMGB1 was quantitated by direct immunofluorescence. HUVEC were harvested by trypsin-EDTA treatment and seeded on a glass coverslip. Once the cells are settled, they were stimulated with 0.2 µg/ml of LPS (Sigma) for 4 hours. The cells were fixed in 2% paraformaldehyde for 15 min and then permeabilized in 0.2% Triton X-100 for 2 min. Fixed and permeabilized cells were incubated with anti-HMGB1 antibodies at 1 µg/ml for 1 hour at room temperature. Cells were then washed to remove excess or nonspecifically bound primary antibody followed by incubation with anti human IgG conjugated with fluorescence (Pierce). The sections were mounted with fluoromount (Southern Associates, Birmingham, Ala.), and the images were processed with a Nikon microscope (Japan) and a SPOT imaging system (Diagnostic Instrument).

Immunoprecipitation and Western. Blot.: Anti-HMGB1 mAbs (G4 and S6) and isotype control were first biotinylated using EZ-Link Sulfo-NHS-LC-Biotin as instructed by the manufacturer (Pierce). After labeling, the mAb was tested for binding to HMGB1 by ELISA with unlabeled mAbs as controls. The biological samples, joint lysate (30 µl), was mixed with 5 mg biotinylated G4, S6 or isotype control overnight at 4° C. in 300 µl IP buffer [containing 1× PBS, pH 7.2 (Invitrogen), 0.1% Tween 20, 0.5 M sodium chloride, 10 mM sodium butyrate, and a 1:100 dilution of Phosphatase Inhibitor Cocktail I (Sigma)]. For sepsis sera, Tween 20, sodium chloride, sodium butyrate, and Phosphatase Inhibitor Cocktail I were added to 500 µl sera with the same final concentration as IP buffer. Streptavidin Sepharose beads (GE Healthcare) were blocked in 4% BSA-PBS overnight at 4° C., then washed three times with PBS and resuspended in 1× PBS resulting in 50% slurry. The bead slurry (60 µl) was then added to the overnight mAb/sample mixture and mixed for 20 minutes at room temperature. The beads were washed once with PBS, five times with IP Buffer and then washed twice with PBS by spinning at 1000 g for two min. The immunoprecipitated proteins were eluted from the beads with 30 ul sample buffer containing 2.5% β-mercaptoethanol at 70° C. for 10 minutes. Eluates were electrophoresed using a 10% NuPAGE Bis-Tris gel in 1× MES Running Buffer, followed by transferring to a PVDF membrane. The membrane was then blocked in 4% BSA/PBS for 1 hour and incubated with a different biotinylated anti-HMGB1 mAb, S16, at 0.5 mg/ml for 1 hour. After washing with PBS/0.1% Triton X-100, the blot was incubated in a 1/40,000 dilution of Streptavidin HRP (GE Healthcare) for 40 min. The bands were detected by LumiGlo substrate solution (KPL) after washing.

6.2.2 Results

ELISA studies demonstrated that most of the antibodies examined bind to immobilized rHMG1 (FIG. 4A). While most antibodies bound to both immobilized and soluble rHMG1 E11, G34 and G20 were seen to bind better to soluble rHMG1 while S10, S12, S16 and G16 bound slightly better to immobilized rHMG1 in this assay (FIG. 4D and data not shown). Many of the antibodies tested show some preference for binding either rHMG1 or one or more forms of the native HMG1 (summarized in Table 1, also see FIGS. 4B-C). For example S16 binds both recombinant and native HMG1 while G4 binds better to native nuclear HMG1 and S2, S6 and S10 all show better binding to rHMG1 (FIG. 4B). Interestingly, while S6 doesn't bind well to any native form of HMG1 it does bind show some binding of released HMG1 (FIG. 4C, top left). S16 and G4 show little difference in binding to the various native forms of HMG1 (FIG. 4C, top right and bottom left). These data indicate that there are differences between rHMGB1 and HMGB1 prepared from mammalian cells that can be detected by our panel of anti-HMGB1 antibodies. The difference may result from the folding or conformations present in the cells which are not found in recombinantly produced material. Alternatively, native HMGB1 may complexed with other proteins or cofactors when prepared from the cells. In addition the antibodies were tested for cross reactivity to the highly related HMG2 protein. E11, S12 and S16 µl showed some binding to HMG2. Interestingly, E11 appears to bind better to HMG2 than to HMG1 when the antigen is immobilized, the conditions used here.

BIAcore Analysis of nearly all of the antibodies was used to determine the $K_d$ of each antibody for recombinant HMG1 (rHMG1, see Table 1). Analysis of several antibodies (G4, G9, S2 and S6) by BIAcore competition assays showed that these anti-HMBG1 antibodies appear to bind to either the same site or sites that are highly related perhaps overlapping (see Table 1).

Figure 5A:
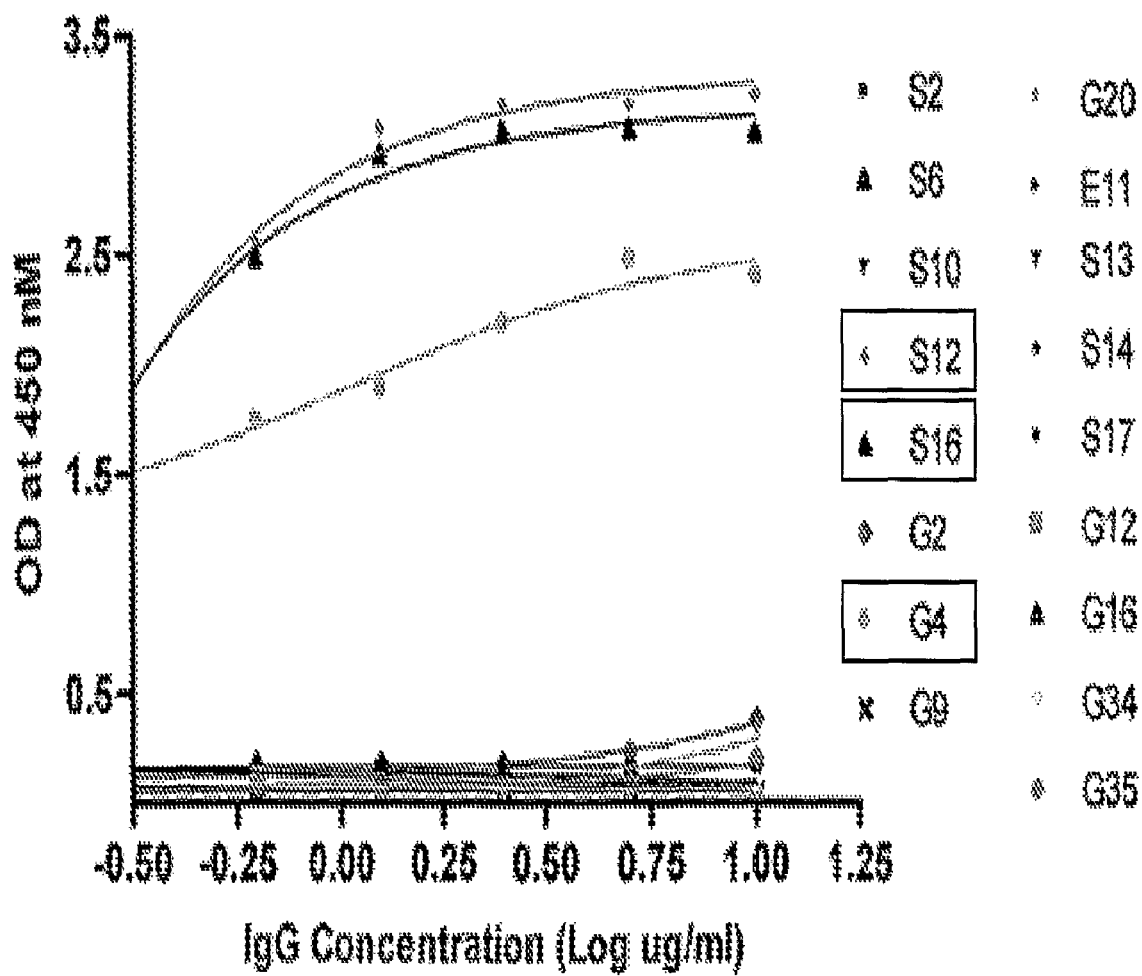
Figure 5B:
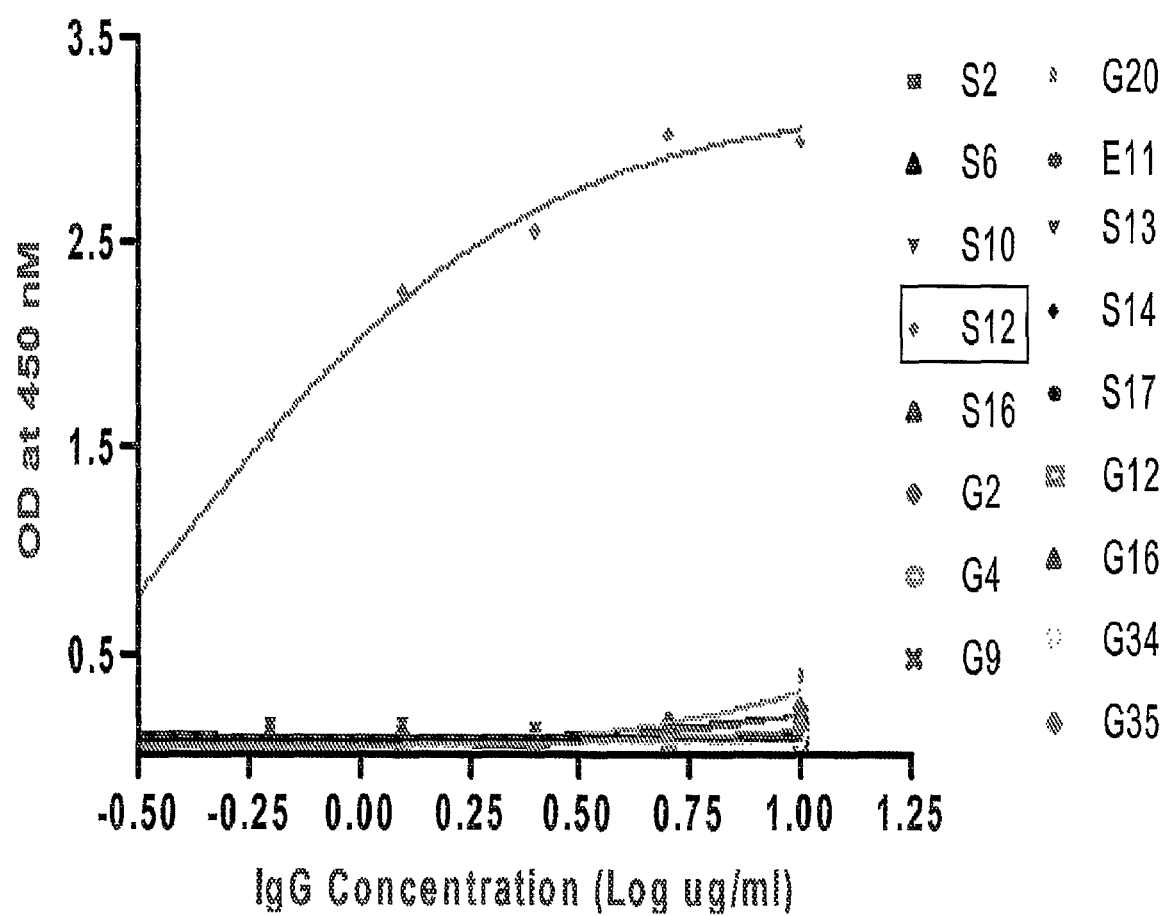
Figure 5C:
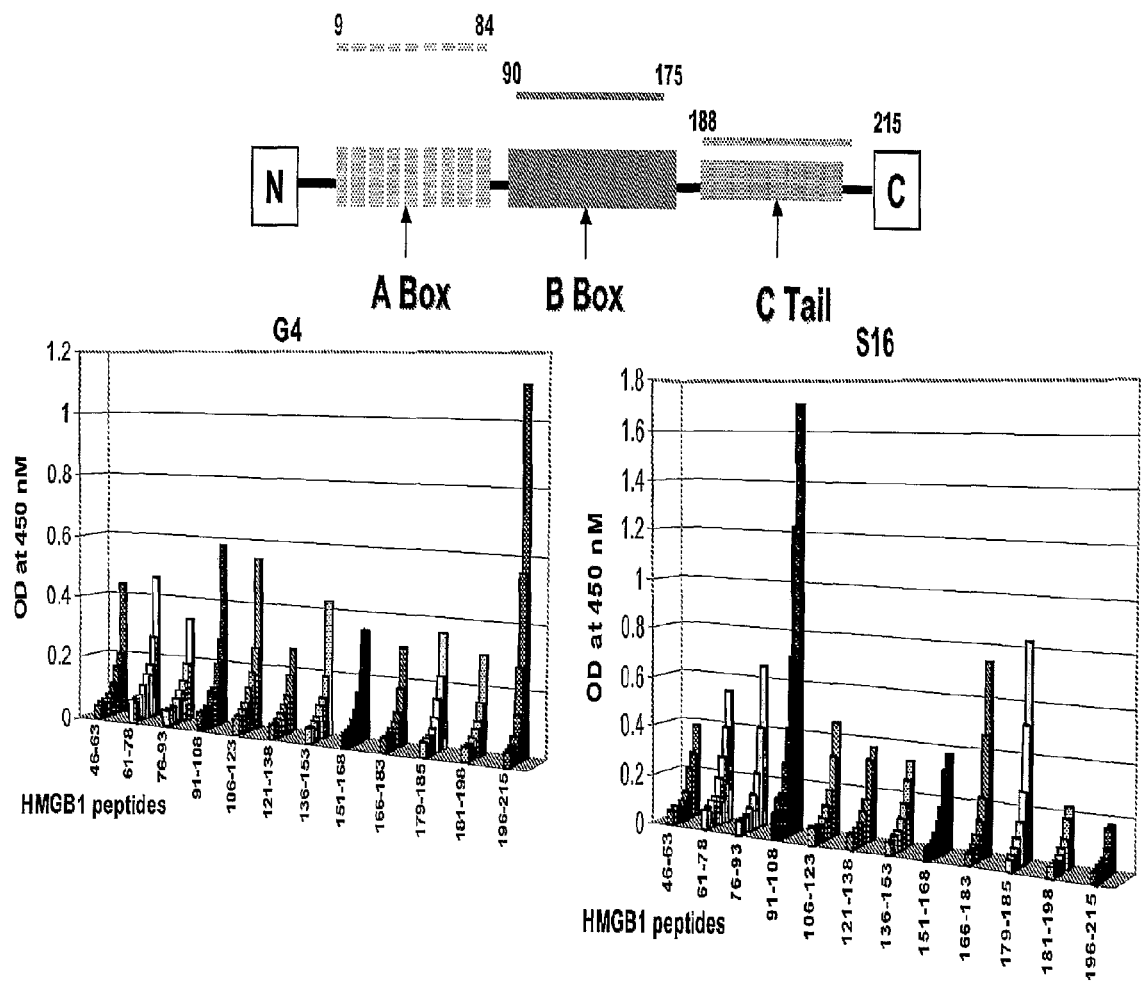

Peptide mapping studies were done on several of the anti-HMG1 antibodies (S2, S6, S10, G2, G4, G9, S12 and S16) to examine binding to HMG1 B Box. As shown in FIGS. 5A-B, G4, S12 and S16 bind to HMG1 peptide 91-169 (FIG. 5A) while only S12 binds to HMG1 peptide 150-183 (FIG. 5B). In addition, it was found that E11 recognizes the HMG1 A-Box (data not shown). Detailed peptide mapping was performed for both G4 and S16 (FIG. 5C, left and right panels, respectively). G4 shows the strongest binding to the C-terminal tail peptide 188-215 and lesser binding to the B-box peptides 91-108 and 108-138. S16 shows the strongest binding to the B-box peptide 91-108 with lesser binding to peptides 166-183 and 179-186.

Figure 4F:
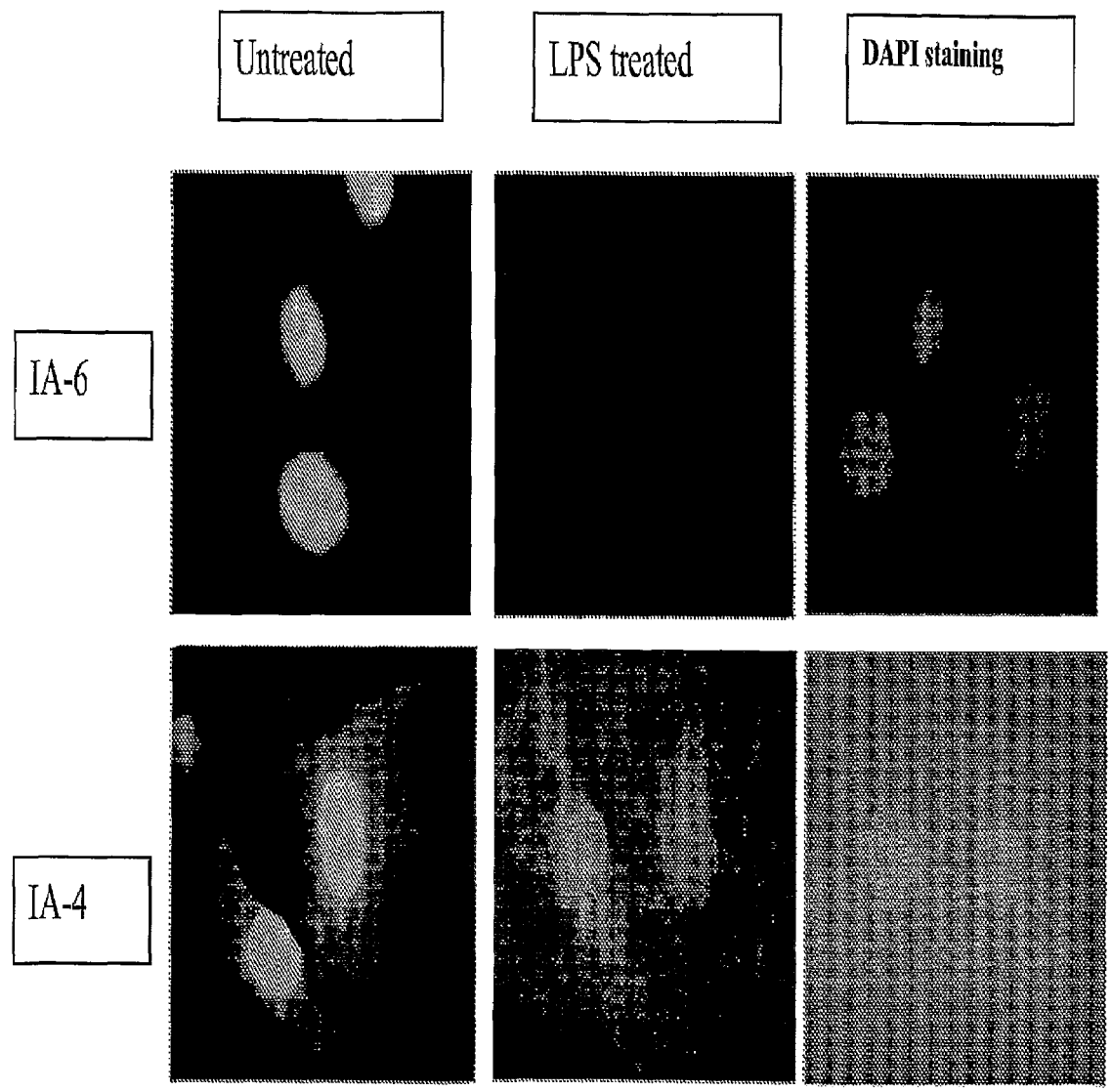
Figure 4G:
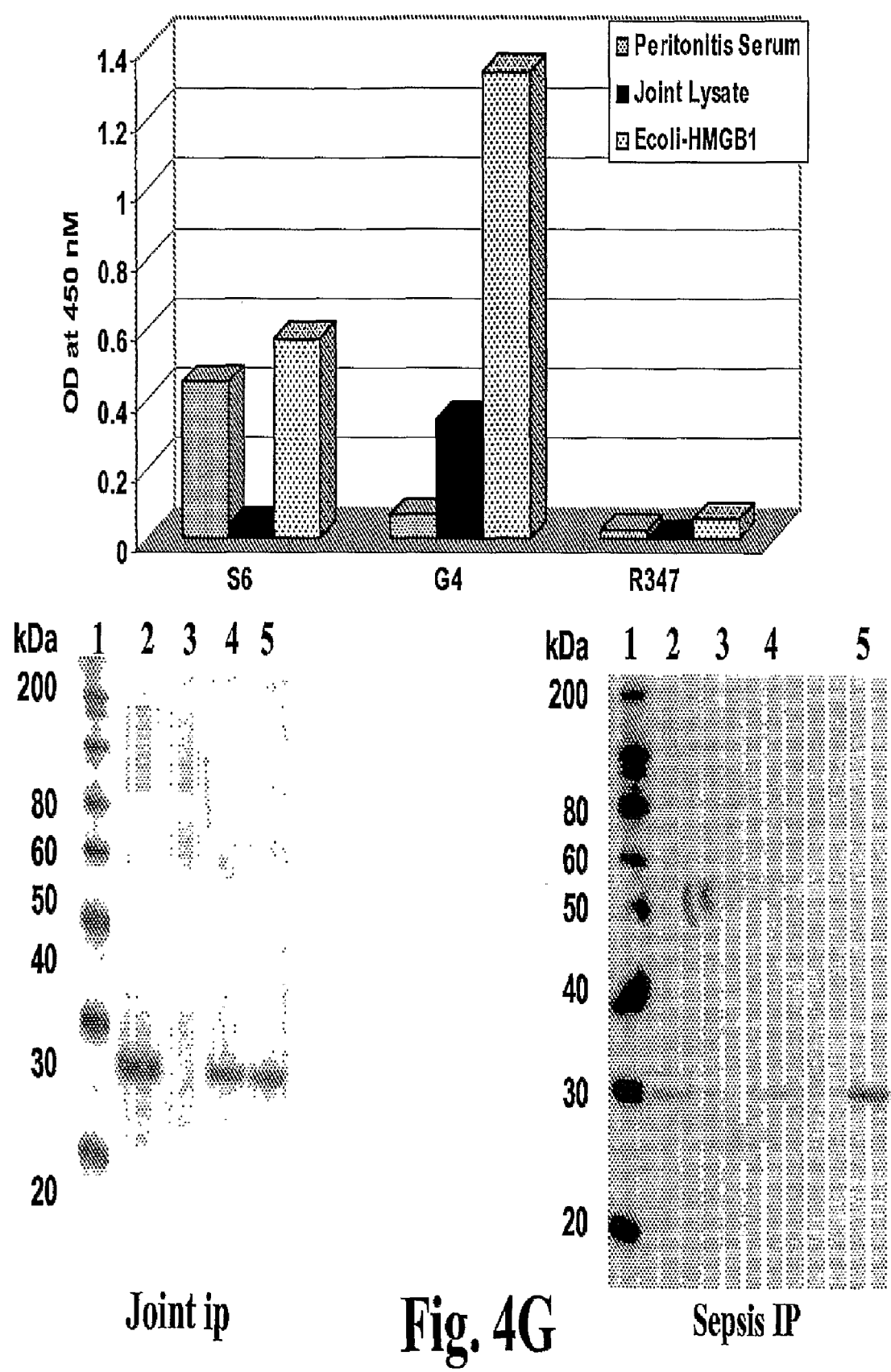

As noted above, the different antibodies bind differently to HMGB1 isolated or prepared from different sources. To expand this observation the anti-HMBG1 antibodies G4 and S6 were used for immunostaining of untreated or LPS activated THp-1 (not shown) and HUVEC cells (FIG. 4F). Consistent with binding data (FIG. 4C, left panels), G4 recognizes both nuclear HMGB1 and actively secreted HMGB1 (FIG. 4F, compare bottom left and middle panels), and S6 did not recognize actively secreted HMGB1 (FIG. 4F, compare top left and middle panels). However, in contrast to binding data, S6 recognized nuclear HMGB1, indicating that the nuclear HMGB1 prepared from freeze thaw cells is different from the native HMGB1 in the nucleus of the cells. As nuclear HMHB1 binds to DNA and histones, which might be disrupted after cell freeze and thaw we immunoprecipitate freeze thaw preparation and probed for histones by Western Blot. No DNA or histones could be detected from this preparation (data not shown). In addition, ELISA and immunoprecipitation analysis was used to examine the binding of the anti-HMGB1 antibodies S6 and G4 to HMGB1 present in lysates prepared from the joints of adjuvant induced arthritis (AIA) rats and sera collected from septic peritonitis mice induced by heat-killed bacteria, *Staphylococcus aureus* (ELISA studies) or human sepsis sera (immunoprecipitation studies). G4 was seen to selectively bind to HMGB1 from arthritis joints by ELISA (FIG. 4G, top) and to immunoprecipitate HMGB1 from both AIA joint lysates and human sepsis sera (FIG. 4G, lane 4 of bottom left and bottom right panels, respectively). In contrast, S6 did not bind or immunoprecipate HMGB1 from arthritis joints (FIG. 4G, top and bottom left, lane 3). S6 shows better binding to HMGB1 from sepsis sera by ELISA (FIG. 4G, top) and was seen to immunoprecipitate smaller band from human sepsis sera (FIG. 4G, bottom right, lane 3). In gel digestion and sequencing confirmed that the smaller band was HMGB1 (data not shown).

In summary, HMGB1 appears to be present in multiple forms in cells and various disease states, and the human anti-HMG1 antibodies isolated show a wide variety of binding characteristics with some binding all forms of HMG1 (e.g., S16) and others discriminating between recombinant and the various native forms (e.g., S10 and S2). In addition, some antibodies (e.g., S6 and G4) appear to preferentially bind HMGB1 present in certain disease states. They also bind a number of different epitopes include the A- and B-boxes. Several human anti-HMG1 antibodies were selected for use in a number of addition in vitro and in vivo experiments (see below).

6.3 Example 3

Anti-HMGB1 Antibodies Inhibit Cytokine Release from Human PBMC's

The ability of a panel of human anti-HMG1 antibodies to inhibit HMG1 induced cytokine release from human peripheral blood mononuclear cells (PBMCs) was determined. The effect on the following cytokines were examined, IL-12, IL-1β, TNF-α, and IL-6. A number of anti-HMG1 antibodies are capable of inhibiting the release of one or more of these cytokines induced by HMG1. In addition, it was determined that HMG1 can stimulate the release of NO and that antibodies against HMG1 can inhibit this release. The ability of several human anti-HMG1 antibodies to reduce HMG1 induced cytokine gene expression in mouse macrophages was also demonstrated.

6.3.1 Materials and Methods

Inhibition of Cytokine Release: Human peripheral blood mononuclear cells (PBMCs) were isolated from the peripheral blood of healthy volunteers by a density gradient centrifugation. Freshly drawn heparinized whole blood was mixed with two volume of PBS. The diluted blood was gently layered on the surface of Histopaque-1077 (Sigma-Aldrich) and centrifuged at 400×g, at RT for 30 minute. PBMCs were collected from the interface between the plasma and the density gradient solution. After washing in PBS 3×, the purified PBMCs were resuspended in RPMI-1640 medium (GIBCO BRL) containing 100 U/ml penicillin, 100 µg/ml streptomycin and 50 µM β-mercaptoethanol. $1 \times 10^5$ of cells was added in each well of 96-well cell culture plates.

The PBMCs were incubated for two hours at 37° C. with 5% $CO_2$. recombinant HMG1, at 4 µg/ml, or native activated HMG1 from $2.4 \times 10^5$ LPS stimulated THP-1 cells, and different concentrations of human anti-HMGB-1 monoclonal antibodies, a RAGE-Fc fusion protein or an HMG1 A-box-Fc fusion protein were added into each well. The culture media was supplemented with 8 U/ml (1 µg/ml) Polymyxin B sulphate (Sigma-Aldrich) to inhibit potential endotoxin. PBMCs from the same donor without stimulation with HMG1 were used as controls. The cell-free culture media were harvested after 14 hours and stored at −20° C.

The culture media were analyzed for inflammatory cytokines using Beadlyte human multi-cytokine flex kit from Upstate by Luminex100 (Luminex Corp.). Proinflammatory cytokines TNF-α, IL-6, IL-1 β and IL-12 p40) were measured for cells stimulated with recombinant HMG1. In addition, TNF-α, IL-6, IL-1 β and IL-8 were measured for cells stimulated with native activated HMG1.

Cytokine release data is presented as mean of triplicates±standard deviations. $IC_{50}$ for anti-HMGB1 monoclonal antibody is defined as the concentration of antibody required yielding one-half maximal inhibition of the cytokine release from PBMCs stimulated by HMGB1. It was calculated by PRISM program.

Inhibition of NO Release: Macrophages employed in the NO assay included RAW cells (mouse macrophage cell line), as well as bone marrow-derived macrophages (mBMMf) obtained from C57BL/6 mice. The mBMMf were used after maturing for 3 days in culture in the presence of M-CSF ("fresh mBMMf"). Cells were plated at $10^5$ cells/well into 96-well plates and stimulated with HMG1 over night in 100 µl of serum-free a-medium. HMGB-1 (5 µg/ml) and LPS (1 µg/ml) were used as positive controls to stimulate NO production by the macrophages at various concentrations; dose dependent response observed with these stimuli. Antibodies were tested at a molar ration of 4:1 against HMG1. The next day plates are spun at 1500 rpm for 5 min and the supernatant is harvested. To another 96-well plate the following components are mixed, A50 µl of stimulated supernatant and standards (diluted in a-medium), 25 µl of NADH, 25 µl of Nitrate Reductase, 50 µl of Griess Reagent I and the plate is incubated for 30 min. at 37° C. Then 50 µl of Griess Reagent II is added to each well and the plate is incubated for 10 minutes at room temp. The absorbance of each well is read at 540 nm and the values of Nitrate are calculated against a standard curve.

Tagman Analysis of Mouse Macrophages (mMØ) Stimulated with HMG1: Mouse bone marrow was harvested by rinsing the femurs of normal C57BL/6 mice. The isolated bone marrow cells were then cultured in Dulbecco's modified Eagle's medium (DMEM) supplemented with 10% fetal bovine scrum (FBS) and 50 ng/ml M-CSF for 24 h, nonadherent cells were collected and grown for 6 days in complete DMEM supplemented with 10% FBS and 50 ng/ml M-CSF in T-75 flasks ($1 \times 10^7$ cells/15 ml/flask). On day 6, adherent cells were harvested and reseeded with 5 ng/ml MCSF in α-MEM containing 10% FBS in 96-well plates ($1 \times 10^5$ cells/200 µl/well) overnight.

The culture medium was replaced with α-MEM and incubated for 2 hours before stimulation to starve cells. HMGB1 (recombinant CBP-HMGB1 fusion protein generated from E. coli at 10 µg/ml), mouse-RAGE-Fc or human-RAGE-Fc fusion protein were pre-mixed with various blocking reagents at 100 µg/ml in α-MEM for 20 min at RT, then 100 µl of the mixtures was added to the cells and incubated at 37° C. for 2 hours. The supernatant was then removed, and the RNA was extracted using Ambion's MagMAX™-96 Total RNA Isolation Kit. All of the recovered RNA were used in a reverse transcriptase (RT) reaction with SuperScript™ III and oligo (dT) primer (Invitrogen) for synthesis of cDNA. 1 µl or 2 µl of the resulting cDNA was used for real time quantitative PCR analysis (TaqMan) using ABI Prism 7700 or 7000.

6.3.2 Results

Figure 6A:
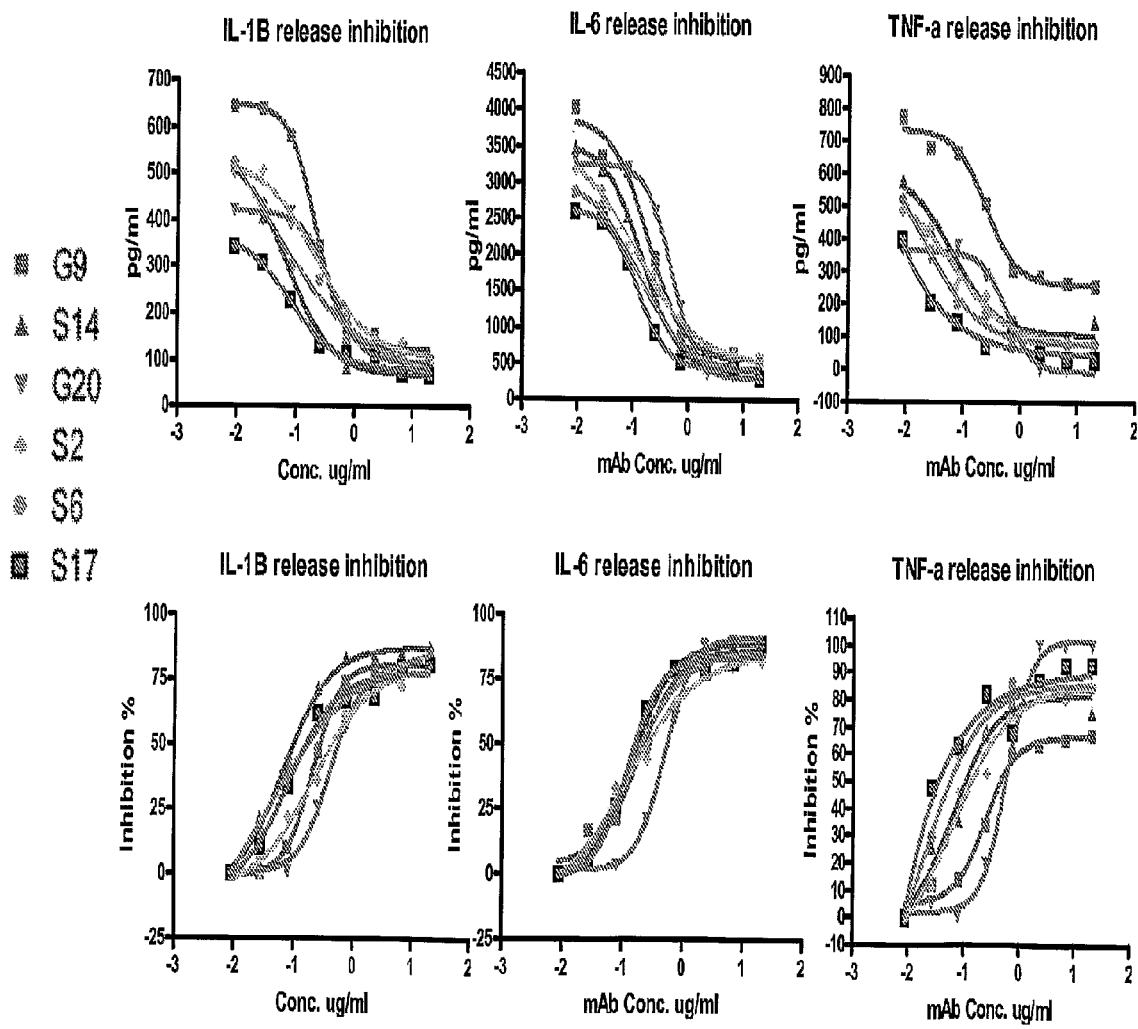
Figure 6B:
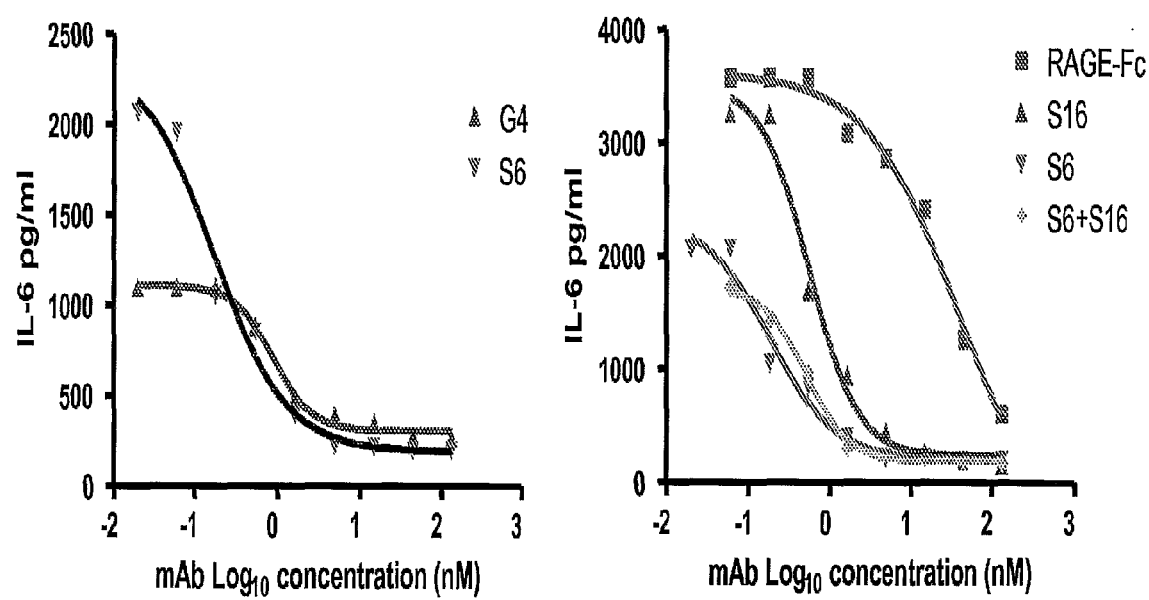
Figure 6C:
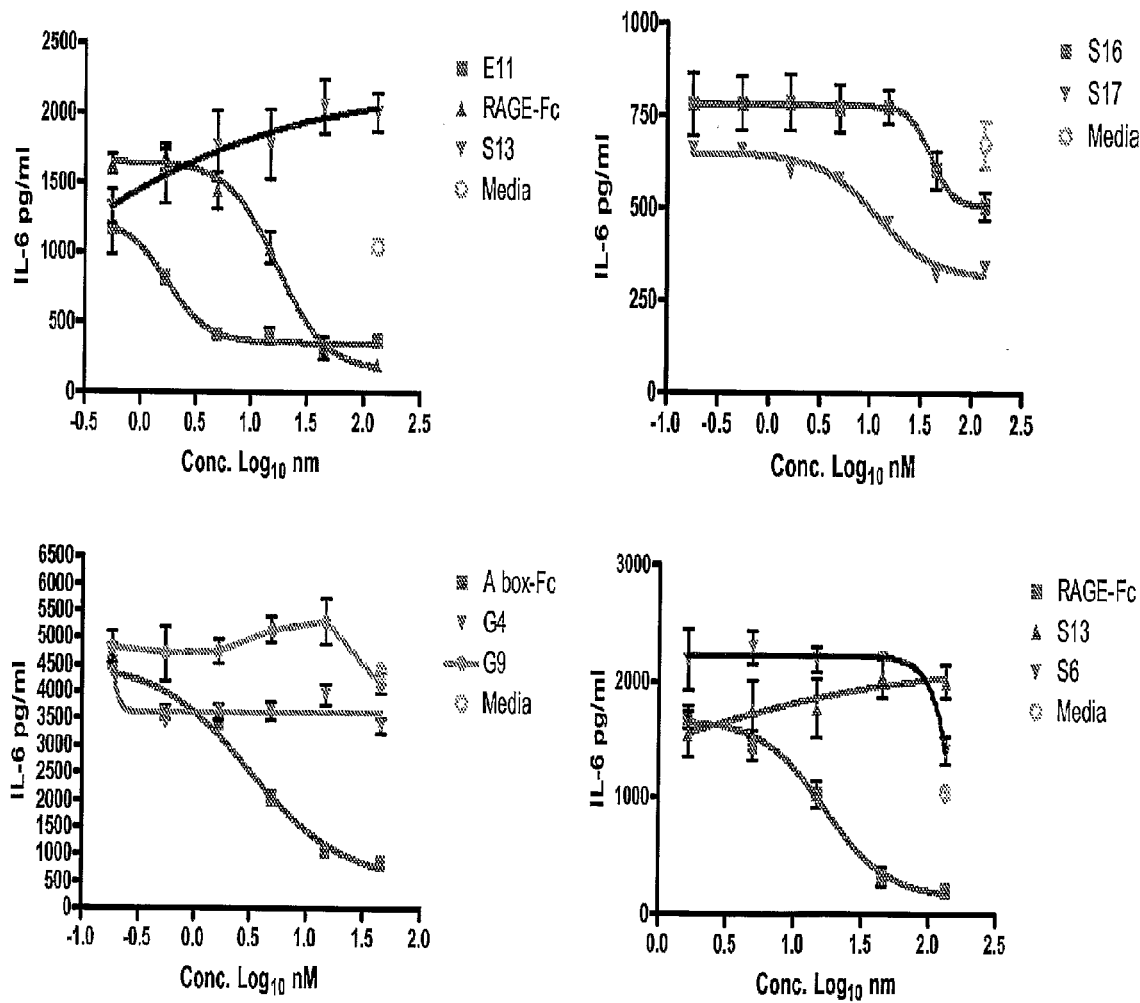

Representative HMG1-induced cytokine release titration curves for several antibodies are shown in FIG. 6A-B. $IC_{50}$ values were calculated for each antibody examined (see Table 1). A few antibodies were also tested for their ability to block native activated HMG1 (from LPS stimulated THP-1 cells, see above). E11, S16 and S17 along with the RAGE-Fc fusion protein were able to block IL-6 released induced by native activated HMG1 while S6, S13, G4 and G9 were less effective (FIG. 6C). The results of these studies and numerous other studies for which the data are not shown are summarized in Table 1. It is apparent that several antibodies are capable of inhibiting cytokine release at low antibody concentrations. Of the antibodies thus far examined, S6 is among the best inhibitor of IL-1β, TNF-α, IL-6 and NO release while G4 is the best inhibitor of IL-12. Note that not all antibodies have been examined for the ability to inhibit the release of all cytokines. A few antibodies were also examined for their ability to inhibit rHMG1-induced cytokine gene expression in isolated mouse macrophages (mMØ). E11, G2 and G4 were able to significantly reduce HMG1-induced IL-1b gene expression (FIG. 7, left and Table 1)). G2 was also able to significantly reduce HMG1-induced TNF-α gene expression (FIG. 7, right and Table 1). Several antibodies were chosen for further analysis to determine their effect on HMG1 binding to cell surface receptors.

6.4 Example 4

Anti-HMG1 Antibodies Block HMG1 Binding to Cell Surface Receptors

Both RAGE and TLR4 have been identified as putative receptors for HMG1. To demonstrate that human anti-HMG1 antibodies are capable of blocking the interaction of HMG1 with one or more of these putative receptors, several of the human anti-HMG1 antibodies were assayed for their ability to block recombinant HMG1 binding to a RAGE-Fc fusion in an ELISA assay (FIG. 8) and/or for their ability to block HMG1-induced activation of TLR4 in a cell reporter system (FIG. 9). In addition, the ability of the human anti-HMG1 antibodies to specifically block the binding of HMG1 to the cell surface of THP-1 cells was also demonstrated (FIG. 10).

6.4.1 Materials and Methods

HMG1 binding to THP-1 Cells: Recombinant rat HMGB-1 was labeled using Eu-labelling Kit from PerkinElmer. Molar ratio of HMGB-1 to Eu is 1:5. THP-1 were cultured as the protocol from ATCC. Cells were harvested and suspended at concentration $1 \times 10^6$/ml in assay buffer containing 1× DELFIA L*R binding buffer (PerkinElmer), 50% of DELFIA stabilizer (PerkinElmer) and 0.05% of sodium azide. 100 µl of cells ($1 \times 10^5$) was added into wells in 96 well cell culture plate. The plate was incubated with gentle shaking at 4° C. for one hour. 100 µl of assay buffer containing 2 nM of Europium-labeled HMGB-1 mixed with various concentrations (333, 166.5, 83.25, 41.6, 20.8, 10.4 and 5.2 DM) of human anti-HMGB1 antibodies E11 or G2 or soluble human RAGE-Fc, were added into each wells respectively. After one hour incubation with gentle shaking at 4° C., the cells were washed four times with 1× L*R wash buffer (PerkinElmer) by centrifuging at 1200 rpm×5 min. 200 µl of enhancement solution was added into each well to dissociate and enhance Eu fluorescence at 615 nm. The fluorescence was measured with Wallac Victor Fluorometer. Assay was performed in triplicate and human antibody R3-47 was used the negative isotype control.

HMG1 binding to RAGE-Ig by ELISA: 50 µl/well of RAGE-Fc fusion protein at 5 µg/ml in PBS was added to each well of an ELISA plate and incubated overnight at 4° C. The plate was then blocked with 200 µl of 5% milk at 37° C. for 1 hr and washed 3× with PBS/Tween. 50 µl/well of diluted HMGB1 solution. For dose curves, HMGB1 concentrations started at 4 ug/ml in PBS. For antibody blocking the HMGB1 was preincubated in another plate with human anti-HMG1 antibodies or buffer, then transferred to the RAGE-coated plate. The plates were then incubated at room temperature for 2 hours and washed 3×. To detect any HMG1 bound to the immobilized RAGE-Fc a mixture of biotinylated mouse anti-HMG1 mAbs (10D4, 4H11, 3E10 and 5C12) each at 1 ug/ml, total Ab: 4 ug/ml, were added to each well and the plate was incubated for 1 hour at room temperature. The plate was then washed and Strepavidin-HPR was added to each well and incubated 15 min. The plate was then washed 3× and blotted dry. 100 µl of TMB developing agent was added and the plate read at 650 nm. Values were calculated as percent of inhibition with HMG1 alone equal to 0% inhibition. The data in FIG. 9 and summarized in Table 1 represent the average of two separate experiments.

TLR4Activation Assay: HuTLR4 and CD14 stably expressed 293 cells (Invitrogen) were seeded in a 96 well plate at $2 \times 10^4$/well in 100 µl of DMEM with 10% FCS overnight. Cells were then transfected with NF-κB/Luc (Stratagene) luciferase reporter construct as indicated by the kit for 24 hr. A mixture of HMGB1 and anti-HMGB1 was added to cells at 100 µl/well overnight. The luciferase activity was then measured to reflect TLR4 activation (Promega).

6.4.2 Results

These studies demonstrate that several of the antibodies tested inhibited recombinant HMG1 binding to RAGE by at least 35% (e.g., G2, G4, S10, S16, S2 and S6), two of the antibodies tested, G2 and 64, inhibited binding by nearly 75% under the conditions tested (FIG. 8, and Table 2). Several antibodies did not inhibit RAGE binding (e.g., G9, G12, G16, S14, etc, see Table 1) at the concentrations tested. E11 was seen to inhibit HMG1 binding to RAGE at higher concentrations (data not shown) and can block native HMG1 binding (see example 14). E11 and G20 were able to inhibit HMG1 activation of TLR4 (FIG. 9 and Table 1). In addition, both E11 and G2 human anti-HMG1 antibodies block the binding of HMG1 to THP-1 cells (FIG. 10 and Table 1). E11 was able to block both TLR4 activation and HMG1 binding to THP-1 cells. Several antibodies were chosen for further analysis to demonstrate their effect on inflammatory responses in vivo (see below).

6.5 Example 5

Anti-HMG1 Antibodies Inhibit Sepsis in the Cecal Ligation and Puncture (CLP) Model To demonstrate that human anti-HMG1 antibodies can inhibit lethality in sepsis, we established sepsis in mice and monitored the survival rates for several antibody treatment protocols. Mice were subjected to cecal ligation and puncture (CLP), a well characterized model of sepsis caused by perforating a surgically-created cecal diverticulum, that leads to polymicrobial peritonitis and sepsis (Fink and Heard, supra; Wichmann et al., supra; and Remick et al., supra). The survival rates for mice treated with several human anti-HMG1 antibodies was compared to mice treated with isotype control antibodies. Several human anti-HMG1 antibodies demonstrated significant protection in the CLP model including G4, S6 and S16 (FIG. 11A-D and Table 1).

6.5.1 Materials and Methods

Anti-HMGB1 in Sepsis: To establish live intra-abdominal infection and sepsis, Balb/C mice (9-11 per group) were subjected to the CLP procedure as described previously (Fink and Heard, 1990, *J Surg Res* 49:186-196; Wichmann et al., 1996, *J Surg Res* 65, 109-114). After anesthesia with an intramuscular injection of ketamine (75 mg/kg, Fort Dodge Laboratories, Fort Dodge, Iowa) and xylazine (20 mg/kg, Boehringer Ingelheim), a 15-mm midline incision was made to expose the cecum. After ligation 5.0 mm from the tip, the cecal stump was punctured once with a 22-gauge needle, and small amount of stool (1-mm length) was extruded. The cecum was placed back into its normal intra-abdominal position, and the wound was closed with two layers of running suture. All animals received saline-solution (0.9% s.c., 20 ml/kg of body weight) resuscitation, and a single dose of antibiotic (0.5 mg of imipenem per mouse in 200 µl of sterile saline injected s.c.) (Primaxin, Merck) 30 min after surgery.

Figure 11A:
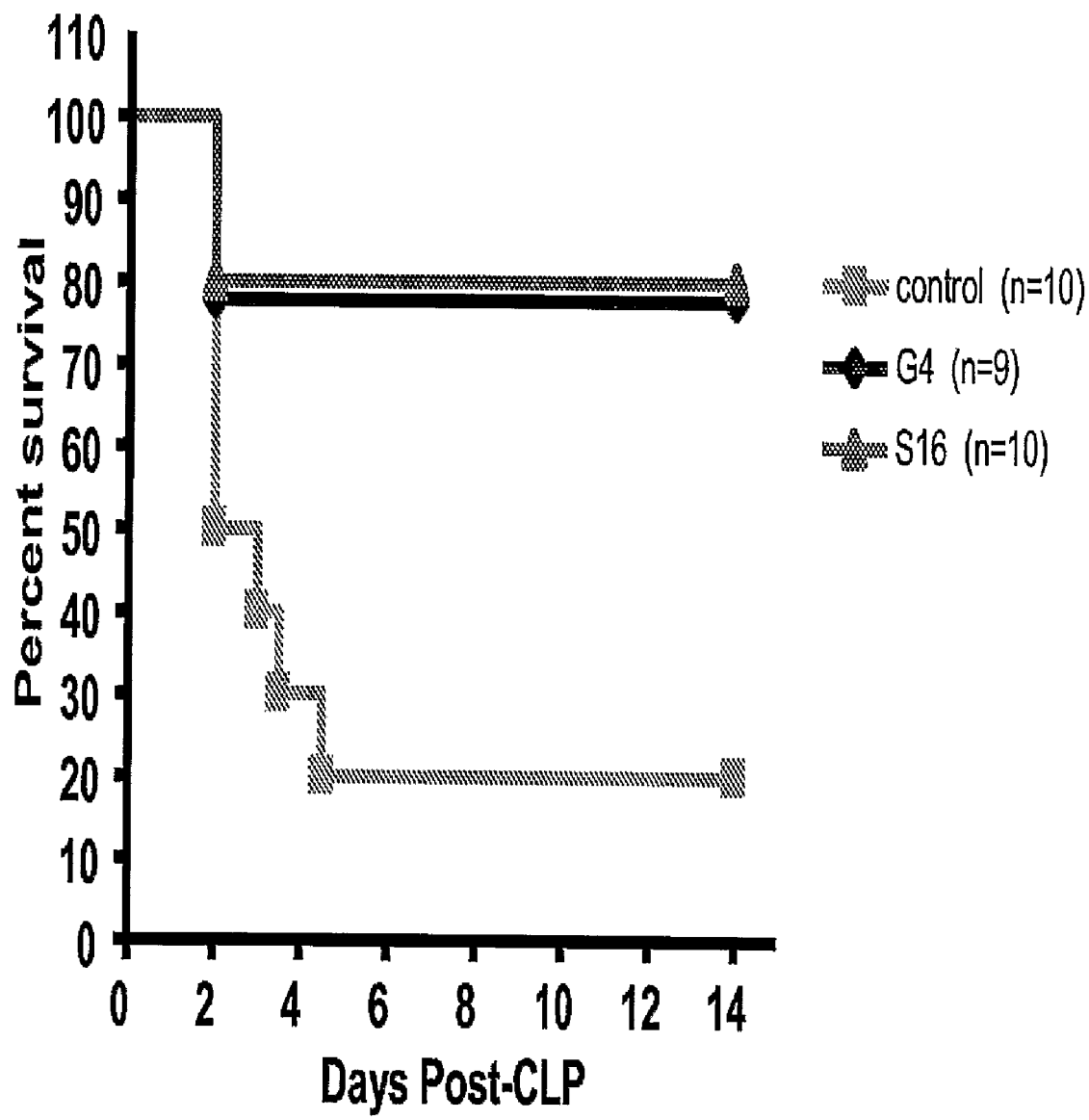
Figure 11B:
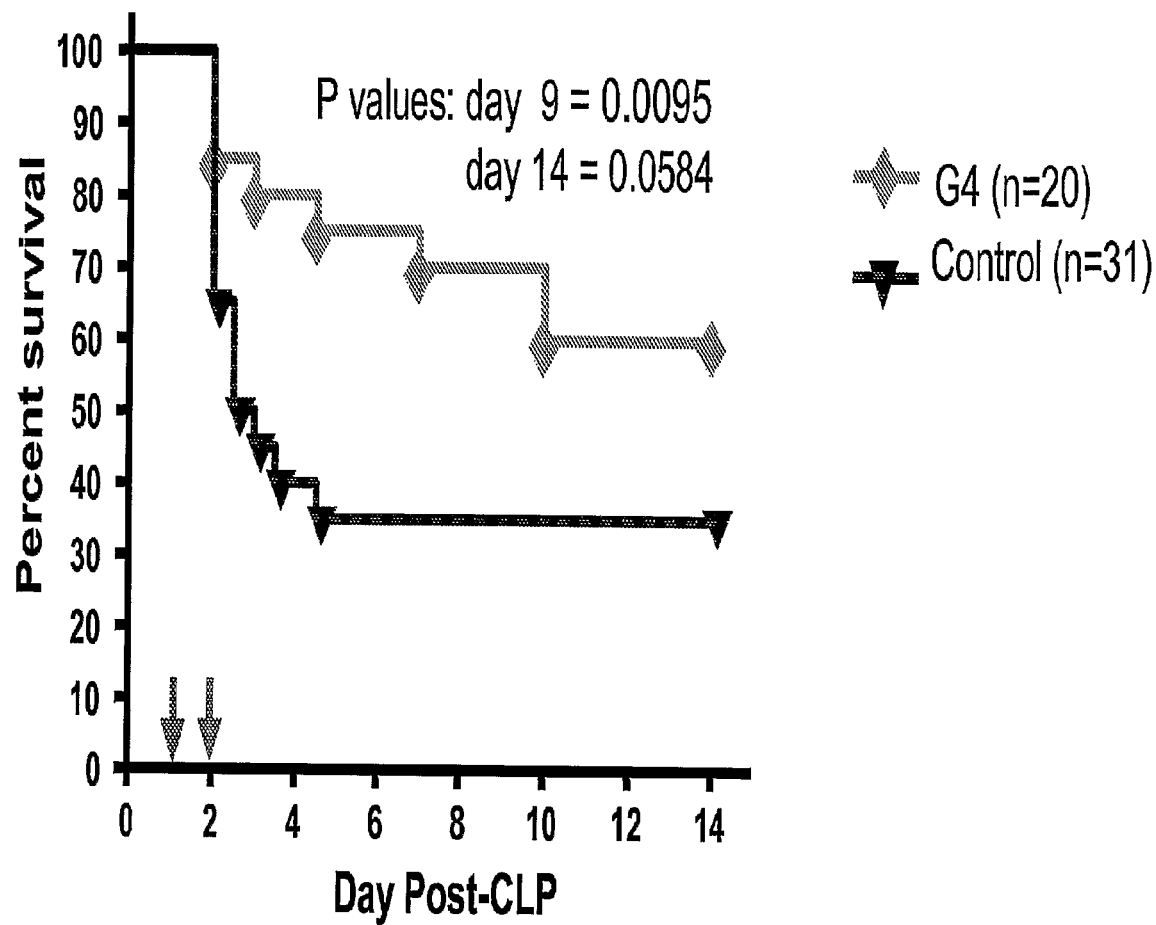
Figure 11C:
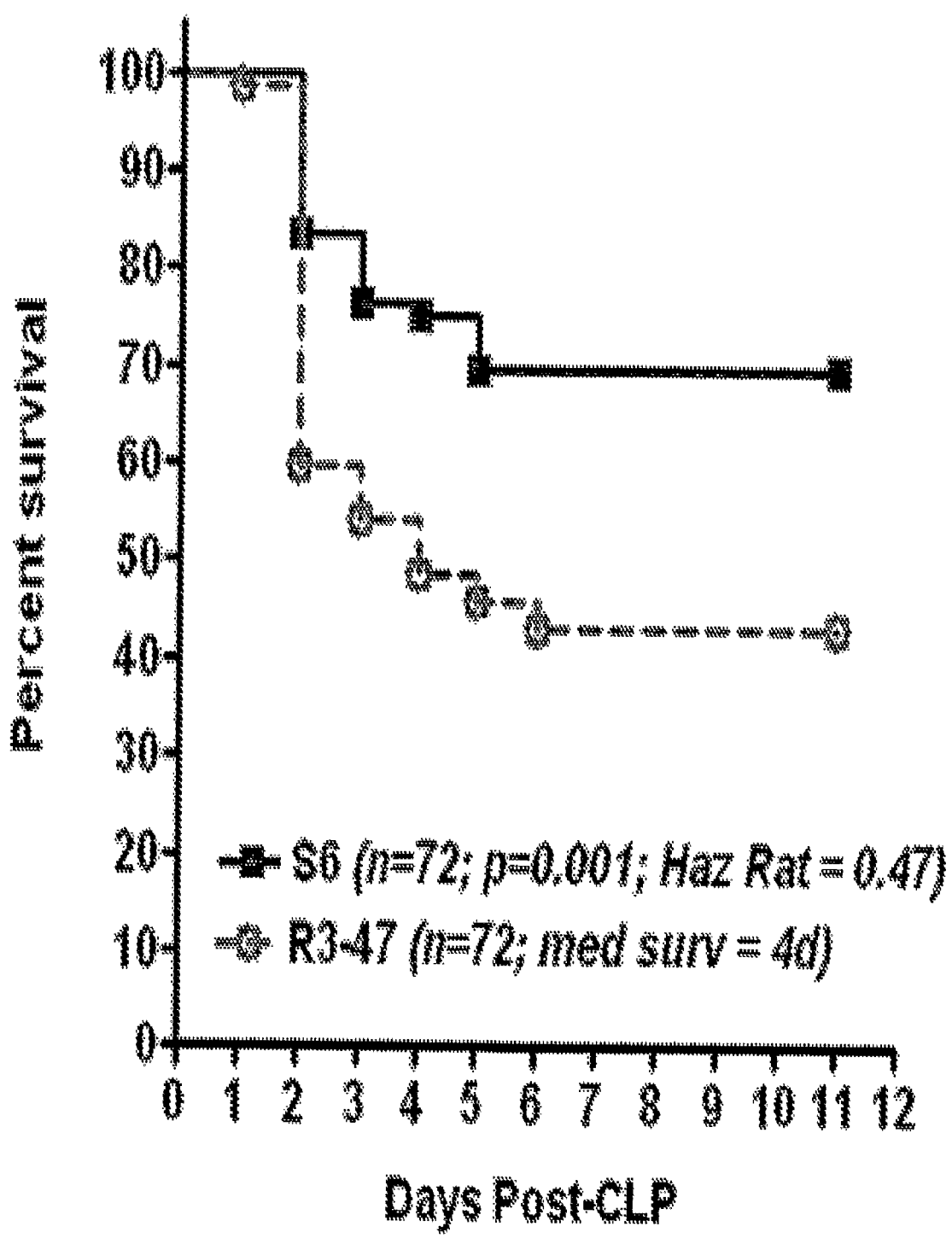
Figure 11D:
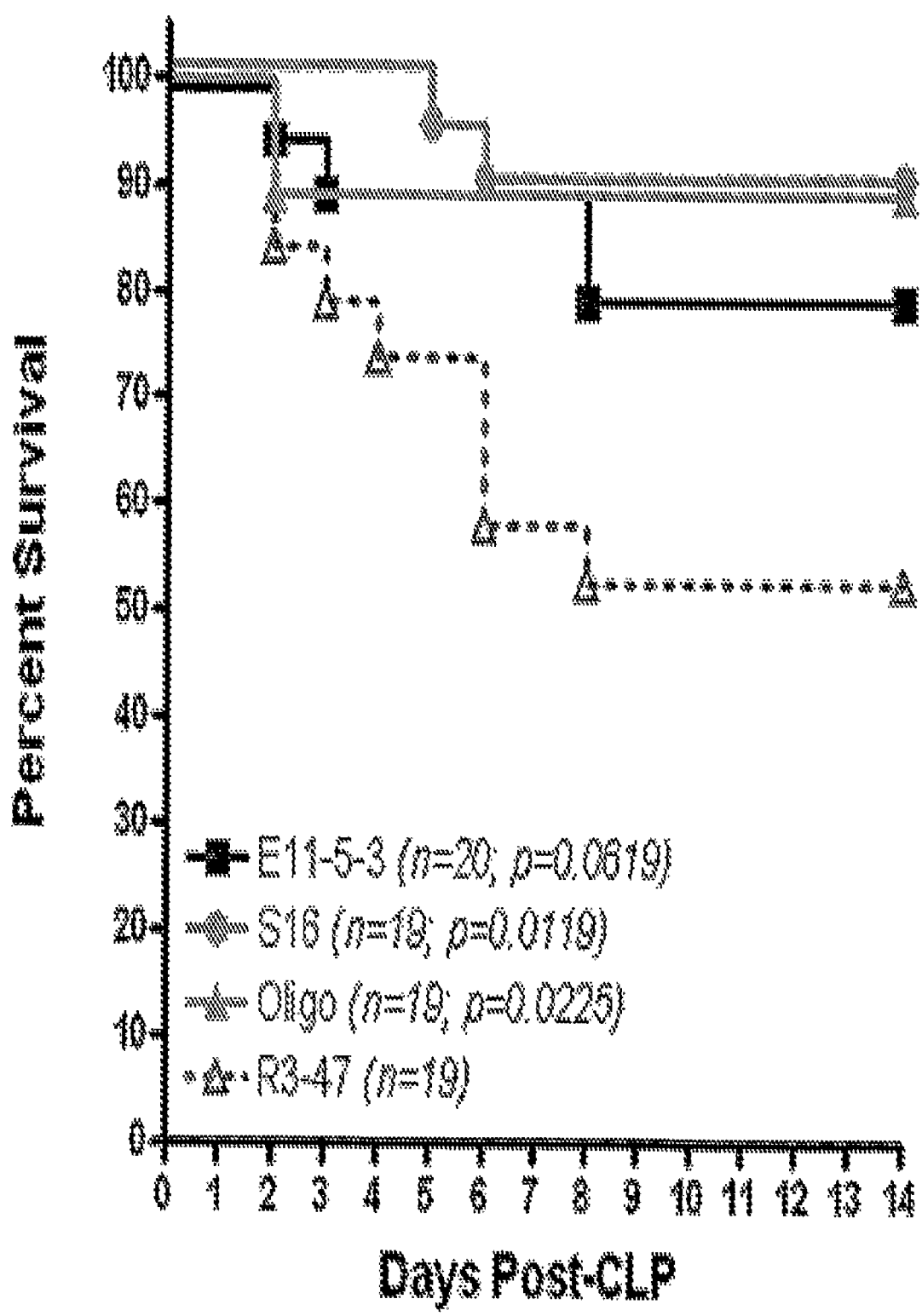

Anti-HMG1 antibodies or isotype control antibodies (50 µg/mouse in a 200 µl volume), were administered intraperitoneally at 24 and 48 hours, post surgery. In certain follow up experiments anti-HMG1 antibodies or isotype control antibodies (8 mg/kg) were administered intraperitoneally at 24 hours, post surgery (FIG. 11C-D). These experiments were blinded—the surgeons randomized the cages, and the encoded antibodies were dosed by another investigator. The survival of the mice was monitored twice daily for a total of 14 days. The survival curves for several representative experiments where the antibodies were delivered at 50 µg/mouse at times 24 and 48 are shown in FIGS. 11A and 11B. The survival curve generated by combining several representative experiments where the antibodies were delivered at 8 mg/kg 24 hours post surgery is shown in FIG. 11C. Several additional antibodies and the oligoclonal antibody pool were tested at 8 mg/kg administered 24 hours post surgery (FIG. 11D).

6.5.2 Results

These studies demonstrate that the passive immunization of critically ill septic mice with human anti-HMG1 antibodies was protective. In particular the human anti-HMG1 antibodies S6, S16, E11 and G4 were protective in the CLP model (see FIG. 11A-D). In several studies the survival rates at day 9 were better than those at day 14 (FIG. 11B). This difference in longer term survival rate is likely due to the reduced half life of the human antibodies in the mouse system. However, for the majority of animals treatment with human anti-HMG1 antibodies did not merely delay death but rather, conferred complete protection from lethal sepsis. The anti-HMG1 antibody S6 has been most extensively studied in this model and has reproducibly provided at least 30% protection in numerous experiments (representative cumulative data is represented in FIG. 11C).

6.6 Example 6

HMG1 is Upregulated in Animal Models of Several Inflammatory Conditions

Serum HMG1 levels have been shown to increase during sepsis/septic shock, in humans. We examined the level of HMG1 protein and/or gene expression in a number of different animal models of inflammatory disease including several arthritis models, acute lung injury and peritonitis. In all models thus far examined we found that HMG1 levels rise with disease progression. In addition, we found that the levels of several cytokines and/or putative HMG1 receptor molecules also rise.

6.6.1 Materials and Methods

Induction of Inflammatory Disease: Please see below for detailed description for the methods used for the induction of each disease model. The levels of HMG1 and the various cytokines were examined in untreated animals in which disease had been induced and compared to normal animals.

Figure 12A:
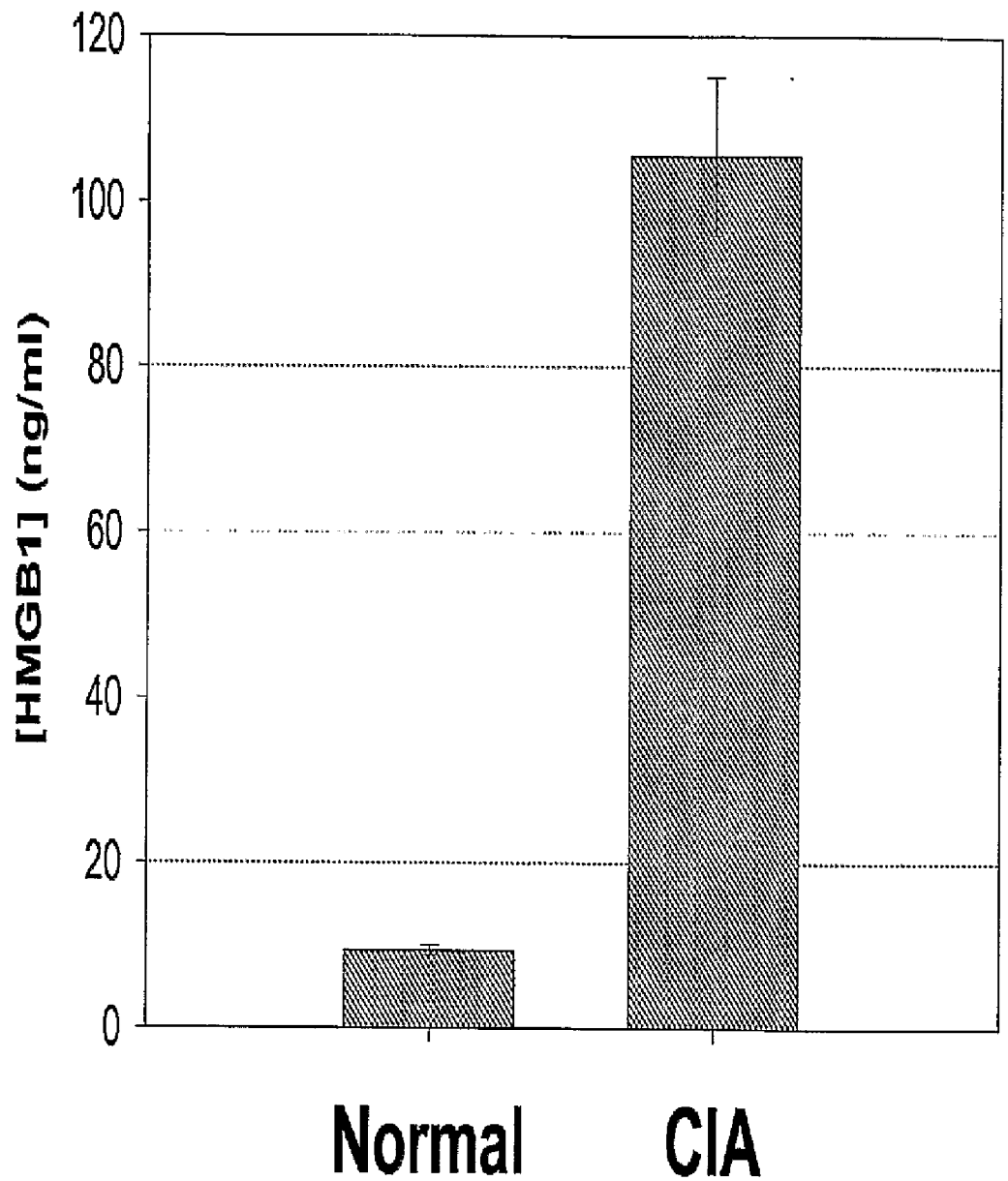

HMG1 Levels in the Passive CIA Mouse: The front paws of normal or passive CIA mice were collected at day 10, snap frozen in liquid nitrogen and stored at −80° C. until assayed. Joint sample and lysis buffer was added to impact-resistant 2 ml tubes pre-filled with specialized lysing matrix A particles (Q biogene). The joint was homogenized with a FastPrep® homogenizer then centrifuged. The supernatant was collected and the HMG1 level was determined by ELISA using MesoScale technology (Meso Scale Discovery). The data shown in FIG. 12A are the average of five paws in each group.

Figure 12B:
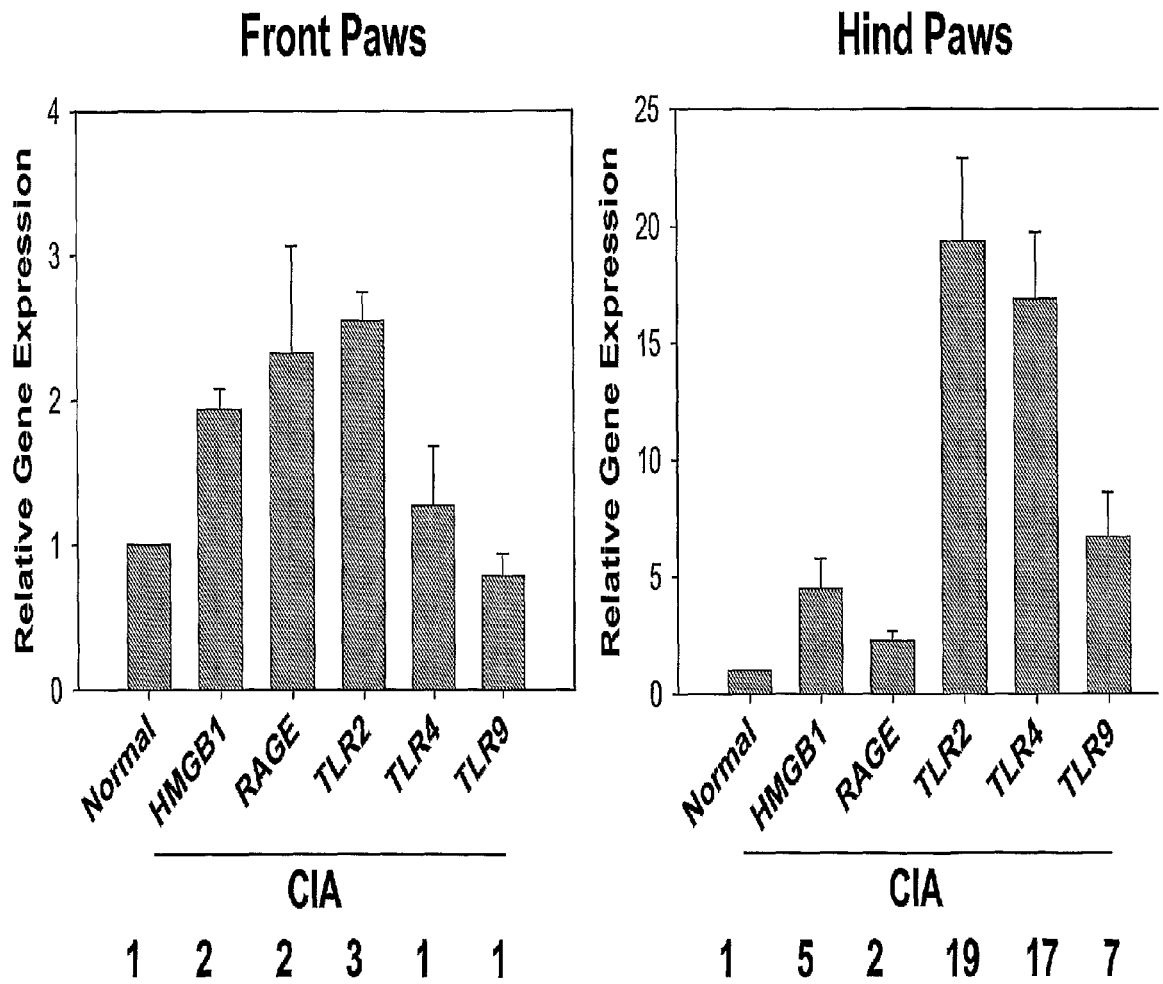
Figure 12C:
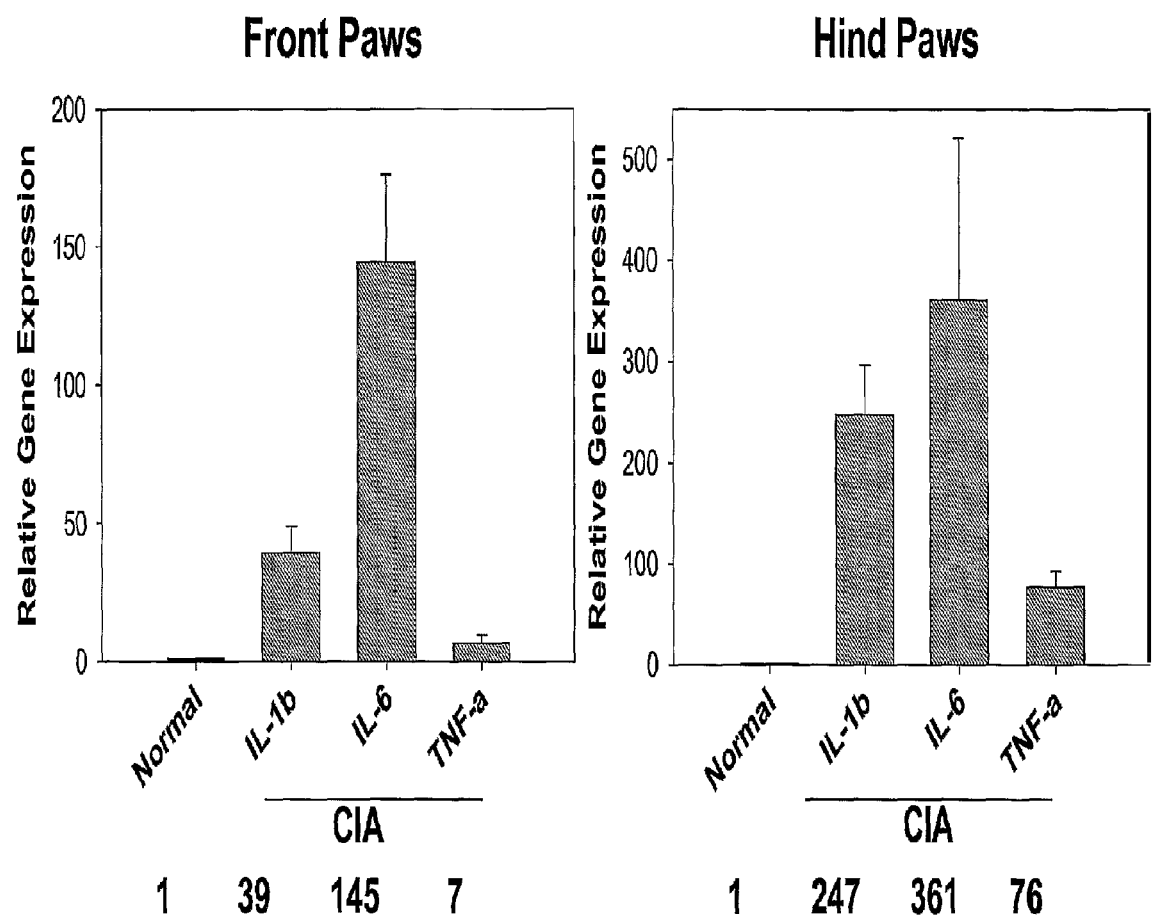
Figure 12D:
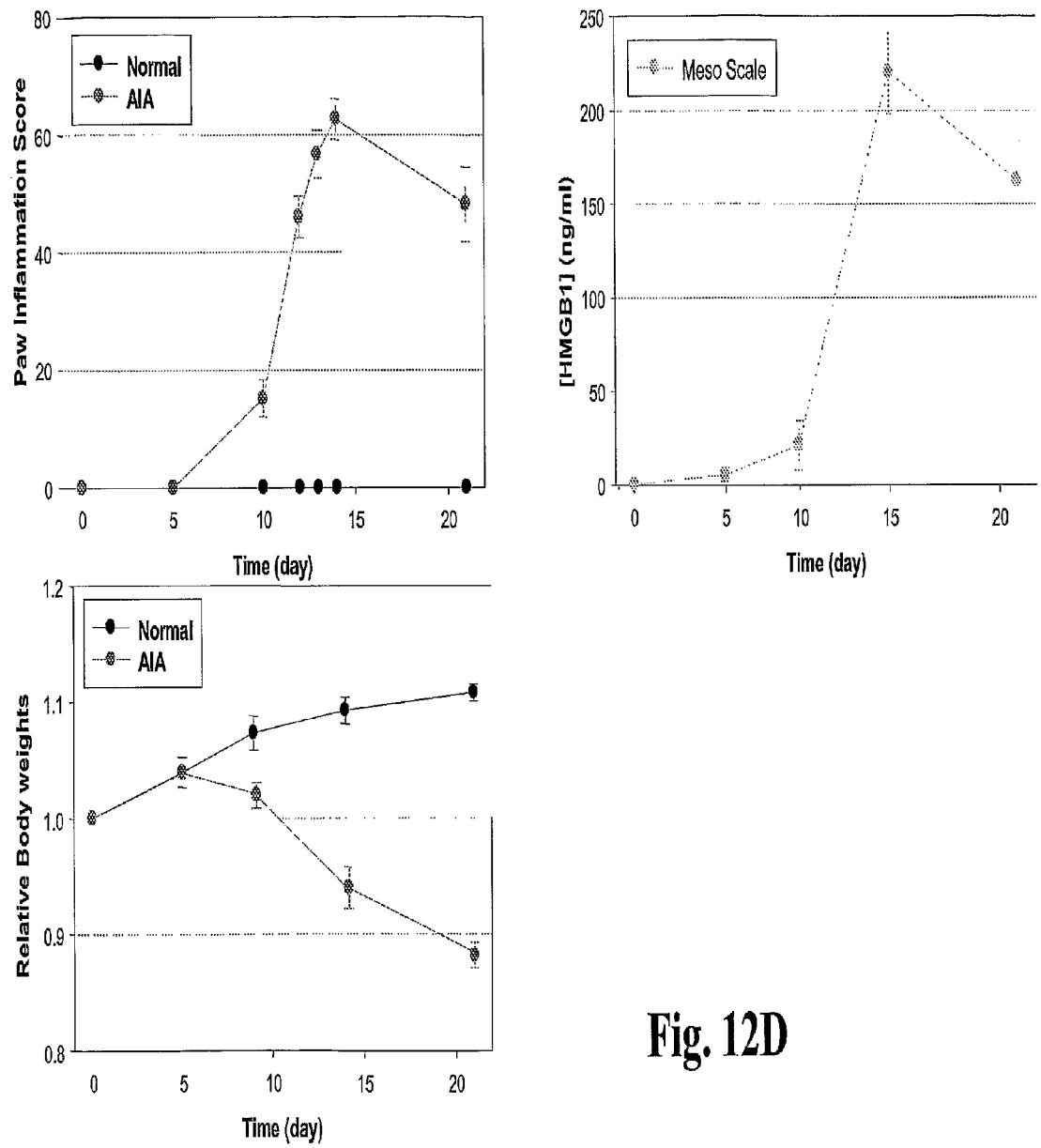

Taqman Analysis of the Active CIA Mouse: The front and hind paws of normal or active CIA mice were collected at day 35, snap frozen in liquid nitrogen and stored at −80° C. until assayed. Joint sample and lysis buffer was added to impact-resistant 2 ml tubes pre-filled with specialized lysing matrix A particles (Q biogene). The joint was homogenized with a FastPrep® homogenizer and RNA was prepared from the homogenate using Qiagen's RNAse mini kit or RNA STAT-60 according to the manufacture's instructions. All of the recovered RNA was used in a reverse transcriptase reaction with SuperScript™ III and oligo(dT) primer (Invitrogen) for the synthesis of cDNA. 1 µl or 2 µl of the cDNA were used for real time quantitative PCR analysis (TaqMan) using an ABI Prism 7700 or 7000. The relative gene expression of HMGB1 and several putative receptor molecules, RAGE, TLR2, TLR4 and TLR9 were examined in both the hind and front paws separately (FIG. 12B). The relative gene expression of several cytokines, IL-1b, IL-6 and TNF-a, were also determined in both the hind and front paws separately (FIG. 12C). The gene expression of each molecule in the normal mouse was set to 1, and the relative gene expression of each molecule is plotted. The numbers under each molecule indicate the values.

HMG1Levels in the AIA Rat: The hind paws of AIA rats were harvested at day 0, 5, 10, 15 and 20 snap frozen in liquid nitrogen and stored at −80° C. until assayed. The AIA joints were processed and assayed using the same protocol as was used for the passive CIA Mouse above. The level of HMG1 present in the joint homogenate is plotted over time in FIG. 12D (upper right graph). Two key indicators of disease progression, joint inflammation and weight loss are also plotted (upper left and lower left graphs, respectively)

Figure 12E:
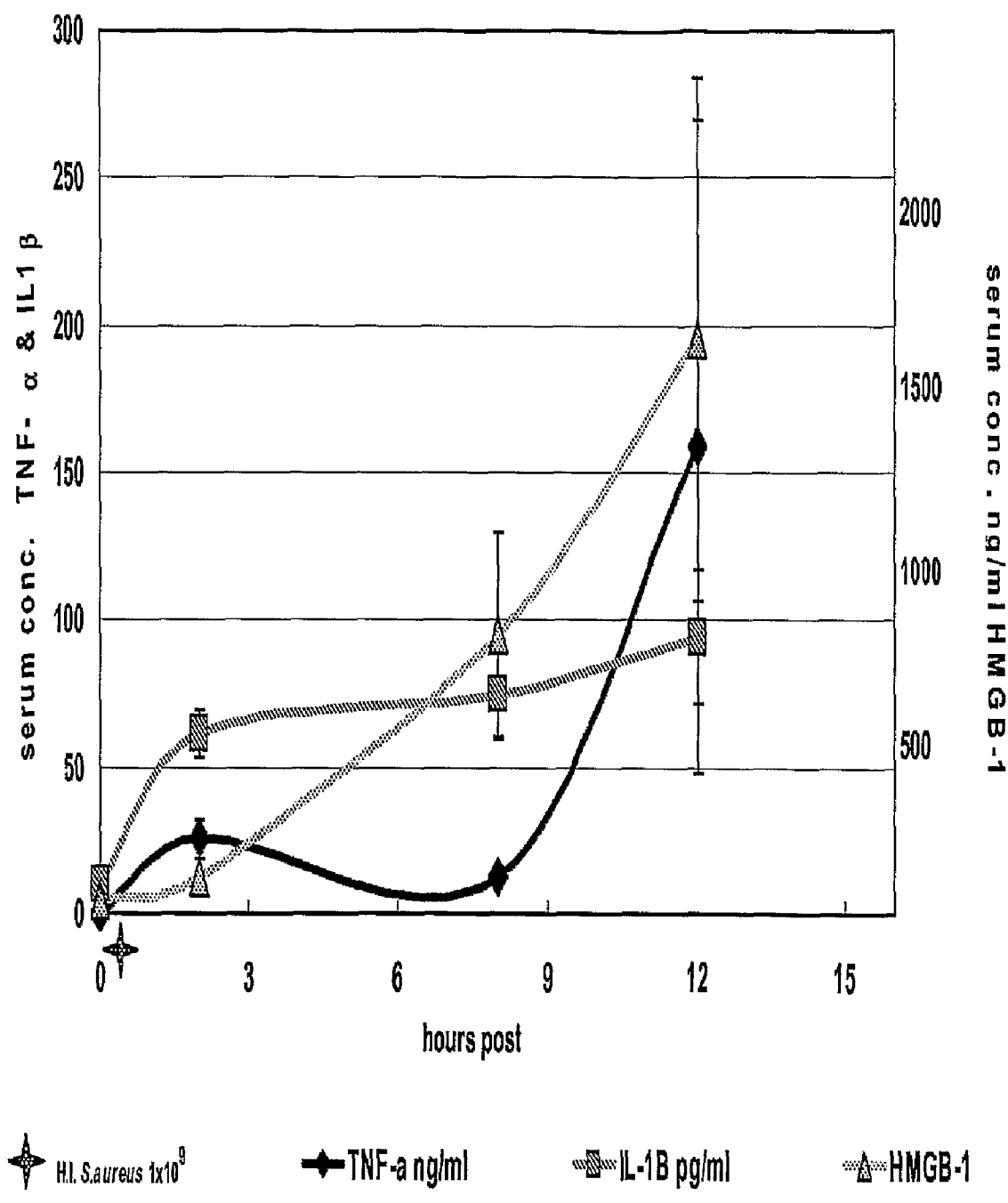

HMG1 and Cytokine Levels in Mouse Sera After S. Aureus challenge: Serum from mice challenged with S. aureus was collected at 2, 8, and 12 hours post challenge. The levels of HMG1, IL-1b and TNF-a were determined by ELISA using MesoScale technology (Meso Scale Discovery). The levels of HMG1, IL-1b and TNF-a are plotted over time (FIG. 12E). Note the different scales used for HMG1 and the cytokines (right and left axes, respectively). Mice challenged with galactosamine alone or receiving no challenge did not show a similar increase in HMG1 or cytokines (data not shown).

Figure 12F:
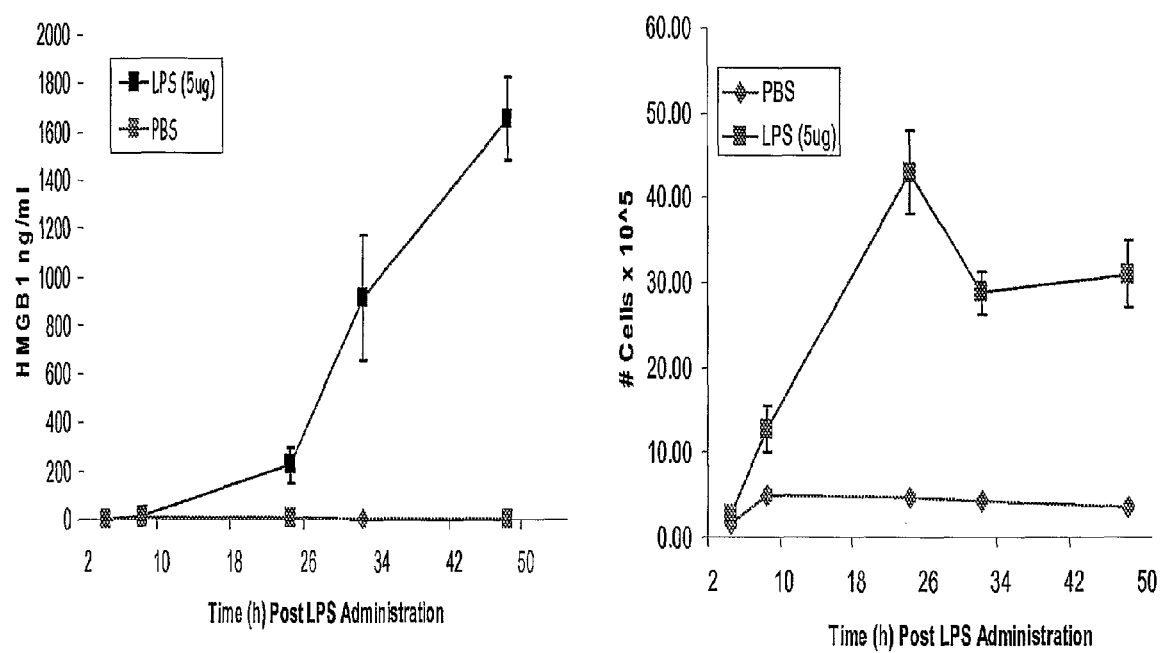

HMG1 Levels in the BAL fluid of the ALI Mouse: BAL fluid from mice challenged with either PBS (control) or LPS (lung injury) were harvested at the indicated times after challenge and the level of HMG1 was determined by MesoScale ELISA. The level of HMG1 is plotted over time (FIG. 12F, left plot). The total cell count present, an indicator of disease progression, is plotted over time as well (FIG. 12F, right plot).

HMG1 Levels in the AIA Rat Post Treatment: The hind paws of AIA rats after treatment (see Experiment 9, below) were processed as above and the levels of HMG1, IL-6 and TNF-a were determined by MesoScale ELISA.

MesoScale ELISA: Briefly, plates were pre-coated with capture antibodies for HMGB1 or cytokines (e.g., IL-1b, TNF-a, IL-6, etc) and blocked with MSD blocker buffer (MSD, Cat#R93AA-1) for 1 hour. Standards (diluted in appropriate sample buffer, for example, normal mouse BAL fluid, serum or joint homogenate) and samples were added to the plate in 20 ul volumes. 20 ul of a mixture of primary and detection antibodies were added to each well and allowed to incubate at room temperature while shaking for 4 hours. Plates were then washed, read buffer (MSD, Cat #R92TD-2) added and read on Sector Imager 6000. For HMG1 detection primary antibody was Affinity Rabbit anti-HMGB1 polyclonal antibody (Becton Dickinson Biosciences, Cat # 556528) and detection antibody was goat anti-rabbit MSD detection antibody (MSD, Cat # R32AB-1).

6.6.2 Results

Figure 15A:
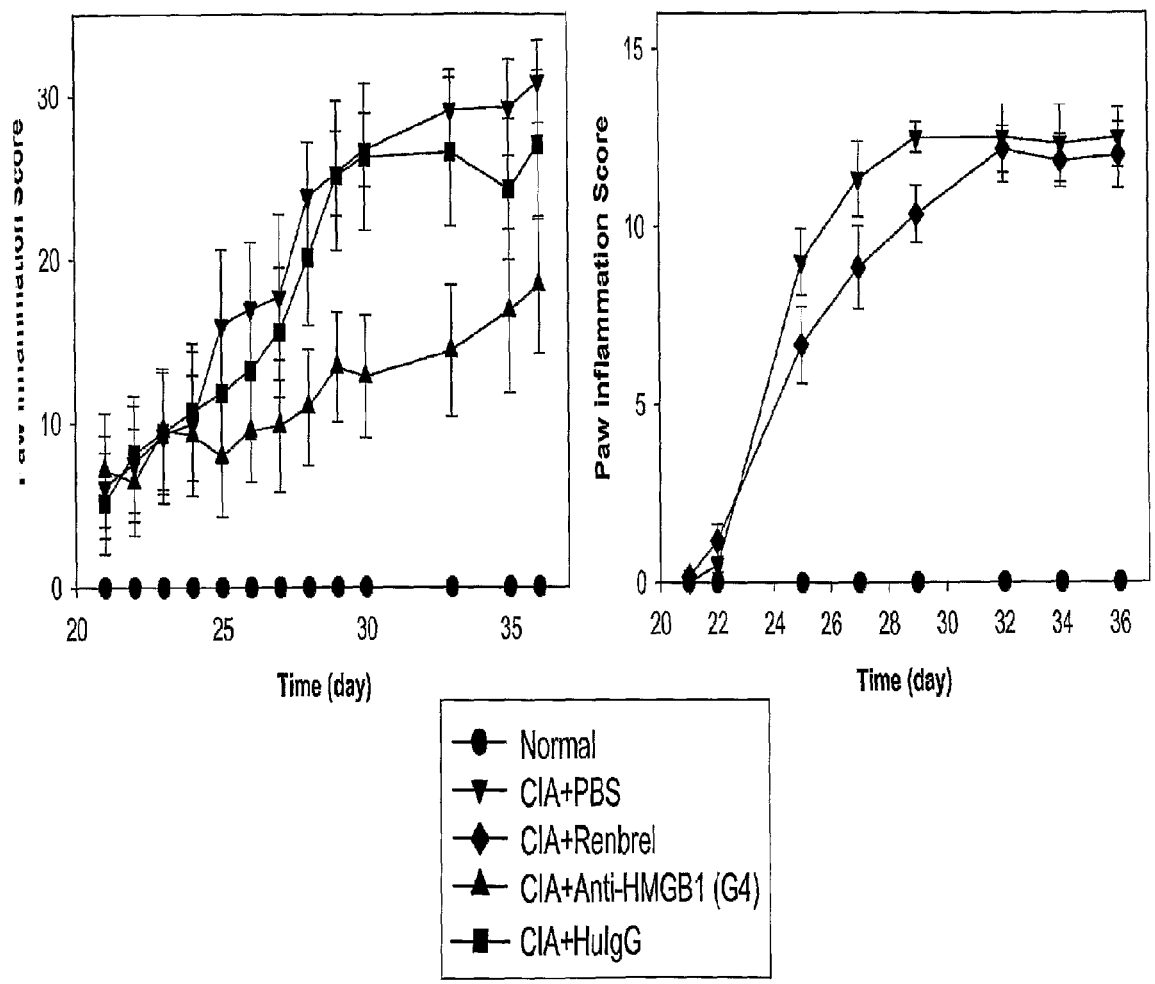

Three arthritis models were examined. In each model HMG1 levels in the joint were seen to rise concurrently with disease progression. In the passive CIA mouse, the level of HMG1 increased about 10 fold by day ten (FIG. 12A) when extensive joint inflammation is seen (see below and FIG. 13A). In the active CIA mouse the level of HMG1, several cytokine and several receptors known to be involved in inflammatory disease were also seen to rise concurrent with disease progression (FIGS. 12B-C and 15A). The RAGE receptor showed about a 2-fold increase in both the front and hind paws, the TLR2 and TLR4 receptors showed a modest 2 and 3 fold increase, respectively, in the front paws and a more dramatic 19 and 17 fold increase, respectively, in the hind paws. TLR9 levels only increased in the hind paws (7 fold). The expression levels of the cytokines IL-1b, IL-6 and TNF-a showed a similar trend increasing by 39, 145 and 7 fold, respectively in the front paws and by a more dramatic 247, 361 and 76 fold, respectively in the hind paws. In the AIA rat model HMG1 levels in the joint homogenates rose from undetectable levels to over 200 ng/ml by day 15 when joint inflammation was the most severe (compare FIG. 12D, left and right graphs). When inflammation decreased at about day 20, a corresponding decrease in HMG1 levels was also seen.

Two other disease models were also examined. FIG. 12E shows the consistent rise in HMG1 levels over time starting at about 2 hours post challenge in the S. aureus model of peritonitis. The levels of TNF-a and IL-6 rise sharply immediately after challenge, with the level of TNF-a peaking at 2 hours, dropping and then rising again at about 9 hour post challenge. IL-6 levels peak at about 2 hours and then generally hold steady with only a slight increase after that. In a mouse model of acute lung injury HMG1 levels in BAL fluid were since to rise from undetectable levels to over 1500 ng/ml by 48 hour post LPS challenge (FIG. 12F, left graph). This rise in HMG1 levels correlates with the increase in cellular infiltrate (total cell numbers) present in the BAL fluid from LPS challenged mice (compare FIG. 12F left and right graphs). HMG levels were undetectable in the BAL fluid from mice challenged with PBS buffer (FIG. 12F left graph). These studies indicate that the level of HMG1 increases with disease progression in a number of inflammatory disease models including three arthritis models an acute lung injury model and a peritonitis model. Several human anti-HMG1 antibodies were chosen for further study in these models to demonstrate that anti-HMG1 antibodies are useful in other inflammatory diseases associated with an increase in HMG1 levels.

Figure 12G:
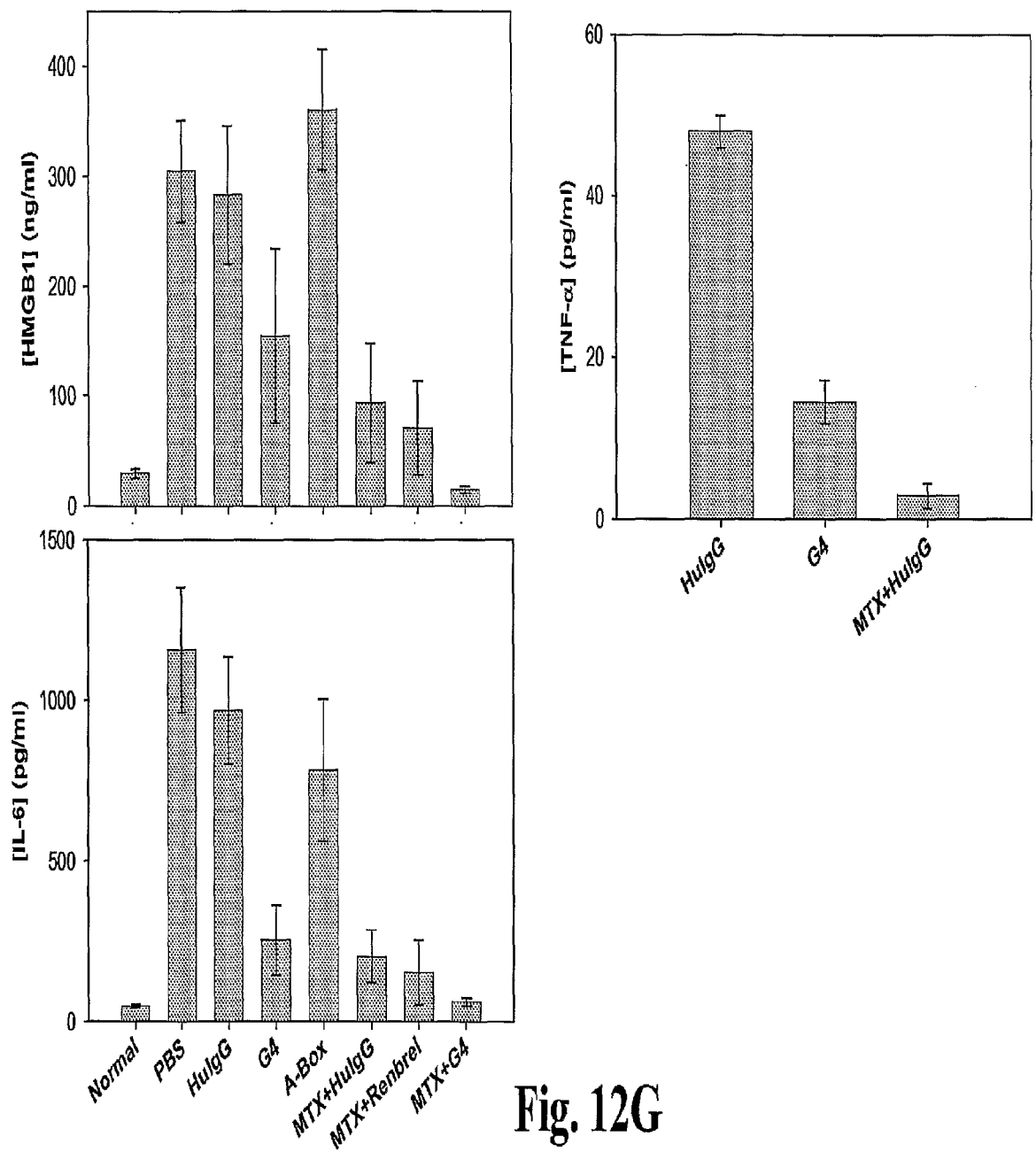

We also examined the levels of HMG1, IL-6 and TNF-a in the joints of AIA rats after treatment with either PBS, a human isotype control (HuIgG), G4, A-box-Fc fusion and methotrexate (MTX) in combination with either HuIgG or Renbrel or G4. FIG. 12 G shows the level of HMG1 (top left) and IL-6 (bottom left) after each treatment. Treatment with HuIgG or A-box-Fc did not significantly reduce the levels of HMG1 or IL-6. G4 alone, and MTX in combination with either HuIgG or Renbrel showed similar reductions in the levels of HMG1 and IL-6 however, the combination of MTX and G4 reduced the levels to normal. G4 also significantly reduced the level of TNF-a although MTX+HuIgG showed more of a reduction for this cytokine (FIG. 12G, top right).

6.7 Example 7

Anti-HMG1 Antibodies Inhibit The Severity of Disease Progression in the Passive Collagen-Induced Arthritis (CIA) Mouse Model To demonstrate that a human antibody against HMG1 was a useful therapeutic we tested a panel of human anti-HMG1 antibodies to treat collagen-induced arthritis in a passive mouse model. For this series of experiments we utilized a prevention model in which treatment is initiated prior to the onset of clinical arthritis. In this study we directly compared the efficacy of anti-HMG1 antibodies with that of known treatment protocols, either Renbrel (an accepted Enbrel™ surrogate molecule for use in rodent model systems) alone or the combination of Renbrel™ and methotrexate (MTX).

We demonstrate here, for the first time, that an antibody against HMG1 demonstrated efficacy in prevention in a passive CIA mouse RA model. In fact, the anti-HMG1 antibody G4 was shown to be more effective then Renbrel alone while the anti-HMG1 antibody S6 was more effective then even MTX/Renbrel therapy in reducing paw inflammation and in reducing bone loss and cartilage damage.

6.7.1 Materials and Methods

Induction of Passive Collagen Induced Arthritis (CIA): To establish an arthritis model six-eight week old male DBA/1J mice (Jackson Labs, Bar Harbor, Me.) were used. Generally 5-8 mice per group are used, On day 0, mice were immunized with 2 mg/mouse of anti-collage mAb cocktail (Chemicon # ECM1100, 10 mg/ml) intravenously, i.v. at tail. Mice were subsequently injected with 50 µg LPS/mouse, i.p. on day 3. Each experiment had several groups of animals as follows: groups A-E in experiment 1, groups G-J in experiment 2 and groups L-N). An additional group of mice (groups F, K and O) were untreated as normal controls. The following treatments were administered as shown in Table 5.

TABLE 5

Treatment Groups For CIA Mouse Model

| Group | Day | Treatment |
|---|---|---|
| A | 3, 5, 7, 9, 11, 13 | PBS alone |
| B | 3, 6, 9, 12 | 0.2 mg Renbrel i.p. |
|   | 3, 10 | 0.033 mg methotrexate i.p. |
| C | 3, 5, 7, 9, 11, 13 | 2 mg Human IgG control |
| D | 3, 5, 7, 9, 11, 13 | 2 mg anti-HMG1 (G16) |
| E | 3, 5, 7, 9, 11, 13 | 2 mg anti-HMG1 (S6) |
| F | N/A | No treatment |
| G | 3, 5, 7, 9, 11, 13 | PBS alone |
| H | 3, 5, 7, 9, 11, 13 | 10 mg/kg Renbrel |
| I | 3, 5, 7, 9, 11, 13 | 10 mg/kg anti-HMG1 (G4) |
| J | 3, 5, 7, 9, 11, 13 | 10 mg/kg Human IgG control |
| K | N/A | No treatment |
| L | 3, 6, 9, 12 | PBS alone |
| M | 3, 6, 9, 12 | 10 mg/kg anti-HMG1 (G4) |
| N | 3, 6, 9, 12 | 10 mg/kg Human IgG control |
| O | 3, 6, 9, 12 | No treatment |

Monitoring Disease: Beginning at day 0 all animals were observed daily to assess the status of the disease in their paws, which was done by assigning a qualitative clinical score to each of the paws. Every day, each animal has its 4 paws scored according to its state of clinical disease. The scoring is done by two observers, with at least one blinded. In addition, each mouse is weighed, to follow body weight changes, at the same time the paws are scored (see FIGS. 6A and 6D)

Grading scales for the ankle/wrist/midfoot/forfoot are as follows:

```
0 = Normal
1 = definite swelling
2 = severe swelling
3 = maximally severe swelling and non-weight bearing
```

The grading scale for the 4 lateral digits of each paw are graded as involved or not involved, i.e., 1 or 0. For example, a maximally involved left rear paw would be scored: ankle=3, midfoot=3, digits=4 (clinical score=10 units) We would repeat this for each paw and sum the scores. Mice are euthanized at day 14, or sooner if total clinical score reaches 40 and a histological evaluation of joints is performed.

Histology: Hind-limb tibiotalus joints from each animal were evaluated and scored for histologic changes as described in Badger et al., 2001, *Arthritis & Rheumatism* 44:128-37. Briefly, animals were sacrificed on day 32 and the hind legs were fixed in formaline and decalcified in Cal-Rite (Richard-Allen Scientific, Kalamazoo, Mich.). The paws were then removed from the legs at the distal tibial diaphysis. After routine processing, the samples were embedded and coronal sections were cut in the plane midway through the tibiotalus and talartarsal joints. Sections were stained with Safranin 0 and counterstained with fast Green (data not shown).

Figure 13A:
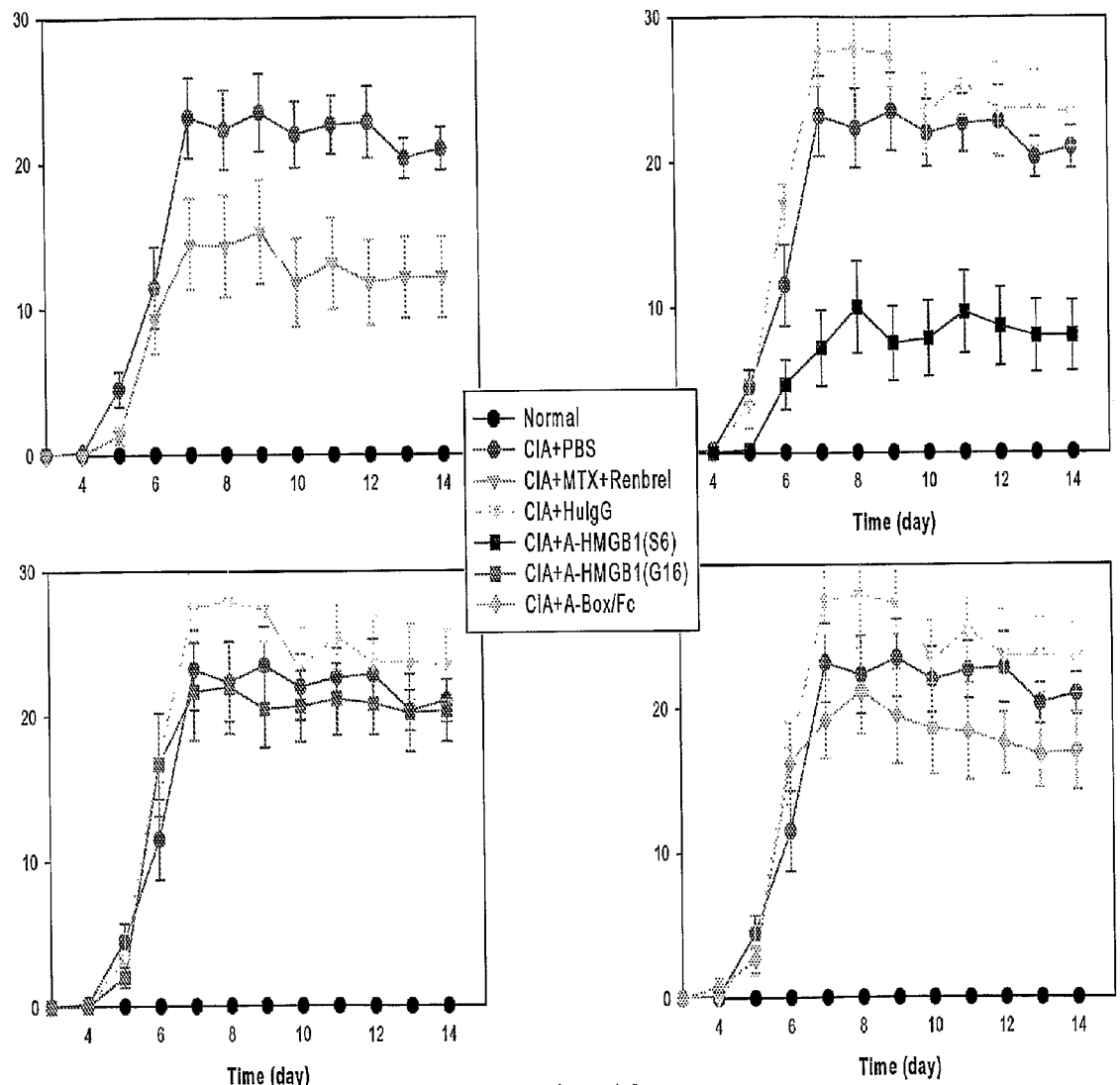
Figure 13B:
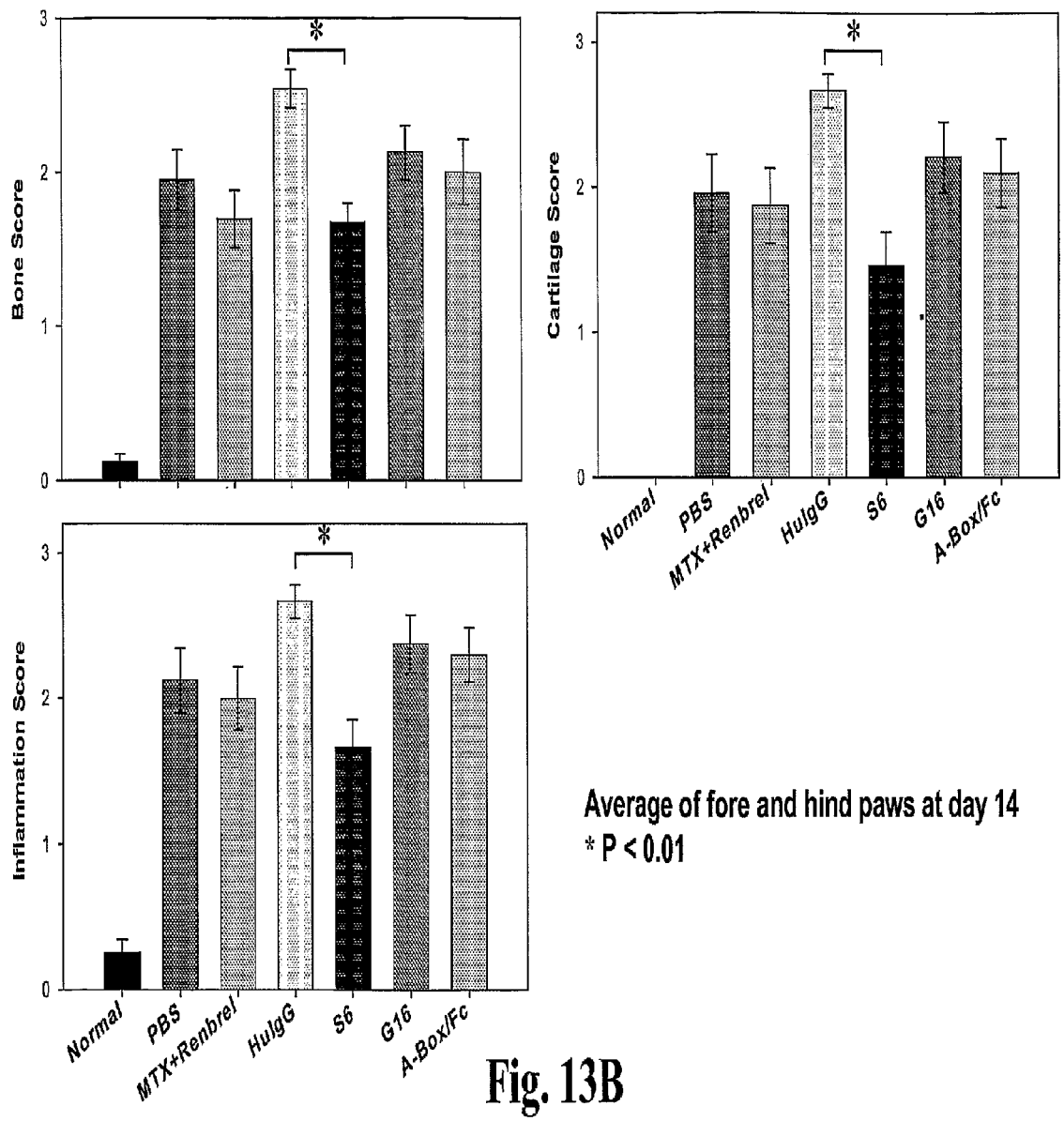
Figure 13C:
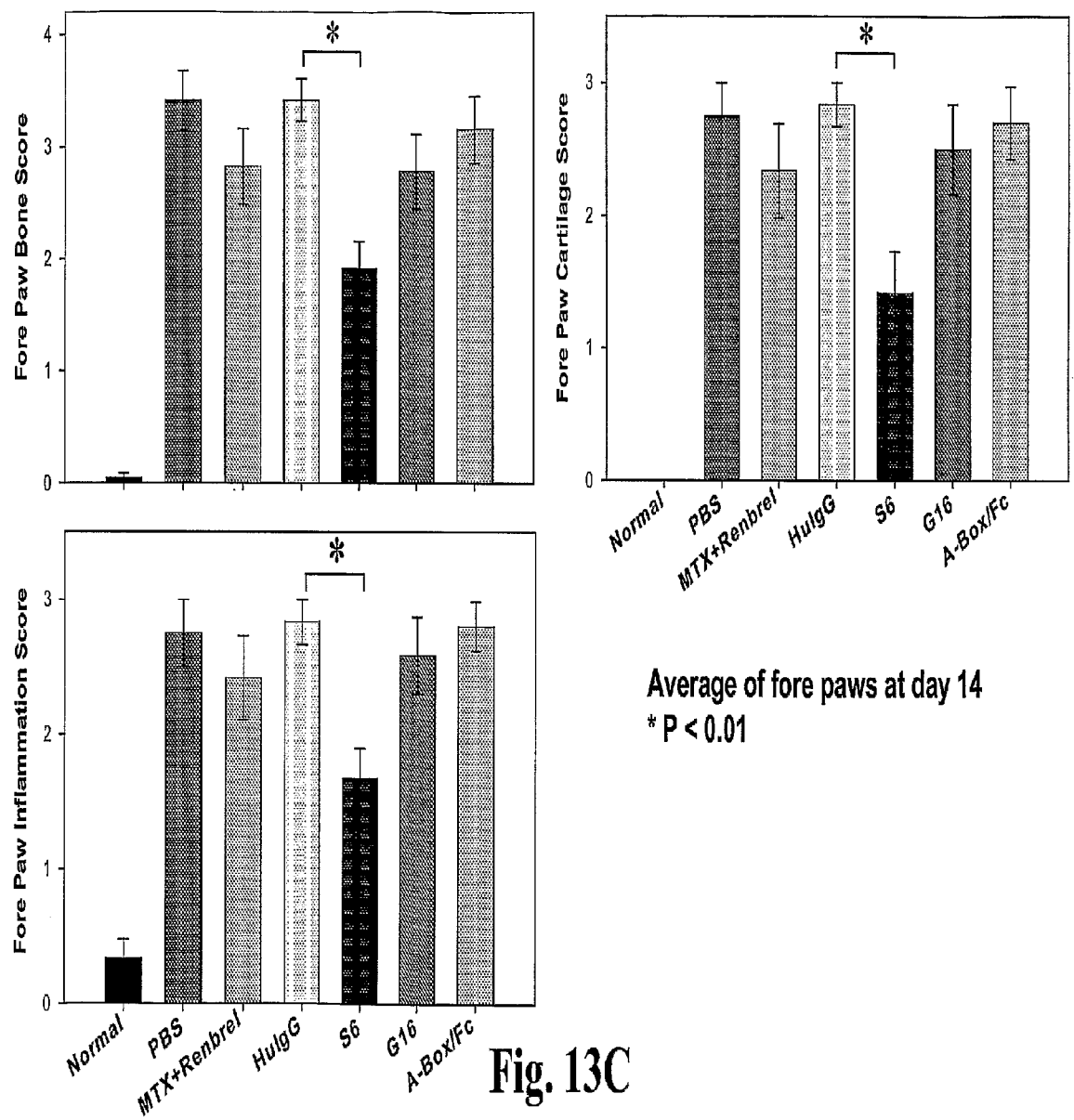

The histological characteristic of the bone and articular cartilage/periarticular soft tissue were scored separately by a blinded observer (FIGS. 13B and 13C). The bone was graded as follows: 0=normal, 1=subperiosteal fibrosis with periosteal woven bone formation, 2=Marrow inflammation, endosteal and trabecular bone resorption, 3=extensive inflammation, 4=marrow replaced by granulation tissue, little trabecular bone remaining, extensive obliteration of cortical contours. The cartilage/synovium was graded as follows: 0=normal, 1=mild lymphocytic inflammation in synovium and surrounding tissues, 2=synovial fibrosis and edema, partial lymphocytic infiltration of the joint space, minor pannus crosion of the cartilage, 3=extensive infiltration of joint space, peripheral and subchondral cartilage erosion, extensive fibrosis of soft tissue with regional necrotic liquefaction.

6.7.2 Results

Several experiments were performed to demonstrate that treatment with HMG1 antibodies could prevent or reduce disease severity in the passive CIA mouse model. In experiment mice were treated with anti-HMG1 antibody S6 or G16 (0.2 mg/mouse) starting on day 3 after mice had been injected with LPS. Mice received a total of 6 doses over a thirteen day period. At the same time control mice received either human mAb (0.2 mg/mouse). A final group received a combination therapy of MTX (0.2 mg/mouse, 4 doses over a twelve day period) and Renbrel (0.2 mg/mouse, 2 doses over a ten day period). The development of arthritis was assessed daily after the initial treatment. The graphs in FIG. 13A shows the paw inflammation scores for each of the treatment groups over the course of the study. FIG. 133B shows the total histological scores for bone, cartilage and inflammation for the prevention model of CIA. It is important to note that in this model the fore paws are a more predictable indicator of disease state as the hind paws can be variably affected. FIG. 13C is the histological scores for bone, cartilage and inflammation for just the fore paws alone. The administration of human IgG had no effect on the development of arthritis. However, the anti-HMG1 S6 antibody treated animals have greatly reduced bone, cartilage and total inflammation scores compared to the control animals. Strikingly, the animals treated with the anti-HMG1 S6 antibody did significantly better then those treated with the MTX/Renbrel combination therapy (FIGS. 13B and 13C).

Figure 13D:
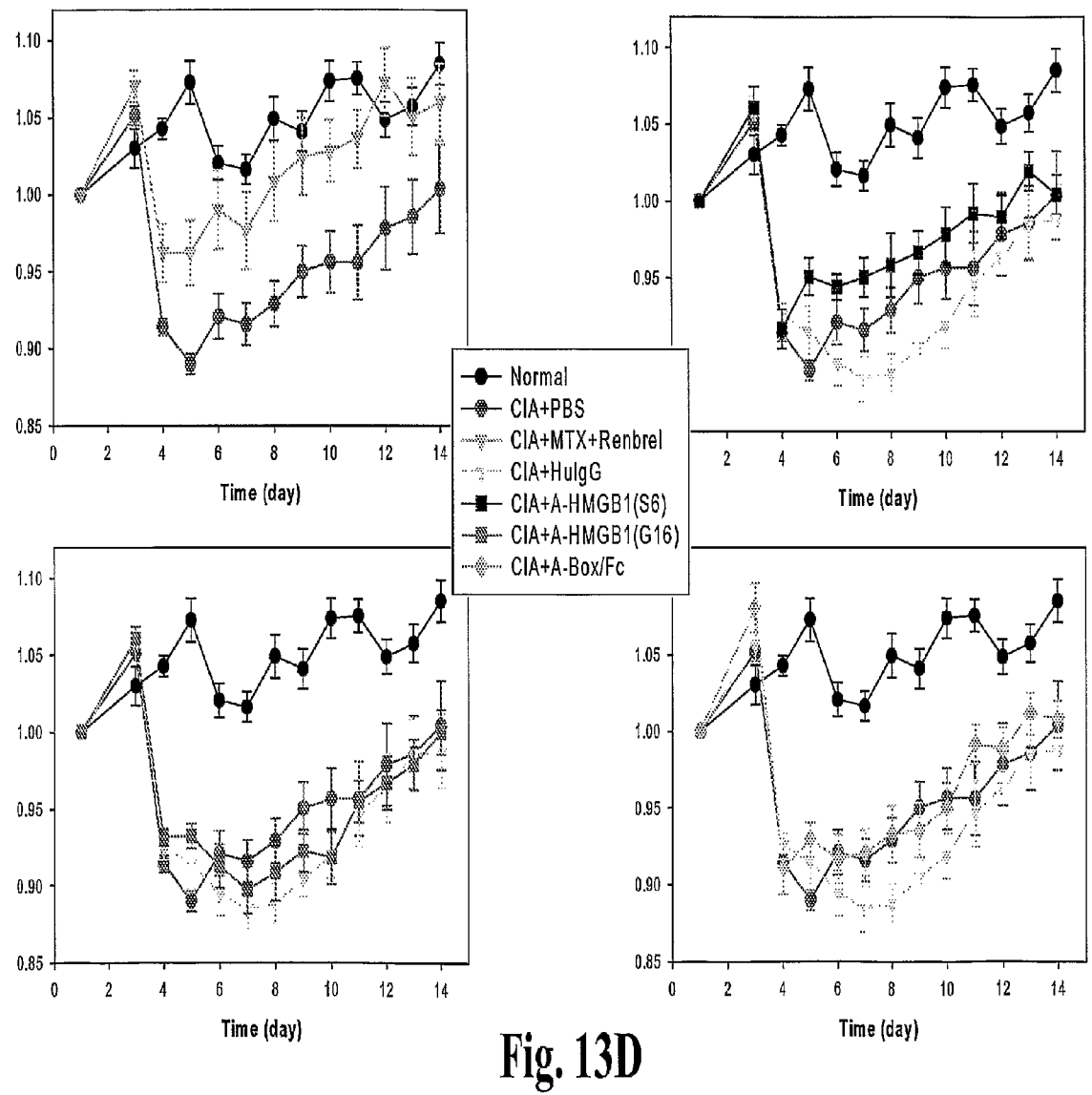

Another clinical feature of disease progression is weight loss. The relative body weight scores for the control animal show a net decrease during the course of the study. Although the clinical scores for the mice treated with anti-HMG1 S6 antibody showed significant protection, this group of animals also showed a net decrease in bodyweight. However the anti-HMG1 S6 antibody treated animals did not lose as much as the control group. The MTX/Renbrel treated animals also showed a net decrease in bodyweight early in the study however they had caught up with untreated animals by the end (FIG. 13D). These results demonstrate that anti-HMG1 antibodies can effectively protect against joint damage and other symptoms when administered prior to the onset of disease. In particular, these results indicate that anti-HMG1 S6 antibody treatment had a profound effect in diminishing the disease severity in CIA mice. It should be noted that this experiment may not be representative of the protective effect of S6 in an arthritis model. While anti-HMG1 S6 antibody treatment has repeatedly shown excellent protection in the mouse CLP model of sepsis (see Example 5 above) the results have been more variable in arthritis models. This variability may reflect differences in antibody preparations, the animal models, antibody pharmacokinetics and other similar parameters.

Figure 14A:
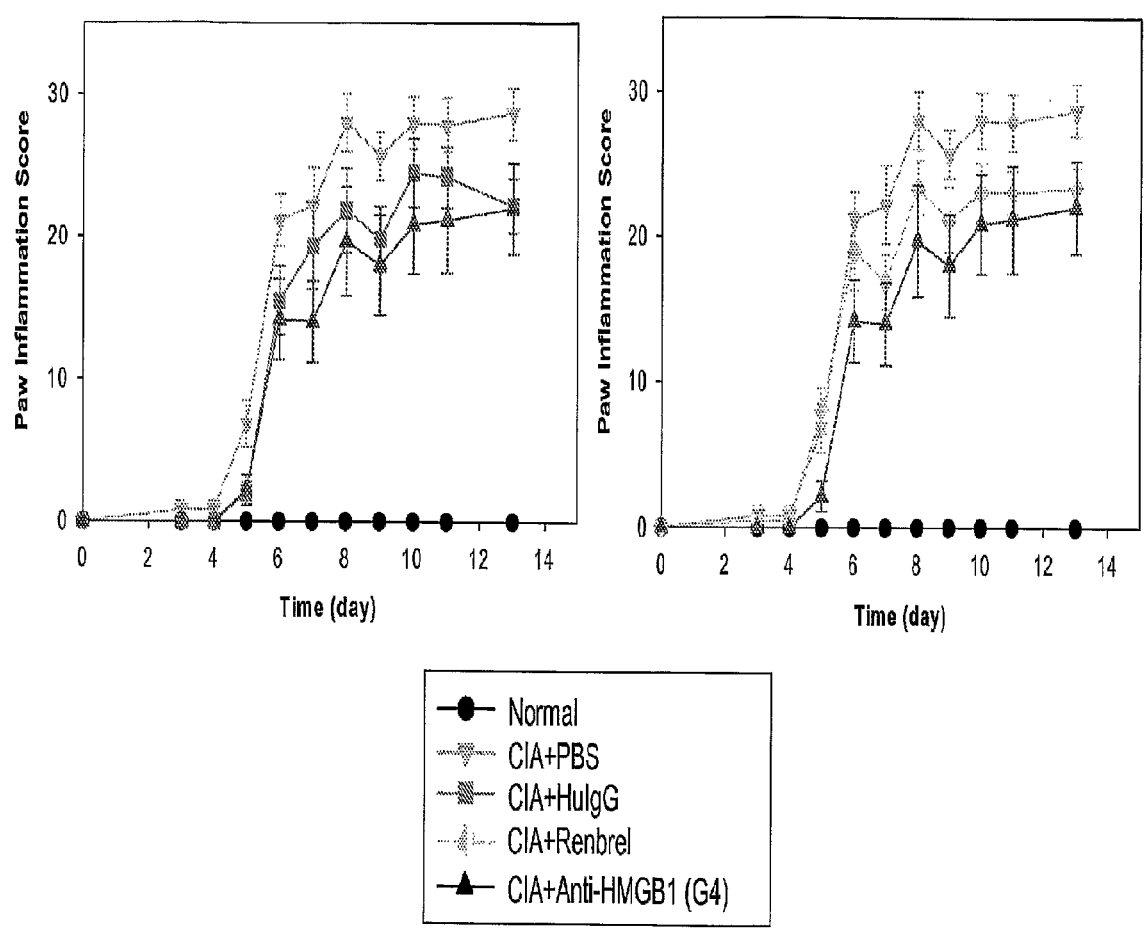
Figure 14B:
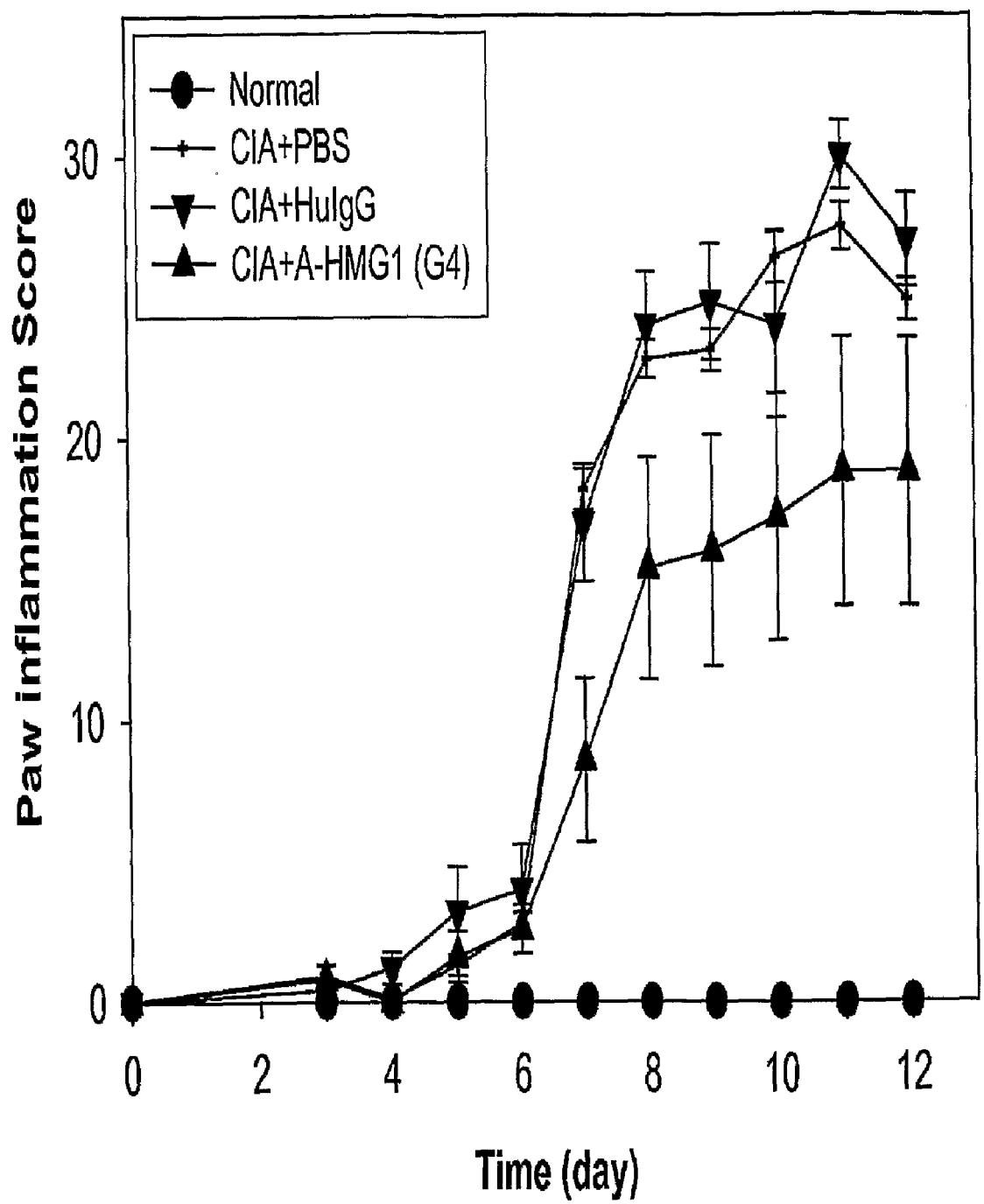

In experiments 2 and 3 mice were treated with the anti-HMG1 antibody G4 (10 mg/kg) starting on day 3 after mice had been injected with LPS. Mice received a total of 6 doses over a thirteen day period in experiment 2 and a total of 4 doses over the same time period in experiment 3. At the same time control mice received either human mAb (10 mg/kg) or PBS. In experiment 2 final group received Renbrel (dosing was the same as for G4). The development of arthritis was assessed daily after the initial treatment. The graphs in FIG. 14A-B shows the paw inflammation scores over the course of the study. It is clear from experiment 2 (FIG. 14A) that the anti-HMB1 antibody G4 is more effective than Renbrel alone at reducing paw inflammation (right panel). The data from experiment 3 (FIG. 14B) show that the anti-HMB1 antibody G4 can be administered less frequently as still paw inflammation. The G4 antibody repeatedly provided significant protection in this and several other models of arthritis (see Examples 8 and 9 below).

6.8 Example 8

Anti-HMG1 Antibodies Inhibit the Severity of Disease Progression in the Active Collagen-Induced Arthritis (CIA) Mouse and Rat Models To demonstrate that a human antibody against HMG1 was a useful therapeutic we tested a panel of anti-HMG1 antibodies to treat active collagen-induced arthritis in a mouse model. For this series of experiments we utilized a prevention model in which treatment is initiated prior to the onset of clinical arthritis. In this study we compared the efficacy of anti-HMG1 antibodies with that of Renbrel.

We demonstrate here, for the first time, that an antibody against HMG1 demonstrated efficacy in reducing paw inflammation and weight loss in an active CIA mouse RA model. In fact, the anti-HMG1 antibody G4 was shown to be more effective then Renbrel alone in reducing paw inflammation.

6.8.1 Materials and Methods

Induction of Active Collagen Induced Arthritis (CIA) in Mice: Six-eight week old male DBA/1J mice (Jackson Labs, Bar Harbor, Me.) were used. On day 0, isoflurane anesthetized animals were given an intradermal injection, at base of tail, of 200 µg bovine Type II collagen (CII) dissolved in 50 µl 0.1 N acetic acid and emulsified with an equal volume of complete Freund's adjuvant (Chondrex, Redmond, Wash.). Three weeks later on day 21 they were given a second similar intradermal injection of 100 µg of CII dissolved in 25 µl 0.1N acetic acid and emulsified with an equal volume of incomplete Freund's adjuvant (Difco, Detroit, Mich.).

Monitoring Disease in Mice: Beginning at day 14 all animals were observed daily to assess the status of the disease in their paws, which was done by assigning a qualitative clinical score to each of the paws. Every day, each animal has its 4 paws scored according to its state of clinical disease. The scoring is done by two observers, with at least one blinded. In addition, each mouse is weighed, to follow body weight changes, at the same time the paws are scored.
Grading scales for the ankle/wrist/midfoot/forfoot are as follows:

0 = Normal
1 = definite swelling
2 = severe swelling
3 = maximally severe swelling and non-weight bearing The grading scale for the 4 lateral digits of each paw are graded as involved or not involved, i.e., 1 or 0. For example, a maximally involved left rear paw would be scored: ankle=3, midfoot=3, digits=4 (clinical score=10 units) We would repeat this for each paw and sum the scores. Mice are euthanized at day 36, or sooner if total clinical score reaches 40 and a histological evaluation of joints is performed.

Induction of Active Collagen Induced Arthritis (CIA) in Rats: Six-eight week old female DA rats were used. On day 0, anesthetized animals were given an intradermal injection, at base of tail, of 2 mg/kg bovine Type IT collagen (CTT) dissolved in 50 µl 0.1 N acetic acid and emulsified with an equal volume of incomplete Freund's adjuvant (Chondrex, Redmond, Wash.). One week later, on day 7 they were given a second similar intradermal injection of 100 µg of CII prepared as described above.

Monitoring Disease Rats: Beginning once inflammation and swelling is apparent in the control group (~day 18) all animal were observed daily to assess the status of the disease in their paws, which was done by assigning a qualitative clinical score to each of the paws. Every day, each animal has its 4 paws scored according to its state of clinical disease. The scoring is done by two observers, with at least one blinded. In addition, each rat is weighed, to follow body weight changes, at the same time the paws are scored.
Grading scales for the ankle/wrist and midfoot/forfoot are as follows:

0 = Normal
1 = barely perceptible swelling
2 = definite swelling
3 = severe swelling
4 = maximally severe swelling and non-weight bearing The grading scale for the 4 lateral digits of each paw are graded as involved or not involved, i.e., 1 or 0. For example, a maximally involved left rear paw would be scored: ankles=4, midfoot=4, MTP=4, PIP=4, DIP=4 (20 units). We would repeat this for each extremity and sum the scores for each extremity. Rats are euthanized at day 42, or sooner if total clinical score reaches 80.

6.8.2 Results

We examined whether treatment with human anti-HMG1 antibodies could prevent or reduce disease severity CIA in an active CIA model. Mice were treated with either anti-HMG1 antibody G4, an isotype control antibody or Renbrel at 10 mg/kg, every three days starting on day 21. The development of arthritis was assessed daily. The graphs in FIG. 15A show the paw inflammation scores for each of the treatment groups over the course of the study. The administration of human IgG had no effect on the development of arthritis. However, the anti-HMG1 G4 antibody treated animals have greatly reduced inflammation scores compared to the control animals. Strikingly, the animals treated with the anti-HMG1 G4 antibody did significantly better then those treated with Renbrel therapy (FIG. 15A compare left and right panels).

Figure 15B:
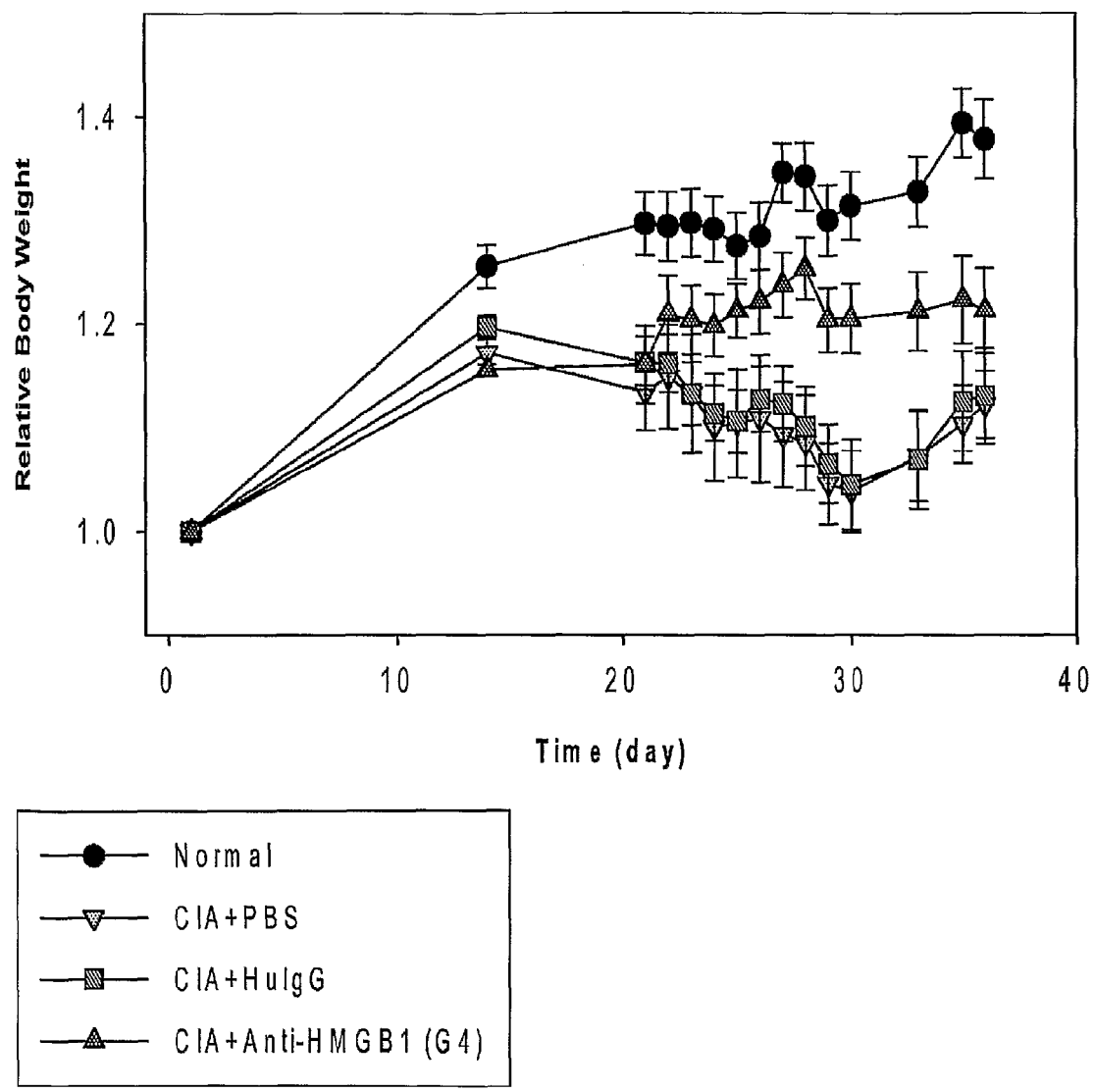

Another clinical feature of disease progression in this model is weight loss. The relative body weight scores for the control animal show a net decrease during the course of the study. Although the clinical scores for the mice treated with anti-HMG1 G4 antibody showed significant protection, this group of animals also showed a net decrease in bodyweight. However the anti-HMG1 G4 antibody treated animals did not lose as much as the control group (FIG. 15B). These results demonstrate that anti-HMG1 antibodies can effectively protect against joint damage and other symptoms when administered prior to the onset of disease. In particular, these results indicate that anti-HMG1 G4 antibody treatment had a profound effect in diminishing the disease severity in the active CIA mouse model.

Figure 15C:
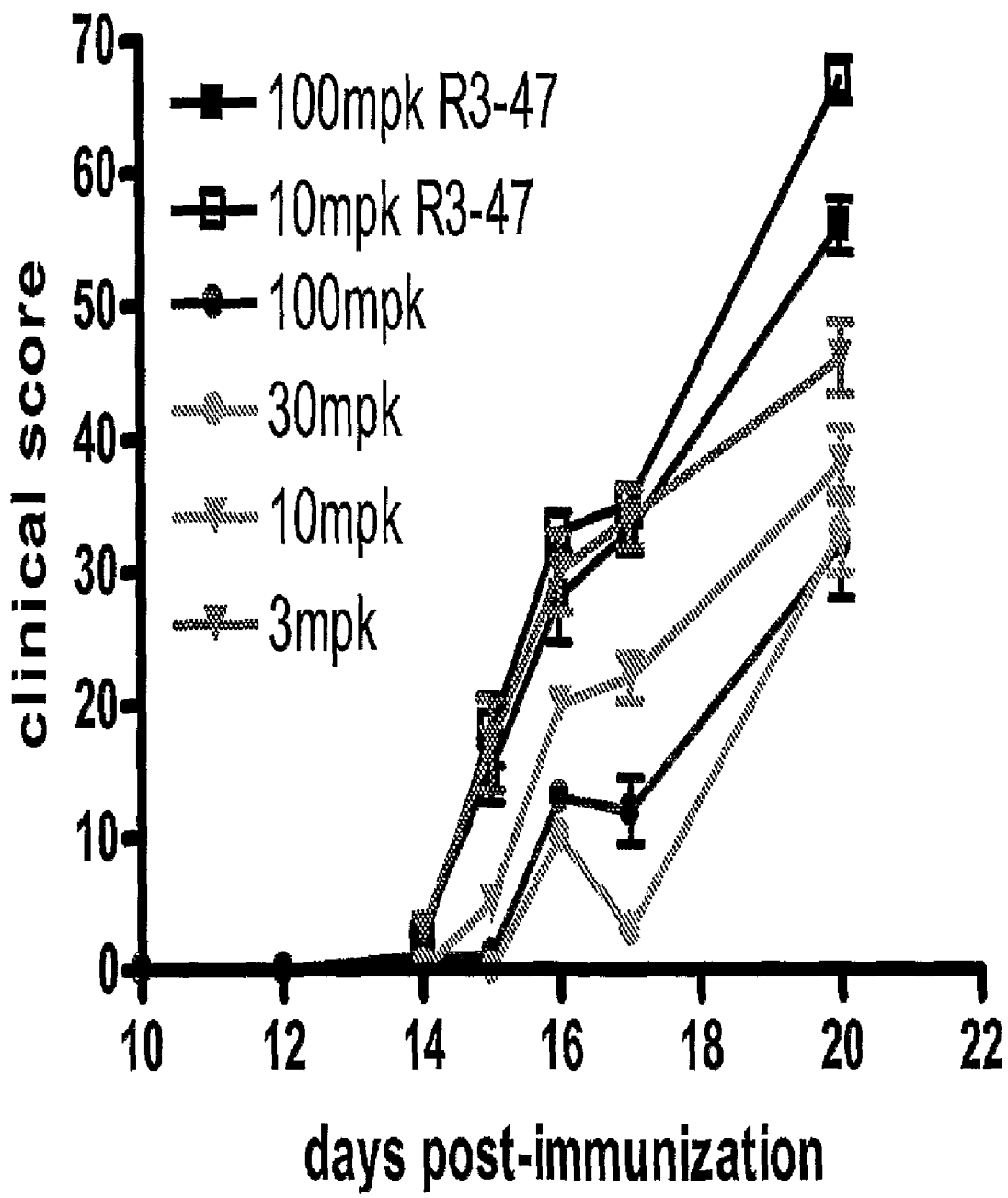

Additional studies to examine dose titration of the G4 anti-HMGB1 antibody in an active collagen-induced arthritis in a rat model showed increasing effectiveness up to doses of 30 mg/kg. No additional improvement in clinical scores was seen for the highest dose, 100 mg/kg (FIG. 15C).

6.9 Example 9

Anti-HMG1 Antibodies Inhibit The Severity of Disease Progression in the Adjuvant-Induced Arthritis (AIA) Rat Model We further tested the human anti-HMG1 antibody G4 in the Adjuvant-Induced Arthritis (AIA) Rat Model. For this series of experiments we utilized a prevention model in which treatment is initiated prior to the onset of clinical arthritis. In this study we compared the efficacy of anti-HMG1 antibodies with that of Renbrel.

We demonstrate here, for the first time, that an antibody against HMG1 (G4) demonstrated efficacy in reducing paw inflammation in the AIA Rat RA model. In fact, the anti-HMG1 antibody G4 was shown to be more effective then Renbrel alone in reducing paw inflammation. An approximately 34% reduction in clinical scores was seen for the anti-HMG1 G4 animals while only an approximately 11% reduction was seen for the Renbrel treated animals. We also demonstrate inhibition of hyperostosis in the anti-HMG1 G4 treated animals. In addition we demonstrate that the combination of methotrexate and G4 was more effective at reducing paw inflammation scores than a combination of methotrexate and Renbrel.

6.9.1 Materials and Methods

Induction of Adjuvant Induced Arthritis (AIA): Six-eight week old female DA rats (Harlen) were used. On day 0, isoflurane anesthetized animals were given an intradermal injection, at base of tail, 0.75 mg of mycobacterium butyricum (Difco #0640-33-7) mixed in 100 μl incomplete Freund's adjuvant (Difco, Detroit, Mich.). The following treatments for the experiments were administered as shown in Table 6.

TABLE 6

Treatment Groups for AIA Rat Model

| Group No. | Test Material | Dose | Total Animals |
|---|---|---|---|
| 1 | Normal | | 6 |
| 2 | PBS | | 6 |
| 3 | HuIgG (R3-47) | 10 mg/kg | 6 |
| 4 | MTX + HuIgG (R3-47) | 0.8 mg/kg MTX 10 mg/kg HuIgG | 6 |
| 5 | Renbrel Alone | 2.5 mg/kg | 6 |
| 6 | MTX + Renbrel | 0.8 mg/kg MTX 2.5 mg/kg Renbrel | 6 |
| 7 | Anti-HMGB1 (G4) | 10 mg/kg | 6 |
| 8 | MTX + Anti-HMGB1mAb (G4) | 0.8 mg/kg MTX 10 mg/kg G4 | 6 |
| 9 | A-Box/Fc | 10 mg/kg | 6 |
| A | Normal | | 8 |
| B | HuIgG (R3-47) | 10 mg/kg | 8 |
| C | Anti-HMGB1 (G4) | 10 mg/kg | 8 |
| D | Renbrel + HuIgG | 4 mg/kg + 10 mg/kg | 8 |
| E | Renbrel + HMGB1 (G4) | 4 mg/kg + 10 mg/kg | 8 |

The human anti-HMG1 antibody G4, the A-box-Fc fusion and the huIgG isotype control were administered at 10 mg/kg, every 3 days, day 0-15. Methotrexate was administered at 0.8 mg/kg, every 6 days, day 0-15 and Renbrel was administered at either 2.5 mg/kg every two days, day 0-15 for treatment group 5 or at 4 mg/kg, every 3 days, day 0-15 for treatment group 6. For treatment groups B, C, D and E the antibodies were administered at 10 mg/kg every three days starting at day 0, for groups D and E, Renbrel was administered at 4 mg/kg every three days starting at day 0.

Monitoring Disease: Beginning at day 6 all animals were observed daily to assess the status of the disease in their paws, which was done by assigning a qualitative clinical score to each of the paws. Every day, each animal has its 4 paws scored according to its state of clinical disease. The scoring is done by two observers, with at least one blinded. In addition, each mouse is weighed, to follow body weight changes, at the same time the paws are scored.

Grading scales for the ankle/wrist/midfoot/forfoot are as follows:

0 = normal
1 = barely perceptible swelling
2 = definite swelling but not severe
3 = severe swelling
4 = maximally severe swelling and non weight bearing The joints of the 4 lateral digits of each paw are graded as involved or not involved, i.e., 1 or 0. For example, a maximally involved left rear paw would be scored: ankles=4, midfoot-4, MTP=4, PIP=4, DIP=4 (20 units). We would repeat this for each paw and sum the scores. Rats are euthanized at day 21, or sooner if total clinical score reaches 80 and a histological evaluation of joints is performed.

Monitoring Bone Morphometry: Hind paws, with attached distal tibia and fibula, were fixed by immersion in 3.7% neutral buffered formaling prior to measurement on a microCT-40 device (computed tomography) (Scanco). MicroCT images were evaluated for the severity and distribution of the periosteal hyperostosis, evident as roughened thickenings and projections from the bony surface and joint boundaries. A severity and distribution score of 0-6 was assigned to the distal tibia, fibula, and talus; a second score of 0-6 was assigned to the tarsal bones and the proxminal metatarsal bones and joints. The total microCT score comprises the composite score of these two areas.

Monitoring Histopathology: After Micro-CT scans, the intact foot was decalcified in formic-acid solution (Cal-EXII, Fischer Scientific, Fair Lawn, N.J.) for approximately 12 hours. Sagittal hemi-sections were then decalcified for 28 hours, washed in water and routinely processed for paraffin embedding; 4-6 micron sections were mounted on glass slides. The sections were stained with Hematoxylin and Eosin, Hematoxylin-Phloxin-Saffron, or Toluidine blue, and examined by light microscopy.

Histological assessment included inflammation and joint damage, as well as confirmation of the presence of the hyperostosis. For inflammation, a numeric score of 0 (normal) through 4 (severe) was assigned for the presence of inflammation of tendon sheaths (tenosynovitis), and a second score assigned for the presence of inflammatory cells and fibrovascular proliferation, in the parosteal tissues (cellulitis). The total inflammation score comprises the composite score of periost bone, tenosynovitis, and cellulitis.

For joint damage, load-beating non-articulating joints (tarsal bones) were assessed separately from load-bearing non-articulating joints (Tibial-talus, metatarsal-phalangeal and inter-phalangeal joints). A score of 0 (normal) through 4 (severe) was assigned for the presence and extent of pannus formation, and a second score assigned for the severity and extent of inflammation of the articular soft tissues (synovitis). The total joint damage score comprises the composite score of pannus formation and synovitis. Cartilage erosion was not scored in the AIA rat model because it has been found to be a minor feature and therefore not reliable for evaluation of potential treatment effects.

6.9.2 Results

Figure 16A:
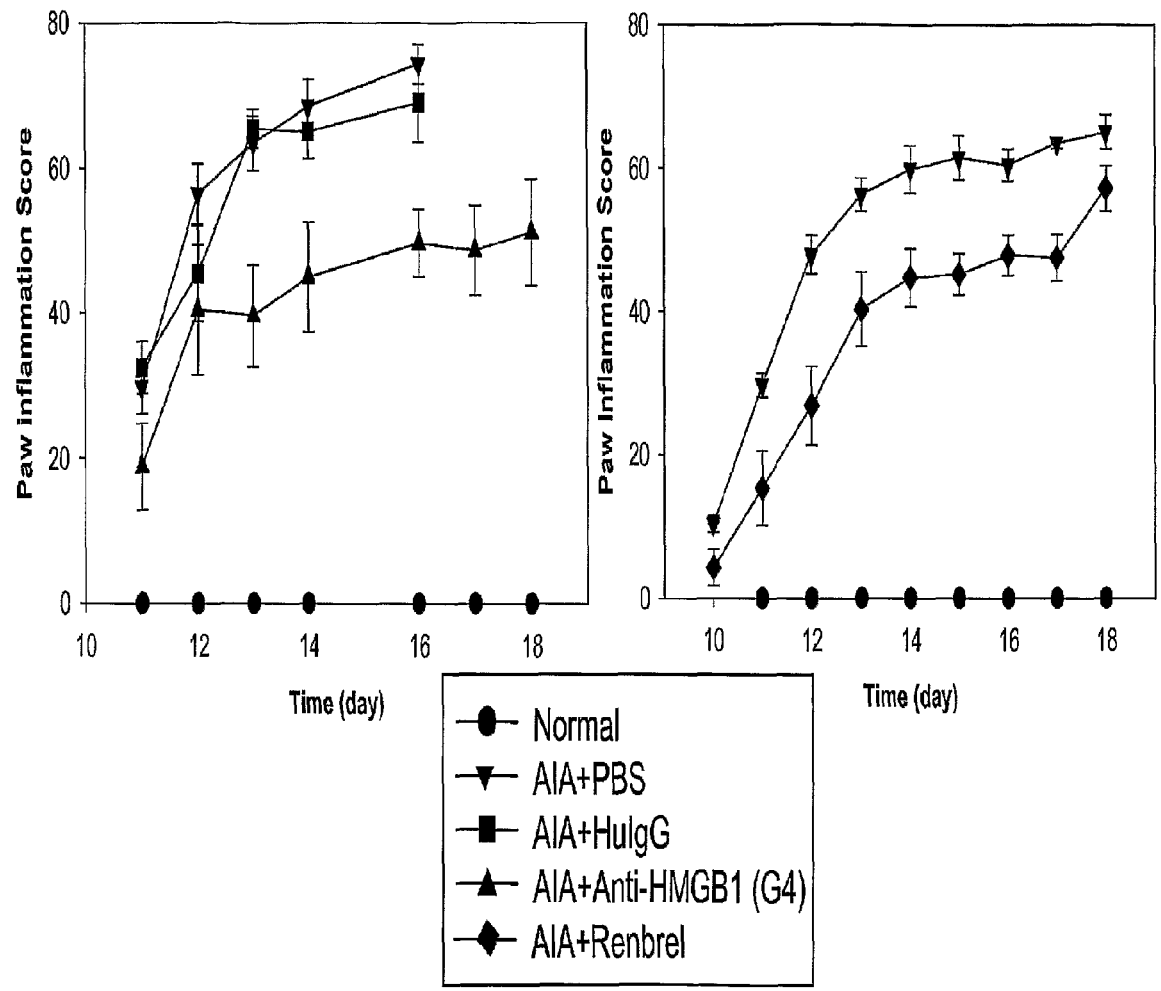

We determined that the human anti-HMG1 antibody G4 could prevent or reduce the severity of AIA in rats. AIA rats were treated with either PBS, anti-HMG1 antibody G4, an isotype control antibody (HuIgG) at 10 mg/kg, every there days or Renbrel at 2.5 mg./kg, every two days starting on day 21. In addition, AIA rats were treated with methotrexate in combination with several other therapies including Renbrel, G4 or HuIgG. AIA rats were also treated with an HMG1 A-box-Fc fusion protein. The development of arthritis was assessed daily. The graphs in FIG. 16A show the paw inflammation scores for each of the antibody or Renbrel alone treatment groups as well as the PBS and normal control groups over the course of the study. The administration of human IgG had no effect on the development of arthritis. However, the anti-HMG1 G4 antibody treated animals have greatly reduced inflammation scores compared to the control animals. Strikingly, the animals treated with the anti-HMG1 G4 antibody did significantly better then those treated with Renbrel therapy alone (FIG. 16A compare left and right panels). An approximately 30% reduction in clinical scores was seen for the anti-HMG1 G4 animals while only an approximately 25% reduction was seen for the Renbrel treated animals.

Figure 16B:
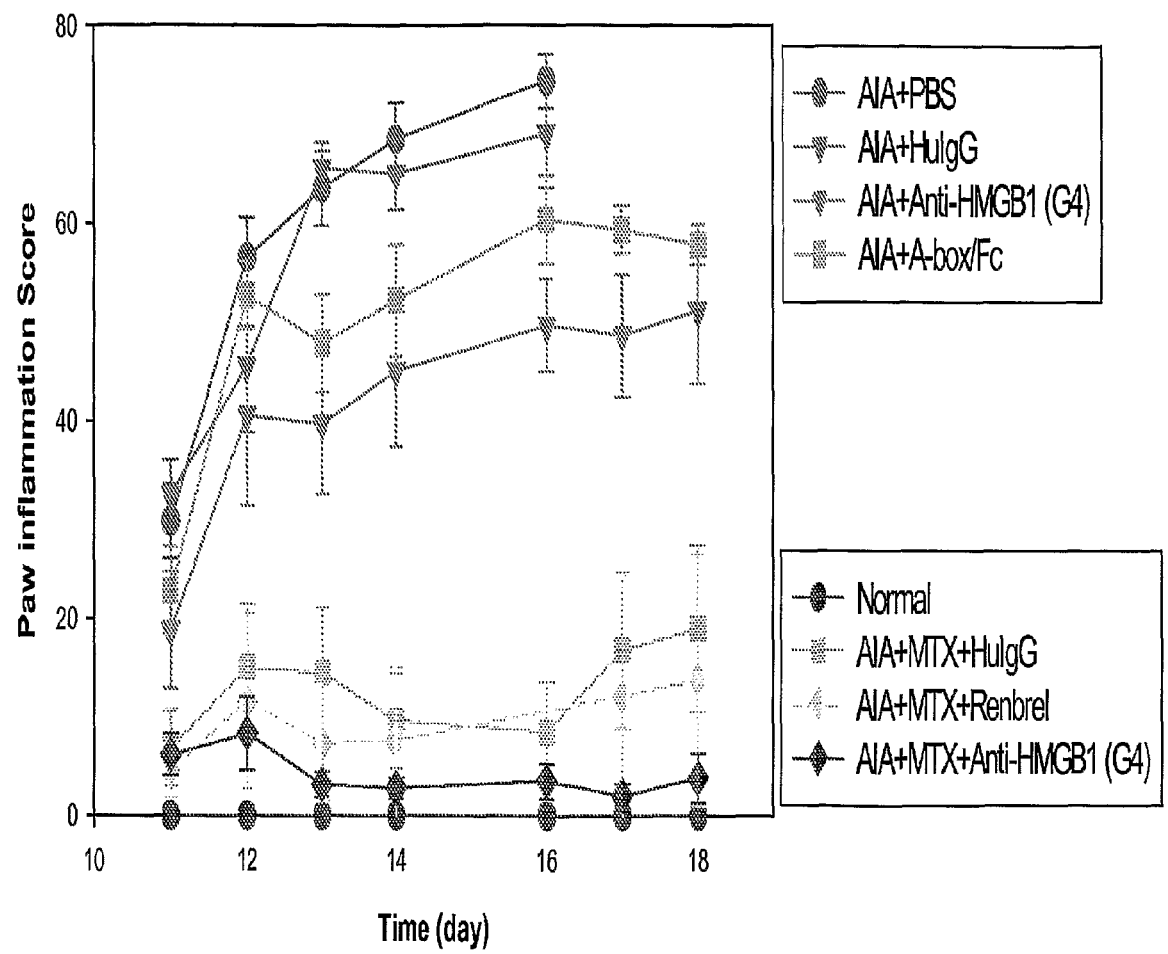

The graphs in FIG. 16B show the paw inflammation scores over time for the combination therapy treatment groups for comparison the antibody alone and HMG1 A-box-Fc fusion protein treatment groups are also included. The A-Box-Fc fusion protein alone reduced inflammation scores but was less effective than G4 alone. The combination of and Renbrel reduced inflammation scores compared to G4 alone. The MTX was likely the largest contributor to this reduction as the combination of MTX and the HuIgG control antibody showed a similar reduction in inflammation as the MTX/Renbrel combination. However, the combination of MTX and G4 was even more effective then even the MTX/Renbrel combination, reducing inflammation scores to nearly normal. The reduction in paw inflammation scores seen for the various treatment groups correlated with a reduction in the levels of HMG1, IL-6 and TNF-a seen in the joint of AIA rats (see FIG. 12G).

Figure 16C:
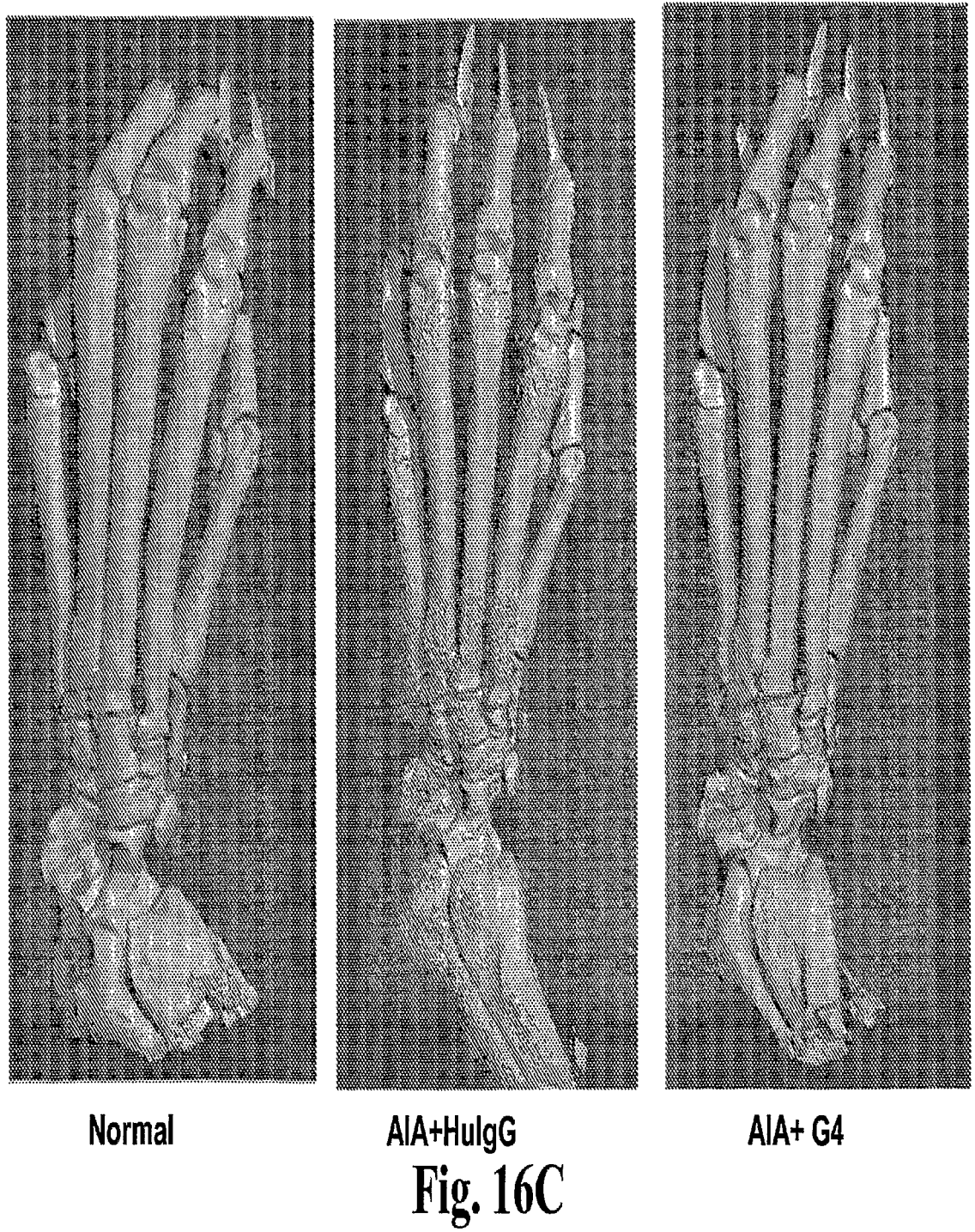
Figure 16D:
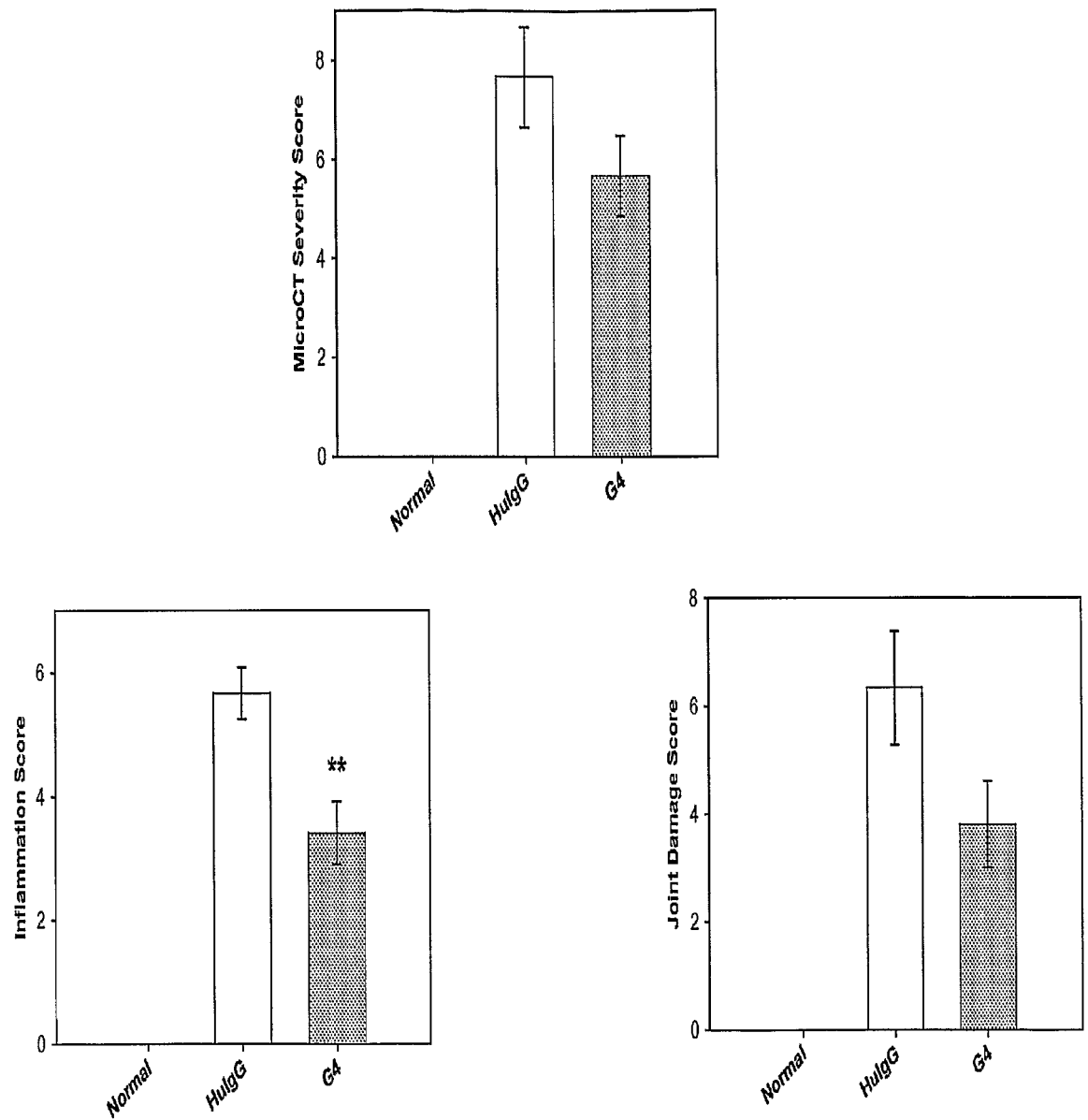

The beneficial effects of anti-HMG1 treatment on paw inflammation were further confirmed by both micro-CT and histopathologic evaluation of the paws. In FIG. 16C, micro-CT revealed prominent hyperostosis in AIA rats, evidenced as thick, radiating projections of subperiosteal cortical bone and mural thickening of the cortex itself. Microscopic evaluation of joints confirmed the overlying periosteum was hypertrophic, consisting of up to 2-3 layers of plump oval cells. The hyperostosis was most severe and extended around the tibial-talus, elevating the Achilles tendon and partially disrupting the plantar tendons. Treatment with anti-HMG1 G-4 resulted in a 30% reduction of hyperostosis (FIGS. 16C and 16D, top panel).

Figure 16E:
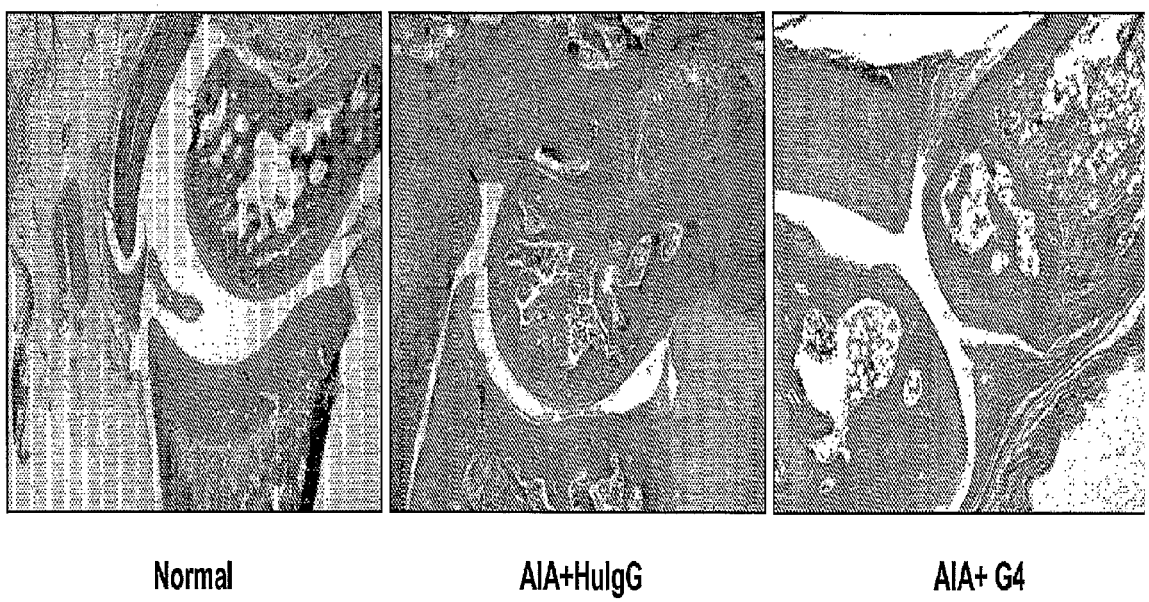

Consistent with clinical observation, histological evaluation revealed severe inflammatory changes in AIA rats (FIG. 16E). Marked edema about the tibial-talus, the palmar surface, and even the distal phalanges was noted clinically and histologically. Marked dilation of the tibal-talar joint space by clear fluid was also noted. Inflammatory cells (admixed lymphocytes, plasma cells, histiocytes and some neutrophils) extended throughout the edematous soft tissues, along with tenosynovial infiltrates extended into and separated tendons. In comparison, rats treated with G-4 had significantly lower inflammatory response (FIG. 16D, bottom left panel). Furthermore, evaluation of articular changes including synovitis and pannus formation also showed milder joint damage in rats treated with G-4 (FIG. 16D, bottom right panel). Taken together, both micro-CT and histopathologic evaluation of the paws confirmed that the beneficial effects of treatment on paw inflammation were associated with a return to normal morphology in animals given the anti-HMG1 therapy.

Figure 16F:
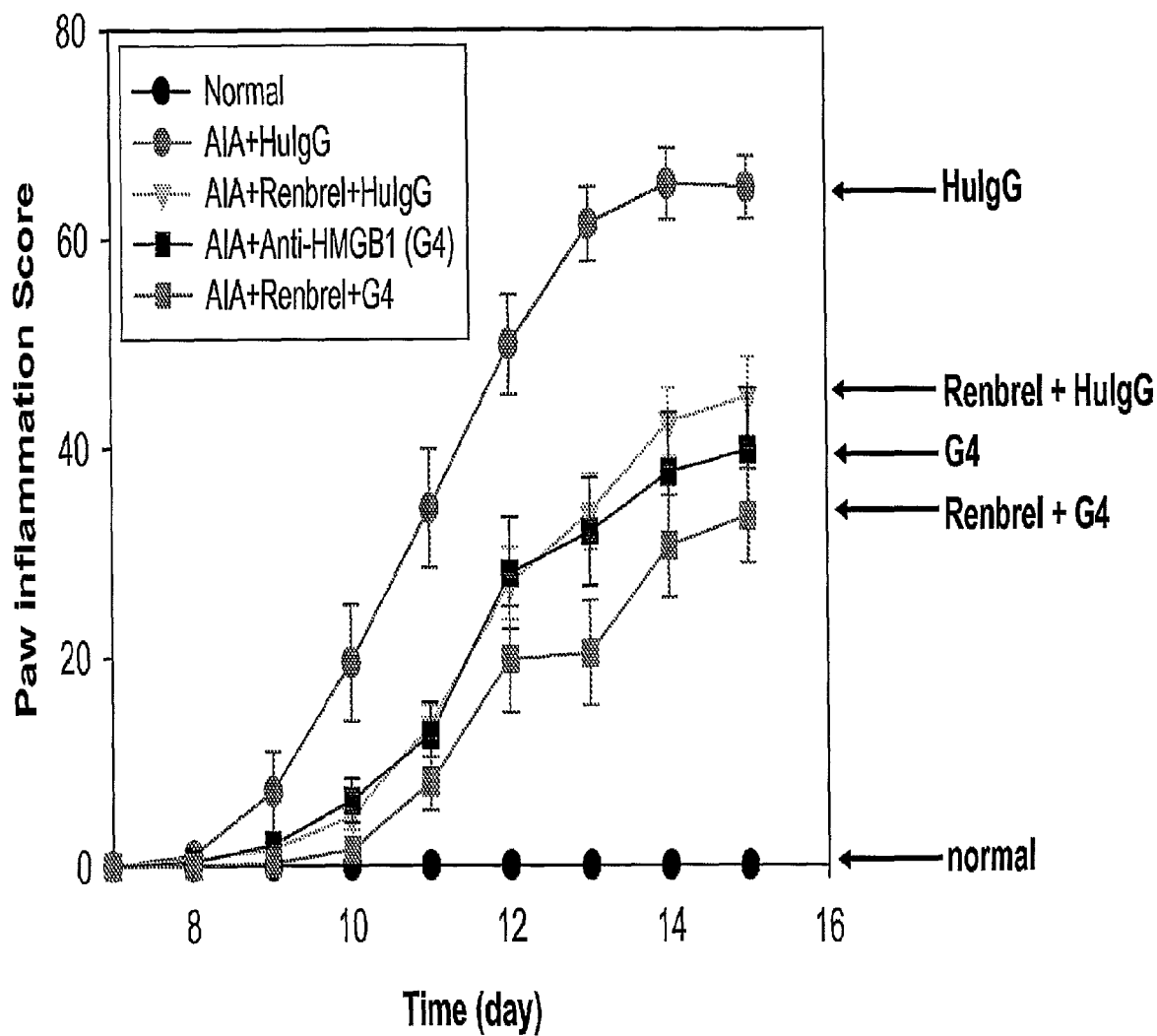

In further studies, higher doses of Renbrel were examined alone or in combination with G4. As shown in FIG. 16F G4 and Renbrel at the higher dose were comparable (48% and 44% inhibition in clinical scores, respectively). However, when combined there was an improvement in the clinical score over either treatment alone (62% inhibition). An improvement was also seen in the combination treatment for several histological evaluation scores including hyperostosis, cellulites, tenosynovitis and artic synovitis scores (data not shown). Similar results were obtained using a delayed treatment regime in which antibodies (control IgG or G4) were administered at 10 mg/kg in combination with Renbrel at 17 mg/kg every three days starting at day 6 (data not shown). These data further confirm the beneficial effects of anti-HMGB1 therapy and suggest that combination therapies may further improve clinical outcomes.

6.10 Example 10

Anti-HMG1 Antibodies Improve Survival in the *S. aureus* Mouse Model of Peritonitis We also tested several human anti-HMG1 antibody in a severe mouse model of peritonitis where the serum levels of HMG1 were seen to rise (see above). Here we demonstrate that treatment with a human anti-HMG1 antibody improves survival by nearly 30% over controls.

6.10.1 Materials and Methods

Induction of Peritonitis: Four-six week old female BALB/c mice were used. An initial study with mice challenged i.p. with heat inactivated *S. aureus* premixed with galactosamine demonstrated that the $LD_{100}$ was between $1 \times 10^7$ and $1 \times 10^9$ cells (data not shown). For determination of HMG1 levels on day 0 approximately $10^9$ heat inactivated *S. aureus* (strain 8325-4) cells premixed with 20 mg of galactosamine or galactosamine alone in a 200 µl volume of PBS was administered i.p. A third group of animals was not challenged. Animals were euthanized at 2, 8, and 12 hours after challenge by $CO_2$ inhalation and blood was collected by cardiac puncture. For the antibody treatment studies on day 0 approximately $10^9$ heat inactivated *S. aureus* (strain 8325-4) cells premixed with 20 mg of galactosamine were administered i.p. in a 200 µl volume and the following treatments were administered i.p. in a 100 µl volume 30 minutes prior to challenge as shown in Table 7.

TABLE 7

Treatment Groups for Peritonitis Model

| Group No. | Test Material | Dose 1 × LD$_{100}$ | Dose Galactosamine | Treatment | Treatment Time | Total Animals |
|---|---|---|---|---|---|---|
| A | S. aureus | 1 × 10$^9$ | 20 mg | none | | 30 |
| B | none | none | 20 mg | none | | 15 |
| C | none | none | none | none | | 7 |
| 1 | S. aureus | 1 × 10$^9$ | 20 mg | PBS | −30 mins. | 10 |
| 2 | S. aureus | 1 × 10$^9$ | 20 mg | R347 200 ug | −30 mins. | 10 |
| 3 | S. aureus | 1 × 10$^9$ | 20 mg | G4-12-3 200 ug | −30 mins. | 10 |

Monitoring Disease: Starting on day 1 and continuing through day 14 the animals were observed daily for signs of morbidity (severely decreased mobility, ruffled fur, and/or loss of >20% of highest body weight) and mortality. The animals were also weighed 2× weekly. Animals showing signs of significant morbidity were euthanized. On day 15 all surviving animals were euthanized (euthanized sooner if significant morbidity observed).

6.10.2 Results

Human anti-HMG1 antibodies were also tested in a severe gram-positive bacterium induced septicemia model in which mice were challenged with a lethal dose of heat inactivated S. aureus. In this model none of the mice treated with either PBS or the antibody isotype control (R347) survived. In contrast 27% of the mice treated with the human antibody against HMG1 G4 survived (FIG. 17) and 8% of the mice treated with E11 survived (data not shown). Differences in mortality were seen as early as 24 hours after treatment and continued over the course of the study. These data support the CLP studies (see above) and indicate that human anti-HMG1 antibodies are useful for the treatment of sepsis induced by a wide range of pathogenic organisms.

6.11 Example 11

Anti-HMG1 Antibodies Reduce Cellular Infiltration Associated with Acute Lung Injury Two human anti-HMG1 antibodies, were tested in the lipopolysaccharide (LPS) induced acute lung injury (ALI) mouse model. Here we demonstrate for the first time that treatment with a human anti-HMG1 antibody reduces total cellular infiltration by approximately 40% compared to controls (FIG. 18).

6.11.1 Materials and Methods

Induction of LPS-induced ALI: LPS (E. coli strain 0111: B4. Sigma, St. Louis, Mo.) was administered intranasally to isoflurane (Baxter Pharmaceuticals, Deerfield, Ill.) anesthetized adult BALB/c mice on day 1 at a dose of 5-10 ug per mouse in 50-100 µl. For determination of HMG1 levels animals were euthanized by CO$_2$ asphyxiation at 4, 8, 24, 32 and 48 hours post LPS administration, and BronchoAlveolar Lavarge (BAL) and other samples collected for protein analysis and histopathology. For treatment protocols 24 hours post LPS dosing, anti-HMGB1 antibodies, HMG1 A-box Fc fusion or controls were administered intraperitoneally (i.p.) at a dose of 10 mg/kg in 100 ul volumes. On day 3 (48 h post LPS dosing), animals were euthanized by CO$_2$ asphyxiation and samples (BALs, blood, and lungs) collected for analysis.

BAL Sample Collection: lungs were flushed three times with ~0.8 ml Phosphate buffered saline (PBS, pH 7.2, GIBCO, Rockville, Md.) using a syringe with a catheter tubing. BAL samples collected were centrifuged at 1,200 rpm for 10 min at 4 C, supernatant collected and stored at −80 C for protein (e.g. HMGB1) quantitation, and cells in pellet were resuspended and transferred to cytoslides, fixed, GIEMSA stained, and BAL cellularity determined visually with the aid of a microscope.

6.11.2 Results

Human anti-HMG1 antibodies were tested in an acute lung injury model induced by intranasal administration of LPS. In this model the HMG1 A-box, a known competitive inhibitor of HMG proinflammatory action, only reduced infiltration by about 23% compared to controls. In contrast G4 and E11 were seen to reduce the total cellular infiltrate present in the BAL fluid by 37%-40% compared to controls, demonstrating that anti-HMG1 antibodies are useful for the treatment of acute lung injury.

6.12 Example 12

HMGB1 Staining Patterns in Multiple Sclerosis (MS) Plaques

Figure 19A:
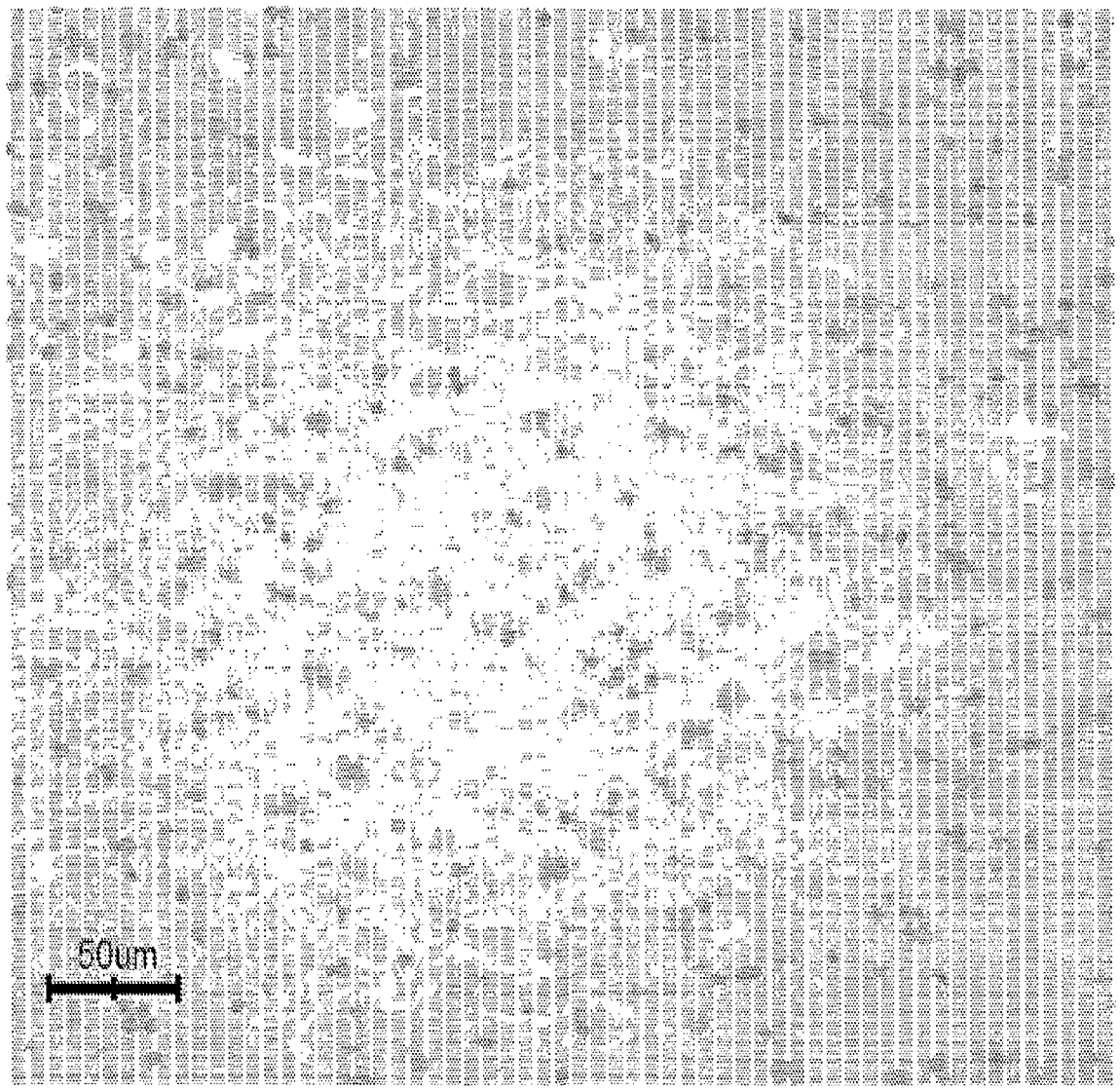
Figure 19B:
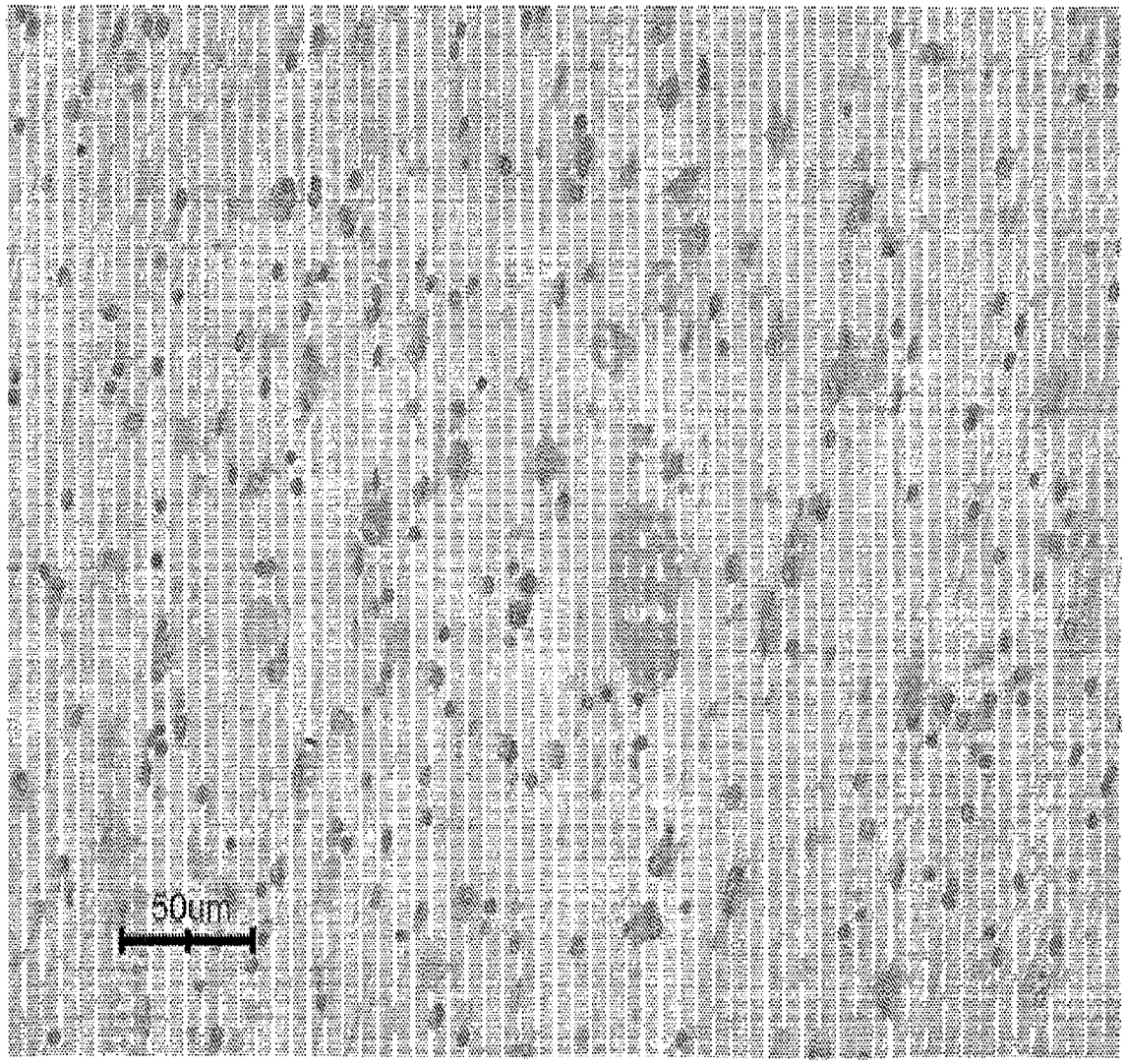
Figure 19C:
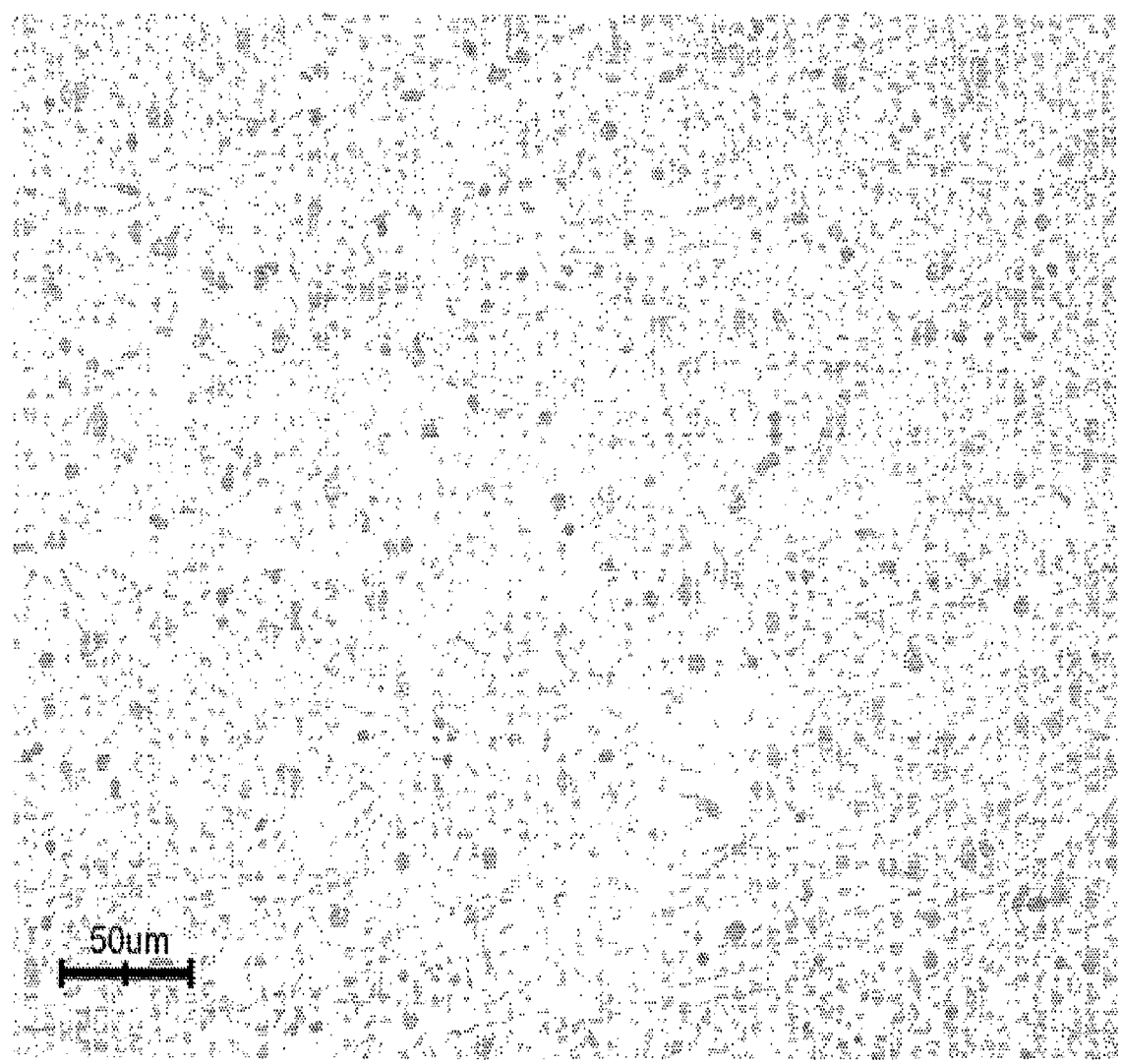

HMGB staining patterns were examined in MS plaques from human brain tissue using the G16 human anti-HMGB antibody. Plaques with demyelination and numerous activated microglia as well as plaques with predominantly demyelination, few activated microglia and numerous lymphocytes were examined. FIG. 19A shows the low level of background staining in Plaques with demyelination and numerous activated microglia using an isotype control antibody. HMGB1 was detected in the cytoplasm of microglia by human mAb G16 in human brain tissue from MS patients. Plaques with demyelination and numerous activated microglia show extensive staining in the cytoplasm of microglia and in the interstitial of the demyelination (FIG. 19B). In contrast, plaques with predominantly demyelination, few activated microglia and numerous lymphocytes showed little or no staining (FIG. 19C) when probed with the human mAb G16. These results reinforce the critical role of HMGB1 as an extracellular modulator of inflammation, and indicate that HMGB1 is likely involved in the inflammatory process of MS.

6.13 Example 13

Synergy Between Recombinant HMGB1 and Toll-Like Receptor (TLR) Ligands

E. coli produced recombinant HMGB1 (designated "rHMG1" or "rHMGB1") is able to bind recombinant RAGE, and induces cytokine secretion in fresh human peripheral blood mononuclear cells (PBMCs) and murine bone marrow mononuclear cells (BMMC). This activity can be blocked by HMGB1 specific monoclonal antibodies (see above). While some rHMG1 preparations still contain trace amounts of endotoxin, the activity of the preparation is the same whether polymyxin B is present or not. However, when rHMG1 is further extracted with Triton-X114 (designated "Tx- HMGB1") to remove residual hydrophobic/lipophilic contaminants the protein retains the same RAGE-binding potency as untreated HMGB1, although it loses the ability to stimulate cytokine release. When cells are treated with this Tx-HMGB1 in combination with suboptimal concentrations of TLR ligands a greatly enhanced cytokine and chemokine release, much greater than that induced by either component alone, is observed. This enhanced cytokine production can be blocked by either HMGB 1-specific or TLR-specific monoclonal antibodies. The synergistic activity of Tx-HMGB1 and LPS is not seen in cells defective in TLR4 activity.

6.13.1 Materials and Methods

Cytokine Release Assays: Human PBMCs were treated with rHMG1 in the presence or absence of Polymyxin B (FIG. 20). Human PBMCs were treated with rHMG1 and Tx-HMGB1 at concentrations up to 4 µg/ml (FIG. 21). ~16 µg/mL (512 nM) Tx-HMGB1 was incubated with 61.5 EU/mL (6.15 ng/mL; approx. 0.615 nM) LPS overnight at 4° C. The sample was diluted as indicated and added to human PBMCs (FIG. 22). In all assays the cells were incubated overnight at 37° C., 5% $CO_2$ and the supernatants were assayed for cytokine levels by Bioplex assay. When present Polymyxin B was used at 8 U/mL.

HMG1-RAGE Binding: Rage binding assays (FIG. 21, left panel) were performed as described above.

Inhibition of HMG1 Mediated Enhancement of TLR Signaling Human PBMCs were treated with Tx-HMGB1+LPS (as described above) in combination with either the Anti-HMG1 antibody E11, S16 or G4, anti-TLR4 antibody, or isotype control antibodies (R3, IgG2a) and incubated overnight at 37° C., 5% $CO_2$ in the presence of 8 U/mL Polymyxin B. The supernatants were assayed for cytokine levels (FIG. 22, right panel).

Intracellular Cytokine Measurements: Human PBMCs were stimulated with 4 ug/ml purified rHMG1 (left panels), Tx-HMGB1 (middle panels) or left untreated overnight (right panels). Intracellular staining of IL-6 (top row) or TNF-a (bottom row) was analyzed by Flow cytometry (all FIG. 23). The Tx-HMGB™ treated coils had reduced levels of intracellular staining for both IL-6 and TNF-a.

Cytokine mRNA Measurements: Human PBMCs were stimulated with medium alone, 400 EU/mL LPS (40 ng/mL), 4 µl/mL Tx-HMGB1 or 4 µg/mL rHMG1 and total RNA was extracted at 1, 4 and 24 hours post treatment. RT-PCR was performed using a human cytokine multiplex PCR kit (Maxim Biotech, San Francisco, Calif.).

Other TLR Ligands: Bone marrow cells from C3H/HcN (normal mice) were stimulated with various TLR ligands alone, rHMG1 (97 pg/mL endotoxin) alone or TLR ligand+4 µg/mL rHMG1. The TLR ligands used were as follows: TLR2-0.01 µg/1 mL PAM3-CSK4, TLR3-0.25 µg/mL Poly (I:C), TLR5-0.01 µg/mL Flagelin, TLR7-0.25 µg/mL Imiquinod and TLR9-0.10 µg/mL CpG. After overnight incubation 23 cytokines in the supernatants were measured by Bioplex (FIG. 24A).

In other experiments bone marrow cells from C3H/HeN (normal mice) or from HeJ (TLR4 defective) mice were treated overnight with Tx-HMGB1, LPS or a mixture of both. Supernatants were harvested and cytokine concentration determined by Bioplex (FIG. 24B).

6.13.2 Results

Figure 23A:
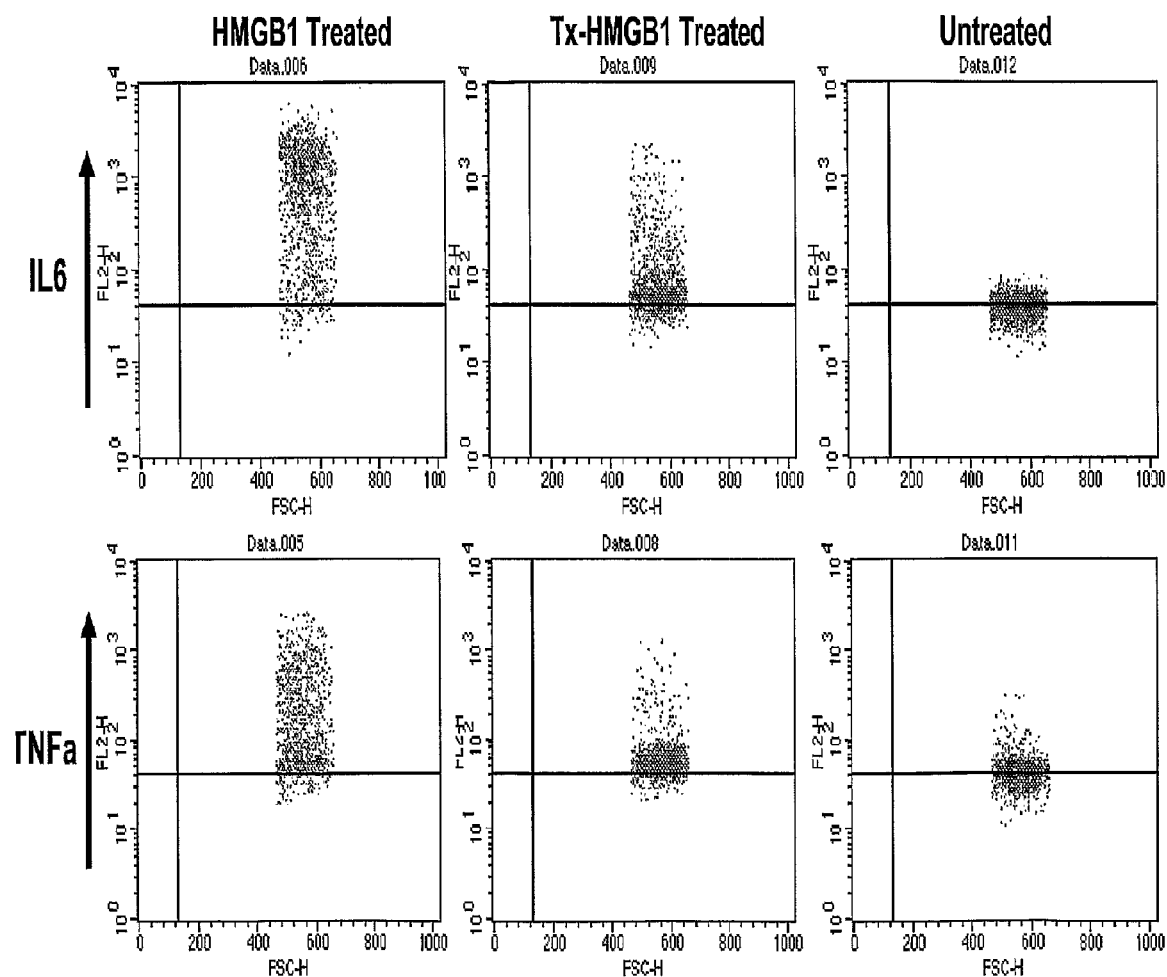
Figure 23B:
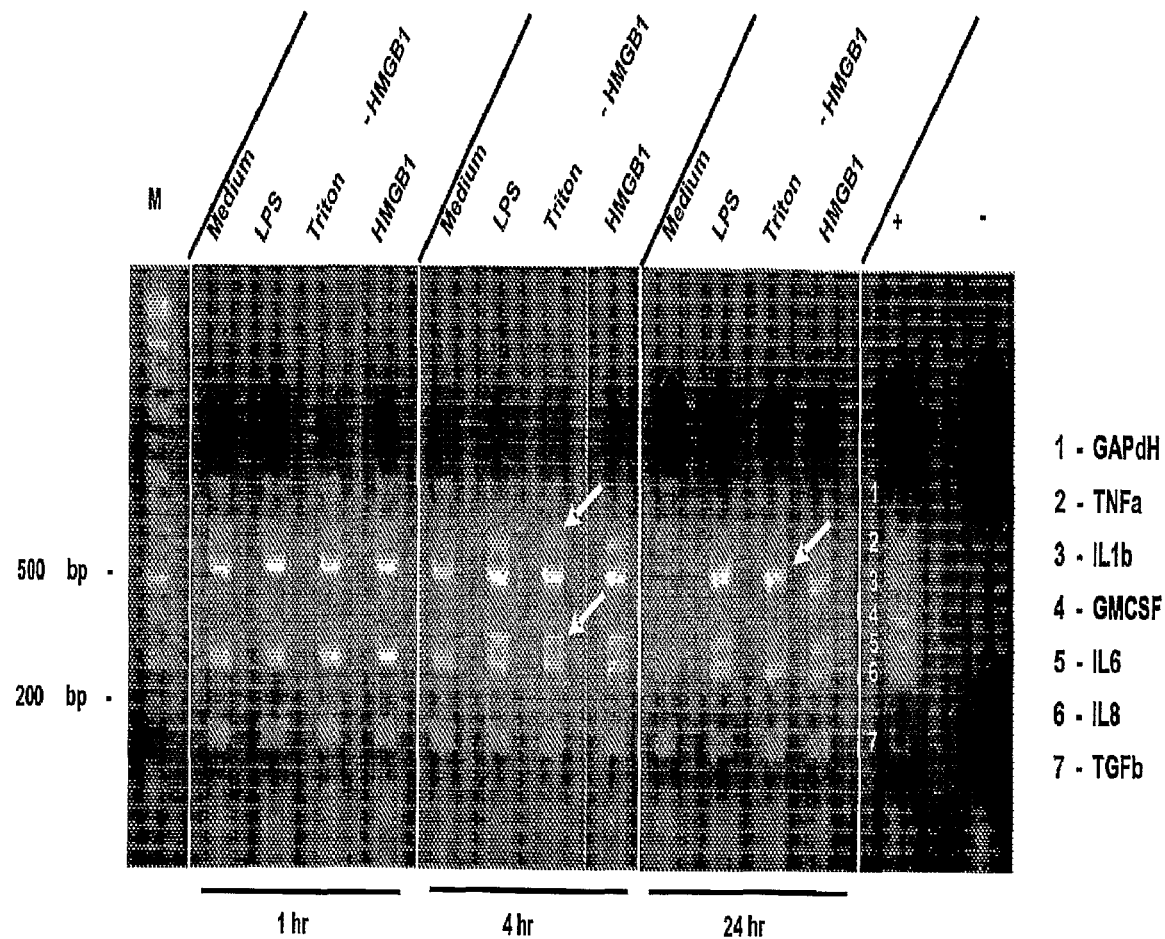

*E. coli* produced rHMG1 contains trace amounts of endotoxin. To examine the relative contribution of the endotoxin present in the rHMG1 the activity of increasing amounts of rHMG1 to stimulate cytokine release (IL-6) was determined in the presence and absence of Polymyxin B. Using two different PBMCs donors the activity of rHMG1 was the same whether Polymyxin B was present or not (FIG. 20). However, when rHMG1 is further extracted with Triton-X114 (Tx-HMGB1) to remove the residual hydrophobic/lipophilic contaminants, the protein retains the same RAGE-binding potency as untreated HMG1 (FIG. 21, left panel), although it loses the ability to stimulate cytokine release even when added at concentrations of up to 4 µg/mL (FIG. 21, right panel). In addition, cells treated with rHMG1 show a dramatic increase in the intracellular levels of both IL-6 and TNF-a (FIG. 23, compare left and right panels), while cells treated with Tx-HMGB1 did not show similar increases (FIG. 23A, compare left and middle panels). However cells treated with Tx-HMGB1 did show an increase in TNF-a, IL-1b and IL-6 mRNA levels (FIG. 23B, red arrows).

As described above, Tx-HMGB1 does not stimulate cytokine release however, when suboptimal concentrations of the TLR4 ligand, LPS, was added back to Tx-HMGB1 the release of several cytokines including IL-6, MIP-1b and TNF-a was largely restored. The addition of suboptimal concentrations of LPS alone did not stimulate cytokine release. Thus, Tx-HMGB1 appears to enhance the ability of suboptimal concentrations of the TLR ligand, LPS, to induce TLR cytokine release (FIG. 22, left panel). Antibodies specific for HMG1 (E11, S16 and G4) or TLR4 were found to block the Tx-HMG1 mediated enhancement of TLR4 signaling (FIG. 22, right panel). Studies using bone marrow cells from HeJ mice, which are defective in TLR4 activity, demonstrate that the synergistic effect of Tx-HMGB1 on LPS stimulation is dependent on the activity of TLR4 (FIG. 25).

Cells were then treated with rHMGB1 (contains trace amount of endotoxins) added to suboptimal concentrations of the following TLR ligands: TLR2-PAM3-CSK4, TLR3-Poly (I:C), TLR5-Flagelin, TLR7-Imiquinod and TLR9-CpG. A greatly enhanced IL-6 release, much greater than that induced by either component alone, was observed for each ligand examined (FIG. 24, left panel). Under the assay conditions used here, the relative enhancement of IL-6 release for each TLR ligand was TLR2>TLR9>TLR7>TLR5>TLR3, where ">" is used to mean "has greater enhancement than". A similar response was seen for IL-12 release with the most dramatic enhancement seen for the TLR7 and TLR9 ligands (FIG. 24, right panel).

Together these data indicated that rHMG1 can enhance the signaling of suboptimal concentrations of proinflammatory factors, in particular, TLR signaling stimulated by one or more TLR ligands. The synergistic activity of HMG1 and TLR4 signaling can be inhibited by either the anti-HMG1 antibodies E11, S16 or G4 or an anti-TLR antibody.

6.14 Example 14

Synergy Between Native HMGB1 and Toll-Like Receptor (TLR) Ligands

Figure 32A:
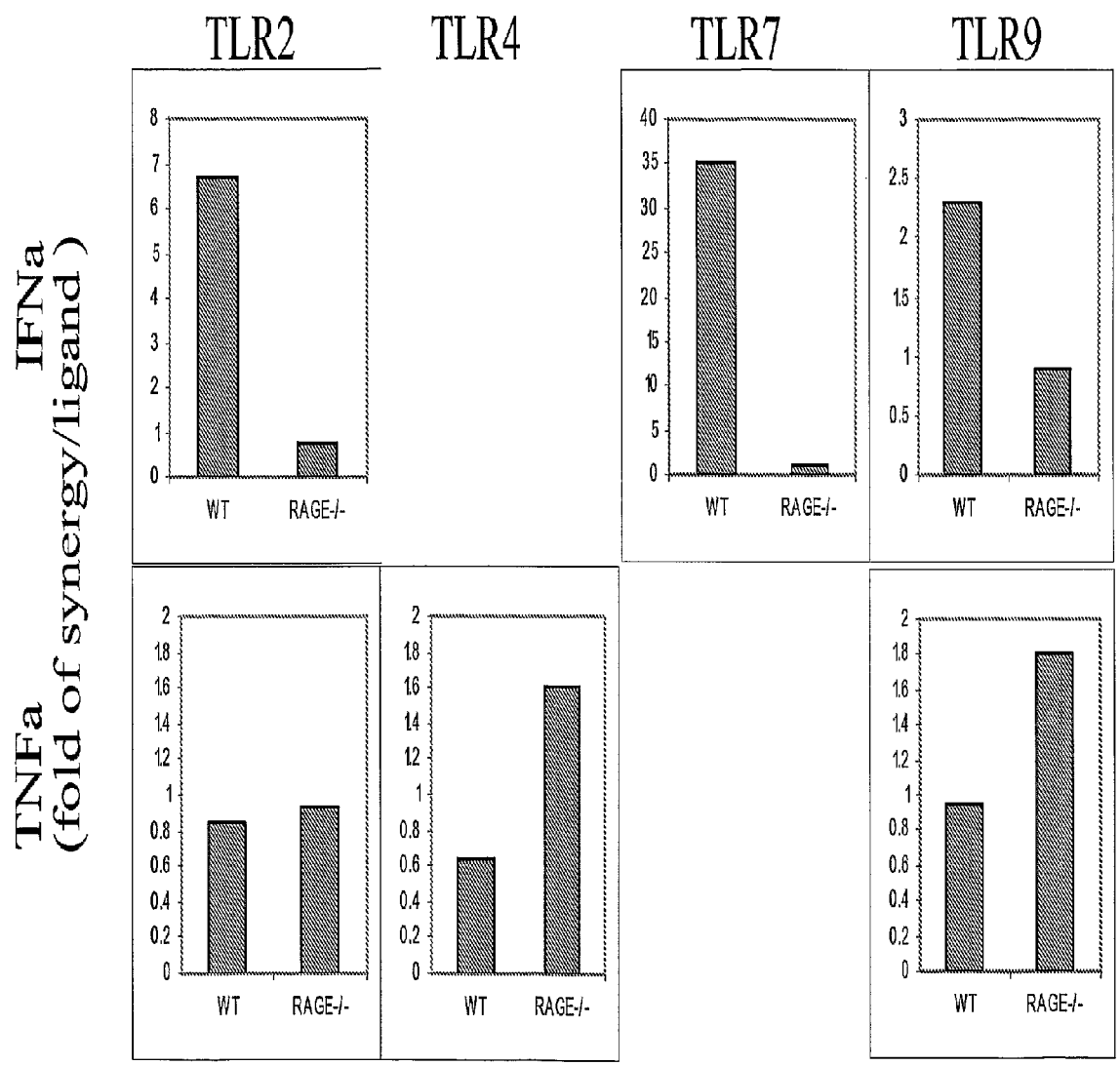
Figure 32B:
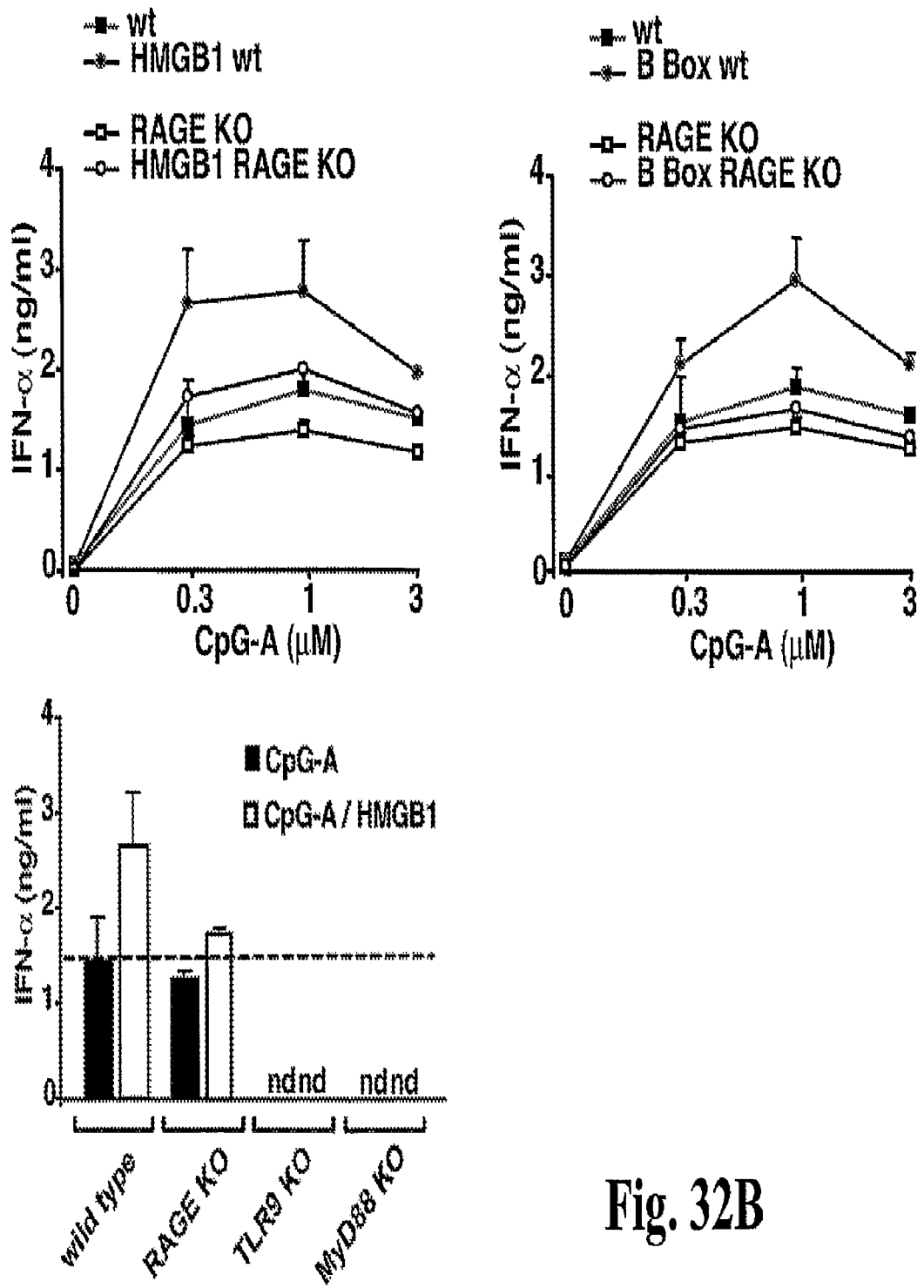

HMGB1 is a chromatin binding protein, to examine the effect of trace amount of bacterial nucleic acids that may be present in *E. coli* produced HMGB1 (rHMG1) the activity of rHMG1 to stimulate cytokine release (IFN-a) was examined in samples pre-treated with benzonase or a mock treatment. The ability of rHMGB1 to induce cytokines is significantly reduced after benzonase treatment, suggesting that HMGB1's ability to induce cytokines is in part dependant upon its bacterial nucleic acid content (FIG. 26). In contrast, thymus derived HMGB1 failed to induce TNF-a secretion (FIG. 27, bottom), although it was effective inducing mRNA transcripts for a number of cytokines including TNF-a mRNA (FIG. 26, top). This is analogous to what was observed for Tx-HMGB1, which was effective at inducing mRNA transcripts for several cytokines although it was not effective at inducing cytokine secretion or intracellular cytokine levels (see Example 13). Like Tx-HMGB1, thymus HMGB1 synergizes with TLR ligands, with the TLR9 ligand CpG2216 showing a strong synergy in inducing the secretion of IFN-a, Rantes, IL-12p70 and IL-6 from bone marrow cells (FIG. 29). The synergy with the TLR9 ligand CpG could be blocked by the anti-HMG1 antibody E11 and to a less extent by G4 and Rage/Fc under the conditions utilized (FIG. 30). The synergy with the TLR4 ligand LPS could be blocked by the anti-HMG1 antibodies E11, G4 and Rage/Fc under the conditions utilized (FIG. 31). In initial experiments the release of IFN-a enhanced by HMG1 by TLR2, 7 and 9 ligands is reduced in Rage knockout mice (FIG. 32A). Subsequent experiments confirm that the synergistic response to CpG-A and HMGB1 complex was reduced in bone marrow cells isolated from RAGE deficient animals and demonstrated similar results for CpG-A and HMGB1 B-box complexes (FIG. 32B).

6.14.1 Materials and Methods

Mice and Bone Marrow Cells: See, Example 15 below.

TNF-a Induction: To examine mRNA levels macrophages were derived from mouse bone marrow using M-CSF. Macrophages were then stimulated by LPS, *E. coli* produced recombinant HMGB1 or HMGB1 purified from bovine thymus for indicated length of time and mRNA is measured by Taqman. To examine protein levels thioglycant activated mouse peritoneal macrophages were stimulated with 10 µg/mL of HMGB1 purified from bovine thymus or recombinant HMGB1 generated from *E. coli* for 24 hr. Cytokines in the supernatant were measured by ELISA.

Inhibition of Native HMG1 Binding to Rage-Fc: Recombinant RAGE/Fc was coated on ELISA plate at 5 µg/mL 0.1 mL/well. HMGB1 (0.5 µg/mL) was pre-incubated with anti-HMGB1 mAb clone E-11 or G-4 at different concentrations for 0.5 hr. After blocking the plate, anti-HMGB1 mAb pre-incubated HMGB1 was added to RAGE/Fc coated plate for 2 hr. RAGE bound HMGB1 was detected with Biotin labeled anti-HMGB1 pAb.

HMGB1+TLR Ligand: Freshly isolated bone marrow cells wore stimulated with TLR ligands (TLR3:PolyIC@5 µg/mL; TLR4:LPS@2.5 ng/mL; TLR5:flagellin@0.25 µg/mL; TLR7:polyU@4 µg/mL or R837@5 µg/mL; TLR9: CpG2216@1 µM) with or without presence of thymus HMGB1 (10 µg/mL) for 24 hr. Cytokines in the supernatant were measured by ELISA.

Inhibition of HMG1 Mediated Enhancement of TLR Signaling: Freshly isolated bone marrow cells were stimulated with TLR9 ligand CpG2216 (0.3 µM) and thymus HMGB1 (10 µg/mL) in the presence of different concentration of the anti-HMGB1 mAb E11 or control human IgG for 24 hr and IFN-a in the supernatant was measured by ELISA. CpG2216, HMGB1 and nonstimulatory DNA were used alone or in combination as controls for the assay.

6.14.2 Results

As described above, rHMG1 isolated from *E. coli* contains trace amounts of endotoxin which enhances signaling through the TLR receptors, when the trace endotoxin is removed by Triton extraction rHMG1 loses the ability to stimulate cytokine release. rHMG1 was also shown to induce INF-a release however, the response was significantly attenuated by pre-treatment of rHMG1 with benzonase to remove contaminating bacterial nucleic acids (FIG. 26). These data support the finding that HMG1 signaling through the TLR receptors is enhanced by trace amounts of TLR receptor ligands including bacterial nucleic acids and/or LPS.

The stimulatory activity of native preparation of HMG1 purified from bovine thymus (thymus HMG1), which does not contain any trace endotoxin or bacterial nucleic acids, to induce TNF-a at both the mRNA level and protein over time was examined in mouse macrophages. Treatment with thymus HMG1 resulted in a roughly 30 fold increase in mRNA levels at two hours while treatment with rHMG1 resulted in ~43 fold increase (FIG. 27, top). At 8 hour post treatment only thymus HMG1 showed a continued increase of mRNA levels at ~15 fold. LPS was included as a positive control and induced an increase in TNF-a mRNA levels at both 2 and 8 hours of ~66 fold and ~7 fold, respectively. Although, thymus HMG1 induced TNF-a mRNA levels only rHMG1 induced an increase in TNF-a protein levels (~10 fold increase) after 24 hours (FIG. 27, bottom).

The ability of several anti-HMG1 antibodies to block the binding of native HMG1 purified from bovine thymus to a RAGE-Fc fusion was examined using an ELISA assay. E11 was found to block native HMG1 while G4 showed little blocking at the concentrations tested here.

To demonstrate that native HMG1 would also enhance signaling by TLR ligands, bone marrow cells were stimulated with the following TLR ligands: TLR2: PAM-CSK; TLR3: PolyIC; TLR4:LPS; TLR5:flagellin; TLR7: R837; TLR9: CpG2216, in the presence or absence of native HMG1 and assayed for the release of IFN-a, Rantes, IL-6 and IL-12p70. Native HMG1 enhanced IFN-a release stimulated by TLR2, TLR7 and TLR9 ligands (FIG. 29, top left), Rantes release stimulated by TLR3, 4, 7 and 9 (FIG. 29, top right), TNF-a release stimulated by TLR2, 4, 7 and 9 (FIG. 29, bottom left) and IL-12p70 release stimulated by TLR4, 7 and 9 (FIG. 29, bottom right).

E11, G4, a Rage/Fc fusion and an HMG1 A-box peptide were further tested for the ability to inhibit the enhancement of TLR9 signaling induced by thymus HMG1 in isolated mouse bone marrow cells. Neither E11, G4 or Rage/Fc inhibited the release of INF-a induced by the TLR9 ligand CpG2216 alone (FIG. 30, bottom right), however both E11 and Rage/Fc inhibited the release of INF-a induced by CpG2216+thymus HMG1 (FIG. 29, bottom left). While HMGB1 A-box did not show inhibition in this assay, after optimization of the assay conditions both RAGE-Fc and the A-box are seen to inhibit HMGB/CpG-A mediated enhanced TLR9 signaling, as measured by IFN-a release, by greater than 95% (FIG. 30, top right). Control reactions were run in parallel in which bone marrow cells were treated with thymus HMG1, stimulatory CpG2216 or non-stimulatory CpG alone or in combination. Only stimulatory CpG induced IFN-a release and this release was enhanced by the presence of thymus HMG1 (FIG. 30, top left).

E11, G4, and a Rage/Fc fusion were also tested for the ability to inhibit the enhancement of TLR4 signaling induced by HMG1. E11, G4 and Rage/Fc were all seen to inhibit the release of TNF-a induced by LPS+HMG1 (FIG. 31, bottom left). E11 was also seen to inhibit signaling by LPS alone (FIG. 31, bottom right). Control reactions were run in parallel in which cells were treated with HMG1, LPS or a combination of HMG1 and LPS. TNF-a release was enhanced by the presence of HMG1 (FIG. 31, top).

The ability of HMG1 to enhance cytokine release stimulated by various TLR ligands was examined in parallel in wild type and Rage knock out (RAGE−/−) mice. In initial experiments the release of both INF-a and TNF-a were examined. The synergistic effect of HMG1 on IFN-a release was significantly reduced for TLR2, 7 and 9 (FIG. 32A, top panels). To extend these observations, we next stimulated total bone marrow cells from either wild type mice or RAGE deficient mice with CpG-A alone (ODN 2336), or CpG-A/HMGB1. The results demonstrate that while the response to CpG-A alone was comparable in cells from wild type and RAGE deficient mice, the response to CpG-A/HMGB1 was reduced by 70% in bone marrow cells from RAGE deficient mice (FIG. 32B, top left). Likewise, as shown in FIG. 32B top right panel, the synergistic response to the CpG-A and HMGB1 B Box complex was abolished in RAGE deficient bone marrow cells. In contrast to what we observed in the RAGE deficient cells, the response to both CpG-A and CpG-A/HMGB1 was completely abolished in bone marrow cells from MyD88 and TLR9 deficient mice (FIG. 32B, bottom left).

These data expand the results described for rHMG1 to native HMG1 demonstrating that native HMG1 can also enhance TLR signaling stimulated by one or more TLR ligands. In addition, these data indicate that HMG1 interacts directly with TLR ligands and may form complexes, which enhances the stimulatory activity of the TLR ligand. The synergistic activity of HMG1 on LPS signaling requires TLR4, and the stimulation of INF-a release by TLR2, 7 and 9 ligands requires RAGE.

TLR ligands belong to a class of molecules having a pathogen-associated molecular pattern (such molecules are known as PAMPs), which are recognized by pattern-recognition family of receptor/molecules (known as PRMs), which includes the TLRs. As HMG1 is known to associate with numerous compounds and molecules, it is likely that HMG1 enhances the stimulatory activity of many other PAMPs. Furthermore, these data demonstrate that the synergistic activity of HMG1 and TLR9 signaling can be inhibited by several anti-HMG1 antibodies with different antibodies exhibiting different inhibitory effects. This indicates that the different antibodies may be useful for inhibiting different TLR signaling pathways.

6.15 Example 15

HMGB1 Binds CpG and Facilitates Intracellular Transport to TLR9

As described above HMGB1 is a chromatin binding protein which can enhance the signaling of CpG DNA through TLR9 (FIG. 34). Using ELISA based assays it was determined that HMGB1 can directly bind CpG (FIG. 33) and that the HMBG1/CpG complex can bind a RAGE/Fc fusion while CpG alone can not (FIG. 35). Microscopic examination of TLR9+/RAGE+ HEK293 cells stimulated with the HMBG1/CpG showed that CpG, RAGE and TLR9 co-localize (FIG. 36). This finding was supported by immunoprecipitation studies of these cells which demonstrated that RAGE and TLR9 co-precipitated only when the cells had boon treated with HMGB1/CpG and that the amount of RAGE co-precipitating with TLR9 increased upon long treatment (FIG. 37). In contrast, another RAGE ligand, S100b failed to induce IFN-α secretion alone or in combination with CpG DNA (FIG. 38).

6.15.1 Materials and Methods

Materials: CpG-A (ODN2216) sequence 5'-GGGGGAC-GATCGTCGGGGGG-3' (SEQ ID NO: 104) and its control ODN sequence 5'-ggG GGA GCA TGC TGg ggg gc-3' (SEQ ID NO: 105) were purchased from Invivogen. Sequence of the random DNA ODNs is 5'-GGT COT TCC ATT TTA CTC CAC-3' (SEQ ID NO: 106). CpG-B (ODN 2006) sequence 5'-TCG TCG TTT TGT CGT TTT GTC GTT-3' (SEQ ID NO: 107). Biotin or fluorescent labeled ODN2216 were synthesized by Qperon Biotechnologies, Huntsville Ala. Mouse RAGE/Fc and various ELISA kits were purchased from R & D system. HMGB1 A-box and B-box were synthesized by New England Peptide. The A-box sequence is: PRGK-MSSYAFFVQTCREEHKKKHPDASVNF-SEFSKKCSERWKTMSAKEKGKFEDM AKADKARY-EREMKTYIPPKGET (SEQ ID NO: 108) and the B-box sequence is PKRPPSAFFLFCSEYRPKIKGEHPGLS IGD-VAKKLGEMWNNTAADDKQPYEK KAAKLKEKY-EK-DIAAYR (SEQ ID NO: 109). HMGB1 was purified from bovine thymus at MedImmune, Inc. as described above. Bovine brain S100b was purchased from Calbiochem. TLR9 (with or without HA tag) stably expressed HEK293 cells wore purchased from Invitrogen. Plasmacytoid dendritic cell isolation kit was purchased from Miltenyibiotec. Fully human monoclonal antibodies to human HMGB1 were generated by Phage display and demonstrated to be specific for binding to HMGB1 (see, Example 1, above). TLR9-Fc protein was purified from HEK293 cells stably expressing a fusion protein containing the ectodomain of human TLR9 linked to the Fc portion of mouse IgG2a. Also, see Example 14.

Mice and Bone Marrow Cells: C57BL/6 mice were obtained from The Jackson Laboratories and maintained in specific pathogen-free conditions in conventional animal facilities at MedImmune, Inc. TLR9 deficient and MyD88 deficient mice and their litter mate controls were maintained in animal facility of University of Massachusetts Medical School. RAGE deficient mice generated were obtained from Heidelburg Germany and maintained at the University of Massachusetts Medical School. Fresh bone marrow cells were collected and pDCs were isolated from bone marrow cells using miltenyibiotec's plasmacytoid dendritic cell isolation kit. pDCs were re-suspended in Opti-MEM (Invitrogen) and stimulated $2.5 \times 10^4$ cell/well for 24 hr and cytokine level in the supernatant was measured by ELISA.

CpG ELISA: Proteins or peptides were diluted in PBS to the concentration of 5 µg/ml and coated onto plates at 4° C. o/n. Plates were blocked with 4% dry milk in PBS. Biotin labeled CpG-A alone or in complex with HMGB1 were incubated in the plates at 37° C. for 1 hr. and detected with HRP labeled strep-avidin.

Tryptophan emission for CpG-A binding to HMGB1: Fluorescence titrations and spectra of HMGB-1 were carried out at 25° C. with a SPEX Fluoromax-3 spectrofluorimeter, monitoring the HMGB-1 intrinsic tryptophan emission at 347 nm (8 nm bandwidth) with 280 nm excitation (3 nm bandwidth) in a masked capped dual-pathlength (0.2×1.0 cm) quartz cell (Hellma Cells, Inc., Jamaica, N.Y.) upon stepwise addition of CpG-A (0.5 mM) to a 1.7 µM solution of HMGB-1 in 1:10 Dulbecco Phosphate Buffered Saline (PBS) solution (Invitrogen, Carlsbad, Calif.). Complex formation between HMGB-1 and the nucleic acid was monitored by the change in the initial fluorescence of the protein. HMGB-1 fractional saturation was inferred from the ratio of observed fluorescence change to maximal change (at saturation), $F_{lim}$, for each of the nucleic acid additions. Binding affinity was calculated from graphs of relative fluorescence intensity versus [nucleic acid base]/[protein].The occluded binding site size (n) was derived from the intersection of the extrapolated initial slope with the limiting fluorescence plateau in the equilibrium binding isotherms. The measurements for assessment of Tryptophan emission are reviewed in detail in Lakowicz, 2000, Photochem. Photobiol. 72, 421-437.

Immunoprecipitation and Immunoblotting: TLR9 with HA tag stably expressed HEK293 cells were transfected with full length human RAGE for 24 hr. Cells were then stimulated with HMGB1 alone (10 µg/ml) or CpG-A alone (0.3 µM) or combination of the two with or without anti-HMGB1 mAb (50 µg/ml) for 1 hr. Cell pellet was harvested and lysed in RIPA buffer containing 1× PBS, 1% Nonidet P-40, 0.5% sodium deoxycholate, 0.1% SDS, and 1 1 mg/ml phenylmethylsulfonyl fluoride. 10% of the samples were loaded on SDS- PAGE gel as input and the rest of the samples were used to pull down TLR9 by immunoprecipitation (IP). Briefly cell lysate was incubated with 1 μg of HA-bead o/n at 4° C., beads were washed five and followed by SDS/PAGE. Membranes were blotted anti-HA (Roche), mouse anti-hu RAGE (Calbiochem) and anti-HMGB1 (Medimmune).

Immunostaining: TLR9 stably express HEK-293 cells were cultured on glass cover slides and transfected with full length human RAGE or vector control plasmid for 48 hr. Cells then were stimulated with complex of PE labeled CpG (0.1 μM) and HMGB1 (10 μg/ml) for 80 minutes, fixed in 2% paraformaldehyde for 10 minute, blocked with 10% serum and permeabilized with 0.2% Triton-100. Goat anti-TLR9 (eBioscience) and mouse anti-RAGE (Calbiochem) were used as primary antibodies at 37° C. for 1 hr. After wash, proper fluorescent-conjugated secondary antibodies were used for detection. Images were viewed under fluorescent microscope.

AlphaScreen (Amplified Luminescent Proximity Homogeneous) binding assay: Rage-Fc protein or TLR9-Fc chimeric proteins were directly coupled on acceptor beads or donor beads, respectively, per the recommendations of the manufacturer (Perkin Elmer). Beads were incubated in buffer (50 mM Tris-Cl, pH7.2, 100 mM NaCl, 0.1% BSA, 0.01% Tween 20) at 20 μg/ml final concentration either alone or in buffer containing increasing amounts of CpG-A or CpG-B DNA. After 30 min incubation at 25° C. in the dark, samples in white 384-well plates (Proxiplate, Perkin Elmer) were read using the Envision HT microplate reader (Perkin Elmer). Data are shown as Alphascreen units without normalization.

6.15.2 Results

The binding of immobilized HMGB1 to soluble CpG-A was determined by ELISA (FIG. 33, top left). In addition, measurements of perturbation of intrinsic tryptophan fluorescence demonstrated that HMGB1 binds to CpG A DNA with an apparent Kd of 70 nM (FIG. 33, top right). As a chromatin protein it was not unexpected that HMGB1 formed tight complex with CpG-A (FIG. 33 top panels). Similarly, A box and B box HMGB1 peptides also bound to CpG DNA with comparable affinity to full-length protein (data not shown). In contrast to CpG-A, CpG-B failed to bind to HMGB1 (data not shown). A box HMGB1, which has been shown to function as a HMGB1 antagonist, prevented the binding of HMGB1 to CpG DNA (FIG. 33 bottom panel).

Figure 34A:
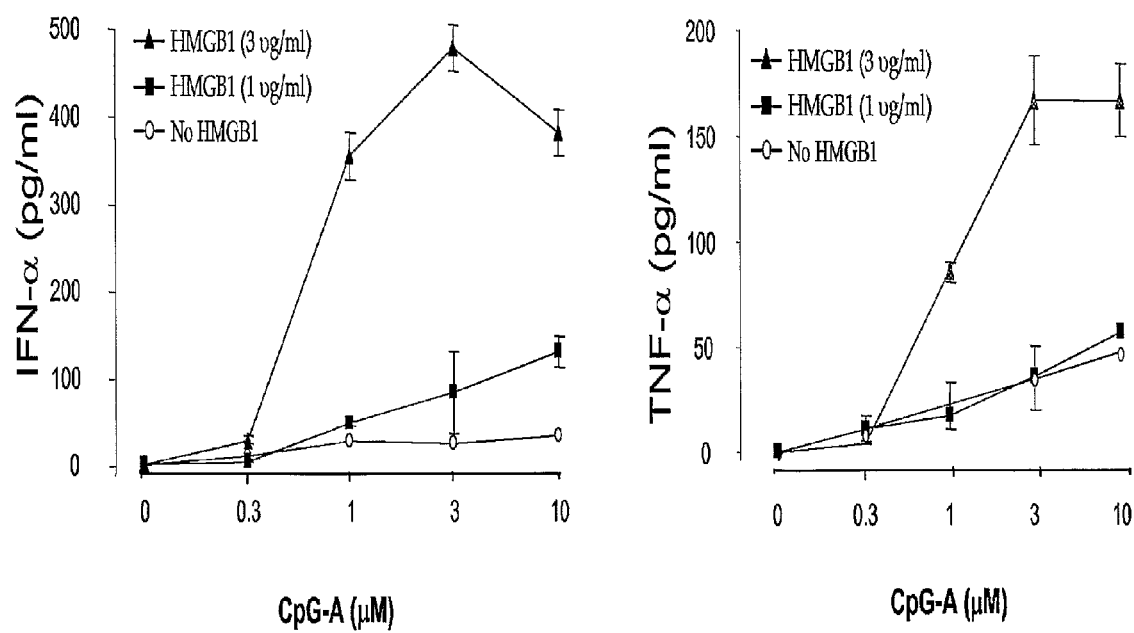
Figure 34B:
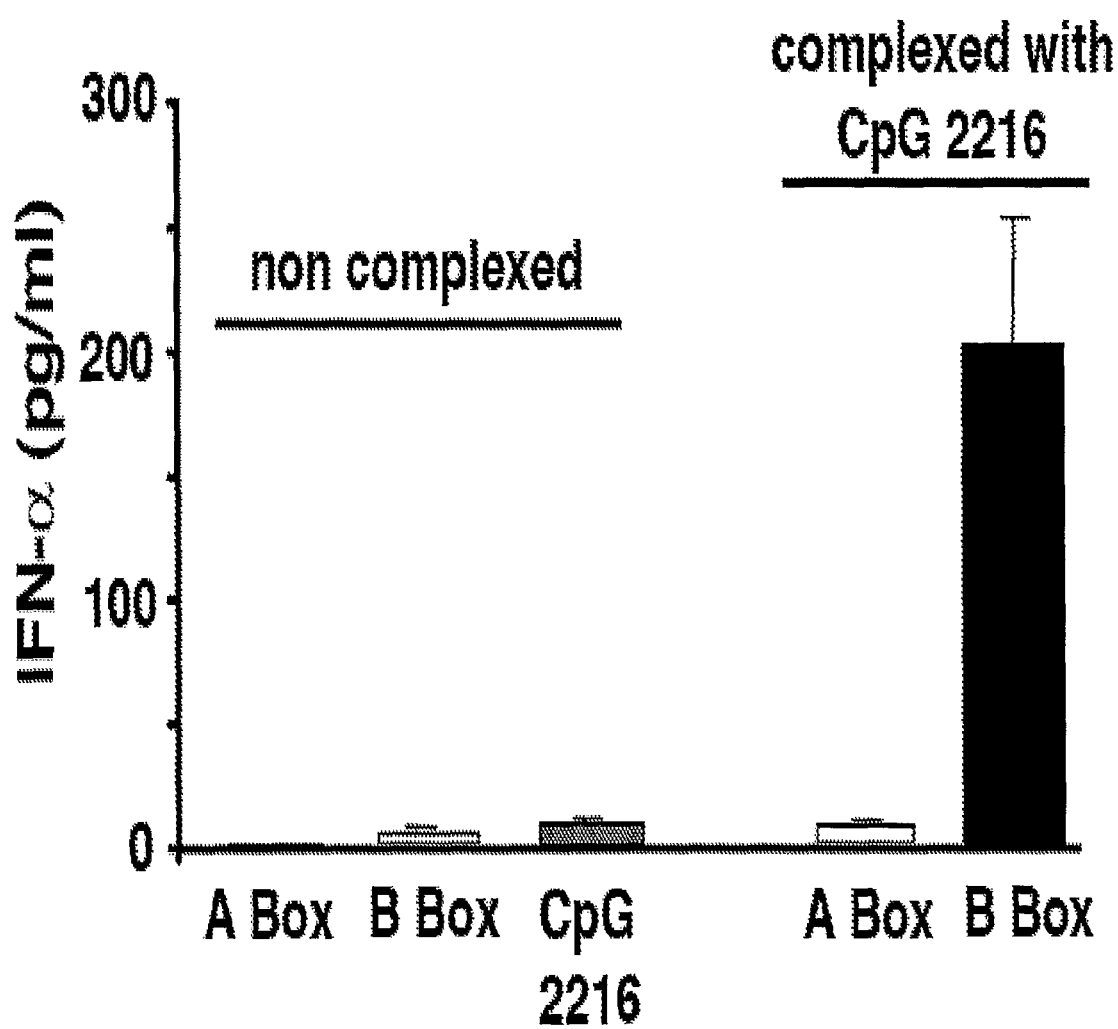

The synergistic immunostimulatory effect of these complexes was confirmed on primary dendritic cells (pDCs) isolated from total bone marrow. CpG DNA alone (open circles) induced a modest but significant increase in IFN-α and TNF-α production as compared to unstimulated cells (IFN-α: 32±5 Vs 0 pg/ml; TNF-α 43±5 Vs 0 pg/ml) (FIG. 34A left and right panels, respectively). HMGB1 alone (not shown) was ineffective in inducing either IFN-α or TNF-a secretion. However co-stimulation with HMGB1 at 3 μg/ml induced a dramatic (20 fold) increase in both IFN-α and TNF-α production (IFN-a: 550±25 pg/ml-TNF a: 172±15 pg/ml respectively (filled triangles). Neither pretreatment with CpG-A prior to HMGB1 treatment, nor HMGB1 treatment prior to CpG-A treatment augmented cytokine secretion (data not shown). Furthermore, non-stimulatory ODN sequences (ODN 2216) were ineffective at inducing IFN-α secretion whether or not they were precomplexed with HMGB1 (data not shown). To address which domain of HMGB1 was required for this synergism, cells were stimulated with either A box or B box of HMGB1 alone, or complexes of A Box/CpG DNA or B Box/CpG DNA. As shown in FIG. 34B, B box/CpG, but not A Box/CpG DNA augmented the production of IFN-α as compared to CpG DNA alone. These data indicate that the B box Domain, which has been reported to contain the RAGE binding region of HMGB1, is required for conferring immunostimulatory activity to HMGB1. As described above studies performed in pDCs obtained from either MyD88 or TLR9 knockout mice revealed that the response to CpG-A alone or HMGB1/CpG-A was completely abolished (FIG. 32B).

Interestingly, the binding of HMGB1 is enhanced by the presence of increasing concentrations of CpG-A (FIG. 35, right panel). The HMGB1/CpG A complex bound to RAGE with an EC50 100-1000 lower than the HMGB1 interaction alone. In contrast to HMGB1/CpG A complex the HMGB1/CpG B complex failed to augment binding to RAGE (data not shown). Furthermore, CpG alone could not bind RAGE, but once bound to HMGB1, CpG was then able to associate with RAGE (FIG. 35, left panel) indicating that the HMGB1/CpG complex binds RAGE. Thus although HMGB1 binds to both A and B class ODN, only CpG-A augments binding of HMGB1 to its receptor.

As described above RAGE/Fc did not block CpG-A induced TFN-α production (FIG. 30), however it significantly blocked CpG/HMGB1 complex induced IFN-α and TNR-α, even beyond HMGB1 amplification effect (FIGS. 30 and 31), which indicated that CpG/HMGB1 induced TLR9 activation was mediated by RAGE. Furthermore, this point was further supported by the experiment in which TLR9+ and RAGE+HEK293 were treated with CpG/HMGB1 complex. Microscopically we found colocalization of CpG, RAGE and TLR9 (FIG. 36). We further demonstrated the association of TLR9 and RAGE in HEK293 cells stably expressing TLR9-HA and transiently transfected with human RAGE by immunoprecipitation. TLR9 was immunoprecipitated, RAGE and MyD88 associated with TLR9 were detected with anti-RAGE, and anti-MyD88 antibodies western blot after cells were stimulated with CpG/HMGB1 complex (FIG. 37, left) but not after HMGB1 or CpG-A stimulation alone (data not shown). In addition, CpG-A alone induced the association of MyD88 with TLR9 (data not shown). To further investigate this interaction, RAGE-Fc and TLR9-Fc were covalently coupled to Alphascreen acceptor and donor beads, respectively. In the absence of CpG DNA, RAGE and TLR9 poorly interacted, however, CpG-A, but not CpG-B augmented RAGE and TLR9 interactions (FIG. 37, right). These data suggest that HMGB1 functions as a chaperone which binds extracellular CpG and through its receptor RAGE, HMGB1 delivers CpG to its endosomal receptor TLR9.

RAGE is a multivalent receptor and binds a number of ligands in addition to advanced glycation end products, such as, for example, proinflammatory cytokine like mediators including members of the calgranulin/S100 family. To determine whether other RAGE ligands would also synergize with CpG DNA, we assessed the both the binding of S100b to RAGE and whether S100b alone or in combination with CpG DNA would induce IFN-α A shown in FIG. 38, S100b and HMGB1 bound in a comparable manner to RAGE, however, despite binding to RAGE, S100b or S100b/CpG DNA failed to induce IFN-a secretion. These data suggest that binding to RAGE per se is insufficient to augment CpG DNA mediated cytokine secretion from pDCs.

6.16 Example 16

Effects of HMGB1 on Osteoclast Differentiation

As described above HMGCB1 levels are seen to increase in the joints as disease progresses in several arthritis models (see, Example 6 above). Osteoclast formation appears to play a role in arthritis. To examine the role of HMGB1 on osteoclast formation precursor cells were treated with HMGB1 from two sources, purified recombinant HMGB1 (rHMGB1) and HMGB1 enriched from synovial fluid fractions (sHMGB1) in the presence or absence of anti-HMBG1 or an isotype control antibody. As shown in FIG. 39 the addition of either rHMGB1 (left panel) or sHMGB1 (right panel) results in increased TRAP-5b activity indicating that HMGB1 can stimulate the production of at least one marker of osteoclast formation in precursor cells. Treatment with HMGB1 in combination with either the G4 or the S16 anti-HMGB1 antibody did not show a similar stimulation of TRAP-5b production. In contrast, treatment with HMGB1 in combination with an isotype control antibody did stimulate TRAP-5b production to similar levels seen with HMGB1 treatment alone. Treatment with antibody alone did not show any increase in production.

6.16.1 Materials and Methods

Osteoclast Precursor Stimulation: Commercially available osteoclast precursor cells (Cambrex) were grown and maintained according to the manufacturers instructions. Cells were treated with M-CSF in the presence or absence of HMGB1 and or anti-HMGB1 antibody for eleven days and then assayed for the TRAP-5b activity. Both purified recombinant HMGB1 (rHMGB1) and HMGB1 enriched from human patient synovial fluid fractions (sHMGB1) over QFF columns were tested. rHMGB1 was used at 4 µg/ml and synovial fluid fractions was used at a final of 1:10 dilution. The anti-HMBG1 antibodies were used at 2 µg/ml.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes. In addition, the following U.S. provisional patent applications: 60/620,726 filed Oct. 22, 2004; 60/651,512 filed Feb. 10, 2005; 60/658,572 filed Mar. 7, 2005; 60/662,944 filed Mar. 18, 2005; 60/713,712 filed Sep. 6, 2005; 60/739,938 filed Nov. 28, 2005; 60/765,746 filed Feb. 7, 2006; 60/799,639 filed May 12, 2006; 60/822,044 filed Aug. 10, 2006 and U.S. patent application Ser. No. 11/254,679 filed Oct. 21, 2005 are incorporated by reference in their entirety.

We claim:

1. An isolated antibody or an antigen-binding fragment thereof that specifically binds a human HMGB1 polypeptide or antigenic fragment thereof comprising:
   a) a light chain variable region having the 3 CDRs of the light chain of the antibody S6, SEQ ID NO:9, and a heavy chain variable region, wherein the heavy chain variable region comprises 3 CDRs; or
   b) a heavy chain variable region having the 3 CDRs of the light chain of the antibody S6, SEQ ID NO:11, and a light chain variable, wherein the light chain variable region comprises 3 CDRs; or
   c) a light chain variable region having the 3 CDRs of the light chain of the antibody S6, SEQ ID NO:9, and a heavy chain variable region having the 3 CDRs of the heavy chain of the antibody S6, SEQ ID NO:11.

2. The antibody or antigen-binding fragment thereof of claim 1, wherein said antibody or antigen-binding fragment thereof comprises a light chain variable region having the 3 CDRs of the light chain of the antibody S6, SEQ ID NO:9, and a heavy chain variable region having the 3 CDRs of the heavy chain of the antibody S6, SEQ ID NO:11.

3. An isolated antibody or an antigen-binding fragment thereof comprising a light chain variable region from the antibody S6, SEQ ID NO:9 and a heavy chain variable region from the antibody S6, SEQ ID NO:11.

4. The antibody or antigen-binding fragment thereof of claim 1, wherein said antibody or antigen-binding fragment thereof is selected from the group consisting of: a monoclonal antibody, a chimeric antibody; a single-chain Fv (scFv); an Fab fragment; and a F(ab') fragment.

5. The antibody or antigen-binding fragment thereof of claim 3, wherein said antibody or antigen-binding fragment thereof is selected from the group consisting of: a monoclonal antibody, a chimeric antibody; a single-chain Fv (scFv); an Fab fragment; and a F(ab') fragment.

6. The antibody or antigen-binding fragment thereof of claim 1, wherein said antibody or antigen-binding fragment thereof is a human antibody or an antigen binding fragment thereof.

7. The antibody or antigen-binding fragment thereof of claim 1, wherein said antibody or antigen-binding fragment thereof has a pI of between 6.5 and 9.5 and has a Tm of between 65 degrees Celsius and 95 degrees Celsius.

8. The antibody or antigen-binding fragment thereof of claim 3, wherein said antibody or antigen-binding fragment thereof has a pI of between 6.5 and 9.5 and has a Tm of between 65 degrees Celsius and 95 degrees Celsius.

9. The antibody or antigen-binding fragment thereof of claim 1, wherein said antibody or antigen-binding fragment thereof inhibits the release of proinflammatory cytokine from a vertebrate cell treated with an HMGB1 polypeptide.

10. The antibody or antigen-binding fragment thereof of claim 9, wherein the cytokine is selected from the group consisting of: IL-1β, TNF-α, and IL-6.

11. The antibody or antigen-binding fragment thereof of claim 3, wherein said antibody or antigen-binding fragment thereof inhibits the release of a proinflammatory cytokine from a vertebrate cell treated with an HMGB1 polypeptide.

12. The antibody or antigen-binding fragment thereof of claim 11, wherein the cytokine is selected from the group consisting of: IL-1β, TNF-α, and IL-6.

13. The antibody or antigen-binding fragment thereof of claim 1, wherein said antibody or antigen-binding fragment thereof when administered to a rodent is at least 30% protective in at least one rodent sepsis model.

14. The antibody or antigen-binding fragment thereof of claim 13, wherein the rodent sepsis model is a rodent cecal ligation and puncture model.

15. A composition comprising the antibody or antigen-binding fragment thereof of claim 3 in a pharmaceutically acceptable excipient.

16. A composition comprising the antibody or antigen-binding fragment thereof of claim 6 in a pharmaceutically acceptable excipient.

* * * * *